United States Patent
English et al.

(10) Patent No.: US 11,970,705 B2
(45) Date of Patent: Apr. 30, 2024

(54) INSECTICIDAL PROTEINS AND METHODS FOR THEIR USE

(71) Applicant: PIONEER HI-BRED INTERNATIONAL, INC., Johnston, IA (US)

(72) Inventors: James J English, San Ramon, CA (US); Jimei Wang, Johnston, IA (US); Nasser Yalpani, Kelowna (CA)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 17/805,016

(22) Filed: Jun. 1, 2022

(65) Prior Publication Data

US 2022/0333128 A1    Oct. 20, 2022

Related U.S. Application Data

(63) Continuation of application No. 16/611,962, filed as application No. PCT/US2018/031746 on May 9, 2018, now Pat. No. 11,555,203.

(60) Provisional application No. 62/504,650, filed on May 11, 2017.

(51) Int. Cl.
C12N 15/82    (2006.01)
A01N 63/50    (2020.01)

(52) U.S. Cl.
CPC ......... *C12N 15/8286* (2013.01); *A01N 63/50* (2020.01)

(58) Field of Classification Search
CPC .................................................. C12N 15/8286
USPC ......................................................... 800/300
See application file for complete search history.

(56) References Cited

U.S. PATENT DOCUMENTS

| | | |
|---|---|---|
| 10,006,014 B2 | 6/2018 | Singh |
| 11,555,203 B2 | 1/2023 | English et al. |
| 2005/0138685 A1 | 6/2005 | Flannagan et al. |
| 2014/0283208 A1 | 9/2014 | Abad et al. |
| 2015/0139976 A1 | 5/2015 | Singh et al. |
| 2016/0201044 A1 | 7/2016 | Singh et al. |

FOREIGN PATENT DOCUMENTS

| | | |
|---|---|---|
| CN | 106834318 A | 6/2017 |
| WO | 2009151748 A1 | 12/2009 |
| WO | 2013098858 A2 | 7/2013 |
| WO | 2016061206 A1 | 4/2016 |
| WO | 2016144688 A1 | 9/2016 |

OTHER PUBLICATIONS

Hill et al Biochem. Biophys. Res. Comm. 244:573-577 (Year: 1998).*
Lazar et al. Mol. Cell. Biol. 8:1267-1252 (Year: 1988).*
Guo et al. Proc. Natl. Acad. Sci. USA 101: 9205-9210 (Year: 2004).*
Falcon-Perez JM et al. J Biol Chem. 274:23584-90 (Year: 1999).*
Guo, Haiwei H.; et al.: "Protein tolerance to random amino acid change," Proceedings of the National Academy of Sciences (PNAS), Jun. 22, 2004 (Jun. 22, 2004), vol. 101, No. 25, pp. 9205-9210.
Lazar, Eliane; et al.: "Transforming Growth Factor: Mutation of Aspartic Acid 47 and Leucine 48 Results in Different Biological Activities," Molecular and Cellular Biology, Mar. 1988 (Mar. 1988), vol. 8, No. 3, pp. 1247-1252.
Unknown: "AFR32946" Feb. 14, 2014 (Feb. 14, 2014), XP55486005, URL:https://www.ebi.ac.uk/ena/data/view/AFR32946&display=text.
International Search Report and Written Opinion for International Application No. PCT/US18/31746, dated Jul. 5, 2018.
International Preliminary Report on Patentability for International Application No. PCT/US2018/031746, dated Nov. 21, 2019, 8 Pages.
Shukla A.K., et al., "Expression of an Insecticidal Fern Protein in Cotton Protects Against Whitefly," Nature Biotechnology, Oct. 2016, vol. 34, No. 10, pp. 1046-1054.

* cited by examiner

*Primary Examiner* — Li Zheng

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of plant species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

12 Claims, 7 Drawing Sheets

Specification includes a Sequence Listing.

| Gene | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|---|---|---|---|---|---|
| IPD121Aa | SBL | 8 | 0 | FAW | 5.8 | 0.4 | CEW | 5.7 | 1 | ECB | 7 | 0.9 | VBC | 5.7 | 1.6 |
| IPD121Ab | | 1 | 0 | | 1 | 0 | | 2.3 | 3.3 | | 4.3 | 1.2 | | 2.3 | 3.2 |
| IPD121Ac | | 8 | 0 | | 5.3 | 0.8 | | 5 | 1.1 | | 7.2 | 1 | | 4.7 | 2.1 |
| IPD121Ad | | 8 | 0 | | 3.3 | 2.2 | | 5.7 | 1 | | 6.5 | 1.2 | | 5.2 | 1.3 |
| IPD121Ae | | 8.3 | 0.5 | | 3 | 2 | | 5.2 | 2 | | 7.5 | 1.4 | | 5.5 | 1.9 |
| IPD121Af | | 7.7 | 1 | | 4 | 1.1 | | 4.7 | 2.5 | | 5.7 | 1.2 | | 5.3 | 2.2 |
| IPD121Ah | | 7.5 | 0.8 | | 5.5 | 0.5 | | 4.8 | 2.7 | | 5.3 | 0.5 | | 5.2 | 1.3 |
| IPD121Aj | | 7.5 | 0.8 | | 4.5 | 1 | | 4.7 | 2.3 | | 5 | 1.5 | | 4.3 | 1.9 |
| IPD121Ba | | 7.3 | 0.5 | | 5.5 | 0.6 | | 5.5 | 1.1 | | 6 | 0 | | 8 | 1.4 |
| IPD121Bb | | 6.8 | 1 | | 5.5 | 0.6 | | 4.8 | 2.4 | | 6 | 0 | | 6 | 0 |
| IPD121Bc | | 7.8 | 1 | | 6 | 0 | | 7.5 | 1.7 | | 6 | 0.5 | | 6.3 | 1.7 |
| IPD121Bd | | 7.8 | 0 | | 6.5 | 0.6 | | 4.5 | 1.3 | | 6.3 | 0 | | 5.8 | 0.5 |
| IPD121Be | | 1 | 1.4 | | 3.8 | 3.6 | | 1.5 | 1 | | 1 | 0.4 | | 1 | 0 |
| IPD121Bf | | 7.7 | 1.5 | | 3.8 | 0.8 | | 4.5 | 1 | | 5.8 | 0.6 | | 2 | 0.9 |
| IPD121Bg | | 7 | 0 | | 5.2 | 0.8 | | 3.7 | 1.9 | | 6 | 3.1 | | 3.3 | 1.4 |
| IPD121Bk | | 1 | 0.5 | | 2.2 | 2 | | 1.3 | 0.8 | | 2.8 | 1.2 | | 1 | 0 |
| IPD121Bl | | 1.5 | 0.5 | | 3.2 | 2.1 | | 1 | 0 | | 2.3 | 1.1 | | 1 | 0 |
| IPD121Bm | | 7.8 | 0.5 | | 3.2 | 2.7 | | 4 | 1.9 | | 6 | 0.5 | | 3.3 | 2.3 |
| IPD121Ca | | 7.7 | 0 | | 4.5 | 0.8 | | 6 | 0 | | 5.7 | 1 | | 6 | 0.6 |
| IPD121Cb | | 8 | 1.2 | | 4 | 0.9 | | 6 | 0 | | 6.3 | 1.7 | | 6.8 | 0.8 |
| IPD121Cc | | 6.7 | 1 | | 4.3 | 0.8 | | 5.7 | 0.5 | | 7.2 | 0.6 | | 6.2 | 1 |
| IPD121Cd | | 7.3 | 0.8 | | 2.8 | 1.5 | | 6 | 0.6 | | 6 | 0.8 | | 5 | 1.3 |
| IPD121Ce | | 7.2 | 0 | | 1.7 | 1.6 | | 4.7 | 1.6 | | 4.8 | 1.9 | | 2 | 1.1 |
| IPD121Cf | | 1 | 0 | | 1 | 0 | | 1 | 0 | | 2.8 | 0.6 | | 1.8 | 2 |
| IPD121Cg | | 5.2 | 3.3 | | 1 | 0 | | 2.5 | 1.4 | | 4.2 | 1.5 | | 1.5 | 0.8 |

*FIG. 2A*

| Gene | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|---|---|---|---|---|---|
| IPD121Ch | SBL | 3.3 | 2.9 | FAW | 1 | 0 | CEW | 2.3 | 1.8 | ECB | 3.2 | 1.2 | VBC | 1 | 0 |
| IPD121Ci |  | 7.8 | 0.5 |  | 6 | 0 |  | 6 | 1.4 |  | 5 | 1.2 |  | 7.3 | 1.3 |
| IPD121Cj |  | 1 | 0 |  | 1.3 | 0.5 |  | 1 | 0 |  | 1.8 | 1.5 |  | 2.8 | 1.7 |
| IPD121Ck |  | 7.3 | 1 |  | 5.3 | 1 |  | 4.5 | 2.4 |  | 5.8 | 2.1 |  | 7.8 | 1.3 |
| IPD121Cl |  | 7.8 | 0.5 |  | 6 | 0 |  | 6.5 | 1 |  | 6.8 | 1.5 |  | 8.5 | 0.6 |
| IPD121Cm |  | 7.5 | 1 |  | 6 | 0 |  | 5.5 | 0.6 |  | 6.8 | 1 |  | 7 | 1.6 |
| IPD121Cn |  | 7 | 0.8 |  | 6.3 | 0.5 |  | 5.3 | 1 |  | 6.3 | 0.5 |  | 8 | 1.4 |
| IPD121Co |  | 7.8 | 0.5 |  | 6 | 0 |  | 5.3 | 2.9 |  | 6.3 | 0.5 |  | 7.8 | 1.5 |
| IPD121Cp |  | 6.7 | 1 |  | 5 | 1.7 |  | 4.7 | 1.9 |  | 5.5 | 0.5 |  | 6.2 | 0.4 |
| IPD121Cq |  | 7.8 | 0.4 |  | 5.7 | 0.5 |  | 4.8 | 1.2 |  | 6.8 | 0.8 |  | 6.5 | 0.5 |
| IPD121Cr |  | 7 | 0.9 |  | 5.8 | 0.4 |  | 5.7 | 1 |  | 7.2 | 1.2 |  | 6 | 0 |
| IPD121Cs |  | 6.8 | 0.8 |  | 4.7 | 0.8 |  | 4.2 | 2.3 |  | 6 | 2.1 |  | 6 | 0 |
| IPD121Ct |  | 7 | 0.8 |  | 2.8 | 0.5 |  | 4.5 | 2.4 |  | 5 | 1.4 |  | 3.5 | 2.1 |
| IPD121Cu |  | 7.8 | 1.3 |  | 2.3 | 1.5 |  | 3.3 | 1.7 |  | 4.5 | 2.6 |  | 1.8 | 1.5 |
| IPD121Cv |  | 6.8 | 1 |  | 3.8 | 2.6 |  | 3.8 | 2.1 |  | 2.5 | 0.6 |  | 1 | 0 |
| IPD121Cw |  | 7.8 | 0.5 |  | 3.5 | 1.9 |  | 6 | 2.2 |  | 4.3 | 1.5 |  | 2 | 1.4 |
| IPD121Cx |  | 8.3 | 0.5 |  | 5.8 | 2.1 |  | 4.8 | 1.9 |  | 7 | 1.4 |  | 4 | 1.6 |
| IPD121Cy |  | 7.5 | 0.6 |  | 3.5 | 2.4 |  | 5.5 | 0.6 |  | 5.5 | 0.6 |  | 2.3 | 2.5 |
| IPD121Cz |  | 7.5 | 0.6 |  | 3.3 | 2.2 |  | 3.5 | 1.9 |  | 4.5 | 1.9 |  | 2.5 | 2.4 |
| IPD121Caa |  | 7.8 | 0.5 |  | 2.3 | 1.5 |  | 1.3 | 0.5 |  | 3.8 | 1.9 |  | 1.8 | 1.5 |
| IPD121Cab |  | 7.3 | 1 |  | 3.5 | 0.6 |  | 4 | 2.4 |  | 5.3 | 1 |  | 2.3 | 1.9 |
| IPD121Cac |  | 2.3 | 1 |  | 1 | 0 |  | 1 | 0 |  | 3 | 4 |  | 1 | 1.9 |
| IPD121Cad |  | 2.8 | 2.2 |  | 2.5 | 1.7 |  | 1.3 | 0.5 |  | 1.8 | 1.5 |  | 2 | 1.4 |
| IPD121Cae |  | 7.3 | 1 |  | 6 | 0.6 |  | 4.3 | 1.4 |  | 6.5 | 1.2 |  | 6.3 | 0.8 |
| IPD121Cag |  | 4.5 | 2.6 |  | 2.3 | 1.9 |  | 1.5 | 0.6 |  | 4.5 | 1.7 |  | 2.3 | 2.5 |

*FIG. 2B*

| Gene | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|---|---|---|---|---|---|
| IPD121Cah | SBL | 1 | 0 | FAW | 2.3 | 2.5 | CEW | 2 | 2 | ECB | 1.8 | 1.5 | VBC | 1.3 | 0.5 |
| IPD121Cai | | 1 | 0 | | 1 | 0 | | 3.5 | 3.8 | | 1 | 0 | | 1 | 0 |
| IPD121Caj | | 1 | 0 | | 2.5 | 1.3 | | 1 | 0 | | 2.3 | 1.5 | | 1 | 0 |
| IPD121Cak | | 7.7 | 0.5 | | 5.5 | 0.5 | | 5.3 | 1.2 | | 5.3 | 1 | | 6.5 | 0.5 |
| IPD121Cal | | 1 | 0 | | 1.2 | 0.4 | | 1 | 0 | | 3.2 | 1.6 | | 5.7 | 0.8 |
| IPD121Cam | | 7.3 | 0.8 | | 5.3 | 1 | | 5.2 | 0.8 | | 6.2 | 0.4 | | 6 | 0 |
| IPD121Can | | 7.8 | 1 | | 5.2 | 0.8 | | 3.5 | 1.4 | | 7.2 | 1.2 | | 5.5 | 0.5 |
| IPD121Cap | | 1 | 2.6 | | 3 | 3.6 | | 1 | 2.6 | | 1 | 2.6 | | 1 | 2.6 |
| IPD121Cat | | 7.2 | 0.8 | | 5.3 | 1.2 | | 4.5 | 0.8 | | 6.3 | 0.5 | | 6.2 | 1 |
| IPD121Cau | | 7.8 | 1 | | 5.5 | 0.5 | | 4.5 | 1.9 | | 6 | 0 | | 5.5 | 0.8 |
| IPD121Cav | | 5.8 | 3.3 | | 1.5 | 0.8 | | 1 | 0 | | 4.5 | 1.7 | | 2.2 | 1.9 |
| IPD121Caw | | 5 | 2.5 | | 4.3 | 0.8 | | 3.8 | 1.6 | | 5 | 0 | | 2 | 1.3 |
| IPD121Cay | | 6.5 | 1.4 | | 5.3 | 1.6 | | 3.7 | 0.8 | | 6.8 | 1.9 | | 1.5 | 0.8 |
| IPD121Caz | | 3.3 | 2.6 | | 1.2 | 0.4 | | 1.3 | 0.5 | | 3.7 | 1.3 | | 1.2 | 0.4 |
| IPD121Cba | | 2.3 | 2 | | 1.7 | 0.5 | | 1.7 | 0.5 | | 3 | 1.6 | | 1.7 | 0.8 |
| IPD121Cbc | | 1 | 0.8 | | 1.5 | 0.8 | | 1.2 | 0.8 | | 1.2 | 0.8 | | 1 | 0.8 |
| IPD121Cbd | | 7.7 | 1.5 | | 2 | 1.1 | | 4.2 | 0.4 | | 6 | 1.4 | | 5 | 1.2 |
| IPD121Cbe | | 7.7 | 1.1 | | 3.8 | 1.3 | | 4.5 | 0.5 | | 5.3 | 0.4 | | 5.7 | 1.8 |
| IPD121Cbf | | 7.3 | 0.7 | | 2.8 | 1.6 | | 3.3 | 1.5 | | 1 | 0.8 | | 4.7 | 1.7 |
| IPD121Cbh | | 8.2 | 0.6 | | 2.7 | 1.7 | | 3 | 1.9 | | 5 | 1.1 | | 3.8 | 2 |
| IPD121Cbk | | 7.8 | 0.4 | | 1.5 | 2.6 | | 2.2 | 2.3 | | 4 | 2.3 | | 4 | 2.1 |
| IPD121Cbm | | 5.2 | 2.9 | | 1.8 | 0.5 | | 2.2 | 1.2 | | 4.7 | 1.7 | | 2 | 1.9 |
| IPD121Cbo | | 7.8 | 2.2 | | 2 | 0.6 | | 1.5 | 1.1 | | 4.7 | 1.3 | | 2 | 1.4 |
| IPD121Da | | 2 | 2.4 | | 1 | 0 | | 1 | 0 | | 1 | 0 | | 1 | 0 |
| IPD121Db | | 1 | 0 | | 1 | 0 | | 2 | 2.4 | | 1.3 | 0.5 | | 1 | 0 |

FIG. 2C

| Gene | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|---|---|---|---|---|---|
| IPD121Dc | SBL | 1 | 0 | FAW | 1 | 0 | CEW | 3.8 | 4 | ECB | 1.7 | 0.8 | VBC | 1 | 0 |
| IPD121Dd | | 1 | 0 | | 1 | 0 | | 1.8 | 2 | | 1 | 0 | | 1 | 0 |
| IPD121De | | 1 | 0.8 | | 1.5 | 1 | | 1 | 0.8 | | 3.2 | 1.8 | | 1 | 0.8 |
| IPD121Df | | 1 | 1.1 | | 1 | 1.1 | | 1 | 1.1 | | 1.2 | 1.1 | | 1 | 1.1 |
| IPD121Dg | | 8.2 | 1.3 | | 2 | 1.4 | | 3 | 2.3 | | 3.7 | 0.7 | | 3.3 | 2.1 |
| IPD121Dh | | 3 | 1.6 | | 1.3 | 1.8 | | 2.5 | 3.2 | | 4.3 | 1.5 | | 2.7 | 2.4 |
| IPD121Ea | | 1 | 0 | | 2.3 | 1 | | 2.5 | 2.6 | | 1.8 | 0.5 | | 2.3 | 1.5 |
| IPD121Eb | | 1 | 0 | | 4 | 2.2 | | 1 | 1.8 | | 1.8 | 0.5 | | 2 | 2 |
| IPD121Ec | | 1 | 0 | | 2.3 | 1.9 | | 1 | 0 | | 1.3 | 0.5 | | 1 | 0 |
| IPD121Ed | | 1.3 | 0.5 | | 3.5 | 1 | | 1.5 | 0.9 | | 1.5 | 1 | | 1.5 | 1 |
| Negative | | 1.2 | 0.4 | | 1 | 0 | | 1.7 | 0.8 | | 4.2 | 1 | | 1 | 0 |

*FIG. 2D*

INSECTICIDAL PROTEINS AND METHODS FOR THEIR USE

CROSS-REFERENCE TO RELATED APPLICATIONS

This Application is a continuation application of U.S. patent application Ser. No. 16/611,962, filed Nov. 8, 2019, granted as U.S. Pat. No. 11,555,203, which is a National Stage application of International Patent Application number PCT/US2018/031746, which claims the benefit of priority to U.S. Provisional Application No. 62/504,650 filed on May 11, 2017, the disclosures of each of which are incorporated herein by reference in their entireties.

REFERENCE TO SEQUENCE LISTING SUBMITTED ELECTRONICALLY

The official copy of the sequence listing is submitted electronically via EFS-Web as an ASCII formatted sequence listing with a file named "7440 WO_PCT_Sequence_Listing" created on May 2, 2018, and having a size of 334 kilobytes and is filed concurrently with the specification. The sequence listing contained in this ASCII formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants may provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera, including but not limited to insect pests that have developed resistance to existing insecticides.

SUMMARY

In one aspect compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect isolated or recombinant nucleic acid molecules are provided encoding IPD121 polypeptides including amino acid substitutions, deletions, insertions, and fragments thereof. Provided are isolated or recombinant nucleic acid molecules capable of encoding IPD121 polypeptides of SEQ ID NOS: 124-234, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect IPD121 polypeptides are encompassed. Also provided are isolated or recombinant IPD121 polypeptides of SEQ ID NO: 124-234, as well as amino acid substitutions, deletions, insertions, fragments thereof and combinations thereof.

In another aspect, methods are provided for producing the polypeptides and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. It will be understood by one of skill in the art that the transgenic plant may comprise any gene imparting an agronomic trait of interest.

In another aspect, methods for detecting the nucleic acids and polypeptides of the embodiments in a sample are also included. A kit for detecting the presence of an IPD121 polypeptide or detecting the presence of a polynucleotide encoding an IPD121 polypeptide in a sample is provided. The kit may be provided along with all reagents and control samples necessary for carrying out a method for detecting the intended agent, as well as instructions for use.

In another aspect the compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of IPD121 polypeptides.

BRIEF DESCRIPTION OF THE FIGURES

FIGS. 1A-C show an amino acid sequence alignment, using the ALIGNX® module of the Vector NTI® suite, of the IPD121Aa polypeptide (SEQ ID NO: 124), the IPD121Ab polypeptide (SEQ ID NO: 125), the IPD121Ac polypeptide (SEQ ID NO: 228), the IPD121Ad polypeptide (SEQ ID NO: 229), the IPD121Ae polypeptide (SEQ ID NO: 230), the IPD121Af polypeptide (SEQ ID NO: 231), the IPD121Ca polypeptide (SEQ ID NO: 126), the IPD121Cb polypeptide (SEQ ID NO: 127), the IPD121Cc polypeptide (SEQ ID NO: 128), the IPD121Cd polypeptide (SEQ ID NO: 129), the IPD121Ce polypeptide (SEQ ID NO: 139), the IPD121Cf polypeptide (SEQ ID NO: 225), the IPD121Cg polypeptide (SEQ ID NO: 226), the IPD121Ch polypeptide (SEQ ID NO: 227), the IPD121 Da polypeptide (SEQ ID NO: 142), the IPD121db polypeptide (SEQ ID NO: 232), the IPD121Dc polypeptide (SEQ ID NO: 233), and the IPD121Dd polypeptide (SEQ ID NO: 234). The amino acid sequence diversity between the amino acid sequences is highlighted. Conservative amino acid differences are indicated by (A) shading.

FIGS. 2A-D show activity of selected IPD121 polypeptides, transiently expressed in bush bean, against leaf feeding damage from a selection of Lepidoptera.

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding IPD121 polypeptides. In particular, the nucleic acid sequences of the embodiments are useful for preparing plants and microorganisms that possess pesticidal activity. Thus, transformed bacteria, plants, plant cells, plant tissues and seeds are provided. The compositions include pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered IPD121 polypeptides by methods known in the art, such as site directed mutagenesis, domain swapping or DNA shuffling. The IPD121 polypeptides find use in controlling or killing Lepidopteran, Coleopteran, Dipteran, fungal, Hemipteran and/or nematode pest populations and for producing compositions with pesticidal activity. Insect pests of interest include, but are not limited to, Lepidoptera species including but not limited to: Corn Earworm, (CEW) (*Helicoverpa zea*), European Corn Borer (ECB) (*Ostrinia nubialis*), Fall Armyworm (FAW), (*Spodoptera frugiperda*), soybean looper (SBL), e.g., *Pseudoplusia includens* Walker; and velvet bean caterpillar (VBC), e.g., *Anticarsia gemmatalis* Hubner.

By "pesticidal toxin" or "pesticidal protein" is used herein to refer to a toxin that has toxic activity against one or more pests. For example, pests may include members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*.

In some embodiments the IPD121 polypeptide includes an amino acid sequence deduced from the full-length nucleic acid sequence disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are isolated or recombinant nucleic acid sequences conferring pesticidal activity. Also provided are the amino acid sequences of IPD121 polypeptides. The polypeptides resulting from translation of these IPD121 genes allows cells to control or kill pests that ingest it.

IPD121 Proteins and Variants and Fragments Thereof

Figure 1A:
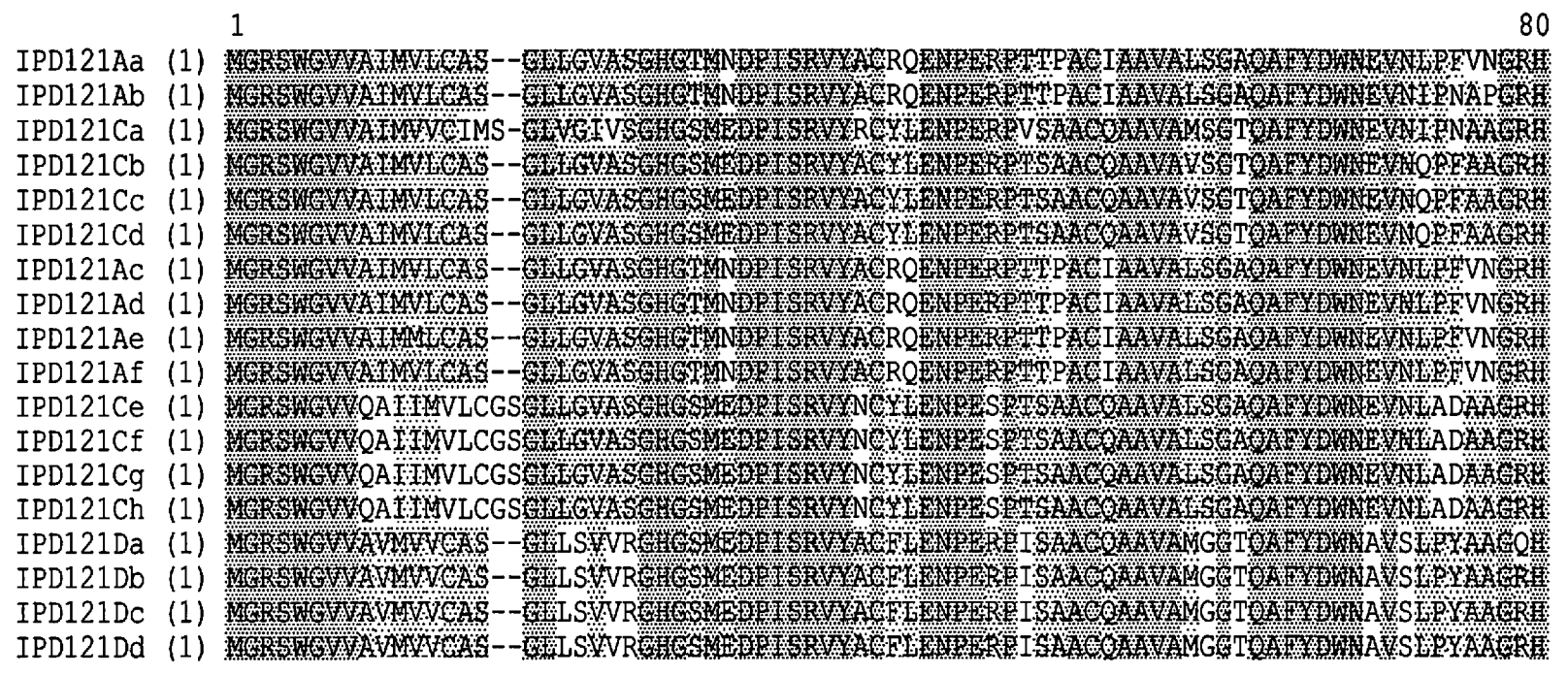
Figure 1B:
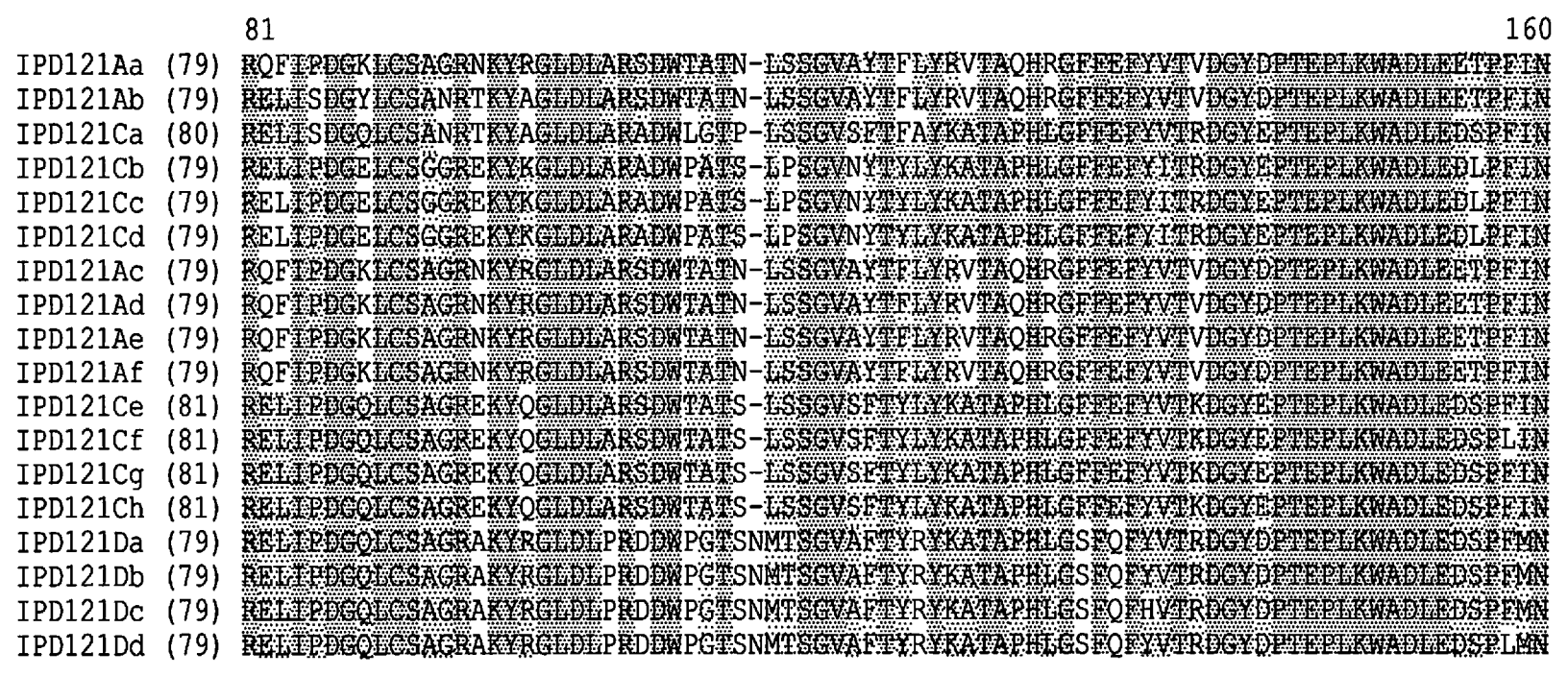
Figure 1C:
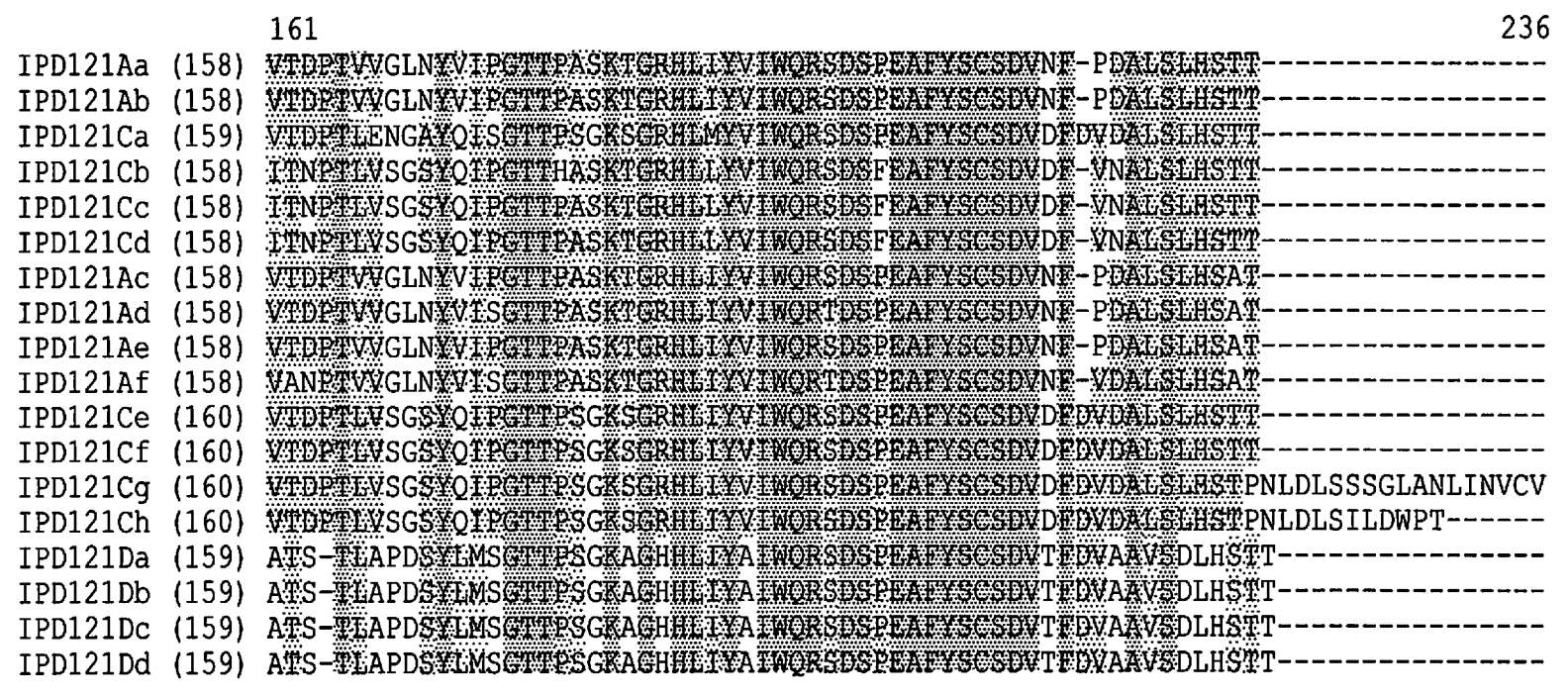

IPD121 polypeptides are encompassed by the disclosure. "IPD121 polypeptide", and "IPD121 protein" as used herein interchangeably refers to a polypeptide(s) having insecticidal activity including but not limited to insecticidal activity against one or more insect pests of the Lepidoptera and/or Coleoptera orders, and is sufficiently homologous to the IPD121Aa polypeptide of SEQ ID NO: 124. A variety of IPD121 polypeptides are contemplated. Sources of IPD121 polypeptides or related proteins include plant species selected from but not limited to *Polystichum, Davallia, Didymochlaena, Humata, Onoclea,* and *Tectaria* species. Alignment of the amino acid sequences of IPD121 polypeptide homologs (for example, see FIGS. 1A-1C), allows for the identification of residues that are highly conserved amongst the natural homologs of this family.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In one embodiment the IPD121 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOS: 124-234. In some embodiments the sequence identity is against the full length sequence of an IPD121 polypeptide. The term "about" when used herein in context with percent sequence identity means+/−1.0%.

A "recombinant protein" is used herein to refer to a protein that is no longer in its natural environment, for example in vitro or in a recombinant bacterial or plant host cell.

"Substantially free of cellular material" as used herein refers to a polypeptide including preparations of protein having less than about 30%, 20%, 10% or 5% (by dry weight) of non-pesticidal protein (also referred to herein as a "contaminating protein").

"Fragments" or "biologically active portions" include polypeptide fragments comprising amino acid sequences sufficiently identical to an IPD121 polypeptide and that exhibit insecticidal activity. "Fragments" or "biologically active portions" of IPD121 polypeptides includes fragments comprising amino acid sequences sufficiently identical to the amino acid sequence set forth in any one of SEQ ID NOS: 124-234 wherein the IPD121 polypeptide has insecticidal activity. Such biologically active portions can be prepared by recombinant techniques and evaluated for insecticidal activity. In some embodiments, the IPD121 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus relative to any one of SEQ ID NOS: 124-234, e.g., by proteolysis, by insertion of a start codon, by deletion of the codons encoding the deleted amino acids and concomitant insertion of a start codon, and/or insertion of a stop codon. In some embodiments, the IPD121 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 amino acids from the N-terminus of any one of SEQ ID NOS: 124-234. In some embodiments, the IPD121 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to any one of SEQ ID NOS: 124-234.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments an IPD121 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the full length or a fragment of the amino acid sequence of any one of SEQ ID NOS: 124-234, wherein the IPD121 polypeptide has insecticidal activity.

In some embodiments an IPD121 polypeptide comprises an amino acid sequence of any one or more of SEQ ID NOS: 124-234 having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or more amino acid substitutions compared to the amino acid at the corresponding position of any one or more of the respective SEQ ID NOS: 124-234.

Methods for such manipulations are generally known in the art. For example, amino acid sequence variants of an IPD121 polypeptide can be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess the desired pesticidal activity. However, it is understood that the ability of an IPD121 polypeptide to confer pesticidal activity may be improved by the use of such techniques upon the compositions of this disclosure.

Conservative amino acid substitutions may be made at one or more predicted nonessential amino acid residues. A "nonessential" amino acid residue is a residue that can be altered from the wild-type sequence of an IPD121 polypeptide without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues.

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

1.) Shuffling

Variant nucleotide and amino acid sequences of the disclosure also encompass sequences derived from mutagenic and recombinogenic procedures such as DNA shuffling. With such a procedure, one or more different IPD121 polypeptide coding regions can be used to create a new IPD121 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) Nature 370:389-391; and U.S. Pat. Nos. 5,605,793 and 5,837,458.

Domain swapping is another mechanism for generating altered IPD121 polypeptides. Domains may be swapped between IPD121 polypeptides resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-21010; Rang, et al., 91999) *Appl. Environ. Microbiol.* 65:2918-2925).

Phylogenetic, Sequence Motif, and Structural Analyses of Insecticidal Protein Families.

A sequence and structure analysis method can be employed, which is composed of four components: phylogenetic tree construction, protein sequence motifs finding, secondary structure prediction, and alignment of protein sequences and secondary structures. Details about each component are illustrated below.

1) Phylogenetic Tree Construction

The phylogenetic analysis can be performed using the software MEGA5. Protein sequences can be subjected to ClustalW version 2 analysis (Larkin M. A et al (2007) *Bioinformatics* 23(21): 2947-2948) for multiple sequence alignment. The evolutionary history is then inferred by the Maximum Likelihood method based on the JTT matrix-based model. The tree with the highest log likelihood is obtained, exported in Newick format, and further processed to extract the sequence IDs in the same order as they appeared in the tree. A few clades representing sub-families can be manually identified for each insecticidal protein family.

2) Protein Sequence Motifs Finding

Protein sequences are re-ordered according to the phylogenetic tree built previously, and fed to the MOTIF analysis tool MEME (Multiple EM for MOTIF Elicitation) (Bailey T. L., and Elkan C., *Proceedings of the Second International Conference on Intelligent Systems for Molecular Biology*, pp. 28-36, AAAI Press, Menlo Park, California, 1994.) for identification of key sequence motifs. MEME is setup as follows: Minimum number of sites 2, Minimum motif width 5, and Maximum number of motifs 30. Sequence motifs unique to each sub-family were identified by visual observation. The distribution of MOTIFs across the entire gene family could be visualized in HTML webpage. The MOTIFs are numbered relative to the ranking of the E-value for each MOTIF.

3) Secondary Structure Prediction

PSIPRED, top ranked secondary structure prediction method (Jones D T. (1999) *J. Mol. Biol.* 292: 195-202), can be used for protein secondary structure prediction. The tool provides accurate structure prediction using two feed-forward neural networks based on the PSI-BLAST output. The PSI-BLAST database is created by removing low-complexity, transmembrane, and coiled-coil regions in Uniref100. The PSIPRED results contain the predicted secondary structures (Alpha helix: H, Beta strand: E, and Coil: C) and the corresponding confidence scores for each amino acid in a given protein sequence.

4) Alignment of Protein Sequences and Secondary Structures

A script can be developed to generate gapped secondary structure alignment according to the multiple protein sequence alignment from step 1 for all proteins. All aligned protein sequences and structures are concatenated into a single FASTA file, and then imported into MEGA for visualization and identification of conserved structures.

In some embodiments the IPD121 polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, IPD121 polypeptide having increased expression, increased solubility, decreased phytotoxicity, and digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In some embodiments an IPD121 polypeptide comprises the amino acid sequence of any one or more of SEQ ID NOS: 124-234.

In some embodiments, chimeric polypeptides are provided comprising regions of at least two different IPD121 polypeptides of the disclosure.

In some embodiments, chimeric polypeptides are provided comprising regions of at least two different IPD121 polypeptides selected from any one or more of SEQ ID NOS: 124-234.

In some embodiments, chimeric IPD121 polypeptide(s) are provided comprising an N-terminal Region of a first IPD121 polypeptide of the disclosure operably fused to a C-terminal Region of a second IPD121 polypeptide of the disclosure.

In other embodiments the IPD121 polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) 1 Biol. Chem., 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) J Biol. Chem., 275:9091-9094).

In another embodiment fusion proteins are provided that include within its amino acid sequence an amino acid sequence comprising an IPD121 polypeptide of the disclosure. Methods for design and construction of fusion proteins (and polynucleotides encoding same) are known to those of skill in the art. Polynucleotides encoding an IPD121 polypeptide may be fused to signal sequences which will direct the localization of the IPD121 polypeptide to particular compartments of a prokaryotic or eukaryotic cell and/or direct the secretion of the IPD121 polypeptide of the embodiments from a prokaryotic or eukaryotic cell. For example, in *E. coli*, one may wish to direct the expression of the protein to the periplasmic space. Examples of signal sequences or proteins (or fragments thereof) to which the IPD121 polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the IPD121 polypeptide may be fused to the pelB pectate lyase signal sequence to increase the efficiency of expression and purification of such polypeptides in Gram-negative bacteria (see, U.S. Pat. Nos. 5,576,195 and 5,846,818).

Plant plastid transit peptide/polypeptide fusions are well known in the art. Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the IPD121 polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. In some embodiments the IPD121 polypeptide is fused to a heterologous signal peptide or heterologous transit peptide.

In some embodiments fusion proteins are provide comprising an IPD121 polypeptide or chimeric IPD121 polypeptide of the disclosure represented by a formula selected from the group consisting of:

$$R^1\text{-L-}R^2,\ R^2\text{-L-}R^1,\ R^1\text{—}R^2 \text{ or } R^2\text{—}R^1$$

wherein $R^1$ is an IPD121 polypeptide or chimeric IPD121 polypeptide of the disclosure and $R^2$ is a protein of interest. In some embodiments $R^1$ and $R^2$ are an IPD121 polypeptide or chimeric IPD121 polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$, or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids EEKKN (SEQ ID NO:249) from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

Nucleic Acid Molecules, and Variants and Fragments Thereof

Isolated or recombinant nucleic acid molecules comprising nucleic acid sequences encoding IPD121 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding IPD121 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding IPD121 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an IPD121 polypeptide is a non-genomic sequence.

A variety of polynucleotides that encode IPD121 polypeptides or related proteins are contemplated. Such polynucleotides are useful for production of IPD121 polypeptides in host cells when operably linked to a suitable promoter, transcription termination and/or polyadenylation sequences. Such polynucleotides are also useful as probes for isolating homologous or substantially homologous polynucleotides that encode IPD121 polypeptides or related proteins.

Polynucleotides Encoding IPD121 Polypeptides

One source of polynucleotides that encode IPD121 polypeptides or related proteins is a *Polystichum, Davallia, Didymochlaena, Humata, Onoclea*, or *Tectaria* species which may contain an IPD121 polynucleotide of any one of SEQ ID NOs: 1-123, encoding an IPD121 polypeptide of SEQ ID NOs: 124-234. The polynucleotides of any one or more of SEQ ID NOS: 1-123, can be used to express IPD121 polypeptides in recombinant bacterial hosts that include but are not limited to *Agrobacterium, Bacillus, Escherichia, Salmonella, Lysinibacillus, Acetobacter, Pseudomonas* and *Rhizobium* bacterial host cells. The polynucleotides are also useful as probes for isolating homologous or substantially homologous polynucleotides encoding IPD121 polypeptides or related proteins. Such probes can be used to identify homologous or substantially homologous polynucleotides derived from *Polystichum, Davallia, Didymochlaena, Humata, Onoclea*, and *Tectaria* species.

Polynucleotides encoding IPD121 polypeptides can also be synthesized de novo from an IPD121 polypeptide sequence. The sequence of the polynucleotide gene can be deduced from an IPD121 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD121 polypeptide sequences that can be used to obtain corresponding nucleotide encoding sequences include, but are not limited to the IPD121 polypeptides of SEQ ID NOS: 124-234. Furthermore, synthetic IPD121 polynucleotide sequences of the disclosure can be designed so that they will be expressed in plants.

In one embodiment, the polypeptide of SEQ ID NO: 124 is encoded by SEQ ID NO: 1; the polypeptide of SEQ ID NO: 125 is encoded by SEQ ID NO: 2; the polypeptide of SEQ ID NO: 126 is encoded by SEQ ID NO: 3; the polypeptide of SEQ ID NO: 127 is encoded by SEQ ID NO: 4; the polypeptide of SEQ ID NO: 128 in encoded by SEQ ID NO: 5; the polypeptide of SEQ ID NO: 129 is encoded by SEQ ID NO: 6; the polypeptide of SEQ ID NO: 130 is encoded by SEQ ID NO: 7; the polypeptide of SEQ ID NO: 131 is encoded by SEQ ID NO: 8; the polypeptide of SEQ ID NO: 132 is encoded by SEQ ID NO: 9 and SEQ ID NO: 81; the polypeptide of SEQ ID NO: 133 is encoded by SEQ ID NO: 10; the polypeptide of SEQ ID NO: 134 is encoded by SEQ ID NO: 11; the polypeptide of SEQ ID NO: 135 is encoded by SEQ ID NO: 12; the polypeptide of SEQ ID NO: 136 is encoded by SEQ ID NO: 13; the polypeptide of SEQ ID NO: 137 is encoded by SEQ ID NO: 14; the polypeptide of SEQ ID NO: 138 is encoded by SEQ ID NO: 15 and SEQ ID NO: 20; the polypeptide of SEQ ID NO: 139 is encoded by SEQ ID NO: 16; the polypeptide of SEQ ID NO: 140 is encoded by SEQ ID NO: 17; the polypeptide of SEQ ID NO: 141 is encoded by SEQ ID NO: 18; the polypeptide of SEQ ID NO: 142 is encoded by SEQ ID NO: 19; the polypeptide of SEQ ID NO: 143 is encoded by SEQ ID NO: 21; the polypeptide of SEQ ID NO: 144 is encoded by SEQ ID NO: 22; the polypeptide of SEQ ID NO: 145 is encoded by SEQ ID NO: 23; the polypeptide of SEQ ID NO: 146 is encoded by SEQ ID NO: 24 and SEQ ID NO: 78; the polypeptide of SEQ ID NO: 147 is encoded by SEQ ID NO: 25 and SEQ ID NO: 82; the polypeptide of SEQ ID NO: 148 is encoded by SEQ ID NO: 26; the polypeptide of SEQ ID NO: 149 is encoded by SEQ ID NO: 27; the polypeptide of SEQ ID NO: 150 is encoded by SEQ ID NO: 28; the polypeptide of SEQ ID NO: 151 is encoded by SEQ ID NO: 29; the polypeptide of SEQ ID NO: 152 is encoded by SEQ ID NO: 30; the polypeptide of SEQ ID NO: 153 is encoded by SEQ ID NO: 31 and SEQ ID NO: 37; the polypeptide of SEQ ID NO: 154 is encoded by SEQ ID NO: 32; the polypeptide of SEQ ID NO: 155 is encoded by SEQ ID NO: 33; the polypeptide of SEQ ID NO: 156 is encoded by SEQ ID NO: 34; the polypeptide of SEQ ID NO: 157 is encoded by SEQ ID NO: 35; the polypeptide of SEQ ID NO: 158 is encoded by SEQ ID NO: 36; the polypeptide of SEQ ID NO: 159 is encoded by SEQ ID NO: 38; the polypeptide of SEQ ID NO: 160 is encoded by SEQ ID NO: 39; the polypeptide of SEQ ID NO: 161 is encoded by SEQ ID NO: 40; the polypeptide of SEQ ID NO: 162 is encoded by SEQ ID NO: 41; the polypeptide of SEQ ID NO: 163 is encoded by SEQ ID NO: 42; the polypeptide of SEQ ID NO: 164 is encoded by SEQ ID NO: 43; the polypeptide of SEQ ID NO: 165 is encoded by SEQ ID NO: 44, SEQ ID NO: 47, SEQ ID NO: 49 and SEQ ID NO: 53; the polypeptide of SEQ ID NO: 166 is encoded by SEQ ID NO: 45; the polypeptide of SEQ ID NO: 167 is encoded by SEQ ID NO: 46; the polypeptide of SEQ ID NO: 168 is encoded by SEQ ID NO: 48; the polypeptide of SEQ ID NO: 169 is encoded by SEQ ID NO: 50; the polypeptide of SEQ ID NO: 170 is encoded by SEQ ID NO: 51; the polypeptide of SEQ ID NO: 171 is encoded by SEQ ID NO: 52; the polypeptide of SEQ ID NO: 172 is encoded by SEQ ID NO: 54; the polypeptide of SEQ ID NO: 173 is encoded by SEQ ID NO: 55; the polypeptide of SEQ ID NO: 174 is encoded by SEQ ID NO: 56 and SEQ ID NO: 109; the polypeptide of SEQ ID NO: 175 is encoded by SEQ ID NO: 57; the polypeptide of SEQ ID NO: 176 is encoded by SEQ ID NO: 58; the polypeptide of SEQ ID NO: 177 is encoded by SEQ ID NO: 59; the polypeptide of SEQ ID NO: 178 is encoded by SEQ ID NO: 60; the polypeptide of SEQ ID NO: 179 is encoded by SEQ ID NO: 61; the polypeptide of SEQ ID NO: 180 is encoded by SEQ ID NO: 62; the polypeptide of SEQ ID NO: 181 is encoded by SEQ ID NO: 63; the polypeptide of SEQ ID NO: 182 is encoded by SEQ ID NO: 64; the polypeptide of SEQ ID NO: 183 is encoded by SEQ ID NO: 65; the polypeptide of SEQ ID NO: 184 is encoded by SEQ ID NO: 66; the polypeptide of SEQ ID NO: 185 is encoded by SEQ ID NO: 67; the polypeptide of SEQ ID NO: 186 is encoded by SEQ ID NO: 68; the polypeptide of SEQ ID NO: 187 is encoded by SEQ ID NO: 69; the polypeptide of SEQ ID NO: 188 is encoded by SEQ ID NO: 70; the polypeptide of SEQ ID NO: 189 is encoded by SEQ ID NO: 71; the polypeptide of SEQ ID NO: 190 is encoded by SEQ ID NO: 72; the polypeptide of SEQ ID NO: 191 is encoded by SEQ ID NO: 73; the polypeptide of SEQ ID NO: 192 is encoded by SEQ ID NO: 74; the polypeptide of SEQ ID NO: 193 is encoded by SEQ ID NO: 75; the polypeptide of SEQ ID NO: 194 is encoded by SEQ ID NO: 76; the polypeptide of SEQ ID NO: 195 is encoded by SEQ ID NO: 77; the polypeptide of SEQ ID NO: 196 is encoded by SEQ ID NO: 79; the polypeptide of SEQ ID NO: 197 is encoded by SEQ ID NO: 80; the polypeptide of SEQ ID NO: 198 is encoded by SEQ ID NO: 83; the polypeptide of SEQ ID NO: 199 is encoded by SEQ ID NO: 84; the polypeptide of SEQ ID NO: 200 is encoded by SEQ ID NO: 85; the polypeptide of SEQ ID NO: 201 is encoded by SEQ ID NO: 88; the polypeptide of SEQ ID NO: 202 is encoded by SEQ ID NO: 89 and SEQ ID NO: 92; the polypeptide of SEQ ID NO: 203 is encoded by SEQ ID NO: 90; the polypeptide of SEQ ID NO: 204 is encoded by SEQ ID NO: 91; the polypeptide of SEQ ID NO: 205 is encoded by SEQ ID NO: 93; the polypeptide of SEQ ID NO: 206 is encoded by SEQ ID NO: 94; the polypeptide of SEQ ID NO: 207 is encoded by SEQ ID NO: 95; the polypeptide of SEQ ID NO: 208 is encoded by SEQ ID NO: 96; the polypeptide of SEQ ID NO: 209 is encoded by SEQ ID NO: 97; the polypeptide of SEQ ID NO: 210 is encoded by SEQ ID NO: 98; the polypeptide of SEQ ID NO: 211 is encoded by SEQ ID NO: 99; the polypeptide of SEQ ID NO: 212 is encoded by SEQ ID NO: 100; the polypeptide of SEQ ID NO: 213 is encoded by SEQ ID NO: 101; the polypeptide of SEQ ID NO: 214 is encoded by SEQ ID NO: 102; the polypeptide of SEQ ID NO: 215 is encoded by SEQ ID NO: 103; the polypeptide of SEQ ID NO: 216 is encoded by SEQ ID NO: 104; the polypeptide of SEQ ID NO: 217 is encoded by SEQ ID NO: 105; the polypeptide of SEQ ID NO: 218 is encoded by SEQ ID NO: 106; the polypeptide of SEQ ID NO: 219 is encoded by SEQ ID NO: 107; the polypeptide of SEQ ID NO: 220 is encoded by SEQ ID NO: 108; the polypeptide of SEQ ID NO: 221 is encoded by SEQ ID NO: 110; the polypeptide of SEQ ID NO: 222 is encoded by SEQ ID NO: 111; the polypeptide of SEQ ID NO: 223 is encoded by SEQ ID NO: 112; the polypeptide of SEQ ID NO: 224 is encoded by SEQ ID NO: 113; the polypeptide of SEQ ID NO: 225 is encoded by SEQ ID NO: 114; the polypeptide of SEQ ID NO: 226 is encoded by SEQ ID NO: 115; the polypeptide of SEQ ID NO: 227 is encoded by SEQ ID NO: 116; the polypeptide of SEQ ID NO: 228 is encoded by SEQ ID NO: 117; the polypeptide of SEQ ID NO: 229 is encoded by SEQ ID NO: 118; the polypeptide of SEQ ID NO: 230 is encoded by SEQ ID NO: 119; the polypeptide of SEQ ID NO: 231 is encoded by SEQ ID NO: 120; the polypeptide of SEQ ID NO: 232 is encoded by SEQ ID NO: 121; the polypeptide of SEQ ID NO: 233 is encoded by SEQ ID NO: 122; and the polypeptide of SEQ ID NO: 234 is encoded by SEQ ID NO: 123.

In some embodiments the nucleic acid molecule encoding an IPD121 polypeptide is a polynucleotide having the sequence set forth in any one of SEQ ID NOS: 1-123, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the IPD121 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an IPD121 polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of any one of SEQ ID NOS: 1-123, wherein the IPD121 polypeptide has insecticidal activity.

In some embodiments the nucleic acid molecule encodes an IPD121 polypeptide variant comprising one or more amino acid substitutions to the amino acid sequence of any one of SEQ ID NOS: 124-234.

Also provided are nucleic acid molecules that encode transcription and/or translation products that are subsequently spliced to ultimately produce functional IPD121 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD121 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length IPD121 polypeptide, but rather encode a fragment or fragments of an IPD121 polypeptide. These polynucleotides can be used to express a functional IPD121 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD121 polypeptides are also encompassed by the embodiments. "Fragment" as used herein refers to a portion of the nucleic acid sequence encoding an IPD121 polypeptide. A fragment of a nucleic acid sequence may encode a biologically active portion of an IPD121 polypeptide or it may be a fragment that can be used as a hybridization probe or PCR primer using methods disclosed below. Nucleic acid molecules that are fragments of a nucleic acid sequence encoding an IPD121 polypeptide comprise at least about 150, 180, 210, 240, 270, 300, 330, 360, 400, 450, or 500 contiguous nucleotides or up to the number of nucleotides present in a full-length nucleic acid sequence encoding an IPD121 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD121 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of any one of the full-length IPD121 polypeptides set forth in SEQ ID NOS: 124-234. In some embodiments, the insecticidal activity is against a Lepidopteran species. In one embodiment, the insecticidal activity is against a Coleopteran species. In some embodiments, the insecticidal activity is against one or more insect pests of the corn rootworm complex: western corn rootworm, *Diabrotica virgifera*; northern corn rootworm, *D. barberi*: Southern corn rootworm or spotted cucumber beetle; *Diabrotica undecimpunctata howardi*, *Diabrotica speciosa*, and the Mexican corn rootworm, *D. virgifera zeae*. In one embodiment, the insecticidal activity is against a *Diabrotica* species.

In some embodiments the IPD121 polypeptide is encoded by a nucleic acid sequence sufficiently homologous to any one of the nucleic acid sequences of SEQ ID NOS: 1-123.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, FASTA, and various other implementations of Smith-Waterman or Needleman-Wunsch algorithms within these tools and in other tools. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments an IPD121 polynucleotide encodes an IPD121 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of SEQ ID NOS: 124-234.

In some embodiments polynucleotides are provided encoding chimeric polypeptides comprising regions of at least two different IPD121 polypeptides of the disclosure.

In some embodiments polynucleotides are provided encoding chimeric polypeptides comprising an N-terminal Region of a first IPD121 polypeptide of the disclosure operably fused to a C-terminal Region of a second IPD121 polypeptide of the disclosure.

The embodiments also encompass nucleic acid molecules encoding IPD121 polypeptide variants. "Variants" of the IPD121 polypeptide encoding nucleic acid sequences include those sequences that encode the IPD121 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the IPD121 polypeptides disclosed as discussed below.

The present disclosure provides isolated or recombinant polynucleotides that encode any of the IPD121 polypeptides disclosed herein. Those having ordinary skill in the art will readily appreciate that due to the degeneracy of the genetic code, a multitude of nucleotide sequences encoding IPD121 polypeptides of the present disclosure exist.

The skilled artisan will further appreciate that changes can be introduced by mutation of the nucleic acid sequences thereby leading to changes in the amino acid sequence of the encoded IPD121 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-

319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene*, 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortie, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA*, 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 1012670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from a plant source, including but not limited to a *Polystichum, Davallia, Didymochlaena, Humata, Onoclea*, and/or *Tectaria* species. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, New York), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential IPD121 polypeptides from plant collections, plant cell extracts can be screened with antibodies generated against IPD121 polypeptides using Western blotting and/or ELISA methods. This type of assay can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of IPD121 polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands to IPD121 polypeptides) with sequence information of an IPD121 polypeptide disclosed herein. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known IPD121 polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding IPD121 polypeptides of the disclosure or a fragment or variant thereof. Methods for the preparation of probes for hybridization and stringency conditions are generally known in the art and are disclosed in Sambrook and Russell, (2001), supra, herein incorporated by reference.

For example, an entire nucleic acid sequence, encoding an IPD121 polypeptide, disclosed herein or one or more portions thereof may be used as a probe capable of specifically hybridizing to corresponding nucleic acid sequences encoding IPD121 polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length Antibodies Antibodies to an IPD121 polypeptide of the embodiments or to variants or fragments thereof are also encompassed. The antibodies of the disclosure include polyclonal and monoclonal antibodies as well as fragments thereof which retain their ability to bind to an IPD121 polypeptide. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against IPD121 polypeptides or antigen-binding portions thereof can be produced by a variety of techniques, including conventional monoclonal antibody methodology, for example the standard somatic cell hybridization technique of Kohler and Milstein, (1975) Nature 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an IPD121 polypeptide as antigens.

A kit for detecting the presence of an IPD121 polypeptide or detecting the presence of a nucleotide sequence encoding an IPD121 polypeptide in a sample is provided. In one embodiment, the kit provides antibody-based reagents for detecting the presence of an IPD121 polypeptide in a tissue sample. In another embodiment, the kit provides labeled nucleic acid probes useful for detecting the presence of one or more polynucleotides encoding an IPD121 polypeptide. The kit is provided along with appropriate reagents and controls for carrying out a detection method, as well as instructions for use of the kit.

Receptor Identification and Isolation

Receptors to the IPD121 polypeptides of the embodiments or to variants or fragments thereof are also encompassed. Methods for identifying receptors are well known in the art (see, Hofmann, et. al., (1988) Eur. J. Biochem.* 173:85-91; Gill, et al., (1995) *J. Biol. Chem.* 27277-27282) can be employed to identify and isolate the receptor that recognizes the IPD121 polypeptide using the brush-border membrane vesicles from susceptible insects. In addition to the radioactive labeling method listed in the cited literatures, an IPD121 polypeptide can be labeled with fluorescent dye and other common labels such as streptavidin. Brush-border membrane vesicles (BBMV) of susceptible insects such as soybean looper and stink bugs can be prepared according to the protocols listed in the references of Hofmann and Gill above and separated on SDS-PAGE gel and blotted on suitable membrane. Labeled IPD121 polypeptide can be incubated with blotted membrane of BBMV and labeled IPD121 polypeptide can be identified with the labeled reporters. Identification of protein band(s) that interact with the IPD121 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the IPD121 polypeptide. Receptor function for insecticidal activity by the IPD121 polypeptide can be verified by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD121 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an IPD121 polypeptide of the embodiments. In some embodiments the DNA construct comprises a polynucleotide encoding a fusion protein comprising an IPD121 polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639. Where appropriate, a nucleic acid may be optimized for increased expression in the host organism.

Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010, herein incorporated by reference. A *Zea maize* usage table can be also found at kazusa.or.jp//cgi-bin/show.cgi?species=4577, which can be accessed using the www prefix. A *Glycine max* usage table can be found at kazusa.or.jp//cgi-bin/show.cgi?species=3847&aa=1&style=N, which can be accessed using the www prefix.

In some embodiments the recombinant nucleic acid molecule encoding an IPD121 polypeptide has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. Plant Cell 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research*, 78:249-264, 2003. In particular, Table 2 of this publication, which is incorporated into the description herewith by reference, discloses 85 proteins from the chloroplast lumen, identified by their accession number (see also US Patent Application Publication 2009/09044298).

Suitable chloroplast transit peptides (CTP) are well known to one skilled in the art also include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea mays* ssRUBISCO, *Zea mays*-beta-glucosidase, *Zea mays*-Malate dehydrogenase, *Zea mays* Thioredoxin M-type (See US Patent Application Publication 2012/0304336).

The IPD121 polypeptide gene to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat.

No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theon. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989)*Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156).

Tissue-preferred promoters can be utilized to target enhanced IPD121 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7): 792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-

772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108. Such seed-preferred promoters include, but are not limited to, Cim 1 (cytokinin-induced message); cZ19B1 (maize 19 kDa zein); and milps (myo-inositol-1-phosphate synthase) (see, U.S. Pat. No. 6,225,529). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1101), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. No. 10/004,357, abandoned and Ser. No. 10/427,692, granted as U.S. Pat. No. 7,462,481); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants are known in the art including, but not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926) and Led transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

In specific embodiments, the sequences of the embodiments can be provided to a plant using a variety of transient transformation methods. Such transient transformation methods include, but are not limited to, the introduction of the IPD121 polynucleotide or variants and fragments thereof directly into the plant or the introduction of the IPD121 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107: 775-784. Alternatively, the IPD121 polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired IPD121 polypeptide. It is also recognized that such a viral polyprotein, comprising at least a portion of the amino acid sequence of an IPD121 polypeptide of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931.

Methods for transformation of chloroplasts are known in the art. See, for example, Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tuhpa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra). Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IPD121 polypeptide.

Methods to Introduce Genome Editing Technologies into Plants

In some embodiments, the disclosed IPD121 polynucleotide compositions can be introduced into the genome of a plant using genome editing technologies, or previously introduced IPD121 polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IPD121 polynucleotide has previously been introduced into a genome, genome editing technologies may be used to alter or modify the introduced polynucleotide sequence. Site specific modifications that can be introduced into the disclosed IPD121 polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed IPD121 polynucleotide compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, one or more of the polynucleotides encoding the IPD121 polypeptide(s) disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to: transgenes that confer resistance to a herbicide; transgenes that confer or contribute to an altered grain characteristic; genes that control male-sterility; genes that create a site for site specific dna integration; genes that affect abiotic stress resistance; genes that confer increased yield genes that confer plant digestibility; and transgenes that confer resistance to insects or disease.

Examples of transgenes that confer resistance to insects include genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens strain CHA*0 *and Pf*-5 (*previously fluorescens*) (Pechy-Tarr, (2008) *Environmental Microbiology* 10:2368-2386: GenBank Accession No. EU400157); from *Pseudomonas taiwanensis* (Liu, et al., (2010) *J. Agric. Food Chem.* 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of US Patent Publication US20140007292; an AFP-1A and/or AFP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; an IPD079 polypeptide of U.S. Ser. No. 62/201,977; an IPD082 polypeptide of U.S. Ser. No. 62/269,482, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin genes and the *B. thuringiensis* cytolytic Cyt1 and Cyt2 genes. Members of these classes of *B. thuringiensis* insecticidal proteins well known to one skilled in the art (see, Crickmore, et al., "*Bacillus thuringiensis* toxin nomenclature" (2011), atlifesci.sussex.ac.uk/home/Neil_Crickmore/Bt/ which can be accessed on the world-wide web using the "www" prefix).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318, abandoned; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009)1 *Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry 1BE & Cry1F (US2012/0311746), Cry1CA & Cry 1 AB (US2012/0311745), Cry 1F & CryCa (US2012/0317681), Cry1DA & Cry 1BE (US2012/0331590), Cry1DA & Cry1Fa (US2012/0331589), Cry 1 AB & Cry 1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

Further transgenes that confer resistance to insects may down-regulation of expression of target genes in insect pest species by interfering ribonucleic acid (RNA) molecules through RNA interference. RNA interference refers to the process of sequence-specific post-transcriptional gene silencing in animals mediated by short interfering RNAs (siRNAs) (Fire, et al., (1998) *Nature* 391:806). RNAi transgenes may include but are not limited to expression of dsRNA, siRNA, miRNA, iRNA, antisense RNA, or sense RNA molecules that down-regulate expression of target genes in insect pests. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus.

RNAi transgenes are provided for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describes polynucleotide silencing elements targeting RyanR and PAT3. PCT publications WO/2016/138106, WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene(s) expressing one or more of the IPD121 polypeptides and desirably provide for improved protection of the pesticide from environmental degradation and inactivation.

Alternatively, the IPD121 polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated IPD121 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient or an agrochemical composition that contains at least one of the IPD121 polypeptide(s) produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus* thuriengiensis, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethy)amino] furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl) methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frupperda* JE Smith (fall armyworm); *S. exigua* Hubner (beet armyworm); *S. litura* Fabricius (tobacco cutworm, cluster caterpillar); *Mamestra configurata* Walker (bertha armyworm); *M. brassicae* Linnaeus (cabbage moth); *Agrotis Ipsilon* Hufnagel (black cutworm); *A. orthogonia* Morrison (western cutworm); *A. subterranea* Fabricius (granulate cutworm); *Alabama argillacea* Hubner (cotton leaf worm); *Trichoplusia ni* Hubner (cabbage looper); *Pseudoplusia includens* Walker (soybean looper); *Anticarsia gemmatalis* Hubner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hubner (American bollworm); *H. zea* Boddie (corn earworm or cotton bollworm); *Melanchra picta* Harris (zebra caterpillar); *Egira (Xylomyges) curialis* Grote (citrus cutworm); borers, casebearers, webworms, coneworms, and skeletonizers from the family Pyralidae *Ostrinia nubilalis* Hubner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hubner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hubner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hubner (Indian meal moth); *Scirpophaga incertulas* Walker (yellow stem borer); *Udea rubigalis* Guenee (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rosslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hubner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Mèneville (Chinese Oak Tussah Moth); *Bombyx mori* Linnaeus (Silkworm); *Bucculatrix thurberiella* Busck (cotton leaf perforator); *Colias* eurytheme Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hubner (elm spanworm); *Erannis tiliaria* Harris (linden looper); *Euproctis chrysorrhoea* Linnaeus (browntail moth); *Harrisina americana* Guerin-Meneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape colaspis); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Galin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; Coreidae spp.; Pyrrhocoridae spp.; Tinidae spp.; Blostomatidae spp.; Reduviidae spp. and Cimicidae spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus,* and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hubner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council.

Some seed treatments that may be used on crop seed include, but are not limited to, one or more of abscisic acid, acibenzolar-S-methyl, avermectin, amitrol, azaconazole, azospirillum, azadirachtin, azoxystrobin, Bacillus spp. (including one or more of cereus, firmus, megaterium, pumilis, sphaericus, subtilis and/or thuringiensis species), Bradyrhizobium spp. (including one or more of betae, canariense, elkanii, iriomotense, japonicum, liaonigense, pachyrhizi and/or yuanmingense), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, trichoderma, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant IPD121 polypeptide of the disclosure. In some embodiments methods are provided for killing an insect pest, comprising contacting the insect pest with an insecticidally-effective amount of one or more of a recombinant pesticidal protein of SEQ ID NOS: 124-234, or a variant or insecticidally active fragment thereof.

In some embodiments methods are provided for controlling an insect pest population, comprising contacting the insect pest population, either simultaneously or sequentially, with an insecticidally-effective amount of one or more of a recombinant IPD121 polypeptide of the disclosure. In some embodiments, methods are provided for controlling an insect pest population, comprising contacting the insect pest population with an insecticidally-effective amount of one or more of a recombinant IPD121 polypeptide of SEQ ID NOS: 124-234, or a variant or insecticidally active fragment thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of one or more of a recombinant IPD121 polypeptide of the disclosure. In some embodiments, methods are provided for controlling an insect pest population resistant to a pesticidal protein, comprising contacting the insect pest population with an insecticidally-effective amount of one or more of a recombinant IPD121 polypeptide of SEQ ID NOS: 124-234, or a variant or insecticidally active fragment thereof.

In some embodiments methods are provided for protecting a plant from an insect pest, comprising expressing in the plant or cell thereof at least one recombinant polynucleotide encoding an IPD121 polypeptide of the disclosure. In some embodiments methods are provided for protecting a plant from an insect pest, comprising expressing in the plant or cell thereof a recombinant polynucleotide encoding one or more IPD121 polypeptides of SEQ ID NOS: 124-234, or variants or insecticidally active fragments thereof.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, in certain instances insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way of increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the IPD121 polypeptides of the disclosure are useful as an insect resistance management strategy in combination (i.e., pyramided) with other pesticidal proteins or other transgenes (i.e., an RNAi trait) including but not limited to Bt toxins, *Xenorhabdus* sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management comprises the presentation of at least one of the IPD121 polypeptide insecticidal proteins to insects in the order Lepidoptera and/or Coleoptera.

In some embodiments the methods of controlling Lepidoptera and/or Coleoptera insect infestation in a transgenic plant and promoting insect resistance management comprises the presentation of at least one of the IPD121 polypeptides of SEQ ID NOS: 124-234, or variants or insecticidally active fragments thereof, insecticidal to insects in the order Lepidoptera and/or Coleoptera.

In some embodiments the methods of controlling Lepidoptera and/or Coleoptera insect infestation in a transgenic plant and promoting insect resistance management comprise expressing in the transgenic plant an IPD121 polypeptide and a Cry protein or other insecticidal protein to insects in the order Lepidoptera and/or Coleoptera having different modes of action.

In some embodiments the methods of controlling Lepidoptera and/or Coleoptera insect infestation in a transgenic plant and promoting insect resistance management comprise expression in the transgenic plant of at least one of an IPD121 polypeptide of SEQ ID NOS: 124-234, or variants or insecticidally active fragments thereof and a Cry protein or other insecticidal protein to insects in the order Lepidoptera and/or Coleoptera, where the IPD121 polypeptide and Cry protein have different modes of action.

Also provided are methods of reducing likelihood of emergence of Lepidoptera and/or Coleoptera insect resistance to transgenic plants expressing in the plants insecticidal proteins to control the insect species, comprising expression of at least one of an IPD121 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins or other insecticidal transgenes (e.g., an RNAi trait) toxic to Lepidoptera and/or Coleoptera insects but each exhibiting a different mode of effectuating its killing activity, wherein two or more of the insecticidal proteins or other insecticidal transgenes comprise an IPD121 polypeptide and a Cry protein. Also provided are means for effective Lepidoptera and/or Coleoptera insect resistance management of transgenic plants, comprising co-expressing at high levels in the plants two or more insecticidal proteins or other insecticidal transgenes (e.g., an RNAi trait) toxic to Lepidoptera and/or Coleoptera insects but each exhibiting a different mode of effectuating its killing activity, wherein two or more insecticidal proteins or other insecticidal transgenes comprise at least one of an IPD121 polypeptide of SEQ ID NOS: 124-234, or variants or insecticidally active fragments thereof and a Cry protein or other insecticidally active protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD121 polypeptide does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that one or more of the IPD121 polypeptides of SEQ ID NOS: 124-234, or variant or insecticidally active fragment thereof does not compete with binding sites for Cry proteins in such insects.

An embodiment of the invention contemplates a recombinant polynucleotide encoding an insecticidal polypeptide having at least 76% sequence identity to a polypeptide selected from SEQ ID NOS: 124-234. In an embodiment, the recombinant polynucleotide encodes a polypeptide having at least 90% sequence identity to a polypeptide selected from SEQ ID NOS: 124-234. In an embodiment, the insecticidal polypeptide is joined to a heterologous signal sequence or a transit sequence. In an embodiment, the recombinant polynucleotide has at least 80% or at least 90% sequence identity to a polynucleotide selected from any one of SEQ ID NOS: 1-123, wherein the polynucleotide is operably linked to a heterologous regulatory element. In an embodiment, the recombinant polynucleotide has codons optimized for expression in an agriculturally important crop. A DNA construct comprising these recombinant polynucleotides is contemplated, as are transgenic plants comprising the recombinant polynucleotides or DNA constructs.

Some embodiments of the invention relate to a method of inhibiting growth or killing an insect pest or pest population, comprising contacting the insect pest with an insecticidal polypeptide having at least 76% sequence identity to a polypeptide selected from SEQ ID NOS: 124-234. An embodiment relates to a method of inhibiting growth or killing an insect pest or pest population comprising expressing in a plant a recombinant polynucleotide encoding an insecticidal polypeptide having at least 76% sequence identity to a polypeptide selected from SEQ ID NOS: 124-234. A method for controlling pest infestation comprising providing in the diet of the pest the transgenic plant expressing a recombinant polynucleotide encoding an insecticidal polypeptide having at least 76% sequence identity to a polypeptide selected from SEQ ID NOS: 124-234 is also contemplated.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing at least one IPD121 polypeptide disclosed herein. Expression of the IPD121 polypeptide(s) results in a reduced ability of a pest to infest or feed on the plant, thus improving plant yield.

Methods of Processing

Further provided are methods of processing a plant, plant part or seed to obtain a food or feed product from a plant, plant part or seed comprising at least one IPD121 polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding one or more IPD121 polypeptides which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds The following examples are offered by way of illustration and not by way of limitation.

EXAMPLES

Example 1—Transcriptome Sequencing of Plants

Transcriptomes for various plant samples were prepared as follows. Total RNA was isolated from frozen tissues with an RNeasy® kit (Qiagen®). Sequencing libraries from the resulting total RNAs were prepared using the TruSeq™ mRNA-Seq kit and protocol from Illumina®, Inc. (San Diego, CA). Briefly, mRNAs were isolated via attachment to oligo(dT) beads, fragmented to a mean size of 180 nt, reverse transcribed into cDNA by random hexamer primers, end repaired, 3' A-tailed, and ligated with Illumina® indexed TruSeq™ adapters. Ligated cDNA fragments were PCR amplified using Illumina® TruSeq™ primers and purified PCR products were checked for quality and quantity on the Agilent Bioanalyzer® DNA 7500 chip. Post quality and quantity assessment, 100 ng of the transcript library was normalized by treatment with Duplex Specific Nuclease (DSN) (Evrogen®, Moscow, Russia). Normalization was accomplished by addition of 200 mM Hepes buffer, followed by heat denaturation and five hour anneal at 68° C. Annealed library was treated with 2 µL of DSN enzyme for 25 minutes, purified by Qiagen® MinElute® columns according to manufacturer protocols, and amplified twelve cycles using Illumina® adapter specific primers. Final products were purified with Ampure® XP beads (Beckman Genomics, Danvers, MA) and checked for quality and quantity on the Agilent Bioanalyzer® DNA 7500 chip.

Normalized transcript libraries were sequenced according to manufacturer protocols on the Illumina® HiSeq® 2500. Libraries were pooled, hybridized and sequenced three per flowcell lane using onboard clustering methods followed by sequencing to a target depth of sixty million 75 bp paired end reads per normalized library.

Example 2—Identification of IPD121Aa and Homologs

Candidate transcriptome DNA assembly sequences harboring the predicted coding sequences for IPD121Aa, IPD121Ab, IPD121Ca, IPD121Cb, IPD121Cc, and IPD121Cd were identified in proprietary sequence databases. The corresponding predicted coding sequences (SEQ ID NOS 1, 2, 3, 4, 5, and 6, respectively) were used to design the primers listed in Table 1. These were used for cloning by polymerase chain reaction using the Kappa HiFi™ polymerase (Kapa Bioscience, Wilmington, MA) and the cDNA prepared from the total RNA from the plants using the SuperScript® II kit (Thermo Fischer Scientific, Waltham, MA) as the template. PCR products were gel purified, digested with NdeI and XhoI restriction enzymes (New England Biolabs) and ligated into pET14b (Novagen®) also digested with the same enzymes. Colonies were sequenced to confirm the clones. The SEQ ID numbers of cloned polynucleotide sequences and their corresponding polypeptide sequences are listed in Table 2.

TABLE 1

| Source | Source species | Forward PCR primer | Reverse PCR primer |
|---|---|---|---|
| PS12415 | Polystichum tripteron | SEQ ID NO: 235 | SEQ ID NO: 236 |
| PS9179 | Davallia fejeensis | SEQ ID NO: 241 | SEQ ID NO: 242 |
| NY006 | Didymochlaena truncatula | SEQ ID NO: 237 | SEQ ID NO: 238 |
| NY008 | Humata tyermanii | SEQ ID NO: 239 | SEQ ID NO: 240 |
| PS12275 | Onoclea sensibilis | SEQ ID NO: 243 | SEQ ID NO: 244 |
| PS9539 | Tectaria milnei | SEQ ID NO: 245 | SEQ ID NO: 246 |

TABLE 2

| Gene Name | Source | Organism | DNA Seq | AA Seq |
|---|---|---|---|---|
| IPD121Aa | PS12415 | *Polystichum tripteron* | SEQ ID NO: 1 | SEQ ID NO: 124 |
| IPD121Ab | PS12415 | *Polystichum tripteron* | SEQ ID NO: 2 | SEQ ID NO: 125 |
| IPD121Ac | PS12415 | *Polystichum tripteron* | SEQ ID NO: 117 | SEQ ID NO: 228 |
| IPD121Ad | PS12415 | *Polystichum tripteron* | SEQ ID NO: 118 | SEQ ID NO: 229 |
| IPD121Ae | PS12415 | *Polystichum tripteron* | SEQ ID NO: 119 | SEQ ID NO: 230 |
| IPD121Af | PS12415 | *Polystichum tripteron* | SEQ ID NO: 120 | SEQ ID NO: 231 |
| IPD121Ca | PS9179 | *Davallia fejeensis* | SEQ ID NO: 3 | SEQ ID NO: 126 |
| IPD121Cb | NY006 | *Didymochlaena truncatula* | SEQ ID NO: 4 | SEQ ID NO: 127 |
| IPD121Cc | NY006 | *Didymochlaena truncatula* | SEQ ID NO: 5 | SEQ ID NO: 128 |
| IPD121Cd | NY008 | *Humata tyermanii* | SEQ ID NO: 6 | SEQ ID NO: 129 |
| IPD121Ce | PS12275 | *Onoclea sensibilis* | SEQ ID NO: 16 | SEQ ID NO: 139 |
| IPD121Cf | PS12275 | *Onoclea sensibilis* | SEQ ID NO: 114 | SEQ ID NO: 225 |
| IPD121Cg | PS12275 | *Onoclea sensibilis* | SEQ ID NO: 115 | SEQ ID NO: 226 |
| IPD121Ch | PS12275 | *Onoclea sensibilis* | SEQ ID NO: 116 | SEQ ID NO: 227 |
| IPD121Da | PS9539 | *Tectaria milnei* | SEQ ID NO: 19 | SEQ ID NO: 142 |
| IPD121Db | PS9539 | *Tectaria milnei* | SEQ ID NO: 121 | SEQ ID NO: 232 |
| IPD121Dc | PS9539 | *Tectaria milnei* | SEQ ID NO: 122 | SEQ ID NO: 233 |
| IPD121Dd | PS9539 | *Tectaria milnei* | SEQ ID NO: 123 | SEQ ID NO: 234 |

Example 3—Identification of Homologs

Gene identities were determined by conducting BLAST™ (Basic Local Alignment Search Tool; Altschul, et al., (1993) *J. Mol. Biol.* 215:403-410; see also ncbi.nlm.nih.gov/BLAST/, which can be accessed using the www prefix) searches under default parameters for similarity to sequences. The polynucleotide sequence for IPD121Aa (SEQ ID NO: 1) was analyzed. Gene identities conducted by BLAST™ in a DUPONT PIONEER internal proprietary database identified multiple homologs of the IPD121Aa protein, as represented by the polynucleotide sequences of SEQ ID NOs 2-123 and the corresponding polypeptide sequences of SEQ ID NOs 125-234.

Example 4—Expression and Insect Bioassay on Transient Leaf Tissues

To confirm activity of IPD121Aa (SEQ ID NO: 124) and the homologs IPD121Ab, IPD121Ac, IPD121Ad, IPD121Ae, IPD121Af, IPD121Ca, IPD121Cb, IPD121Cc, IPD121Cd, IPD121Ce, IPD121Cf, IPD121Cg, IPD121Ch, IPD121 Da, IPD121db, IPD121Dc, and IPD121Dd, the corresponding genes were cloned into a transient expression system under control of the viral promoter dMMV promoter (Dey, et. al., (1999) *Plant Mol. Biol.* 40:771-782; PCT Patent Publication WO2011133387). The expression plasmids were transformed into *Agrobacterium tumefaciens* AGL1, and the resulting strains were used for transient expression in bush bean (common bean, *Phaseolus vulgaris*). The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, the unifoliate stage of bush bean (common bean, *Phaseolus vulgaris*) were agro-infiltrated with normalized bacterial cell suspensions of test and control strains. Leaf discs were excised from each plantlet and infested with neonates of Soy Bean Looper (SBL) (*Pseudoplusia includens*), Corn Earworm, (CEW) (*Helicoverpa zea*), (FAW), Velvet Bean Caterpillar (VBC) (*Anticarsia gemmatalis*) or European Corn Borer (ECB) (*Ostrinia nubialis*). Leaf discs from a control were generated with *Agrobacterium* containing only empty expression vector. Leaf discs from a non-infiltrated plant were used as a second control.

The consumption of green leaf tissue was scored three days after infestation and given scores of 0 to 9 as indicated by Table 3. The transiently expressed IPD121Aa (SEQ ID NO: 124) and several homologs protected bush bean leaf discs from consumption by the infested insects while total green tissue consumption was observed for the negative control and untreated tissue. Transient protein expression of IPD121Aa (SEQ ID NO: 124) and IPD121Ab (SEQ ID NO: 125) was confirmed by a mass spectrometry-based protein identification method using extracted protein lysates from infiltrated leave tissues (Patterson, (1998) 10(22):1-24, Current Protocol in Molecular Biology published by John Wiley & Son Inc). As shown in FIGS. 2A-2D, transient protein expression of IPD121Aa (SEQ ID NO: 124), IPD121Ca (SEQ ID NO: 126), IPD121Cb (SEQ ID NO: 127), IPD121Cc (SEQ ID NO:128), IPD121Cd (SEQ ID NO:129), and IPD121Ce (SEQ ID NO: 139) resulted in protection of bush bean against leaf feeding damage from a diversity of Lepidoptera.

TABLE 3

| Leaf Feeding Score | % Consumed |
|---|---|
| 1 | 86-100 |
| 2 | 71-85 |
| 3 | 61-70 |
| 4 | 51-60 |
| 5 | 36-50 |
| 6 | 11-35 |
| 7 | 7-10 |
| 8 | 1-3 |
| 9 | 0 |

Activity of selected IPD121 polypeptides, transiently expressed in bush bean, against leaf feeding damage from a selection of Lepidoptera is shown in FIGS. 2A-2D. The average score and standard error (SE) for 6 replicate measurements are shown. Samples with Average Leaf Damage Scores which were greater than one Standard Error different from the negative control were considered to be active under test conditions. Accordingly, samples which were not considered active under test conditions are shaded grey.

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed is:

1. A DNA construct comprising a heterologous regulatory element and a recombinant polynucleotide encoding an insecticidal polypeptide comprising an amino acid sequence having at least 95% sequence identity to SEQ ID NO: 126, or a fragment thereof having insecticidal activity.

2. The recombinant polynucleotide of claim 1, wherein the polynucleotide has codons optimized for expression in an agriculturally important crop.

3. A transgenic plant comprising the polynucleotide of claim 1.

4. A method of inhibiting growth or killing an insect pest or pest population, comprising contacting the insect pest with an insecticidal polypeptide comprising an amino acid sequence having at least 95% sequence identity to SEQ ID NO: 126 or a fragment thereof having insecticidal activity.

5. A method of inhibiting growth or killing an insect pest or pest population comprising expressing in a plant the polynucleotide of claim 1.

6. A method of controlling insect pest damage to plants comprising providing the insecticidal polypeptide of claim 1 to an insect pest or pest population for ingestion, wherein said insecticidal polypeptide is produced by a transgenic plant and is present in at least one of said plants.

7. A method for controlling pest infestation comprising providing in the diet of the pest the transgenic plant of claim 3, or a part thereof.

8. A method for improving the yield of a crop comprising growing the transgenic plant of claim 3, wherein the yield of the crop is increased in the presence of the insect pest relative to the crop not comprising said transgenic plant.

9. The method of claim 4, wherein the insect pest or pest population is resistant to at least one Cry insecticidal protein.

10. The method of claim 6, wherein the transgenic plant is selected from corn, soybean, wheat, rice, sorghum, sunflower, canola, barley, sugarcane, potatoes, tomatoes, cotton, rape seed, peanut, and alfalfa.

11. The method of claim 4, wherein the insect pest or insect pest population is an agriculturally important species in the Order Lepidoptera.

12. The method of claim 11, wherein the insect pest or insect pest population is selected from corn earworm, European corn borer, fall armyworm, soybean looper, velvet bean caterpillar, and diamondback moth.

* * * * *

SEQUENCE LISTING

<160> NUMBER OF SEQ ID NOS: 249

<210> SEQ ID NO 1
<211> LENGTH: 637
<212> TYPE: DNA
<213> ORGANISM: Polystichum tripteron

<400> SEQUENCE: 1

```
atgggcaggt catggggagt tgtggctatt atggtgttgt gcgccagcgg cctgctgggc      60
gtagcgagcg gccatggcac catgaacgac cccatcagtc gcgtctacgc ctgcaggcag     120
gagaatccgg agcgacccac tacgccggct tgcatagcgg cggtggcgct gagtggggcc     180
caagcgttct atgattggaa tgaggtgaac ctgcccttg tcaatggccg gcaccgccag      240
ttcattccgg atgggaaact ctgcagcgcc gggcggaaca agtataggg tctcgacctg      300 gcacgctccg actggacagc cacaaacttg tcctccggcg tcgcctacac attcctctac     360
agggtcaccg cccagcacag gggcttcttc gagttctacg tcaccgtgga tggttacgac     420
cccactgagc cgctcaaatg ggcagacttg gaggaaacgc cgttcatcaa cgtcaccgac     480
cccacagttg taggcctcaa ctatgtaatc cccggtacca cgcctgccag caagaccggc     540
cgccacctca tctacgtcat ttggcagcgc tccgacagcc ccgaggcctt ctactcctgc     600
tccgacgtca actttcccga tgccctgtct ctccact                             637
```

<210> SEQ ID NO 2
<211> LENGTH: 637
<212> TYPE: DNA
<213> ORGANISM: Polystichum tripteron

<400> SEQUENCE: 2

```
atgggcaggt catggggagt tgtggctatt atggtgttgt gcgccagcgg cctgctgggc      60
gtagcgagcg gccatggcac catgaacgac cccatcagtc gcgtctacgc ctgcaggcag     120
gagaatccgg agcgacccac tacgccggct tgcatagcgg cggtggcgct gagtggggcc     180
caagcgttct atgattggaa tgaggtgaac attcctaatg ccctggtcg gcaccgtgag      240 ctcatttctg atggctacct atgcagcgcc aatcggacca agtatgcagg tctcgacctg     300
gcacgctccg actggacagc cacaaacttg tcctccggcg tcgcctacac attcctctac     360
agggtcaccg cccagcacag gggcttcttc gagttctacg tcaccgtgga tggttacgac     420
cccactgagc cgctcaaatg ggcagacttg gaggaaacgc cgttcatcaa cgtcaccgac     480
cccacagttg taggcctcaa ctatgtaatc cccggtacca cgcctgccag caagaccggc     540
cgccacctca tctacgtcat ttggcagcgc tccgacagcc ccgaggcctt ctactcctgc     600
tccgacgtca actttcccga tgccctgtct ctccact                             637
```

<210> SEQ ID NO 3
<211> LENGTH: 643
<212> TYPE: DNA
<213> ORGANISM: Davallia fejeensis

<400> SEQUENCE: 3

| | | | | | |
|---|---|---|---|---|---|
| atgggcaggt | catggggagt | tgttgcaatt | atggtggtgt | gcatcatgag | tggcctggtg | 60 |
| ggcatagtga | gtggccatgg | cagcatggag | gaccccatca | gtcgcgtcta | tagatgctac | 120 |
| ttagagaatc | cggagcgtcc | tgtatcggca | gcttgccaag | cagcggtggc | gatgagtggt | 180 |
| acccaagcct | tctacgattg | gaatgaggtg | aacattccta | acgccgctgg | ccggcaccgt | 240 |
| gagctcattt | ccgatggcca | actatgcagc | gccaatcgca | caagtatgc | aggccttgac | 300 |
| ttggcacgcg | ctgactggct | aggcaccccc | ttgtcctcgg | gtgtctcctt | cacatttgcc | 360 |
| tacaaggcca | ccgcaccaca | cttgggcttt | ttcgagttct | acgttacccg | ggatggttac | 420 |
| gagcccaccg | agccgctcaa | atgggcggac | ttagaggact | cgcccttat | caatgtcacc | 480 |
| gaccccacac | ttgaaaatgg | cgcctaccaa | atctctggca | ctacaccttc | tggtaagtcg | 540 |
| gggcgccact | tgatgtatgt | catttggcag | cgctctgata | gccctgaggc | gttctactcg | 600 |
| tgctccgatg | ttgacttcga | cgtcgatgcc | ctctctctcc | act | | 643 |

<210> SEQ ID NO 4
<211> LENGTH: 635
<212> TYPE: DNA
<213> ORGANISM: Didymochlaena truncatula

<400> SEQUENCE: 4

| | | | | | |
|---|---|---|---|---|---|
| atgggcaggt | catggggagt | tgtggctatt | atggtgttgt | gcgccagcgg | cctgctgggc | 60 |
| gtagcgagtg | ccatggcag | catggaggac | cctatcagtc | gcgtctacgc | ctgctacctg | 120 |
| gagaatccgg | agcgtcccac | gtcggcagct | tgccaagcgg | cggtggcagt | gagtgggacc | 180 |
| caagcgttct | atgattggaa | tgaggtgaac | cagcccttcg | ccgctggccg | gcaccgcgag | 240 |
| ctcattccgg | atggcgaact | gtgcagcggc | gggcgggaga | agtataaggg | cctcgacttg | 300 |
| gcacgcgccg | actggccagc | cacctccttg | ccctccggtg | tcaactacac | atacctctac | 360 |
| aaggccaccg | ccccgcactt | gggcttcttc | gagttctaca | tcacccggga | tggctacgag | 420 |
| cccactgagc | cgctcaaatg | gcagacttg | gaggacttgc | cgttcatcaa | catcaccaac | 480 |
| cccacgcttg | tcagcggctc | ctaccaaatc | cccggcacca | cgcatgccag | caagactggc | 540 |
| cggcacctcc | tctatgtcat | ttggcagcgc | tccgacagct | cgaggccttc | tactcctgc | 600 |
| tccgacgtcg | acttcgtcaa | tgccctctct | ctcca | | | 635 |

<210> SEQ ID NO 5
<211> LENGTH: 636
<212> TYPE: DNA
<213> ORGANISM: Didymochlaena truncatula

<400> SEQUENCE: 5

| | | | | | |
|---|---|---|---|---|---|
| atgggcaggt | catggggagt | tgtggctatt | atggtgttgt | gcgccagcgg | cctgctgggc | 60 |
| gtagcgagtg | ccatggcag | catggaggac | cctatcagtc | gcgtctacgc | ctgctacctg | 120 |
| gagaatccgg | agcgtcccac | gtcggcagct | tgccaagcgg | cggtggcagt | gagtgggacc | 180 |
| caagcgttct | atgattggaa | tgaggtgaac | cagcccttcg | ccgctggccg | gcaccgcgag | 240 |
| ctcattccgg | atggcgaact | gtgcagcggc | gggcgggaga | agtataaggg | cctcgacttg | 300 |
| gcacgcgccg | actggccagc | cacctccttg | ccctccggtg | tcaactacac | atacctctac | 360 |

| | |
|---|---|
| aaggccaccg ccccgcactt gggcttcttc gagttctaca tcacccggga tggctacgag | 420 |
| cccactgagc cgctcaaatg gcagacttg gaggacttgc cgttcatcaa catcaccaac | 480 |
| cccacgcttg tcagcggctc ctaccaaatc cccggcacca cgcctgccag caagactggc | 540 |
| cggcacctcc tctatgtcat ttggcagcgc tccgacagct tcgaggcctt ctactcctgc | 600 |
| tccgacgtcg acttcgtcaa tgccctctct ctccac | 636 |

<210> SEQ ID NO 6
<211> LENGTH: 636
<212> TYPE: DNA
<213> ORGANISM: Humata tyermanii

<400> SEQUENCE: 6

| | |
|---|---|
| atgggcaggt catggggagt tgtggctatt atggtgatgt acattggtgg cctgctaagc | 60 |
| atagcaagcg gccatggcag catggaggac cccatcagcc gcgtctatag gtgctacttg | 120 |
| gagaatccgg agagtcccac atcggcagct tgccaagcgg cagtggcagt gagtggggcc | 180 |
| caagccttct acgattggaa tgaggtgaac attgctgacg ccaatggccg acaccgggag | 240 |
| ctcatttctg atggccaact atgtagcgca atcggagta agtatgcggg cctcgacctg | 300 |
| gcacgcgcag attggctagg caccaccttg tcctcgggcg cctccttcac atttgcctac | 360 |
| aaggccaccg cgccgcactt gggcttcttt gagttctacg tcacccggga tggttacgag | 420 |
| cccaccgacc cgctcaaatg gcagacttg gaggactcgc ccttcatcaa cgtcaccaac | 480 |
| cccacacttg ataatggcgc ctaccagatc tccggcacca cgcctgccgg taagtcgggg | 540 |
| cgtcatctga tctacgtcat ttggcagcgc tctgatagcc cagaggcatt ctattcgtgc | 600 |
| tccgacgtcg actttgtcga tgctctctct ctccac | 636 |

<210> SEQ ID NO 7
<211> LENGTH: 726
<212> TYPE: DNA
<213> ORGANISM: Cyrtomium fortunei

<400> SEQUENCE: 7

| | |
|---|---|
| atggggagtt gtggctatta tggtgttgtg cgccagcggc ctgctgggcg tggcggcaat | 60 |
| tctgttggtc atagtgtggg gatggggagg tcatggggag ttgtggctat tatggtgctg | 120 |
| tgcaccagcg gctgctggg cgtggcgagc ggccatggca ccatgggcga ccccatcagc | 180 |
| cgcgtctaca actgcttcca ggagaatccg gagagaccca cgtcggcagc ttgcatcgcg | 240 |
| gcggtggcgc tcagtggaac ccaagcgttc tatgattgga tgaggtgaa cctgcccgac | 300 |
| gtcaatggcc gccaccgcga gttcattccg gatggccaac tgtgcagcgc cgggcgggac | 360 |
| aagtataagg gtctcgacct ggcacgctcc gactggacag ccaccaactt gtcctccggc | 420 |
| gtcgcctaca cattcctcta cagggtcacc gcccagcaca ggggcttctt cgagttctac | 480 |
| gtcaccgtgg atgattacga tcccactgtg gcgctcaaat gggaggactt ggaggaaaca | 540 |
| ccgttcctca acgtcaccga ccccacggtt gtaggcgtca actaccaaat ctccggcacc | 600 |
| acgcctgcca gcaagaccgg ccgccacctc atctacgtca tttggcagcg ctccgacagc | 660 |
| cctgaggcct tctacgcctg ctccgatgtc gacttcgtcg atgccgtctc tctccactcc | 720 |
| accacc | 726 |

<210> SEQ ID NO 8
<211> LENGTH: 741
<212> TYPE: DNA
<213> ORGANISM: Adiantum hispidulum

<400> SEQUENCE: 8

```
atgaagaagt catggggact tgcagtagta gtaggttcac atctgattgt aaggatgaag    60
aagtcatggg gagttgcagt agtagtagga gtagtagctt tgtgcctgct gggcatggca   120
agcggccatg gcagcatgca ggaccccatc agtcgcgtct acaactgcta cctagagggc   180
ccggagcgcc aacgtcggc agcttgcata gctgcggtgg caatgagtgg cacacaacca    240
ttctacgatt ggaatgaggt gaacttgccc gacgccgctg gccggcaccg cgagctcatc   300
cccgatggca agctgtgcag cgccggccgg gataagtatc agggcctcga cctggcgcgc   360
gacgactggg tagcctcctt atcctctggc gtcgcctaca cattccttta ccagtcact    420
gcccagcact tgggcttctt tgaaatttac gtcacccgtg acctacga ccccactcag     480
gcgctaacat gggatgacct ggaagactcg cccttcatca acgttaccaa cccctccgtt   540
gtcagtacga cgttgggtaa cgcctacgca atccccaccc ccacgccatc cggcaagact   600
ggtcgccacc tcatctacgt aatctggcag cgcagcgaca gccccgaggc gttctactcc   660
tgctccgacg tcgagttcga cgtggcatcg acagtcgagg acgacgtcat catctctctc   720
cgctccgcag ctctagacgt c                                              741
```

<210> SEQ ID NO 9
<211> LENGTH: 750
<212> TYPE: DNA
<213> ORGANISM: Polystichum acrostichoides

<400> SEQUENCE: 9

```
atggtcacct atatatatat gtgtgaaatg catgttggaa ggtgtagcaa tatgcgtgca    60
gtaattagag aagccaatta tattgatcat agtgtgagtg tgagcatggg gaggtcatgg   120
ggagttgtgg ctattatggt gttgtgcgct agcggcctgc tgggtgtagc gagcggccat   180
ggcagcatga cgaccccat cagccgcgtc tacaactgcc gtctggagaa tccggagagt    240
cccacgtcag cagcttgcat agcggcgtg gcgctgagtg ggacccaagc gttctatgat    300
tggaatgagg tgaacctgcc cgacgtcaat ggccggcacc gccagctcat tccggatggc   360
aaattgtgca gcgccgggcg ggacaagtat aagggcctcg acctggcacg ctccgactgg   420
gtagccacca acttgtcctc cggcgtcgcc ttcacattcc tctacagggt caccgcccag   480
cacagggct tcttcgagtt ctacgtcacc gtggatgatt acgaccccac tgagctgctc    540
aaatgggaag acttggagga acgccgttc atgaacgtca ccgacccac ggttgtaggc     600
gtcaactacg aaatccccgg caccacgcct gccaataaga ccggccgcca tctcatctat   660
gtcatttggc agcgctccga cagccccgag gccttctact cctgctccga cgttgacttc   720
gtcgatgccg tgtctctcca ctccaccacc                                     750
```

<210> SEQ ID NO 10
<211> LENGTH: 729
<212> TYPE: DNA
<213> ORGANISM: Thelypteris kunthii

<400> SEQUENCE: 10

```
atgcatgttg gaatatacag cacgagtgca gtagtaggga ggatgagaga aagcaatatt    60
ggtcataaca ccgtgaggat ggagagggct gcatggggcg ttgtgggcat tattatggtg   120
ttgtgcgcca gcggcctgct gggcgtagcg agtggccacg gcagcatgga ggaccccatc   180
agtcgcgtct acctctgcta cctcgagaat ccggagcgtc ccacgtcggc agcttgccaa   240
```

| | |
|---|---|
| gcggcggtgg cgctgagtgg gacccaagca ttctatgatt ggaatgaggt gaacatcgcc | 300 |
| gacgccgctg gccggcaccg cgagctcatt ccggatggcc aactgtgcag cgccgggcgg | 360 |
| gacaagtata agggcctcga cctggcacgc tccgactggg tagccaccaa cttgtcctcc | 420 |
| ggcgtcgcct tcacattcct ctacagggtc accgccgagc acaggggctt cttcgagttc | 480 |
| tacgtcaccg tggatgatta cgaccccact gagctgctca atgggaaga cttggaggca | 540 |
| acgccgttca tgaatgtcac cgaccccacg gttgtaggcg acaactacga aatcccggc | 600 |
| accacgcctg ccaacaagac cggccgccat ctcatctatg tcatttggca gcgctccgac | 660 |
| agccccgagg ccttctactc ctgctctgac gtcgtcttcg ccgatgccgt gtctctccac | 720 |
| tccaccacc | 729 |

<210> SEQ ID NO 11
<211> LENGTH: 747
<212> TYPE: DNA
<213> ORGANISM: Cyrtomium fortune (clivicola)

<400> SEQUENCE: 11

| | |
|---|---|
| atgcattctg gaatgggcag cagtatgcgt gcagcaatta ggaggacgag acaaggcaat | 60 |
| tatactggtc atagtgtgag gatggggaca ttggggaggt catggggagc tgtggctatt | 120 |
| atggtgttgt cgccagcgg tctcctgggc gtagccagcg ccatggcag catgaacgac | 180 |
| cccatcagcc gcgtctacaa ctgctacctg gagaatccgg agagacccac ctcggcagct | 240 |
| tgcatagcgg ccgtggcgct cagtgggacc caagcgttct atgattggaa tgaggtgaat | 300 |
| ctgcccgacg ccaatggccg gcaccgccag ctcattccgg atggccaact gtgcagcgcc | 360 |
| gggcgggaca gtataaagg cctcgacctc gcacgctccg actggacggc caccaattta | 420 |
| tcctccggcg tcgccttcac attcctctac agggtcaccg cccagcacag gggcttcttc | 480 |
| gagttctacg tcaccgtgga tgattacgat cccactgtgg cgctcaaatg gaggacttg | 540 |
| gaggaaacac cgttcctcaa cgtcaccgac cccacggttg taggcgtcaa ctaccaaatc | 600 |
| tccggcacca cgcctgccag caagaccggc cgccacctca tctacgtcat ttggcagcgc | 660 |
| tccgacagcc ccgaggcttt ctatgcctgc tccgacgtcg actttgtcga tgccgtctct | 720 |
| ctccactcca ccaccttgac cctgatc | 747 |

<210> SEQ ID NO 12
<211> LENGTH: 729
<212> TYPE: DNA
<213> ORGANISM: Polystichum tripteron

<400> SEQUENCE: 12

| | |
|---|---|
| atgcatgttg gaatgtgcag caatatgctt gcagtaatta ggaggacgag acatttaggc | 60 |
| acttattttg gtcatagtgt gaggatgggc aggtcatggg gagttgtggc tattatggtg | 120 |
| ttgttttcca gtggcctgct gggagtagca agcggccatg gcagcatggg cgaccccatc | 180 |
| agtcgcgtct acaactgcag gcaggagaat ccggagcgac ccactacgcc ggcttgcata | 240 |
| gcggcggtgg cgctgagtgg ggcccaagcg ttctatgatt ggaatgaggt gaacctgccc | 300 |
| tttgtcaatg gccggcaccg ccagttcatt ccggatggga actctgcag cgccgggcgg | 360 |
| aacaagtata ggggtctcga cctggcacgc tccgactgga cagccacaaa cttgtcctcc | 420 |
| ggcgtcgcct acacattcct ctacagggtc accgccagc acaggggctt cttcgagttc | 480 |
| tacgtcaccg tggatggtta cgaccccact gagccgctca atgggcaga cttggaggaa | 540 |
| acgccgttca tcaacgtcac cgaccccaca gtagaaggcc tcaactatgt tcgagttcta | 600 |

```
cgtcaccgtg gatgcaagag tggccgccac ctcatctacg tcatttggca gcgctccgac    660
agccccgagg ccttctactc ctgctccgac gtcaactttc ccgatgccct gtctctccac    720
tccgccacc                                                            729
```

<210> SEQ ID NO 13
<211> LENGTH: 744
<212> TYPE: DNA
<213> ORGANISM: Didymochlaena truncatula

<400> SEQUENCE: 13

```
atgatcacct gtatatatat gtgtgaaatg catgttgaaa tgtgcaacat gcgtgcagta     60
gggaggctga gacaaggcaa tattggtcat agtgtgagga tggggagatc atggggagtt    120
gtggctatta tggtgttgtg cgccagcggc ctgctgggcg tagcgagtgg ccatggcagc    180
atggaggacc ctatcagtcg cgtctacgcc tgctacctgg agaatccgga gcgtcccacg    240
tcggcagctt gccaagcggc ggtggcagtg agtgggaccc aagcgttcta tgattggaat    300
gaggtgaacc agcccttcgc cgctggccgg caccgcgagc tcattccgga tggcgaactg    360
tgcagcggcg ggcgggagaa gtataagggc ctcgacttgg cacgcgccga ctggccagcc    420
acctccttgc cctccggtgt caactacaca tacctctaca aggccaccgc cccgcacttg    480
ggcttcttcg agttctacat cacccgggat ggctacgagc ccactgagcc gctcaaatgg    540
gcagacttgg aggacttgcc gttcatcaac atcaccaacc ccacgcttgt cagcggctcc    600
taccaaatcc ccggcaccac gcctgccagc aagactggcc ggcacctcct ctatgtcatt    660
tggcagcgct ccgacagctt cgaggccttc tactcctgct ccgacgtcga cttcgtcaat    720
gccctctctc tccactccac cacc                                           744
```

<210> SEQ ID NO 14
<211> LENGTH: 750
<212> TYPE: DNA
<213> ORGANISM: Asplenium antiquum

<400> SEQUENCE: 14

```
atgtcgagac gctggctgtc attcaatcac acaaacattg ggttgcattt tttgagtagt     60
gctatgagaa tggggaggtc ggcatcttgc atcagagcta atatggcgat catgctggtg    120
ttgttttggg ctagctgctc ctgcctgctg gcatagtga gcgggcatgg cagcatggag    180
gatcccatca gtcgtgtcta cgcctgcttc ttggagaatc cggagaggcc cacatctgca    240
gcttgcatag cggcggtggc gttgagtggg acgcaagcgt tctacgattg gaacgaggtt    300
aaccagccca cgccgccgg tcggcaccgc gagatcattc cggatggcca gctttgcggc    360
gccggacggg acaagtataa gggcctcaac ttggcacgtg ccgactggcc ggcaaccacc    420
ttgtcctccg acatcagctt cacatacctc ttcaaggcaa ccgcccctca ccgcggtttc    480
ttcgagttct acgtcacccg ggatggttac gatcccaccg agcccctcaa atgggcggac    540
ttggaggacc accattcct caacgtcacc gacccccacgc ttgcttccgg ctcctaccaa    600
atccccggca ccacaccagc cggcaagact ggccgccatc tcatttacgt catatggcag    660
cgctccgata gccccgaagc cttctactct tgctctgacg tggactttga cagcagcgat    720
accgtgatct ctctccgctc tgccaccacc                                     750
```

<210> SEQ ID NO 15
<211> LENGTH: 720
<212> TYPE: DNA

<213> ORGANISM: Cyrtomium falcatum (Butterfieldii)

<400> SEQUENCE: 15

```
atgttggaat gtgcagcaaa tatgcgtgca gtaattagca ggacgagaca aggcaattct    60
attgtgagtg tgaggatggg gaggtcatgg ggagttgtgg ctattatggt gttgtgcgcc   120
accggcctcc tgggcgtggc gagcggccat ggcagcatgg gcgaccccat cagccgcgtc   180
tacaactgct tcctggagaa tcctgagaga cccacgtcgg cagcttgcat cgcggccgtt   240
gcgctcagtg gaacccaagc gttctatgat tggaatgagg tgaacctgcc cgacgtcaat   300
ggccgccacc gccagttcat tccggatggc caactgtgca gcgccgggcg ggacaagtat   360
aagggtctcg acctggcacg ctccgactgg acagccacca acttgtcctc cggcatcgcc   420
tacacattcc tctacagggt caccgcccag cacaggggct tcttcgagtt ctacgtcacc   480
gtggatgatt acgatcccac tgtggcgctc aaatgggagg acttggagga aacgccgttc   540
ctcaacgtca ccgaccccac ggttgtaggc gtcaactacc agatcaacgg caccacgcct   600
gccagcaaga cgggccgcca cctcatctac gtcatttggc agcgctccga cagccccgag   660
gccttctacg cctgctccga cgtcgacttc gtcgatgccg tctctctcca ctccaccacc   720
```

<210> SEQ ID NO 16
<211> LENGTH: 741
<212> TYPE: DNA
<213> ORGANISM: Onoclea sensibilis

<400> SEQUENCE: 16

```
atgcgtgcag tcattagtaa gaagatattg agacaaggca atattggtga tattggtgat    60
agtgtgatca ctgattcagc cttgaggatg gggaggtcat ggggagtggt gcaggctata   120
attatgtgt tgtgcggcag cggcctgctg gcgtagcga gcggccatgg cagcatggag   180
gaccccatca gtcgcgtcta caactgctac ctggagaatc ccgagagtcc cacgtcggca   240
gcttgccaag cggcggtggc gctgagtggg cccaagcgt tctatgattg gaatgaggtg   300
aacctggccg acgccgctgg ccggcatcgc gagctcattc cggatggcca actgtgcagc   360
gccgggcggg agaagtatca gggcctcgac ctggcacgct ccgactggac agccacttcc   420
ttgtcctccg gcgtctcctt cacatacctc tacaaggcca ccgccccgca cttgggcttc   480
ttcgagttct acgtcaccaa ggatggttac gagcccactg agccgctcaa atgggcagac   540
ttggaggact cgcccttcat caacgtcacc gaccccacgc ttgtcagcgg ctcctaccaa   600
atccccggca ccacgccttc cggcaagtcc ggccgccacc tcatctacgt catttggcag   660
cgctccgaca gccccgaggc cttctactcc tgctccgacg tcgacttcga cgtcgatgcc   720
ctctctctcc actccaccac c                                             741
```

<210> SEQ ID NO 17
<211> LENGTH: 738
<212> TYPE: DNA
<213> ORGANISM: Platycerium superbum

<400> SEQUENCE: 17

```
atggagaagt tatctgaggt ggaggaaaag tggataatgg agagttggca gtgggcgaag    60
gtgctgatgc aggtgagggt gagggtgagg atgaggaggt catgggtagc tgtggctgtt   120
accttggtgg tgtgcgccgg cagcctgctg gcgtagcga gcggtcatgg cagcatggag   180
gatcccatca gccgcgtcta ctggtgctac ctggagaatc cggagaatcc tacgtcggca   240
gcgtgcatcg cggcggtggc ggcaagtggc actcaagcct tctacgactg gaatgaggtg   300
```

```
aatcagccct tgccgctgg ccaacaccgc cagatcattc ctgacggcca gctctgcagc    360
gccgggcggg acaagtataa aggcctcgac ctggcacgcg ccgactggcc tgccacctcc    420
ttatcttcgg gcgtcgatta cactttctc ttcaaggcca ccgcccccca ccggggctac    480
ttcgagttct acgtcacccg cgatagctac gaccccactg agccctggc ctgggccgac    540 ctggaggaca cgcccttcat caacgtcacc gacccgaccc ttgtgagcgg ctcctatcag    600
atctccagca ccacgccttc cggcaagacc ggccgtcacc tcatctacgt catttggcag    660
cgcaccgaca gcactgaggc cttctactcc tgctccgatg tcgactttga cgagaccctc    720
cgccttcact ccgccacc                                                  738

<210> SEQ ID NO 18
<211> LENGTH: 714
<212> TYPE: DNA
<213> ORGANISM: Davallia tyermannii

<400> SEQUENCE: 18
atgtggagca tgcatttgtg tggagtaagg aggatcttga dacaaggcaa aatcggtcat     60
agtgtgagaa tggggaggtc atggggagtt gtggctatta tggtgatgta cattggtggc    120
ctgctaagca tagcaagcgg ccatggcagc atggaggacc ccatcagccg cgtctatagg    180
tgctacttgg agaatccgga gagtcccaca tcggcagctt gccaagcggc agtggcagtg    240
agtggggccc aagccttcta cgattggaat gaggtgaaca ttgctgacgc caatggccgg    300
caccgcgagc tcatttccga tggccaccta tgtagcgcca atcgaactaa gtatgcaggc    360
ctcgacctgg catgccccga ttggctaggc accctcttgt tctcgggcgt ctcctacaca    420
ttttcctaca aggccaccgc gccacacttg ggcttctttg agttctacgt caccccggat    480
ggttacgagc ccaccgaccc gctcaaatgg gcagacttgg aggactcgcc cttcatcaac    540
gtcaccaacc ccacacttga taatggcgcc taccagatct ccggcaccac gcctgccggt    600
aagtcggggc gtcatctgat ctacgtcatt tggcagcgct ctgatagccc agaggcattc    660
tattcgtgct ccgacgtcga ctttgtcgat gctctctctc tccactctac cacc          714

<210> SEQ ID NO 19
<211> LENGTH: 723
<212> TYPE: DNA
<213> ORGANISM: Tectaria milnei

<400> SEQUENCE: 19
atgcatcttg gaatctgcaa cattcgtgct gtagggagga tgagacaagc caatattgga     60
gatagtgtga ggatggggag gtcatgggga gtggtggctg ttatggtggt gtgcgcaagc    120
ggcctattga gcgtagtgag gggccatgga agcatggagg accccatcag tcgtgtgtat    180
gcatgcttcc tagagaatcc ggagcgtccc atatcagcag cttgccaggc ggcagtggca    240
atgggtggga cgcaagcctt ctatgattgg aatgcggtaa gcctgcccta tgctgctggg    300
cagcaccgtg aactcatccc ggatggccaa ttgtgcagtg ctgggcgggc caagtatcgg    360
ggcctggacc tgcctcgtga cgattggcca ggcacctcca atatgacctc cggcgtcgcc    420
ttcacataca ggtacaaggc caccgcccca cacttgggct ccttccagtt ctatgtcact    480
cgggatggct acgatcccac cgagccgctc aaatgggcag acttggagga ctcgcctttc    540
atgaacgcca ccagcacgct tgccccgac tcctacctaa tgtccggcac cacccctagc    600
ggcaaggctg gccaccacct catctacgcc atttggcagc gcagcgacag ccctgaggcc    660
```

```
ttctactcct gctccgatgt caccttcgac gtcgctgctg tctctgatct ccactccacc    720
acc                                                                  723

<210> SEQ ID NO 20
<211> LENGTH: 720
<212> TYPE: DNA
<213> ORGANISM: Cyrtomium falcatum

<400> SEQUENCE: 20
atgttggaat gtgcagcaaa tatgcgtgca gtaattagca ggacgagaca aggcaattct     60
attgtgagtg tgaggatggg gaggtcatgg ggagttgtgg ctattatggt gttgtgcgcc    120
accggcctcc tgggcgtggc gagcggccat ggcagcatgg gcgaccccat cagccgcgtc    180
tacaactgct cctggagaaa tcctgagaga cccacgtcgg cagcttgcat cgcggccgtt    240
gcgctcagtg gaacccaagc gttctatgat tggaatgagg tgaacctgcc cgacgtcaat    300
ggccgccacc gccagttcat tccggatggc caactgtgca gcgccgggcg ggacaagtat    360
aagggtctcg acctggcacg ctccgactgg acagccacca acttgtcctc cggcatcgcc    420
tacacattcc tctacagggt caccgcccag cacaggggct tcttcgagtt ctacgtcacc    480
gtggatgatt acgatcccac tgtggcgctc aaatgggagg acttggagga aacgccgttc    540
ctcaacgtca ccgaccccac ggttgtaggc gtcaactacc agatcaacgg caccacgcct    600
gccagcaaga cgggccgcca cctcatctac gtcatttggc agcgctccga cagccccgag    660
gccttctacg cctgctccga cgtcgacttc gtcgatgccg tctctctcca ctccaccacc    720

<210> SEQ ID NO 21
<211> LENGTH: 720
<212> TYPE: DNA
<213> ORGANISM: Polystichium tsus-simense

<400> SEQUENCE: 21
atgtgcaaca atatgcgtgc agtaattagg agtacgagac aattaggcaa ttatattggt     60
catagtgtga ggatggggag gtcatggtgg ggagttttgg ctgttatggt gttgtgcgcc    120
agcggcctgc tgggcgtagc gagcggccat ggcaccatga atgaccccat cagccgcgtc    180
tacaactgct cctggagaaa tccggagagc cccacgtcgg cagcttgcat agctgcggtg    240
gcgctgagtg ggacccaagc gttctatgat tggaatgagg tgaacctggc caacgccgct    300
ggccgacacc gcgagctcat tccggatggc caactgtgca gcgccgggcg ggacaagtat    360
aagggcctcg acctggcacg ctccgactgg acagccacca acttgtcctc cggcgtcgcc    420
ttcacattcc tctacagggt caccgcccag cacaggggct tcttcgagtt ctacgtcacc    480
gtggatgact acgaccccac tgagctgctc aaatgggaag acttggagga aacgcctttt    540
ctcaacgtca ctgaccccac ggttgtaggc gtcaactatg aaatctccgg caccacgcct    600
gccagcaaga ctggccgcca cctcatctac gtcatttggc agcgctccga cagccccgag    660
gccttctact cctgctccga cgtcgacttc gtcgatagcc tctctctcca ctccaccacc    720

<210> SEQ ID NO 22
<211> LENGTH: 720
<212> TYPE: DNA
<213> ORGANISM: Nephrolepis falcata

<400> SEQUENCE: 22
atgcatcatg gaatctgcaa cattcatgca ataggagga ggagacaagc caatattggt      60
cgtagtgtga ggatggggag gtcatggtgg ggagctgtgg ctattgtatt ggcggtgtgc    120
```

```
gccagcggcc tgctgagcgt agtgagcggc aaggaagca tggcgtaccc catcagtcgc    180
gtctatggat gcttcctaga gaatccgttg agtcccacgt cagcagcttg caacgcggcc    240
gtggcattga gtgggacgca agccttctat gattggaatg aggtgagcct ggccaatgcc    300
tctggccagc accgccaact cattccggat ggtcagttgt gcagtgccgg caggccaag    360 tatcggggcc tcgacctggc tcgcgacgat tggccaggca cctccttgac ctccggtgtc    420
gcctacacat tctactacta tgccaccacc ctgcacttgg gcttcttcga gttctatgtc    480
actcgggatg gctacgatgc cacccagccc ctcaaatggg cagatctgga ggactcgcct    540
ttcctcaacg tcaccagcac gcttgccgcc tcctccttcc agtggtctag catcactccc    600
agtgacaagt ctggccgcca cctcatctac gtcatttggc agcgcaccga cagccctgag    660
gccttctact cctgctccga cgtcgacttc gactatgccg tctctctcca ctccaccacc    720
```

<210> SEQ ID NO 23
<211> LENGTH: 717
<212> TYPE: DNA
<213> ORGANISM: Nephrolepis exaltata

<400> SEQUENCE: 23

```
atgcatcttg gaatctgcaa cattcgtgca atagggagga ggagacaagc caatattggt     60
ggtagtgtga ggatggggag gtcatgggga gttgcggcta ttgtagtggc ggtgtgcgcc    120
agcggcctgt tgagcgtagt gagcggccat ggaagcatgc aggaccccat cagtcgcgtc    180
tatgcatgct acctagagaa tccggagcgt cccacgtcag cagcttgcca ggcggcagtg    240
gcattgagtg ggacgcaagc cttctatgat tggaatgagg tgaacctgcc caatgccgct    300
ggccggcacc gcgaactcat tccggatggt cagttgtgca gtgctgggcg gccaagtat    360 cagggcctcg accaggctcg caacgattgg ccacacaccg acttgatctc cggcgtcgcc    420
ttcacattca actacagggc caccgcccca cacttgggca tcttcgagtt ctatgtcact    480
cgggatgggt acgatgccac ccagcccctc aaatgggcag atctggagga ctcgcctttc    540
ctcaccgcca ccagcacgct tgcccccctc tctaccagt ggcccggcac cactcccagt    600
ggcaagtctg gccgccacct catctacgtc atttggcagc gcaccgacag ccccgaggcc    660
ttctactcct gctccgacgt cgagttcgtc gatgccgtct ctctccactc caccacc       717
```

<210> SEQ ID NO 24
<211> LENGTH: 717
<212> TYPE: DNA
<213> ORGANISM: Nephrolepis exaltata

<400> SEQUENCE: 24

```
atgcatcttg gaatcttcaa cattctggca atagggatga gtatgcaagc caatattggt     60
ggtagtgtga ggatggggag gtcatgggga gttgcggcta ttgtagtggc ggtgtgcgcc    120
agcggcctgt tgagcgtagt gagcggccat ggaagcatgc aggaccccat cagtcgcgtc    180
tatgcatgct acctagagaa tccggagcgt cccacgtcag cagcttgcca ggcggcagtg    240
gcattgagtg ggacgcaagc cttctatgat tggaatgagg tgaacctgcc caatgccgct    300
ggccggcacc gcgaactcat tccggatggt cagttgtgca gtgctgggcg gccaagtat    360 cagggcctcg accaggctcg caacgattgg ccacacaccg acttgatctc cggcgtcgcc    420
ttcacattca actacagggc caccgcccca cacttgggca tcttcgagtt ctatgtcact    480
cgggatgggt acgatgccac ccagcccctc aaatgggcag atctggagga ctcgcctttc    540
```

```
ctcaccgcca ccagcacgct tgcccctcc tcctaccagt ggcccggcac cactcccagt    600
ggcaagtctg gccgccacct catctacgtc atttggcagc gcaccgacag ccccgaggcc    660
ttctactcct gctccgacgt cgagttcgtc gatgccgtct ctctccactc caccacc       717
```

```
<210> SEQ ID NO 25
<211> LENGTH: 744
<212> TYPE: DNA
<213> ORGANISM: Humata termanii

<400> SEQUENCE: 25
atgagtatat atatacacac aaatgttcga atgtggagca tgcatttgtg tggagtaagg     60
aggatcttga gacaaggcaa atcggtcat agtgtgagaa tggggaggtc atggggagtt    120
gtggctatta tggtgatgta cattggtggc ctgctaagca tagcaagcgg ccatggcagc    180
atggaggacc ccatcagccg cgtctatagg tgctacttgg agaatccgga gagtcccaca    240
tcggcagctt gccaagcggc agtggcagtg agtgggccc aagccttcta cgattggaat    300
gaggtgaaca ttgctgacgc caatggccga caccggagc tcatttctga tggccaacta    360
tgtagcgcaa atcggagtaa gtatgcgggc ctcgacctgg cacgcgcaga ttggctaggc    420
accaccttgt cctcgggcgc ctccttcaca tttgcctaca aggccaccgc gccgcacttg    480
ggcttctttg agttctacgt cacccgggat ggttacgagc ccaccgaccc gctcaaatgg    540
gcagacttgg aggactcgcc cttcatcaac gtcaccaacc ccacacttga taatggcgcc    600
taccagatct ccggcaccac gcctgccggt aagtcggggc gtcatctgat ctacgtcatt    660
tggcagcgct ctgatagccc agaggcattc tattcgtgct ccgacgtcga ctttgtcgat    720
gctctctctc tccactctac cacc                                          744
```

```
<210> SEQ ID NO 26
<211> LENGTH: 747
<212> TYPE: DNA
<213> ORGANISM: Adiantum tenerum (Scutum Roseum)

<400> SEQUENCE: 26
atgactcaag gtgtttcgaa tttgcatacg aatcatctta cggtccttag gtcacctagc     60
tttattggtc gtagtgtgag tgttagtatg ggctggtgca ggtcatgggg agttgtggct    120
gtgatggtgt tgtgcaccag cggcctcctg ggcgtagcga gcgggcatgg cagcatgaag    180
gaccccatca gccgcgtcta caactgctac ctggagaatc cggagaggcc cacgtcggca    240
gcttgccaag cggcggtggc gctgagcggg acccaagcat tctatgattg gaatgaggtg    300
aacctgccca cgccgcgggg tcggcaccgt gagctcattc cggatggcga actgtgcagc    360
gccgggcggg aaaagtatca gggcctcgac ctggcgcgcg ccgactggac agccacgtcc    420
ttgacctccg gcctcgactc gttcacatgg ctctacaagg ccaccgctcc gcacttgggc    480
ttcttcgagt tctacgttac ccgggacggt tacgacccga ccgaggcgct cacatgggca    540
gacctggagg actcgccgtt cataaacgtc accaaccccg cgcttgtcag cggcgactac    600
caaatctccg gcaccatacc tgccggcaag agcggccgcc acctcatcta cgtcatttgg    660
cagcgctccg acagcccgga ggccttctac tcctgctccg acgtcgactt cgtcgatgat    720
gccctgatct ctctccgctc cgccaca                                       747
```

```
<210> SEQ ID NO 27
<211> LENGTH: 723
<212> TYPE: DNA
<213> ORGANISM: Polystichum setiferum (compacta)
```

<400> SEQUENCE: 27

```
atgtatatat gtgaaatgca tgttggaatg tgcagcaata tgcgtgcagt agttagacac      60
ggcaatcata gtgtgaggat ggggaggtca tggggagttg cggctattat ggtgttgtgc     120
gccagcggcc tgctgggtgt agcgagcggc catggcacca tgcatgaccc catcagtcgt     180
gtctacaact gcttcctgga gaatccagag agtcccacgt cggcagcttg catagaggcg     240
gtggaggtga gtgggaccca accattctat gattggaatg aggtgaacct ggccaacgcc     300
gctggccggc accgcgagct cattccggat ggcaaactgt gcagcgccgg cgggacaag      360
tataagggcc tcgacctggc acgctccgac tgggtagcca ccaacttgtc ctccggcgtc     420
gccttcacat tcctctacag ggtcaccgcc gagcacaggg gcttcttcga gttctacgtc     480
accgtggatg attacgaccc cactgagctg ctcaaatggg aagacttgga ggaaacgccg     540
ttcatgaatg tcaccgaccc cacggttgta ggcgccaact acgaaatccc cggcaccacg     600
cctgccaaca agaccggccg ccatctcatc tatgtcattt ggcagcgctc cgacagcccc     660
gaggccttct actcctgctc cgacgtcgtc ttcgccgatg ccgtgtctct ccactccacc     720
acc                                                                 723
```

<210> SEQ ID NO 28
<211> LENGTH: 723
<212> TYPE: DNA
<213> ORGANISM: Polystichum setiferum (compacta)

<400> SEQUENCE: 28

```
atgtatatat gtgaaatgca tgttggaatg tgcagcaata tgcgtgcagt agttagacac      60
ggcaatcata gtgtgaggat ggggaggtca tggggagttg cggctattat ggtgttgtgc     120
gccagcggcc tgctgggtgt agcgagcggc catggcacca tgcatgaccc catcagtcgt     180
gtctacaact gcttcctgga gaatccagag agtcccacgt cggcagcttg catagaggcg     240
gtggaggtga gtgggaccca accattctat gattggaatg aggtgaacct gcctgacgtc     300
aatggccggc accgcgagct cattccagat ggcaaactgt gcagcgccgg cgggagaag      360
tataagggcc tcgacctggc acgctccgac tgggtagcca ccaacttgtc ctccggcgtc     420
gccttcacat tcctctacag ggtcaccgcc gagcacaggg gcttcttcga gttctacgtc     480
accgtggatg attacgaccc cactgagctg ctcaaatggg aagacttgga ggcaacgccg     540
ttcatgaatg tcaccgaccc cacggttgta ggcgacaact acgaaatccc cggcaccacg     600
cctgccaaca agaccggccg ccatctcatc tatgtcattt ggcagcgctc cgacagcccc     660
gaggccttct actcctgctc cgacgtcgtc ttcgccgatg ccgtgtctct ccactccacc     720
acc                                                                 723
```

<210> SEQ ID NO 29
<211> LENGTH: 729
<212> TYPE: DNA
<213> ORGANISM: Lepisorus bicolor

<400> SEQUENCE: 29

```
atgtcctggg gagttgtggc tattatggtg gccgtgtgtg ccagcggcct gcttttggta      60
attatttttt atagaagtgt gaggatgagg tcctgggag ttgtggctat tatggtggcc     120
gtgtgtgcca gcggcctgct gggcgtcgcg agtggccatg gcagcatgtc ggaccccatc     180
agtcgcgtct ataggtgccg cctcgagaat ccggagcgtc ccacgtccgc agcctgcatc     240
```

| | |
|---|---|
| gcggcggtgg cgcttagcgg caagcaagcc ttctacgatt ggaatgaggt gaatctgccc | 300 |
| ttcgccaatg gccggcaccg cgagctcatc cctgacggta aactttgcag cgccgggcgg | 360 |
| gacaaatata aaggcctcga cctgccacgc gccgactggc tggccacctc cttgtcttct | 420 |
| ggctccgcct acacattcct ctaccgggcc accgcccccc acctgggcta ctttgagttc | 480 |
| tacgtcacgc gggatagcta cgaccccact cagccgctcg catggtcgga cttggaggac | 540 |
| tcgccgttca tcaaggtcac caacccgccc ctcgtcagcg gatttacga atttcctggc | 600 |
| accacgcctt ccggcaaaac cggccgccac ctcatctacg tcatttggca gcgcaccgac | 660 |
| agcaccgagg ctttctactc ctgctccgac gtcgactttg acgaggccct ctctctttcc | 720 |
| tccaccatc | 729 |

<210> SEQ ID NO 30
<211> LENGTH: 750
<212> TYPE: DNA
<213> ORGANISM: Pyrrosia lingua

<400> SEQUENCE: 30

| | |
|---|---|
| atgagatcct gtataaaaag ggcgggactg gaaaggagga gcagcagcga agatcctgag | 60 |
| agacatctgg tgcttttag atacagagtg tgtgagagga tgaggacgag ggtatgggga | 120 |
| gttgtggctt ttatggtggc cgtgtgtgcc tgcgacctgc tgggcctagc gagtgggcat | 180 |
| ggctccatgg gggaccccgt cagtcgcgta ttgaattgct acctcgagaa tccggagagg | 240 |
| cccacgtcgg cagcctgcat cgcggcggtg gcgctgagtg gcacccaagc tttctacgac | 300 |
| tggaatgagg tgaacctggc ctccgcctgt ggccggcacc gcgagctcat ttctgacggc | 360 |
| gaactctgca gcgccgggcg cgacaagtat aaaggcctca acctggcacg cgccgactgg | 420 |
| gtggccacct ccctgtcttc gggcgtcgat tacacattcc tctttaacgc caccgccgcc | 480 |
| cacctgggct acttcgagtt ctgggtcacc cgtgatagct acgaccccac tcagccgctc | 540 |
| gcctgggcgg acttggagga ctcgccattc atcaacatca ccaaccccac cattgtcagc | 600 |
| gatgcctacc aagtgcccgc caccacgcct tccggcaaga ccggccgcca cctcatctac | 660 |
| gtcatttggc agcgcactga cagcaccgag gccttctact cctgctccga cgtcgacttt | 720 |
| gacgaggccc tccctctctc ctccaccacc | 750 |

<210> SEQ ID NO 31
<211> LENGTH: 735
<212> TYPE: DNA
<213> ORGANISM: Blechnum appendiculatum

<400> SEQUENCE: 31

| | |
|---|---|
| atgcaggacc cccgactcac agtttatctt atctgcatgt atacactcac tgatctgatt | 60 |
| aggatgaaga agtcatccgg agttgtagta gtggtagtag cagctatatt actgttgtgc | 120 |
| ctgctgggcg tggcaaacgg ccatggcagc atgcaggacc ccatcagtcg cgtctacaac | 180 |
| tgcttcctag agaacccgga gagtccgaca tcggcagctt gccaagctgc ggtagcagtg | 240 |
| gccgggacgc aaccattcta cgattggaat gaggtgaacc tggccaacgc caatggccgg | 300 |
| caccgcgagc tcatttcaga tggcatgctg tgcagcgcca accggtccaa gtatcatggc | 360 |
| ctcgacctgg cgcgcgccga ctggacggcc acctccttat cctctggcgt cgcctacaca | 420 |
| ttcctgtacc gggtcaccgc ccaccacagg ggtttcttcg agttctacat cacccgtgac | 480 |
| agctacgacc ccacccagcc gctcgcatgg gcagacctgg aggactcacc gttcatcaac | 540 |
| attaccgacc ccacgactgt gagtacgact ctgggtgaag cctacgaaat ctccggcacc | 600 |

```
acgcccgcca gcaagagcgg tcgccacctc atctatgtca tctggcagcg cagcgacagc    660
cccgaggcat tctactcctg ctccgacgtc gacttctctg ccgatgccct gatctctctc    720
cgctccgcag tactc                                                     735
```

<210> SEQ ID NO 32
<211> LENGTH: 717
<212> TYPE: DNA
<213> ORGANISM: Polystichum munitum

<400> SEQUENCE: 32

```
atgcatcttg gaatgtgcag caatatgcgt gcagtaatta cacaaggcaa ttatattggt     60
catagtgtga ggatggggag gtcatgggga gttgtggcta ttatggtgtt gtgcgctagc    120
ggcctgctgg gcgtagcgag cggccatggc accatgaaca accccatcag ccgcgtctac    180
aactgccgcc tggagaatcc ggagcgtccc acgtcagcag cttgcatagc ggcggtggcg    240
ctgagtggga cccaagcgtt ctatgattgg aatgaggtga acctgcccga cgtcaatggc    300
cggcaccgcg agctcattcc ggatggcaaa ctgtgcagcg ccgggcggga caagtataag    360
ggcctcgacc tggcacgctc cgactgggta gccaccaact tgtcctccgg cgtcgccttc    420
acattcctct acagggtcac cgcccagcac aggggcttct tcgagttcta cgtcaccgtg    480
gatgattacg accccactga gctgctcaaa tgggaagact tggaggaaac gccattcatg    540
aacgtcaccg accccacggt tgtaggcgtc aactacgaaa tcccaggcac cacgcctgca    600
aacaagaccg gccgccatct catctatgtc atttggcagc gctccgacag ccccgaggcc    660
ttctactcct gctccgacgt agacttcgtc gatgccgtgt ctctccactc caccacc      717
```

<210> SEQ ID NO 33
<211> LENGTH: 696
<212> TYPE: DNA
<213> ORGANISM: Stenochlaena tenuifolia

<400> SEQUENCE: 33

```
atgaggcgac acaatactgg ttataatagt gagcgagcac tgtgcatggg gatggggagg     60
tcaaactcat ctaaagttgt agctatcgtg gtgttgtgca gtggcctgct gagcctagtg    120
agcggccatg gcagtatgca gaaccccatc agtcgcgtcc tcaactgcta cctggagaat    180
ccggagcgtc ccacgtcggc agcttgccaa gcggcggtgg cgatgagtgg gacccaagcc    240
ttctatgatt ggaatgaggt gaacctgccc aacgccgctg gcggcaccg ccaactcatt     300 cccgatggcc aactgtgcag cgccgggcgg cagaagtatc ggggcctcga cttggctcgc    360
gacgactggg aagccaccac cttgtcctcc gggaccgcct tcacatacaa ctacagggcc    420 accgcccgc acctgggctt cttcgagttc tacgtcactc gggatggcta cgagcccact     480
gagcctctca atggtccga cttgcaggac tcgcccttca tcaacgtcac caccacgctt     540
tctagcgact cctaccaaat caccggcacc acgcctgctg gcaagtccgg ccgccacctc    600
atctacgtca tttggcagcg ctccgacagc cccgaggcct tctactcctg ctccgacgtc    660
gagttcgacg ttgccctctc tctccattcc gccacc                              696
```

<210> SEQ ID NO 34
<211> LENGTH: 693
<212> TYPE: DNA
<213> ORGANISM: Asplenium bulbiferum (G.Forst.)

<400> SEQUENCE: 34

| | |
|---|---|
| atgagaatgg ggagatcgac atcttgcatg ggagcaaata tggctttcat gctgctgctg | 60 |
| ctgttgtttt gggctagctg ctgctgcctg ctgggcaaag tgagcgggca tggcagcatg | 120 |
| gaggatccca tcagccgtgt ctacgcctgc ttcttggaga atccggagag ccgacgtcg | 180 |
| gcagcatgcc aagcggcggt ggcgttgagt gggacgcaag cgttctatga ttggaacgag | 240 |
| gtcaaccagc ccaacgctgc cggccggcac cgcgagataa tcccggacgg ccagctctgc | 300 |
| agcggcgggc gggagaagta tcagggcctc gacttggcac gtgacgactg gacgccacc | 360 |
| tccttgtccc caaacgtctc cttcacgttc ctctacaagg cgacagcgcc tcaccgcggt | 420 |
| ttcttcgagt tctacgtcac ccgggatggt tacgacccta ccgaggccct cacatgggcc | 480 |
| gacttggagg aaccgccatt catcaacgtc accgacccca cggttgcctc cggcgcctac | 540 |
| cagatccccg gcaccacacc ggccggcaag actggccgcc atctcatcta cgtcatatgg | 600 |
| cagcgctctg atagccccga ggccttctac tcttgctccg acgtcgactt cgagagtgcc | 660 |
| gataccgtca atatctctct ccgctctacc acc | 693 |

<210> SEQ ID NO 35
<211> LENGTH: 699
<212> TYPE: DNA
<213> ORGANISM: Athyrium filix-femina

<400> SEQUENCE: 35

| | |
|---|---|
| atgaatattg caggtcatac tagtgtgagg gtgaggatgg ggaggtcatg gggagttgtg | 60 |
| gctattctta tggtgttgtg cggctgcctg ctgggcgtag cgagcgggca tggcagcatg | 120 |
| gaggacccca tcagtcgcgt ctacaactgc tacctcgaga atccggagag tcccacgtcg | 180 |
| gcagcttgcc aagcggcggt ggcgctgggt gggccccaac cgttctatga ttggaatgag | 240 |
| gtgaaccagc ccaacgccga tggccactcc cgcgagatca ttccggatgg ccaactgtgc | 300 |
| agcggcgggc gggagaagta taagggcctc gacctggcac gctccgactg gacagccacc | 360 |
| tccttgtcct ccggcgtcgc cttcacattc ctcttcaagg ccactgcccc gcacgcgggc | 420 |
| ttcttcgagt tctacgtcac ccaggatggt tacgacccca ctgagccgct caaatgggca | 480 |
| gacttggagg actcgccctt catcaacgtc accgacccca cgcttctcag cggctcctac | 540 |
| caaatccccg gcaccacgcc tgccggcaag tccggccgcc acctcatcta cgtcatttgg | 600 |
| cagcgctccg acagccccga ggccttctac tcctgctccg acgtcgactt cgtcgatgcc | 660 |
| ctctctagtg atctccactc caccatggca ccaatagct | 699 |

<210> SEQ ID NO 36
<211> LENGTH: 693
<212> TYPE: DNA
<213> ORGANISM: Adiantum capillus-veneris

<400> SEQUENCE: 36

| | |
|---|---|
| atggggatga agatgtcatg gaagttgca ctagcagaaa tagtagcttt gtgcctactg | 60 |
| ggcatggcaa gcagccatgg caccatgcag acccccataa gtcgtgtcta caactgctttt | 120 |
| ctggagaacc cggagaggcc aacgtcggca gcttgtcaag ctgcagtagc gttgggtggc | 180 |
| acacaaccac tctatgattg gaatgaggtg aacatccatg atgccgctgg caaccaccgc | 240 |
| gatctcatcc ccgatggcaa gctctgcagc gccggccgcc aaaagtttca gggcctcgac | 300 |
| ttggcgcgcg cggattggat agcaacctcc ctatcctctg gcgtcgacgt cgactacaca | 360 |
| ttcctctacc gcgccaccgc cccgcacttg ggcttctttg aatttttacat cacccgtgac | 420 |
| acctacgacc ccacccagcc gctcgcatgg ggtgacctgg aagactcgcc cttcatcaac | 480 |

```
attaccaatc cctccatcgt cagtacgact ttgggtcccg cctactcgat ccccagcact    540
acaccattca gcaaaagtgg tcgccacctc atctacgtca tctggcagcg caccgacagc    600
ctcgaggcgt tctactcctg ctccgacgtc gacttctcga catcttccat cgaggatgat    660
gtcatcgtct ctctccgttc tgcagctcta ctc                                 693
```

<210> SEQ ID NO 37
<211> LENGTH: 699
<212> TYPE: DNA
<213> ORGANISM: Coniogramme emeiensis (Golden Zebra)

<400> SEQUENCE: 37

```
atgtatacac tcactgatct gattaggatg aagaagtcat ccggagttgt agtagtggta     60
gtagcagcta tattactgtt gtgcctgctg ggcgtggcaa acggccatgg cagcatgcag    120
gaccccatca gtcgcgtcta caactgcttc ctagagaacc cggagagtcc gacatcggca    180
gcttgccaag ctgcggtagc agtggccggg acgcaaccat ctacgattg gaatgaggtg     240 aacctggcca acgccaatgg ccggcaccgc gagctcattt cagatggcat gctgtgcagc    300
gccaaccggt ccaagtatca tggcctcgac ctggcgcgcg ccgactggac ggccacctcc    360
ttatcctctg gcgtcgccta cacattcctg taccgggtca ccgcccacca caggggtttc    420
ttcgagttct acatcacccg tgacagctac gaccccaccc agccgctcgc atgggcagac    480
ctggaggact caccgttcat caacattacc gaccccacga ctgtgagtac gactctgggt    540
gaagcctacg aaatctccgg caccacgccc gccagcaaga gcggtcgcca cctcatctac    600
gtcatttggc agcgcagcga cagccccgag gcattctact cctgctccga cgtcgacttc    660
tctgccgatg ccctgatctc tctccgctcc gcagtactc                           699
```

<210> SEQ ID NO 38
<211> LENGTH: 693
<212> TYPE: DNA
<213> ORGANISM: Asplenium nidus var plicatum

<400> SEQUENCE: 38

```
atgagaatgg ggagatccat atcacgcatg gcagctagga tggctattat gctggtgttg     60
tgctgggcta taagctgctg cctgctgggc acagtgagcg ggcatggcag ctctgaggat    120
cccatgagcc gtgtctatgg gtgctacttg cagaatccgg agaggcccgc atcggcagcc    180
tgccgagcgg cagtggcgat gagtgggacg caagcgttct atgattggaa cgaggtcaac    240
cagccccatg ctgccggtcg gcaccgcgag atcattccgg atggcagct ctgcggcggc     300 gggcgggcga agtatcgggg cctcaacttg gcacgtgccg actggtggtc caccccttg    360 tactccaaca ccccccttcat gttcctctat agggctaccg ccctcacag gggtttcttc    420 gagttctatg tcacccggga tggttacgat cccactgaac ccctcaaatg gtcggacttg    480
gagtacccac cattcatcaa cgtcaccgac cccacgcttg ccttcggcgc ctacaagatc    540
cccggcttca caccgtatgg caagactggc cgccatctca tctacatcat atggcaacgc    600
tctgatagcc cagaagcctt ctactcttgc tccgacgtgg acttcgtgga cttcaagagc    660
gatgaaaccg tgatccctct ccactctacc acc                                 693
```

<210> SEQ ID NO 39
<211> LENGTH: 693
<212> TYPE: DNA
<213> ORGANISM: Polystichum polyblepharum

<400> SEQUENCE: 39

```
atgcttgcag taattagaca aggcaattat attggtcata gtgtgaggat ggggaggtca        60
tggggagttg tggctattat ggtgctgtgc gctagcggcc tgctggacgt agcgagcggc       120
catggcagca tgaacgaccc catcagccgt gtctacaact gccgcctgga gaatccggag       180
agtcccacgt cagatgcttg catagcggcg gtggcgctga gtgggaccca agcgttctat       240
gattggaatg aggtgaacct gcccaacgcc gctggcaggc accgagagct cattccggat       300
ggcaaactgt gcagcgccgg gcgggacaag tataagggcc tcgacctcgc acgctccgac       360
tgggtagcca ccaacttgtc ctccggcgtc gccttcacat tcctctacag ggtcaccgcc       420
cagcacaggg gcttcttcga gttctacgtc accgtggatg attacgaccc cactgagctg       480
ctcaaatggg aagacttgga ggaaacaccg ttcatgaatg tcaccgaccc cacggttgta       540
ggcgtcaact acgaaatggc cggcaccacg cctgccaaca gaccggccg ccatctcatc        600
tatgtcattt ggcagcgctc cgacagcccc gaggccttct actcctgctc cgacgtcgac       660
ttcgtcgatg ccgtgtctct ccactccagc acc                                   693
```

<210> SEQ ID NO 40
<211> LENGTH: 699
<212> TYPE: DNA
<213> ORGANISM: Adiantum venustum

<400> SEQUENCE: 40

```
atggggagac gtcgtgcagt aaggaaaggt cataatagtg tgaggaggat atccatgggg        60
aggtcatggg gagacgttgt ggctattatg gtgttgtgcg ccagcggcct gctgggcgta       120
gcgagcggcc atgcagcat gcaggacccc atcagtcgcg tctacaactg ctacctggag        180
ggtccggaga gtcccacgtc ggcagcttgc atagcggcgg tggcgctgag tgggacccaa       240
gcattctatg actggaatga ggtgaaccag cccaacgccg ctggccggca ccgcgagatc       300
atcccggatg ccaactctg cagcggcggg cgggacaagt atagcggcct cgaccttgcg        360
cgctccgact ggacagccac ctccttgtcc tccaacgtct cctacacata cctcttcaag       420
gccaccgccc cgcacaaggg cttcttcgag ttttacgtca cccgggacag ctacgagccc       480
actgaggcgc tcaaatgggc agacttggag gactcaccct tcattaacat caccgacccc       540
acgcttgaca gcgcgccta ccaaatcccc ggcaccacgc ctgccggcaa gtctgggcgc        600
cacctcatct acgtcatttg gcagcgctcc gacagcggcg aggccttcta cgcctgctgc       660
gacgtcgact cgatgtcga tgtcctccac tccaccaca                              699
```

<210> SEQ ID NO 41
<211> LENGTH: 699
<212> TYPE: DNA
<213> ORGANISM: Actiniopteris australis

<400> SEQUENCE: 41

```
atgaggcaag gcagtagtat tgctgatatg agtgtgagaa tgggggagt taacgctgtt         60
gctatcatat tgctgttgtg ctgcgctagc agcggcttgc tgggcatagc ccgcgggcat       120
ggcagcatgc aagatcccat cagccgtgtc tacgcctgct acttggagaa tccggagcgt       180
cccacatcgg cagcttgcca agcggcagtg gccttgagtg ggacgcaagc cttctatgac       240
tggaacgagg tgaaccagcc gtttgctgct ggccgccacc gcgagatcat tcccgacggc       300
cagctttgca gcggtgggcg gaccaagtat gcggcctcg acctggcacg cgacgactgg        360
acagccacct ccttgtccgc cggcatctcc tacacattcc tctacagagg caccgccccg       420
```

```
caccttggct tcttcgagtt ctacgtcacc cgggatggtt acgatcccac tgagcccctc    480
aaatgggcag acttggagga cccgcctttc atcaacatca ccaaccccac tcttgtcagc    540
ggcgtttacc agatccccgg gaccacacct gccggaaaga ctggccgcca tctcatctac    600
gttatctggc agcgcaccga cagccccgag gcgttctact cctgctccga cgtcgtcttc    660
agcgacgatg ccgccctcta tctccgctct accactgag                           699
```

<210> SEQ ID NO 42
<211> LENGTH: 693
<212> TYPE: DNA
<213> ORGANISM: Marsilea crenata

<400> SEQUENCE: 42

```
atgaggagga gcgggatgag cagcagcgtg ctagccgctg tcgccgccgg agttcttcta     60
gtggcggcac taggcagcca cgtggcgtac gggcacggca gcatgaagga accaatcagc    120
cgcgcttaca actgctacct cgaaattgct gacaatgcca cgtcagacgc gtgcggggcg    180
gcggcagcgc tttgcatccc tgaagccttc aacgactgga acgctgtact tatccctgac    240
gtcgccggcc gccaccgcca gctcatcccg gacggacagc tgtgcagcgc cggaagagcg    300
aagtacgccg gcctgaatct cgcaagtgtg gactgggagg ccgccacctt ggctgccggc    360
gtgaactaca cgtttctgta caaggccgta gtggtccaca aaggctactt cgagttctac    420
gtcaccaagg acggctacga cgccacgcaa gcgctcacat ggtccgactt ggaagacgcc    480
cctttcgtca cgtcaccga tcccatagtc aattccgaca gtgacttcga aattcccggc    540
accattccct ccgggaagtc cggccgccac gtgatctacg tcatttggca gcgcaccgac    600
agccccgaag ctttctactc ctgctcggac gtcgacttcg acgacaccat ctccgacgac    660
accatctccg acaccgtcct acatgccagc tca                                 693
```

<210> SEQ ID NO 43
<211> LENGTH: 687
<212> TYPE: DNA
<213> ORGANISM: Asplenium prolongatum x Asplenium antiquum (Kurata)

<400> SEQUENCE: 43

```
atgagaatgg ggaggtcggc atcttgcatc agagctaata tggctatcat gctggtgttg     60
ttttgggcta gctgctgctg cctgctgggc atagtgagcg ggcatggcag catggaggat    120
cccatcagtc gtgtctacgc ctgctacttg gagaatccgg agcggcccac atctgcagct    180
tgcatagcgg cggtggcgtt gagtgggacg caagcgttct acgattggaa cgaggttaac    240
cagcccaacg ccgccggtcg gcaccgcgag tcattccgg atggccagct tgcagcggt    300 gggcgggaga agtatcaggg cctcgacctg gcacgtgccg actggacggc cacctccctg    360
acctccggta tcaccttcac tttcctctac aaggcaacag cccctcaccg tggtttcttt    420
gagttctacg tcacccgcga tacttatgat ccaccgagc ccctcacatg gcggacttg    480 gaggacacgc cattcatcaa cgccaccgac cccacgcttg cttccggctc ctaccagatc    540
cccggcacca ccagccggg caagactggc cgccatctca tctacgtcat atggcagcgc    600
tctgatagcc ccgaagcctt ctactcttgc tctgacgtgg actttgagag cagcgatacc    660
gtgatctctc tccgctctgc caccacc                                        687
```

<210> SEQ ID NO 44
<211> LENGTH: 687
<212> TYPE: DNA

<213> ORGANISM: Adiantum raddianum (Fritz Luthi)

<400> SEQUENCE: 44

```
atggggatga agatgtcatg ggaagttgca ctagcagaaa tagtagcttt gtgcctactg    60
ggcatggcaa gcagccatgg caccatgcag acccccataa gtcgtgtcta caactgcttt   120
ctggagaacc cggagaggcc aacgtcggca gcttgtcaag ctgcagtagc gttgggtggc   180
acacaaccac tctatgattg gaatgaggtg aacatccatg atgccgctgg caaccaccgc   240
gatctcatcc ccgatggcaa gctctgcagc gccggccgcc aaaagtttca gggcctcgac   300
ttggcgcgcg cggattggat agcaacctcc ctatcctctg gcgtcgacta cacattcctc   360
taccgcgcca ccgccccgca cttgggcttc tttgaatttt acatcacccg tgacacctac   420
gaccccaccc agccgctcgc atggggtgac ctggaagact cgcccttcat caacattacc   480
aatccctcca tcgtcagtac gactttgggt cccgcctact cgatcccag cactacacca    540
ttcagcaaaa gtggtcgcca cctcatctac gtcatctggc agcgaccga cagcctcgag    600
gcgttctact cctgctccga cgtcgacttc tcgacatctt ccatcgagga tgatgtcatc   660
gtctctctcc gttctgcagc tctactc                                       687
```

<210> SEQ ID NO 45
<211> LENGTH: 681
<212> TYPE: DNA
<213> ORGANISM: Asplenium australasicum

<400> SEQUENCE: 45

```
atgagaatgg ggagatccac atcacgcatg cagctagga tggctattac gctgctgttg     60
tgctgggcta gctgctgcct gctgggcaca gtgagcgggc atggcagcat gctggatccc   120
atcagtcgca tctacgcctg cttcttggag aatccggaga ggcccacatc ggcagcctgc   180
caggcggcag tggcgttggg tgggacgcaa ccgctctatg attggaacga ggtcaaccag   240
cccaatgctg ccggtcggca ccgcgagatc attccggatg ccagctttg cggcggcggg    300
cgggagaagt atcagggcct caacttggca cgtgccgact ggccggcaac ctccttgtcc   360
tccaacaccg ccttcacgtt cctctacatt gctacagccc ctcaccgcgg tttcttcgag   420
ttctacgtca cccgggatgg ttacgatccc actgagctcc ttaaatgggc ggacttggag   480
tacccacccct tcctcaacgt caccgacccc acgcttgcct ccggcaacta ccagatccct   540
ggcaccacac cagccggcaa gaccggccgc catctcattt acgtcatatg gcagcgctcc   600
gatagccccg aagccttcta ctcctgctcc gacatcgact tcgagagcga tgaaaccgtg   660
atctctctcc actctaccac c                                             681
```

<210> SEQ ID NO 46
<211> LENGTH: 681
<212> TYPE: DNA
<213> ORGANISM: Asplenium australasicum

<400> SEQUENCE: 46

```
atgagaatgg ggagatccac atcacgcatg cagctagga tggctattac gctgctgttg     60
tgctgggcta gctgctgcct gctgggcaca gtgagcgggc atggcagcat gctggatccc   120
atcagtcgca tctacgcctg cttcttggag aatccggaga ggcccacatc ggcagcctgc   180
caggcggcag tggcgttggg tgggacgcaa ccgctctatg attggaacga ggtcaaccag   240
cccaacgctg ccggccgcca ccgcgagatc attcccgatg ccaactttg cagcggcggg    300
cgggagaagt ataagggctt cgacttgcct cgtgccgact ggccggcaac caccttggtc   360
```

| | |
|---|---|
| tccaacatca gcttcacata cctctacaag gcaacagctc ctcaccgtgg tttcttcgag | 420 |
| ttctacgtca cccgggatgg ttacgatccc actgagctcc ttaaatgggc ggacttggag | 480 |
| tacccaccct tcctcaacgt caccgacccc acgcttgcct ccggcaacta ccagatccct | 540 |
| ggcaccacac cagccggcaa gaccggccgc catctcattt acgtcatatg gcagcgctcc | 600 |
| gatagccccg aagccttcta ctcctgctcc gacatcgact tcgagagcga tgaaaccgtg | 660 |
| atctctctcc actctatcac c | 681 |

<210> SEQ ID NO 47
<211> LENGTH: 687
<212> TYPE: DNA
<213> ORGANISM: Adiantum raddianum (Gracillimum)

<400> SEQUENCE: 47

| | |
|---|---|
| atggggatga agatgtcatg ggaagttgca ctagcagaaa tagtagcttt gtgcctactg | 60 |
| ggcatggcaa gcagccatgg caccatgcag acccccataa gtcgtgtcta caactgcttt | 120 |
| ctggagaacc cggagaggcc aacgtcggca gcttgtcaag ctgcagtagc gttgggtggc | 180 |
| acacaaccac tctatgattg gaatgaggtg aacatccatg atgccgctgg caaccaccgc | 240 |
| gatctcatcc ccgatggcaa gctctgcagc gccggccgcc aaaagtttca gggcctcgac | 300 |
| ttggcgcgcg cggattggat agcaacctcc ctatcctctg gcgtcgacta cacattcctc | 360 |
| taccgcgcca ccgccccgca cttgggcttc tttgaatttt acatcacccg tgacacctac | 420 |
| gaccccaccc agccgctcgc atggggtgac ctggaagact cgcccttcat caacattacc | 480 |
| aatccctcca tcgtcagtac gactttgggt cccgcctact cgatcccag cactacacca | 540 |
| ttcagcaaaa gtggtcgcca cctcatctac gtcatctggc agcgcaccga cagcctcgag | 600 |
| gcgttctact cctgctccga cgtcgacttc tcgacatctt ccatcgagga tgatgtcatc | 660 |
| gtctctctcc gttctgcagc tctactc | 687 |

<210> SEQ ID NO 48
<211> LENGTH: 684
<212> TYPE: DNA
<213> ORGANISM: Thelypteris palustris

<400> SEQUENCE: 48

| | |
|---|---|
| atgaggcaag gcaattatat aggtcatagt gtgaggatgg ggaggtcatg gggagttgtg | 60 |
| ggtattatgg tgttgtgcct gctgggcgta gcgagcggcc atggcaccat gcaggacccc | 120 |
| atcagtcgcg tctacaactg ccgcctggag aatccggagc gtcccacgtc ggcagcttgc | 180 |
| atagcggccg tggcgctgag tgggacccaa gcgttctatg attggaatga ggtgaacttg | 240 |
| gccaacgccg ctggccggca ccgcgagctc attccggatg ccaactgtg cagcgccggg | 300 |
| cgggtcaagt accagggcct cgacctggca cgctccgact ggacagccac ctccttgtcc | 360 |
| tccggcgtct ccttcacatt cctctacagg gtcaccgccc agcacttggg cttcttcgag | 420 |
| ttctacgtca cccaggatgg ttacgacccc actgagccgc tcaaatgggc agacttggag | 480 |
| gactcgccgt tcatcaacgt caccaacccc acggttgtca gcacctccct aggccccgcc | 540 |
| taccaaatcg ctggcaccac gcctgccggc aagtctggcc gccacctcat ctacgtcatt | 600 |
| tggcagcgct ccgacagccc cgaggccttc tactcctgct ccgacgtcga cttcgtcgat | 660 |
| gccctctctc tccactccac tgcc | 684 |

<210> SEQ ID NO 49

```
<211> LENGTH: 687
<212> TYPE: DNA
<213> ORGANISM: Adiantum raddianum (Variegatum)

<400> SEQUENCE: 49
atggggatga agatgtcatg ggaagttgca ctagcagaaa tagtagcttt gtgcctactg      60
ggcatggcaa gcagccatgg caccatgcag accccataa gtcgtgtcta caactgcttt     120
ctggagaacc cggagaggcc aacgtcggca gcttgtcaag ctgcagtagc gttgggtggc     180
acacaaccac tctatgattg gaatgaggtg aacatccatg atgccgctgg caaccaccgc     240
gatctcatcc ccgatggcaa gctctgcagc gccggccgcc aaaagtttca gggcctcgac     300
ttggcgcgcg cggattggat agcaacctcc ctatcctctg gcgtcgacta cacattcctc     360
taccgcgcca ccgccccgca cttgggcttc tttgaattt acatcacccg tgacacctac     420
gaccccaccc agccgctcgc atggggtgac ctggaagact cgcccttcat caacattacc     480
aatccctcca tcgtcagtac gactttgggt cccgcctact cgatcccag cactacacca     540
ttcagcaaaa gtggtcgcca cctcatctac gtcatctggc agcgcaccga cagcctcgag     600
gcgttctact cctgctccga cgtcgacttc tcgacatctt ccatcgagga tgatgtcatc     660
gtctctctcc gttctgcagc tctactc                                        687

<210> SEQ ID NO 50
<211> LENGTH: 690
<212> TYPE: DNA
<213> ORGANISM: Asplenium dimorphum X Asplenium difforme

<400> SEQUENCE: 50
atgagaatgg ggagatcgac atcttgcatg ggagctaata tggctatcgt cctgctgctg      60
ctgttgtttt gggctagctg ctgctgcctg ctgggcaaag tgagcgggca tggcagcatg     120
gaggatccca tcagtcgtgt ctacgcctgc ttcctggaga atccggagag gccgacgtcg     180
gcagcctgcc aagcggcggt ggcgttgagt gggacgcaag cgttctatga ttggaacgag     240
gtcaacctgc ccaacgctgc cggccggcac cgcgaaatca tcccggacgg ccagctttgc     300
agcggcgggc gggagaagta taaaggcctc gacttggcac gtgccgactg gacggccacc     360
tccttgtccc caaacgtctc cttcacgttc ctctacaagg ggacagcgcc tcaccgcggt     420
ttcttcgagt tctacgtcac ccgggatggt tacgaccctac cgaggccct cacatgggcc     480
gacttggagg aaccgccatt catcaacgtc accgacccca cgcttgcctc cggcgcctac     540
cagatccccg gcaccacacc agccggcaag acgggccgcc atctcatcta cgtcatatgg     600
cagcgctctg acagccccga agccttctac tcttgctccg acgtcgactt cgagagtgac     660
gataccgtgg tctctctccg ctctaccacc                                     690

<210> SEQ ID NO 51
<211> LENGTH: 687
<212> TYPE: DNA
<213> ORGANISM: Matteuccia struthiopteris

<400> SEQUENCE: 51
atgcttgcag taaggaaagg caatattggt gatagcgtga ggatggggag gtcatggggt      60
gttgtagcta ttatggtgtt gtgcgccagc agcctgctgg gcgtagtgag cggccatggc     120
agcatggcgg accccatcag tcgtgtctat gggtgccgtc tggagggtcc ggagagcccc     180
acatcggcag cttgccaagc ggcggtggcg ctgagtggga cccaagcgtt ctatgattgg     240
aatgaggtga accagccctt cgccgctggc cggcaccgcg agctcattcc ggatggccaa     300
```

```
ctgtgcagcg gcgggcgggt caagtatcag ggcctcgacc tggcacgctc cgactggcca    360
gccaccaact tgtcctccgg cgtctccttc acattcctct acgaggtcac cgccacgcac    420
ttgggctact ttgagttcta cgtcacccgg gatggttacc agccgactga gccgctcaaa    480
tgggcagact tggaggactc gccgttcctc accgccacca caacgcatga gagcagctcc    540
tacataatcc ctggcaccac gccttccgcc aagtccggcc gccacctcat ctacctcatt    600
tggcagcgga ccgacagccc cgaggccttc tactcctgct ccgacgtcga cttcgtcgat    660
gccctctcta gtctccactc caccaac                                        687
```

<210> SEQ ID NO 52
<211> LENGTH: 684
<212> TYPE: DNA
<213> ORGANISM: Athyrium filix-femina (angustum)

<400> SEQUENCE: 52

```
atgatgaata ttgcaggtca tactagtgtg aggatgggga ggtcatgggg agttgtggct     60
attcttatgg tgttgtgcgg ctgcctgctg ggcgtagcga gcgggcatgg cagcatggag    120
gaccccatca gtcgcgtcta caactgctac ctggagaatc cggagagtcc cacgtcggca    180
gcttgccaag cggcggtggc gctgggtggc acccaaccgt tgtatgattg aatgaggtg     240 aaccagccca cgccgctggc cagtcccgc gaaatcattc cggatggcca actgtgcagc    300
ggcgggcggg agaagtatca gggcctcgac ctggcacgct ccgactggac agccacctcc    360
ttgtcctccg gcgtcgcctt cacattcctc ttcaaggcca ccgccccgca cttgggcttc    420
ttcgagttct acgtcaccca ggatggttac gaccccactg agccgctcaa atgggcagac    480
ttggaggact cgcccttcat caacgtcacc gaccccacgc ttctcagcgg ctcctaccaa    540
atccccggca ccacgcctgc cggcaagtcc ggccgccacc taatctacgt catttggcag    600
cgctccgaca gccccgaggc cttctactcc tgctccgacg tcgacttcgt cgatgccctc    660
tctagtgatc tccactccac cacc                                           684
```

<210> SEQ ID NO 53
<211> LENGTH: 687
<212> TYPE: DNA
<213> ORGANISM: Adiantum monocolor

<400> SEQUENCE: 53

```
atggggatga agatgtcatg ggaagttgca ctagcagaaa tagtagcttt gtgcctactg     60
ggcatggcaa gcagccatgg caccatgcag gaccccataa gtcgtgtcta caactgcttt    120
ctggagaacc cggagaggcc aacgtcggca gcttgtcaag ctgcagtagc gttgggtggc    180
acacaaccac tctatgattg aatgaggtg aacatccatg atgccgctgg caaccaccgc    240
gatctcatcc ccgatggcaa gctctgcagc gccggccgcc aaaagtttca gggcctcgac    300
ttggcgcgcg cggattggat agcaacctcc ctatcctctg cgtcgactga cacattcctc    360
taccgcgcca ccgccccgca cttgggcttc tttgaatttt acatcacccg tgacacctac    420
gaccccaccc agccgctcgc atggggtgac ctggaagact cgcccttcat caacattacc    480
aatccctcca tcgtcagtac gactttgggt cccgcctact cgatcccag cactacacca    540 ttcagcaaaa gtggtcgcca cctcatctac gtcatctggc agcgcaccga cagcctcgag    600
gcgttctact cctgctccga cgtcgacttc tcgacatctt ccatcgagga tgatgtcatc    660
gtctctctcc gttctgcagc tctactc                                        687
```

<210> SEQ ID NO 54
<211> LENGTH: 684
<212> TYPE: DNA
<213> ORGANISM: Adiantum pubescens (Bronze)

<400> SEQUENCE: 54

| | | | | | |
|---|---|---|---|---|---|
| atgaagaagt | cttggggagt | tacagctgta | gtgggagtaa | tagctttgtg | cctgctggac | 60 |
| gtggcaagcg | gccatggcag | catgcaggac | cccatcagtc | gtgtctacaa | ctgctttcta | 120 |
| gaaaacccgg | agcgcccaac | gtcggcagct | tgcatagctg | cggtggcaat | gagtggcaca | 180 |
| caaccattct | acgattggaa | tgaggtgaac | ttggccgacg | ccaatggccg | gcaccgcgag | 240 |
| ctcatccccg | atggcaagct | gtgcagcgcc | ggcaggata | agtatcaggg | cctcgaccag | 300 |
| gcgcgcgacg | actgggtagc | aacctcctta | tcctctggcg | tcgcctacac | attcctttac | 360 |
| cgggtcactg | ccccgcactt | gggcttcttt | gaattttacg | tcacccgtga | cacctacgac | 420 |
| cccactcagg | cgctcgcatg | ggatgacctg | gaagactcgc | ccttcatcaa | cattaccaac | 480 |
| ccctccgttg | tcagtacgac | gttgggtaac | gcctactcaa | ttcccggcac | cacgccatcc | 540 |
| ggcaagactg | gtcgccacct | catctacgtc | atctggcagc | gcagcgacag | tcgcgaggcg | 600 |
| ttctactcct | gctccgacgt | cgacttcccg | gcatcgacag | tcgaggatga | cgtcatcatc | 660 |
| tctctccgct | ccgcagctct | agtc | | | | 684 |

<210> SEQ ID NO 55
<211> LENGTH: 681
<212> TYPE: DNA
<213> ORGANISM: Blechnum niponicum

<400> SEQUENCE: 55

| | | | | | |
|---|---|---|---|---|---|
| atgagcgcag | taaggaatat | tggtcatagt | gtgaggatgg | gaaggtcatg | gggagttgtg | 60 |
| gctattatgg | tgttgtgcgc | cagcggcctg | ctgggcgtag | cgagcggcca | tggcagcatg | 120 |
| gacgacccca | tcagtcgtgt | ctacaactgc | tacctggaga | atccggagcg | tcccacgtcg | 180 |
| gcagcttgcc | aagccgcggt | ggcgctgagt | gggacccaag | cgttctatga | ttggaatgag | 240 |
| gtgaaccagc | ccttcgccgc | tggccggcac | cgcgagatca | ttccggatgg | ccaactgtgc | 300 |
| agcggcgggc | gggagaagta | tcagggcctg | gacctggcac | gctccgactg | gacagccacc | 360 |
| tccttgtcct | ccgcgtctc | cttcacatac | ctgtacaagg | ccaccgcccc | gcacttgggc | 420 |
| ttcttcgagt | tctacgtcac | cgtggatggt | taccagccca | ctgagccgct | caaatggtca | 480 |
| gacttggagg | accgccgtt | catcaacgtc | accaacccca | cgcttgtcag | cggctcctac | 540 |
| caaatccccg | gcaccacgcc | tgccggcaag | accggccgcc | acctcatcta | cgtcatttgg | 600 |
| cagcgctccg | acagcccga | ggccttctac | tcctgctccg | acgtcgactt | cgccgatgcc | 660 |
| ctctctctcc | actccaccac | c | | | | 681 |

<210> SEQ ID NO 56
<211> LENGTH: 672
<212> TYPE: DNA
<213> ORGANISM: Platycerium wandae

<400> SEQUENCE: 56

| | | | | | |
|---|---|---|---|---|---|
| atgtatggtg | gtcagcatac | tgggaggatg | gggaagccgt | ggagagtggt | ggtggccatt | 60 |
| gtggtggtgt | gcgccagcgg | cctgctgggc | gtagcgagcg | gccatggcag | catgggtgaa | 120 |
| cccatcagtc | gcgtctataa | ttgctacctg | gagaatccgg | agagaccac | gtcggcagcg | 180 |
| tgcatcgcgg | cggtggcgct | tagtggcacc | caagccttct | acgactggaa | tgaggtgaac | 240 |

```
ctgcccttcg ccgctggccg gcaccgcgag ctcattcctg acggccagct ctgcagcgcc    300
gggcgggaca agtataaagg cctggacctg gcacgcgccg actgggttgc cacctccctg    360
tcttcgggcg tcagctacac cttcctctac agggccaccg ccccccacca gggctacttt    420
gagttctacg tcaccaagga tagctacgac cccactgagc cgctggcctg gcggacctg     480 gaggacacgc ccttcattaa catcaccgat ccgacccttg tcagcggctc ttaccagatc    540
cccagcacca cgccttccga caagaccggc cgccacctca tctacgtcat ttggcagcgc    600
accgacagcc ctgaggcctt ctactcctgc tccgatatcg actttgacga cacccctcccc   660 ctacactcca cc                                                         672
```

<210> SEQ ID NO 57
<211> LENGTH: 675
<212> TYPE: DNA
<213> ORGANISM: Nephrolepis cordifolia (Duffii)

<400> SEQUENCE: 57

```
atgaaacaag ccaatattgg tcatagtgta aggatgggga ggtcatggcg agttgtggct    60
attatggtgg tgtgcgccag cggcctattg agtgtagtga ggggccatgg aagcatggaa    120 gacccctta gtcgcgtcta tgggtgcttc ctagagaatc agagagtcc cacgtcagca     180 gcttgccaag cggcagtggc aatgagtggg accctagctt ctatgattg gtttgatgtg    240 agcttgccca atgcttctgg ccggcaccgc gaactcattc cggatggcca attgtgtggt    300
gctgggctga ccaagtatca gggcctcaac ctggctcgcg atgattggac agccacctcc    360
ttgacctccg gcgtctcctt cacatacctc tacaaggccg ccgcccgaca cttgggcttc    420
tttgagttct atgtcactcg ggatggttac gatcccaccg agccgctcaa atgggcagac    480
ttggaggact tgcctttcat gaacgtcacc agcacgcttg acgaggagtc ctaccaaatc    540
cctggcacca ctcctagtgg caaggctggc cgccacctca tctacgtcat ttggcagcgc    600
agcgacagcc ctgaggcctt ctactcctgc tccgatgtcg acttcgtcga tgctgtctct    660
ctccactcca ccacc                                                      675
```

<210> SEQ ID NO 58
<211> LENGTH: 672
<212> TYPE: DNA
<213> ORGANISM: Adiantum raddianum (Fragrans)

<400> SEQUENCE: 58

```
atggggatga agatgtcatg gaagttgca ctagcagaaa tagtagcttt gtgcctactg     60
ggcatggcaa gcagccatgg caccatgcag acccccataa gtcgtgtcta caactgcttt    120
ctggagaacc cggagaggcc aacgtcggca gcttgtcaag ctgcagtagc gttgggtggc    180
acacaaccac tctatgattg gaatgaggtg aacatccatg atgccgctgg caaccaccgc    240
gatctcatcc ccgatggcaa gctctgcagc gccggccgcc aaaagtttca gggcctcgac    300
ttggcgcgcg cggattggat agcaacctcc ctatcctctg gcgtcgacta cacattcctc    360
taccgcgcca ccgccccgca cttgggcttc tttgaattt acatcacccg tgacacctac    420
gaccccaccc agccgctcgc atgggtgac ctggaagact cgcccttcat caacattacc    480
aatccctcca tcgtcagtac gactttgggt cccgcctact cgatcccag cactacacca    540 ttcagcaaaa gtggtcgcca cctcatctac gtcatatggc agcgcagcga cagcccgaa    600 gctttctatg cctgctccga catcgacttc tccacttctt ccgacatgat ttctctccgc    660
```
tccgcagttc tc                                                              672

<210> SEQ ID NO 59
<211> LENGTH: 675
<212> TYPE: DNA
<213> ORGANISM: Platycerium bifurcatum (Netherlands)

<400> SEQUENCE: 59
atgtatggtg gtcagcatac tgcgagcatg gggaagccgt ggagagtggt ggtggccatt          60
gtggtggtgt gcgccagcgg cctgctgggc gtagcgagcg ccatggcag catgggggat          120
cccatcagtc gcgtctataa ttgctacctg gagaatccgg agaggcccac atcggcagcg         180
tgcatcgcgg cggtggcgct tagtggcacc caagccttct acgactggaa tgaggtgaac         240
ctgccccttcg ccgctggccg gcaccgcgag ctcattcctg acggccagct ctgcagcgcc        300
gggcgggaca agtataaagg cctggacctg gcacgcgccg actgggttgc cacctccttg        360
tcttcgggcg tcagctacac cttcctctac agggttaccg ccccccaccg gggctacttt       420
gagttctacg tcaccaagga tagctacgac cccactgagc cgctgccctg gcggacctg         480
gaggacacgc ccttcattaa catcaccgac ccgaccattg tcagcggctc ttaccagatc        540
tccagcacca cgccttccga caagaccggc cgccacctca tctacgtcat ttggcagcgc        600
accgacagcc ctgaggcctt ctactcctgc tccgatgtcg actttgacga caccctcccc        660
ctccactcct ccacc                                                          675

<210> SEQ ID NO 60
<211> LENGTH: 663
<212> TYPE: DNA
<213> ORGANISM: Pyrrosia polydactyla

<400> SEQUENCE: 60
atgaggatgg ggatgaggat gaggttatgg ggagttgtgg cttttatggt ggccgtgtgt         60
gccggcgagc tgctggacca agcgagtggg catggctcca tgggggaccc cgtcagtcgc        120
gtcttgaatt gctacctcga gaatccggag aaccctcgt cggctgcctg catcgctgcg        180
gtggcggcga gtggcacccca agccttctac gactggaatg aggtgaatct ggccttcgcc       240
gctggccagc accgcacgct cattcctgat ggcgaactct gcagcgccgg tcgggagaag        300
tataaaggcc tcaatctggc acgcgccgac tgggtagcca cttcattgtc ttcaggcgcc        360
aactacacat tcctctacag ggccaccgcc ccccacctgg gctacttcga gttctacgtc        420
acgcaagata gctacgaccc cactgagccg ctcgcatggg cggacttgga ggactcgccg        480
ttcatcaatg tcaccaaccc ggccctcgtc agcggctcct accgaattgc tggcaccacg       540
ccttccggca aaaccggccg ccacctcatc tacgtcattt ggcagcgcac cgacagcccc       600
gaggccttct actcctgctc cgacgtcgac tttgacgagg ccgtctctct tcttccacc         660
acc                                                                       663

<210> SEQ ID NO 61
<211> LENGTH: 666
<212> TYPE: DNA
<213> ORGANISM: Blechnum brasiliense

<400> SEQUENCE: 61
atgaagaagc catggggagt tgtagtagta gtagctatat tactgttgtg cctgctgggc        60
gtggcaagcg gccatggcag catgcaggac cccatcagtc gagtctacaa ctgctaccta       120
gagaacccag agaggccgac atcggcagct tgccaagctg cggtggcgat gagcgggacg        180

```
caagcattct acgattggaa tgaggtgaac ctggccaacg cttctggccg gcaccgcgag      240
ctcattcctg atggcaagct gtgcagtgcc ggccgggaca agtatcgggg cctcgacctg      300
gcgcgcgccg actggacggc cacctcctta tcctctggcg tcgcctacac attcctccac      360
cgggtcaccg cccggcactt gggattcttc gagttctaca tcacccgtga cagctacgac      420
cccaccgagc tgctcacatg ggcagacctg gaggactcgc cgttcatcaa cattaccaac      480
cccacgactg tgagtacgtc tctgggtaac gcctaccaga tccccggcac cacgcccgcc      540
ggcaagagcg gtcgtcacct catctacgtc atctggcagc gcagcgacag ccctgaggca      600
ttctactcct gctgcgacgt cgacttctct tctgataccc tgatctctct ccgctctgca      660
gcactc                                                                666

<210> SEQ ID NO 62
<211> LENGTH: 666
<212> TYPE: DNA
<213> ORGANISM: Blechnum sp. (Silver Lady)

<400> SEQUENCE: 62
atgaagaagc catggggagt tgtagtagta gtagctatat tactgttgtg cctgctgggc       60
gtggcaagcg gccatggcag catgcaggac cccatcagtc gagtctacaa ctgctaccta      120
gagaacccag agaggccgac atcgcagct tgccaagctg cggtggcgat gagcgggacg       180
caagcattct acgattggaa tgaggtgaac ctggccaacg cttctggccg gcaccgcgag      240
ctcattcctg atggcaagct gtgcagtgcc ggccgggaca agtatcgggg cctcgacctg      300
gcgcgcgccg actggacggc cacctcctta tcctctggcg tcgcctacac attcctccac      360
cgggtcaccg cccggcactt gggattcttc gagttctaca tcacccgtga cagttacgac      420
cccaccgagc ccctcacatg ggcagacctg gaggattcgc cgttcctcaa cattaccgac      480
cccacgactg tgggtacgcc tctgggtgat gcctacgaaa tccccggcac cacgcccgac      540
ggcaagagcg gtcgccacct catctatgtc atctggcagc gcagcgacag ccctgaggca      600
ttctactcct gctgcgacgt cgacttctct tctgataccc tgatctctct ccgctctgca      660
gcactc                                                                666

<210> SEQ ID NO 63
<211> LENGTH: 669
<212> TYPE: DNA
<213> ORGANISM: Pteris cretica (Mayi)

<400> SEQUENCE: 63
atggggtcga ggtcagtggg cggcggagga gctgggggcta tttattgtat gctgctaata       60
tgctgcgtta gcagcgggct gctgggcata gcgagcggcc atggcaccat gctgacccc       120 tttagtcgtg tgtacgcctg ccgcttcttc gagaatccgg agcgtcccac atcgccagca      180
tgccaagcag cagtggcggc gagtggaacg caagcgttct atgactggaa cgaggtgaac      240
cagcccttcg ccgctggccg gcaccgcgag atcattccgg acggccaact ttgcagcggt      300
gggcgggaca agtataaggg cctcgacctg gcacgcaacg actggccagc cacctccttg      360
tcctccaaca tcccccttcac ataccctgtac attgccagcg ctccgcaccg cggcttcttc      420
gagttctacg tcacccagga tggttacgat cccactcagc ccctcaaatg ggcagatttg      480
gagtacccgc cattcatcaa catcaccgac cccacgctgc tcagcggctc ctaccaaatc      540
cccggcacca cgccggccgg caagtctggc cgccatctca tctacgtcat ttggcagcgc      600
```

| | |
|---|---|
| tccgacagcc ccgaggcctt ctactcctgc tccgacgtcg acttcgtcga ctctctccac | 660 |
| gcctccgtc | 669 |

<210> SEQ ID NO 64
<211> LENGTH: 663
<212> TYPE: DNA
<213> ORGANISM: Cystopteris fragilis

<400> SEQUENCE: 64

| | |
|---|---|
| atggggagag ttaaccttct ggctattctg gtgttgtgcg ccagctgctg cgccggcctg | 60 |
| ctgggcgtag ccagcggcca tggcaccatg gaggacccca tcagtcgcgt ctacaactgc | 120 |
| ttcctggaga acccggagcg tcccacgtcg gcagcttgcc aagcggcggt tgcgctgagt | 180 |
| ggcacccaag cgttctatga ctggaatgag gtgaacctgg cggacgccgc tggccggcat | 240 |
| cgcgagctca ttccggatgg ccaactgtgc agcgccgggc gggagaagta tcggggcctg | 300 |
| gacctggcac gctccgactg gtagccacc tccttgtcct ccggcgtctc caccacattc | 360 |
| ctctacaagg ccacggctcc gcacttgggc ttcttcgagt tctacgtcac ccgggatgga | 420 |
| tacgacccca ccgaggcgct caaatggtca gacttggagg actcgccgtt cctcaacgtc | 480 |
| accgacccca cccttctcag cagcccctac gtctaccaaa tccctggcac cacgcctgcc | 540 |
| ggcaagtccg ccgccacct gatctacgtc atttggcagc gctccgacag ccctgaggcc | 600 |
| ttctactcct gctccgacgt cgccttcgac gatgcccagc ttgtctctct ccactccacc | 660 |
| acc | 663 |

<210> SEQ ID NO 65
<211> LENGTH: 660
<212> TYPE: DNA
<213> ORGANISM: Dryopteris filix-mas

<400> SEQUENCE: 65

| | |
|---|---|
| atggggaggt catggggagt ggtgcaggct ataattatgg tgttgtgcgg cagcggcctg | 60 |
| ctgggcgtag cgagcggcca tggcagcatg gaggacccca tcagtcgcgt ctacaactgc | 120 |
| tacctggaga atcccgagag tcccacgtcg gcagcttgcc aagcggcggt ggcgctgagt | 180 |
| ggggcccaag cgttctatga ttggaatgag gtgaacctgg ccgacgccgc tggccggcat | 240 |
| cgcgagctca ttccggatgg ccaactgtgc agcgccgggc gggagaagta tcagggcctc | 300 |
| gacctggcac gctccgactg gacagccact tccttgtcct ccggcgtctc cttcacatac | 360 |
| ctctacaagg ccaccgcccc gcacttgggc ttcttcgagt tctacgtcac caaggatggt | 420 |
| tacgagccca ctgagccgct caaatgggca gacttggagg actcgcccct catcaacgtc | 480 |
| accgacccca cgcttgtcag cggctcctac caaatccccg gcaccacgcc ttccggcaag | 540 |
| tccggccgcc acctcatcta cgtcatttgg cagcgctccg acagcccga ggccttctac | 600 |
| tcctgctccg acgtcgactt ctcttccgat gccctcatct ctctcggctc cgcggtactc | 660 |

<210> SEQ ID NO 66
<211> LENGTH: 657
<212> TYPE: DNA
<213> ORGANISM: Bolbitis cladorrhizans

<400> SEQUENCE: 66

| | |
|---|---|
| atggggaggt cattgggagc tgtggttatt acattggtgc tgtgcgcggg cggcctgctg | 60 |
| agcttagcga gcggccatgg cagcatggag gatcccatca gtcgcgttta caggtgctac | 120 |
| cttgagaatc cggagagtcc gacttcggcg gcttgccaag cggcggtggc gctgagtggc | 180 |

```
accgaagcct tctctggtta tgcttggagt gcggtattgg ccaacgctgc aggccagcac      240
cgccagctca ttccagatgg ccaattgtgc agcgcagggc aggagctgta tgcgggccta      300
gacctgccac gcgccgactg ccagccacc tccttgtcct ctggcgttgc cttcacatat       360
ctctacaagg ccgcgatccc gcacatgggc ttcttcgagt tctacatcac ccgggatggt      420
tatgagccca cagagccgct caagtgggca gatttggagg actcgccctt cctcaacgtc      480
actgaccccc cgcttgtcag tagttcctac cagatccctg ctccacacc tgccggcaag       540 tctggccgcc accttatcta tgtcatttgg cagcgctccg acagccccca ggccttctac      600
tcctgttccg atgtcgactt tgttgatgcc accctctctc agctccactc caccacc        657

<210> SEQ ID NO 67
<211> LENGTH: 660
<212> TYPE: DNA
<213> ORGANISM: Dryopteris filix-mas

<400> SEQUENCE: 67
atgaagaagt catggggagt tgttgtagta gtagtagtag ctctagtact gttgtgcctg      60
ctgggcacgg caagcggcca tgcagcatg caggacccca tcagtcgtgt ctacaactgc       120
tacctagaga atcctgagaa cccaacgtcg gcagcttgca aagctgtggt ggcggtgggg      180
ggcacgcaac cactctacga ttggaatgag gtgaacctgg ccaacgccgc tggccggcac      240
cgtgagctca ttcctgatgg caggctgtgc agtgctggcc gggacaaata tcggggcctc      300
gacctggctc gcgacgactg gccagccacc tccttatcct ctggtgtcga ctacacattc      360
ctctaccgcg ccactgcccc tcacttgggc ttcttcgagt tctatgtcac ccgcgacagc      420
tacgacccca cccagccgct cgcatgggca gacctggagg acttgccgtt catcaacgtt      480
accaaccctg ccctaaatgc tggtgcctac caaatccccg gcaccatgcc ggccggaaag      540
agcggtcgcc acctcatcta cgtcatctgg cagcgcagcg acagccccga ggcattctac      600
tcctgctccg acgtcgactt ctcttccgat gccctcatct ctctccgctc cgcggtactc      660

<210> SEQ ID NO 68
<211> LENGTH: 654
<212> TYPE: DNA
<213> ORGANISM: Pyrrosia lanceolata

<400> SEQUENCE: 68
atgaggacga ggtcatgggg agttgtggct tttatggtag ctgtgtgtgc cggcgacctg      60
ctaggcctcg cgagtgggca tggctccatg ggctaccccg tcagtcgcgt cttgaactgc      120
ttccttgaga atccggagag ccccacgtcg gctgcctgca ccgcggcggt ggctatgagt      180
ggcacccaag cctttctacga ctggaatgag gtcaatctgc cctttgccaa tggccagcac     240
cgcgacctca ttcctgacgg ccaactctgc agcgccgggc gcgccaagta tgcaggcctg      300
gacctggcac gcgacgactg ggaagccact tttttgtctt cggccaccag ctacacactc      360
ctctacaggg tcaccgctcg ccacctgggc tacttcgagt tctacgtcac tcgcgatagc      420
tacaactcca ctcagccgct cgcctgggcg gacttggagg attcgccctt catcaacatc      480 accaaccta ccgttgacag cggctactac caagtgcctg tcgacacgcc ttccggcaag       540
actggccgcc acctcatcta cgtcatttgg cagcacaccg acagcctcga ggccttctac      600
tcctgctccg acgttgaatt tgacgtcgag gtcccctctc tccgctccac cacc           654

<210> SEQ ID NO 69
```

```
<211> LENGTH: 654
<212> TYPE: DNA
<213> ORGANISM: Athyrium filix-femina

<400> SEQUENCE: 69
atggggaggt catggggggg agttgtggct attatggtgt tgtgcggctg cctgctgggc      60
gtagcgagcg ggcatggcag catggaggac cccatcagtc gcgtctacaa ctgctacctg     120
gagaatccgg agagtcccac gtcggcagct tgccaagcgg cggtggcgct gagtgggacc     180
caagcgttct atgattggaa tgaggtgaac cagcccttcg ccgctggcca gtcccgcgag     240
atcattccgg atggccaact gtgcagcggc gggcgggaga agtataaggg cctcgacctg     300
gcacgctccg actggacagc cacctccttg tcctccggcg tcgccttcac attcctcttc     360
aaggccaccg ccccgcacgc gggcttcttc gaattctacg tcacccagga tggttacgac     420
cccactgagc cgctcaaatg gcagacttg gaggactcgc ccttcatcaa cgtcaccgac      480
cccacgcttg tcagcggctc ctaccaaatc tccggcacca cgcctgccgg caagtccggc     540
cgccacctca tctacgtcat ttggcagcgc tccgacagcc ccgaggcctt ctactcctgc     600
tccgacgtcg aattcgtcga cgatgccctc tctagtgatc tccactccac cacc           654

<210> SEQ ID NO 70
<211> LENGTH: 654
<212> TYPE: DNA
<213> ORGANISM: Colysis wrightii (Monstifera)

<400> SEQUENCE: 70
atggggagag catgggtagt tgtggctatt atggtcgccg tgtgcgccag cgggctgctg      60
agcttcgcca gtcgcacacg gggccatggc agcatggggg accccatcag tcgagtactt     120
aggtgccgcg aagagaatcc ggagaatccc acgtcgccag cctgcatcgc ggcggtggcg     180
ctcagcggca acaagccctt ctacgattgg aatgaagtga atctgcccct cgccgatggc     240
cagcaccaaa agctcatccc tgacggccaa cttttgcggcg ctgggcgtga caagtataaa     300
ggcctcaacc tggcacgtgc cgactggctg gctacctcct tgtctgccgg cgcccctac     360
acattcctct cctggcctc cgcccccac ctgggctact cgagttcta cgtcactcgg       420
gatagttacg accccactca gccgctcgca tgggcggact tggaggactc gccgttcctc     480
actaccacca cgaccctcga cagcagctcc tacataattc caggcaccac gcccgctggc    540
aaaaccggcc gccacctcat ctacctcatt tggcagcgca ccgacagccc tgaggccttc    600
tactcctgct ccgacgtcga cttgaggag gccatctctc tttcctccac cacc           654

<210> SEQ ID NO 71
<211> LENGTH: 657
<212> TYPE: DNA
<213> ORGANISM: Coniogramme venusta

<400> SEQUENCE: 71
atggggagga gctcgtcgtg ggagggagta ctagtagtag tggtgtgctg cgccagcggc      60
ctgctgggcg tagcgagcgg ccatggcagc atgggcagcc ccatcagtcg cgtctacaac     120
tgccgccagg agaatccgga gcgtccccac tcggcagctt gcagagaggc ggtgaggatt     180
agtgggaccc aagcgttcta tgattggaat gaggtgaacc tgcccgtcgc ctctggccgg     240
caccgcgagc tcattccgga tggcaagctc tgcagcgccg gcggactaa gtatgcgggc     300
ctcgacttgg cacgctccga ctgggtatcc accgtcttgc cctccggcgt ccctacaca     360
ttcctctaca gggtcaccgc tcgccacgtg ggcttcttcg agttctacgt cacccgggat     420
```

```
ggttaccagc cctctgagcc cctcaaatgg tcagacttgg aagagcctcc gttcatcaac    480
gtcaccaatc ccacgatgtc cggcggcttc tatcgaatcc ccggaaccac gccacccgcc    540
aaggccggcc gccacctcat ctacgtcatt tggcagcgct ccgacagccc cgaggccttc    600
tactcctgct ccgacgctgt cttcggcgac gccctctctc tccagtactc ctccacc      657

<210> SEQ ID NO 72
<211> LENGTH: 651
<212> TYPE: DNA
<213> ORGANISM: Platycerium coronarium

<400> SEQUENCE: 72
atgaggaggt cttggggagt tgtggctgtt attatgttgg cagtgtgcgc cgtcggcatg     60
ctgggcgtag ccagcgggca tggtagcatg gaggatccca tcagtcgcgt gtataggtgc    120
ttcctggaga acccggagag gcccacgtca gcagcgtgca tcgccgcggt ggcgcttagt    180
ggcacccaag ccttctacga ctggaatgag gtaaatctgc ccttcgcagc tggccgacac    240
cgcgagctca ttcctgacgg tcagctctgc agcgccgggc gggacaagta taaaggcctc    300
gacctggcac gcgacgactg ggtggccacc tctttgtcct ccggcgtcaa ctacaccttc    360
ctctacaagg ccaccgcccc ccatcggggc tacttcgagt tctacgtcac ccgggatagc    420 tacgaccccca ctgagccgct ggcctgggcg gacctggaag acacgccctt catcaacgtc    480
accgacccgg acctcgccag tggctcctac cagatctcca gcaccacgcc ttccggcaag    540 accgccgcc accttatcta cgtcatttgg cagcgcaccg acagcccga ggccttctac    600 tcctgctccg acatcctttt cgacgaggcc gtcgctctct actctaccgc t              651

<210> SEQ ID NO 73
<211> LENGTH: 654
<212> TYPE: DNA
<213> ORGANISM: Cystopteris bulbifera

<400> SEQUENCE: 73
atggggagag tcaaccttat ggctattttg gcgttgtgcg ccagcttctg cgccgccctg     60
ctgggcgttg ccagcggcca tgcagcatg caggaccccaa tcagtcgcgt ctacaactgc    120
ttcctggaga acccggagcg tcccacgtcg gcagcttgcc aagcggcggt tgcgctgagt    180
ggcacccaag cgttctatga ctggaatgag gtgaacctgg cgaacgccga tggtcggcat    240
cgcgagctca ttccggatgg ccaactgtgc agcgccggga gggagaagta tcagggcctg    300
gacctggcac gcgccgactg gacagccacc tccttgtcct ccggcatctc ctacacattc    360
ctctacaagg ccaccgctcc gcacctgggc ttcttcgagt tctacgtcac ccgggatggt    420 tacgaccccca ccgaggcgct caaatggtca gacttggagg actcgccgtt cctcaacgtc    480 accaaccca cccttgtcag cggctcctac caaatccccg ttaccacgcc tgccgccaag    540 tccgccgcc acctgatcta cgtcatttgg cagcgctccg acagcccga ggccttctac    600 tcctgctccg acgtcgactt cgacgatgcc ctagtctctc tccactccac cacc          654

<210> SEQ ID NO 74
<211> LENGTH: 651
<212> TYPE: DNA
<213> ORGANISM: Platycerium ridleyi

<400> SEQUENCE: 74
atgaggaggt catggggagt tatggctgtt attttgttgg cggtgtgcgc ctgcggcctg     60
```

| | |
|---|---|
| ctgggcgtag cgagcgggca tggcagcatg gaggatccca tcagtcgcgt gtatgggtgc | 120 |
| tacctggaga atccggagag gcccacgtcg gcagcgtgca tcgcggcggt ggcgctcagt | 180 |
| ggcacccaag ccttctacga ctggaatgag gtgaatcagc cctttgcagc tggccgacac | 240 |
| cgcgagctca ttcctgacgg tcagctctgc agcggcgggc gggacaagta taaaggcctc | 300 |
| gacctggcgc gcgacgactg ggaggccacc tccttgtctt ctggcgccaa ctacagcttc | 360 |
| ctcttcaagg ccaccgcccc ccatcggggc tacttcgagt tctacgtcac ccaggatagc | 420 |
| tacgacccca ctgagccgct ggcctggggg gacctggaga gcacgccctt catcaatgtt | 480 |
| acggacccgg acctttcag cggctcctac cagatctcca gcaccacccc tcccggcaag | 540 |
| accggccgcc acctcatcta cgtcatctgg cagcgcaccg acagtcccga ggctttctac | 600 |
| tcctgctccg acgtcctttt cgacgaggcc gtcgctctct actctaccgc t | 651 |

<210> SEQ ID NO 75
<211> LENGTH: 645
<212> TYPE: DNA
<213> ORGANISM: Dryopteris marginalis

<400> SEQUENCE: 75

| | |
|---|---|
| atgggggaggt catggggagt tgtggctatt attatggtgt tgtgcggcag cggcctgctg | 60 |
| ggcgtagcga gcggccatgg cagcatgcag acccccatca gtcgcgtcta caactgctac | 120 |
| ctggagaatc cggagcgtcc cacgtcggca gcttgccaag cggcggtggc gctcagtggg | 180 |
| acccaagcgt tctatgattg aatgaggtg aaccagccct cgcggctgg ccggcaccgc | 240 |
| gaaatcattc cggatggcca actgtgcagc gccgggcggg agaagtatcg gggcctcgac | 300 |
| ctggcacgct ccgactgggt agccacctcc ttgtcctcgg gcgtcaacta cacataccctc | 360 |
| tacaaggcca ccgccccgca cttgggcttc ttcgagttct acgtcaccca ggatggttac | 420 |
| aattcctctg agccgctcaa atgggcagac ttggaggact cgccgttcat caacgtcacc | 480 |
| accacgcttg acagcgcctc ctaccaaatc cccggcacca cgcctgcggg caagaacggc | 540 |
| cgccacctca tctacgtcat tggcagcgc tccgacagcc ccgaggcctt ctactcctgc | 600 |
| tccgacgtcg acttcgccga tgccctctct ctccactcca ccacc | 645 |

<210> SEQ ID NO 76
<211> LENGTH: 648
<212> TYPE: DNA
<213> ORGANISM: Microsorum musifolium (Blume)

<400> SEQUENCE: 76

| | |
|---|---|
| atgagaaggt catggggagt tctggctatc gtgatggccg tgtgcgcaag cggcctgttt | 60 |
| ggcgtcgcga gtggccatgg ctctatggag caccccatta gtcgcgtcta tcaatgctac | 120 |
| cgcgagggtc cggaaaatcc caagtcgcca gcctgcatcg cggcaaaggg gcttagcggc | 180 |
| gctcaagcct tctacgattg aatgaagtg aatcagccct cgccgatgg ccgccaccag | 240 |
| gagatcatcc atgacggcca tctttgcagc ggcgggcgcg acaagtatag aggcctcgac | 300 |
| ctgccacgtg ccgactgggt ggctacctct tgtctgccg aaaaccccta cacattcctc | 360 |
| taccgggcca ccgccaccac cctgggctac ttcgagttct acgtcactcg gacggctac | 420 |
| gaccccacta agccgctcgc atgggcggac ttggaggact cgccgtttat caatgtcacc | 480 |
| aacccgaccc tcgtcagcgg cagctaccga attccacaca ccacgcccgc cagcaaaact | 540 |
| ggccggcacc tcatctacgt catttggcag cgcaccgaca gcttcgaggc tttctactcc | 600 |
| tgctccgacg tcgtctttga tgaggccctc tctctttcct ccaccatc | 648 |

<210> SEQ ID NO 77
<211> LENGTH: 648
<212> TYPE: DNA
<213> ORGANISM: Elaphoglossum sp.

<400> SEQUENCE: 77

| | | |
|---|---|---|
| atgcggagat catgggaagt tgtggctcta attatggtgg tgtgcgcctg cggcctgctg | 60 |
| ggcgtagcga gtggccatgg cagcatggag gaccccatca gtcgtgtcta caggtgctac | 120 |
| ctcgagggag tggagaatcc cacgtcggca gcctgcatag cggccattga ggtgagtggc | 180 |
| aagcaagcct tctacgactg gaatgaagtg aatcagccct tggccgctgg ccggcaccgc | 240 |
| gaaatcattc ctgacggcga gctgtgcagc ggcgggcggg agaagtataa aggcctcgac | 300 |
| ttggcacgcg ccgactggtt agccacctcc ttgtcttcgg gtgtcgacta cacattcctc | 360 |
| tacaaagcca ccgccgaaca caagggctac ttcgagttct acgtcactca ggatagttac | 420 |
| gaccccacgg agcctctcaa atggtcgac ctggaggaca cgcccttcat taacgtcacc | 480 |
| caacccttgc ttgtcagcgg ctcctaccaa attcccggca ccacgccttc cggcaaaacc | 540 |
| ggccgccacc tcatctacgt catctggcag cgcaccgata cgccgaagc cttctactcc | 600 |
| tgctccgatg tcaactttga cgacgccctc cctatctact ctgccacc | 648 |

<210> SEQ ID NO 78
<211> LENGTH: 645
<212> TYPE: DNA
<213> ORGANISM: Nephrolepis exaltata (Tiger Fern)

<400> SEQUENCE: 78

| | | |
|---|---|---|
| atggggaggt catggggagt tgcggctatt gtagtggcgg tgtgcgccag cggcctgttg | 60 |
| agcgtagtga gcggccatgg aagcatgcag gaccccatca gtcgcgtcta tgcatgctac | 120 |
| ctagagaatc cggagcgtcc cacgtcagca gcttgccagg cggcagtggc attgagtggg | 180 |
| acgcaagcct tctatgattg gaatgaggtg aacctgccca tgccgctgg ccggcaccgc | 240 |
| gaactcattc cggatggtca gttgtgcagt gctgggcggg ccaagtatca gggcctcgac | 300 |
| caggctcgca acgattggcc acacaccgac ttgatctccg gcgtcgcctt cacattcaac | 360 |
| tacagggcca ccgccccaca cttgggcatc ttcgagttct atgtcactcg ggatgggtac | 420 |
| gatgccaccc agccctcaa atgggcagat ctggaggact cgcctttcct caccgccacc | 480 |
| agcacgcttg cccctcctc ctaccagtgg cccggcacca ctcccagtgg caagtctggc | 540 |
| cgccacctca tctacgtcat ttggcagcgc accgacagcc cgaggccttc tactcctgc | 600 |
| tccgacgtcg agttcgtcga tgccgtctct ctccactcca ccacc | 645 |

<210> SEQ ID NO 79
<211> LENGTH: 642
<212> TYPE: DNA
<213> ORGANISM: Dryopteris lepidopoda

<400> SEQUENCE: 79

| | | |
|---|---|---|
| atggggaggt catggggagt tgtggctatt atggtgttgt gcggcagcgg cctgctgggc | 60 |
| gtggcgagcg gccatggcag catggaggac cccatcagtc gcgtctacaa ctgctacctg | 120 |
| gagaatccgg agcgtcccac gtcggcagct tgccaagcgg cggtggcgct gagtgggacc | 180 |
| caagcgttct atgattggaa tgaggtgaac cagcccttcg cggctggccg gcaccgcgaa | 240 |
| atcattccgg atggccaact gtgcagcggc gggcgggaga agtatcgggg cctggaccctg | 300 |

```
gcacgctccg actgggaagc cacctccttg tcctccggcg tcagctacac atacctctac    360
aaggccaccg ccccgcactt gggcttcttc gagttctacg tcacccagga tggttacaac    420
tcctctgagc cgctcgaatg ggcagacttg gaggactcac cgttcatcaa cgtcaccacc    480
acgcttgaca gcgcctccta ccaaatcccc ggtaccacgc ctgccggcaa gaccggccgc    540
cacctcatct acgtcatttg gcagcgctcc gacagccccg aggcattcta ctcctgctcc    600
gacgtcgact tcgtcgatgc cctctctctc cactccacca cc                       642
```

<210> SEQ ID NO 80
<211> LENGTH: 642
<212> TYPE: DNA
<213> ORGANISM: Polystichum lepidocaulon

<400> SEQUENCE: 80

```
atgggcaggt catggggagt tgtggctatt atggtgttgt ttgccagcgc tagcggcctg     60
ctgggcgtag cgaacggcca tggctccatg ggcaacccca tcagtcgcgt ctacaactgc    120
aggctggaga atccggagag acccacgtcg gcagcttgca tagcggcggt ggcgctgagt    180
ggcacctatg attggagtga ggtgaacctg cccaacgcca atggccggca ccgcgagctc    240
attccggatg gcaaactgtg cagcgccggg cgggacaagt ataagggcct cgacctggct    300
cgctccgact ggacagccac caacttgtcc tccggcgtcg cctacacatt cctctacagg    360
gtcaccgccg agcacagggg gttcttcgag ttctacgtca ccgtggatga ttacgaaccc    420
actgagctgc tcaaatggga agacttggag gaaacgccgt tcctcaacgt gagtgacccc    480
acggtcgtag gcaacaacta cgaaatctcc ggcaccacgc ctgccagcaa gactggccgc    540
cacctcatct acgtcatttg gcagcgctcc gacagccccg aggccttcta ctcctgctcc    600
gacgtcgact tcgtcgatac cctgtctctc cactccacca cc                       642
```

<210> SEQ ID NO 81
<211> LENGTH: 645
<212> TYPE: DNA
<213> ORGANISM: Polystichum acrostichoides

<400> SEQUENCE: 81

```
atggggaggt catggggagt tgtggctatt atggtgttgt gcgctagcgg cctgctgggt     60
gtagcgagcg gccatggcag catgaacgac cccatcagcc gcgtctacaa ctgccgtctg    120
gagaatccgg agagtcccac gtcagcagct tgcatagcgg cggtggcgct gagtgggacc    180
caagcgttct atgattggaa tgaggtgaac ctgcccgacg tcaatggccg gcaccgccag    240
ctcattccgg atggcaaatt gtgcagcgcc gggcgggaca agtataaggg cctcgacctg    300
gcacgctccg actgggtagc caccaacttg tcctccggcg tcgccttcac attcctctac    360
agggtcaccg cccagcacag gggcttcttc gagttctacg tcaccgtgga tgattacgac    420
cccactgagc tgctcaaatg ggaagacttg gaggaaacgc cgttcatgaa cgtcaccgac    480
cccacggttg taggcgtcaa ttacgaaatc cccggcacca cgcctgccaa taagaccggc    540
cgccatctca tctatgtcat ttggcagcgc tccgacagcc ccgaggcctt ctactcctgc    600
tccgacgttg acttcgtcga tgccgtgtct ctccactcca ccacc                    645
```

<210> SEQ ID NO 82
<211> LENGTH: 645
<212> TYPE: DNA
<213> ORGANISM: Davallia tyermannii

<400> SEQUENCE: 82

```
atggggaggt catggggagt tgtggctatt atggtgatgt acattggtgg cctgctaagc    60
atagcaagcg gccatggcag catggaggac cccatcagcc gcgtctatag gtgctacttg   120
gagaatccgg agagtcccac atcggcagct tgccaagcgg cagtggcagt gagtggggcc   180
caagccttct acgattggaa tgaggtgaac attgctgacg ccaatggccg acaccgggag   240
ctcatttctg atggccaact atgtagcgca aatcggagta agtatgcggg cctcgacctg   300
gcacgcgcag attggctagg caccaccttg tcctcgggcg cctccttcac atttgcctac   360
aaggccaccg cgccgcactt gggcttcttt gagttctacg tcacccggga tggttacgag   420
cccaccgacc cgctcaaatg gcagacttg gaggactcgc ccttcatcaa cgtcaccaac    480
cccacacttg ataatggcgc ctaccagatc tccggcacca cgcctgccgg taagtcgggg   540
cgtcatctga tctacgtcat ttggcagcgc tctgatagcc cagaggcatt ctattcgtgc   600
tccgacgtcg actttgtcga tgctctctct ctccactcta ccacc                   645

<210> SEQ ID NO 83
<211> LENGTH: 645
<212> TYPE: DNA
<213> ORGANISM: Polystichum polyblepharum (C.)

<400> SEQUENCE: 83
atggggaggt catggggagt tgtggctatt atggtgttgt gcgctagcgg cctgctcggc    60
gtagcgagcg gccatggcac catgaatgac cccatcagcc gcgtctacaa ctgccgcctg   120
gagaatccgg agagtcccac gtcagcagct tgcatagcgg cggtggcgct gagtgggacc   180
caagcgttct atgattggaa tgaggtgaac ctgcccaacg ccgctggcag gcaccgagag   240
ctcattccgg atggcaaact gtgcagcgcc gggcgggaca agtataaggg cctcgacctc   300
gcacgctccg actgggtagc caccaacttg tcctccggcg tcgccttcac attcctctac   360
agggtcaccg cccagcacag gggcttcttc gagttctacg tcaccgtgga tgattacgac   420
cccactgagc tgctcaaatg gaagacttg gaggaaacac cgttcatgaa tgtcaccgac    480
cccacggttg taggcgtcaa ctacgaaatg gccggcacca cgcctgccaa caagaccggc   540
cgccatctca tctatgtcat ttggcagcgc tccgacagcc ccgaggcctt ctactcctgc   600
tccgacgtcg acttcgtcga tgccgtgtct ctccactcca gcacc                   645

<210> SEQ ID NO 84
<211> LENGTH: 648
<212> TYPE: DNA
<213> ORGANISM: Lecanopteris sinuosa

<400> SEQUENCE: 84
atgatgaggt catggggagt tgcggcaatt atgatggccg tctgcgccag tggcctgctg    60
ggcgttgcaa gtgggcatgg cagcatggcg dacccatca gtcgggtgta caggtgccgc    120
ctcgagaatc ccgaaaggcc cacgtcgcca gcctgcattg cggcggtggc gcttagcggc   180
actcaagcct tctacgactg gaatgaagtg aatcttccct tcgctgctgg ccgccaccgc   240
cagctcatcc ccgacggaca actttgcagc gccgggcgga acaagtataa aggcctcgac   300
ctcgcacgcg ccgactggct agccaccttcc ctgtctcccg cgccaattca cattcctctc   360
taccgggcga ccgcccccca cgcgggctac tttgagttct acgtcactcg tgatagctac   420
gaccccactg agcagctcgc ttgggcggac ttggaagact cgccgttcat caccatcacc   480
aacccgaccc ttgtcaacgg ctactaccag attcccaaca ccgtccctgc cggcaaaact   540
```

| | |
|---|---|
| ggccgtcacc ttatctacgt catttggcaa cgcacagaca gtcccgaagc cttctactcc | 600 |
| tgctccgacg tcgactttga cgatgccctc cgtctccact actccacc | 648 |

<210> SEQ ID NO 85
<211> LENGTH: 645
<212> TYPE: DNA
<213> ORGANISM: Aglaomorpha splendens

<400> SEQUENCE: 85

| | |
|---|---|
| atgaggaggt catggggagt ggtggtgatt ttggtggtgt gcgtctgcgg cctgctgggc | 60 |
| gtggcgagtg ggcatggctc catgggggac cccatcagtc gcgtctatgg gtgccgcctt | 120 |
| gagaatccgg agagtcccac gtcggcagcc tgcatagcgg cggtggcggt gagtggcacc | 180 |
| caagccttct acgattggaa tgaggtgaat cagcccaacg ccaatggccg gcaccgcgag | 240 |
| atcattccag atggcgaact gtgcagcgcc gggcgggtaa aatatgcagg cctcgatctg | 300 |
| gcacgcgacg actgggtagc cacctccttg tcttctggcg tcaactacac attcctcttc | 360 |
| gtagccaccg cccccacttt gggctacttc gagttctacg tcactcagga tagctacgac | 420 |
| cccacccagc cgctcaaatg gtcggacttg gaggccaccc cgttcatcaa cgtcaccgat | 480 |
| cccacgcttc ttaacggctc ctaccaaatt cccagctcca cgcctccgg caaaaccggc | 540 |
| cgccacctca tctacgtcat ttggcagcgc actgacagcc ctgaggcctt ctactcctgc | 600 |
| tccgacgtcg actttgatgt ggccctccct ctttactcct ccacc | 645 |

<210> SEQ ID NO 86
<211> LENGTH: 645
<212> TYPE: DNA
<213> ORGANISM: Nephrolepis exaltata

<400> SEQUENCE: 86

| | |
|---|---|
| atggggaggt catggggagt tgcggctatt gtagtggcgg tgtgcgccag cggcctgttg | 60 |
| agcgtagtga gcggccatgg aagcatgcag gaccccatca gtcgcgtcta tgcatgctac | 120 |
| ctagagaatc cggagcgtcc cacgtcagca gcttgccagg cggcagtggc attgagtggg | 180 |
| acgcaagcct tctatgattg gaatgaggtg aacctgccca atgccgctgg ccggcaccgc | 240 |
| gaactcattc cggatggtca gttgtgcagt gctgggcggg ccaagtatca gggcctcgac | 300 |
| caggctcgca acgattggcc acacaccgac ttgatctccg gcgtcgcctt cacattcaac | 360 |
| tacagggcca ccgccccaca cttgggcatc ttcgagttct atgtcactcg ggatgggtac | 420 |
| gatgccaccc agcccctcaa atgggcagat ctggaggact cgcctttcct caccgccacc | 480 |
| agcacgcttg cccccctcctc ctaccagtgg cccggcacca ctcccagtgg caagtctggc | 540 |
| cgccacctca tctacgtcat ttggcagcgc accgacagcc ccgaggcctt ctactcctgc | 600 |
| tccgacgtcg agttcgtcga tgccgtctct ctccactcca ccacc | 645 |

<210> SEQ ID NO 87
<211> LENGTH: 645
<212> TYPE: DNA
<213> ORGANISM: Aglaomorpha splendens

<400> SEQUENCE: 87

| | |
|---|---|
| atgaggaggt catggggagt ggtggtgatt ttggtggtgt gcgtctgcgg cctgctgggc | 60 |
| gtggcgagtg ggcatggctc catgggggac cccatcagtc gcgtctatgg gtgccgcctt | 120 |
| gagaatccgg agagtcccac gtcggcagcc tgcatagcgg cggtggcggt gagtggcacc | 180 |
| caagccttct acgattggaa tgaggtgaat cagcccaacg ccaatggccg gcaccgcgag | 240 |

```
atcattccag atggcgaact gtgcagcgcc gggcgggtaa aatatgcagg cctcgatctg      300
gcacgcgacg actgggtagc cacctccttg tcttctggcg tcaactacac attcctcttc      360
gtagccaccg ccccccactt gggctacttc gagttctacg tcactcagga tagctacgac      420
cccacccagc cgctcaaatg gtcggacttg gaggccaccc cgttcatcaa cgtcaccgat      480
cccacgcttc ttaacggctc ctaccaaatt cccagctcca cgccctccgg caaaaccggc      540
cgccacctca tctacgtcat ttggcagcgc actgacagcc ctgaggcctt ctactcctgc      600
tccgacgtcg actttgatgt ggccctccct ctttactcct ccacc                      645
```

<210> SEQ ID NO 88
<211> LENGTH: 648
<212> TYPE: DNA
<213> ORGANISM: Polypodium formosanum

<400> SEQUENCE: 88

```
atgaagagat cgtggggagt tgctgctatt gtgatggccc tgagcacttg cggcttgata       60
ggcgtagcaa gtggccatgg ctccatggga daccccatca gtcgcgtcta taggtgctac      120
cgagagaatc cggagcgtcc cacgtcgcca gcctgcattg cggcggtggc gctgagtggc      180
aagcaagcct tctacgattg gaatgcggtg aatctgttca acgccaacgg tcgacaccgc      240
gagctcattc ctgacggcca gctctgcagt gccgggcggg ccaagtataa aggccttgac      300
ctcccacgcg ccgattggct agccacctcc ttatcctccg gcgtcaactt cacattcctc      360
tacagggtca ccgcccgcca cctgggctat ttcgagttct acgtcactcg cgatggctac      420
gaccccagtg aaccgctcgc atgggcggac ttggaggact cgccgttcat caaaatcacc      480
aacccatccg ttgtcagcaa ctcctatgta attcccggca tcacgcctgc cggcaaaact      540
ggccgccacc ttatttacgt catttggcag cgcaccgaca gccaggaggc cttctactcc      600
tgctccgaca tcgactttga cgaggccgtc cctctctact ccaccacc                   648
```

<210> SEQ ID NO 89
<211> LENGTH: 642
<212> TYPE: DNA
<213> ORGANISM: Nephrolepis obliterata (Sunjest)

<400> SEQUENCE: 89

```
atggggaggt catggggagt tgtggctatt atggtggtgt gcgcttgcgg cctattgagc       60
gtagtgaggg gccatggaag catggaggac cccattagtc gcgtctatgg gtgctaccta      120
gagaatccag agagtcccaa gtcagcagct tgccaagcgg cagtggcatt gagtgggacc      180
caagcgttct atgattggaa tgaggtgaac ttgcccgatg ttgctggccg gcaccgcgca      240
gtcattccgg atggccaatt gtgcagtgct gggcgggcta agtatcaggg cctcaacttg      300
gctcgcgccg attggccagc cacctccttg acctcaggcg tgtccttcac atacctctac      360
aaggtcaccg caaacacttt gggcttcttt gagttctatg tcactcaaga tggttacgat      420
cccaccgaac cgctcaaatg ggcagacttg gaggacttgc ctttcatgaa cgtcaccagc      480
acgtttgacg atgagtccta ccaaatgtct ggcaccactc ctagtggcaa ggctggccgc      540
cacctcatct acgtcatttg gcagcgcagc gacagccctg aggccttcta ctcctgctcc      600
gatgtcgact cgtcgatgc cgtctctctc cgctccacca cc                         642
```

<210> SEQ ID NO 90
<211> LENGTH: 645
<212> TYPE: DNA

<213> ORGANISM: Deparia acrostichoides

<400> SEQUENCE: 90

```
atggggaggt catggggagt tgtggctatt atggtgttgt gcgccagcgg tctgctgggc    60
gtagcgagcg gccatggcag catggagggc cccatcagtc gcgtcctcaa ctgctacctg   120
gagaatccgg agagacccac gtcgggagct tgcatagcgg cggtggcgct gggtgggaca   180
caaccgtttt atgattggaa tgaggtgaac ctggccgatg ccgatggccg gcaccgcgag   240
ctcattccgg atggccaact gtgcagcgcc ggacgggaga agtttaaggg cctcgacctg   300
gcacgctccg actggccagc cacctccttg tcctccggcg tcgccttcac atacctctac   360
aaggccaccg ccccacacgc tggcttcttc gagttctacg tcacccggga tggttacaag   420
cccactgagc cgctcaaatg gcagacttga ggagccac cgttcatcaa cgtcaccgac    480
cccaagcttg tcagcggctc ctaccaaatc cccggcacca cgcctgccgg caaggctggc   540
cgccacctca tctacgtcat ttggcagcgc tccgacagcc ccgaggcctt ctactcctgc   600
tccgacgtcg acttcgtcga agccctctct ctccactcca ccacc                   645
```

<210> SEQ ID NO 91
<211> LENGTH: 648
<212> TYPE: DNA
<213> ORGANISM: Aglaomorpha sp. (Roberts)

<400> SEQUENCE: 91

```
atgaggaggt catggccggg agtggtggcg attatggtgg tgtgtgccctg cggcctgctg    60
ggcgtggcga gtggccatgg ctccatgcag gaccccatca gtcgggtcta taggtgccgc   120
cttgagaatc cggagcggcc cacgtcggca gcctgcatag cggcggtggc gctgagtggc   180
acccaagcct tctacgactg gaatgaggtg aatcagccct cgccaatgg ccgccaccgc    240
gagatcattc cggacggcca actgtgcagc gccgggcggg caaagtatag aggcctcgac   300
ctggcacgcg ccgactggct agcccccctcc ttgtcttctg gcgtcgacta cacatttctc   360
tacatagcca ctgccccca tttgggctac ttcgagttct acatcactcg ggatagctac   420
gaccccaccg agccgctcaa atggtcggac ttggaggact ctccgttcat caacgtcacc   480
aacccctcgc ttgtcagcgg ctcctaccaa attcccggca ccacgccctc aacaaaacc    540
ggccgccacc tcatgtacgt catttggcag cgcaccgaca gccccgaggc cttctacgcc   600
tgctctgacg tcgactttga tgtggccctc cctctctact ccaccact                648
```

<210> SEQ ID NO 92
<211> LENGTH: 642
<212> TYPE: DNA
<213> ORGANISM: Nephrolepis obliterata

<400> SEQUENCE: 92

```
atggggaggt catggggagt tgtggctatt atggtggtgt gcgcttgcgg cctattgagc    60
gtagtgaggg gccatggaag catggaggac cccattagtc gcgtctatgg gtgctaccta   120
gagaatccag agagtcccaa gtcagcagct tgccaagcgg cagtggcatt gagtgggacc   180
caagcgttct atgattggaa tgaggtgaac ttgcccgatg ttgctggccg gcaccgcgca   240
gtcattccgg atggccaatt gtgcagtgct gggcgggcta agtatcaggg cctcaacttg   300
gctcgcgccg attggccagc cacctccttg acctcaggcg tgtccttcac atacctctac   360
aaggtcaccg caaacacttg ggcttcttt gagttctatg tcactcaaga tggttacgat   420
cccaccgaac cgctcaaatg gcagacttga ggacttgc ctttcatgaa cgtcaccagc     480
```

| acgtttgacg atgagtccta ccaaatgtct ggcaccactc ctagtggcaa ggctggccgc | 540 |
| cacctcatct acgtcatttg gcagcgcagc gacagccctg aggccttcta ctcctgctcc | 600 |
| gatgtcgact cgtcgatgc cgtctctctc cgctccacca cc | 642 |

<210> SEQ ID NO 93
<211> LENGTH: 645
<212> TYPE: DNA
<213> ORGANISM: Polypodium attenuatum (Falax)

<400> SEQUENCE: 93

| atggggaagg gatgggaagt tgtgggtata atggtggtgt gcgcctgcgg cctgctgggc | 60 |
| gtggccagtg ggcatggcac catggaggac cccatcagtc gcgtctacag gtgccgcctt | 120 |
| gagaatccgg agcgacccac gtcgccagcc tgcatagcgg cggtggcgct gagcggcact | 180 |
| caagccttct acgattggaa tgaggtgaat ctgcccttcg ccgccggccg gcaccgcgag | 240 |
| atcattcccg acggccagct gtgcagcgcc gggcgcgcca agtataggg gctggatctg | 300 |
| gcacgcgatg actggctagc cacctccttg tcttccggcg tcgactacac attcgtctac | 360 |
| agagtcaccg cgccccaccg tggctacttc gagttctacg tcactcggga cacctacgac | 420 |
| cccactgagc ccctcaaatg gtcggacttg gaggagcccc ccttcatcaa cgttacccaa | 480 |
| ccctcgcttg tcagcggctc ctaccagatt cccggcgcca cgcctaccgg taagaccggc | 540 |
| cgccacctca tctacgtcat ctggcagcgc actgacagcc ccgaagcctt ttactcctgt | 600 |
| tccgacgtcg actttggcga ggctctccgt ctcgacgcca ccgcc | 645 |

<210> SEQ ID NO 94
<211> LENGTH: 645
<212> TYPE: DNA
<213> ORGANISM: Arachniodes simplicior (variegata)

<400> SEQUENCE: 94

| atggggaggt catggggagt tgtggctatt atagtgttgt gcgccagcgg cctgctgggc | 60 |
| gtagcgagcg gccatggcag catggaggac cccatcagtc gcgtctacaa ctgcttcctg | 120 |
| gagggtccgg agaatcccac gtcggacgct tgcatagcag ctgtggcgct gagtgggacc | 180 |
| caagcgttct atgattggac ggaggtgaac ctggccgacg ccgatggcca tcaccgcgag | 240 |
| ctcattccgg atggccaact gtgcagcgcc gggcgggaca agtacaaggg cctcgacctc | 300 |
| gcacgctccg actggacagc cacgtcattg tcctccggcg tcgactacac attcctcttc | 360 |
| aaggccaccg ccccgcactt gggctccttc gagttctacg tcactgtgga tggttacgag | 420 |
| cccactgagc cgctcaaatg ggcagacttg gaggcaacgc cattcatcaa cgtcaccgac | 480 |
| cccacgcttg acagcggctc ctaccaaatc cctggtacca cacctgccgg caagaccggc | 540 |
| cgccacctca tctacgtgat ttggcagcgc tccgacagtg ccgaggcctt ctactcctgc | 600 |
| tccgacgtcg acttcactga tgccctctct ctccactcca ccacc | 645 |

<210> SEQ ID NO 95
<211> LENGTH: 648
<212> TYPE: DNA
<213> ORGANISM: Campyloneurum angustifolium

<400> SEQUENCE: 95

| atgaggaggt catgggaggt tgtggggatg atggtgctgt gcgcctgcgg cctgctgggt | 60 |
| gtagcgagcg gccatggcag catggaggac cccatcagtc gcgtctatag gtgccgcctt | 120 |

```
gagggtccgg agaggccaac gtcgccggcc tgcatagcgg cggtggcggt gaatggcact    180
caggccttct acgactggaa tgaggtgaat cagcccttcg ccgctgggcg gcaccgtgag    240
atcattcccg acggccagct ctgcagcgcc gggcgggaca agtataaagg gttggacctg    300
gcgcgcgccg actggctagc cgtctccttg tcttccggcg ccgactacac attcctctac    360
ctagccaccg ccacccacag gggctacttc gagttctacg tcactcggga tagctacgat    420
cccactgagc cgctcaaatg gtcggacttg gaggactccc cgttcatcaa cgtcacggat    480
cccacagaag tcggccccgt gtaccaaatt cccggcacca cgcctgccgg caaaactggc    540
cgccacctca tctacgtcat ttggcagcgc accgacagcc ccgaagcctt ctactcctgc    600
tccgacgtcg actttggcga gtctctctcc ctctactccg tcaccgag                 648
```

<210> SEQ ID NO 96
<211> LENGTH: 645
<212> TYPE: DNA
<213> ORGANISM: Colysis wrightii (Ching)

<400> SEQUENCE: 96

```
atgaggaagt cattggaagt tgtggctatt atggtggccg tgtgcgccag cggcctactg     60
ggcgtcgcga gtggccatgg caccatgctg gaccccatca gtcgcgtcta taggtgctac    120
ctcgagaatc cggagcgtcc cacgtcccca gcctgcatcg cggcggtggc gctcagcggc    180
aaacaagcct tctacgattg gaatgaagtg aatctgccct tcgcggctgg ccgtcaccgc    240
gagctcatcc ctgacggcca actttgcagc gctgggcggg acaagtataa aggcctcgat    300
caggcacgtg acgactggct ggctacctcc ttgccttccg cgccaactac atattccgc    360 tttgaggtca ccgccgtcca ccgtggctac ttcgagtttt acgtcactcg cgatggttac    420
gaccccactc agccgctcgc atgggcggac ttggaggact cgccgttcct cactaccacc    480
acgaccctcg acagcagctc ctacataatt ccaggcacca cgcccgctgg caaaaccggc    540
cgccacctca tctacctcat ttggcagcgc accgacagcc ctgaggcctt ctactcctgc    600
tccgacgtcg actttgagga ggccatctct ctttcctcca ccacc                    645
```

<210> SEQ ID NO 97
<211> LENGTH: 645
<212> TYPE: DNA
<213> ORGANISM: Colysis wrightii (Ching)

<400> SEQUENCE: 97

```
atggggaggt catgggtagt tgtggctatt atggtcaccg tgtgcgccag cggcctgctg     60
ggcttcgcca gtggccatgg cagcatgggg gaccccatca gtcgagtact taggtgccgc    120
gaagagaatc cggagaatcc cacgtcgcca gcctgcatcg cggcggtggc gctcagcggc    180
aaacaagcct tctacgattg gaatgaagtg aatctgccct tcgcggctgg ccgtcaccgc    240
gagctcatcc ctgacggcca actttgcagc gctgggcggg ccaagtataa aggcctcgat    300
ctggcacgtg acgactggct ggctaccccc ttgccttccg cgccgccta cacattccgc    360 tatcgggtca ccgccgccca ccgtggctac ttcgagttct acgtcactcg ggatggttac    420
gaccccactc agccgctcgc atgggcggac ttggaggact cgccgttcct cactaccacc    480
acgaccctcg acagcagctc ctacataatt ccaggcacca cgcccgctgg caaaaccggc    540
cgccacctca tctacctcat ttggcagcgc accgacagcc ctgaggcctt ctactcctgc    600
tccgacgtcg actttgagga ggccatctct ctttcctcca ccacc                    645
```

<210> SEQ ID NO 98
<211> LENGTH: 648
<212> TYPE: DNA
<213> ORGANISM: Platycerium elephantotis

<400> SEQUENCE: 98

| | | | | | |
|---|---|---|---|---|---|
| atgaggaggt | catgggggt | tgtggctgtt | atgttggcga | tctgcgccag | cggcctgctg | 60 |
| ggcgtagcga | gcggccatgg | cagcatgctg | gatcccatca | gtcgcgtgta | tacgtgctat | 120 |
| ttggagaatc | cggagaggcc | cacgtcggca | gcgtgcatcg | cggcggtggc | ggtcagtggc | 180 |
| tcccaagcgt | tctacgattg | gaatgaggtg | aatctggccg | atgcagatgg | ccagcaccgc | 240 |
| cagctcattc | ctgacggcaa | gctctgcagc | gccgggcggg | aaaagtacag | aggcctcgac | 300 |
| ctcgcacgcg | atgattggcc | tgccacctcc | ttgtcttctg | gagtcaatta | caccttcctc | 360 |
| tacagggcca | ccgcccccca | cctgggcttc | ttcgagttct | acgtcacccg | tgatagctac | 420 |
| gaccccactc | agccctggc | ctgggcggac | ctggaagacc | cccctttat | caacatcacc | 480 |
| gacccaaccc | ttgccagcgg | ctcctaccag | attgttaaca | ccacgccttc | caacaagacc | 540 |
| ggccgccacc | tcatctacgt | catctggcag | cgtactgaca | gccccgaggc | cttctactcc | 600 |
| tgctccgacg | tcgacttcga | cgaagatgac | tctcttctct | ccgcagtt | | 648 |

<210> SEQ ID NO 99
<211> LENGTH: 645
<212> TYPE: DNA
<213> ORGANISM: Platycerium madagascariense

<400> SEQUENCE: 99

| | | | | | |
|---|---|---|---|---|---|
| atgaggaggt | cgtgggggt | tgtggctgtt | atcttggcaa | tgtgcgccgg | tagcctgctc | 60 |
| ggcgtagcaa | gcggccatgg | tagcatggag | gatcccatca | gtcgcgtgta | tgcgtgcttc | 120 |
| ctggagaatc | cggagagacc | cacgtcggca | gcatgcatcg | cggcggtggc | gctgagtggc | 180 |
| acccaagcct | tctacgactg | gaatgaggtg | aatcagccca | atgccgctgg | caaccacaca | 240 |
| atcattcccg | acgccagct | ctgcagtgcc | gggcgggaga | agtacaaagg | cctcgacctc | 300 |
| ccacgcgccg | actggtctgc | catctccttg | tcttccggcg | taaactacac | cttcctttac | 360 |
| aaggctaccg | cccccaccg | gggctactt | gagttctacg | tcacccgtga | tagctacgac | 420 |
| cccactgagc | cccttgcctg | ggcggacctg | aagacaccc | ccttcatcaa | catcaccgac | 480 |
| ccagaccttg | tcagcggctc | ctaccggatt | gctaacacca | cccttccgg | caagaccggc | 540 |
| cgccacctca | tctacgtcat | ttggcagcgt | accgacagcc | ccgaggcctt | ctactcctgc | 600 |
| tccgacgtcg | tcttcgacga | ggatgtctct | ctcgtctccg | cagct | | 645 |

<210> SEQ ID NO 100
<211> LENGTH: 648
<212> TYPE: DNA
<213> ORGANISM: Microsorum musifolium (Blume)

<400> SEQUENCE: 100

| | | | | | |
|---|---|---|---|---|---|
| atgagaaggt | catgggagt | tctggctatc | gtggtggccg | tgtgcgcaag | cggcctgttt | 60 |
| ggcgtcgcga | gtggccatgg | ctctatggag | cacccccatta | gtcgcgtcta | tcaatgctac | 120 |
| cgcgagggtc | cggaaaatcc | caagtcgcca | gcctgcatcg | cggcaaaggg | gcttagcggc | 180 |
| gctcaagcct | tctacgattg | gaatgaagtg | aatcagccct | cgccgatgg | ccgccaccag | 240 |
| gagatcatcc | atgacggcca | tctttgcagc | ggcgggcgcg | acaagtatag | aggcctcgac | 300 |
| ctgccacgtg | ccgactgggt | ggctacctct | ttgtctgccg | gaaaacccta | cacattcctc | 360 |

```
taccgtgcca ccgcccccca cttgggctac ttccagtttt acgtcactcg cgacggctac    420
aaccccacta agccgctcgc atgggcgac ttggaggact cgccgtttat caatgtcacc     480
aacccgaccc tcgtcagcgg cagctaccga attccacaca ccacgcccgc cagcaaaact    540
ggccggcacc tcatctacgt catttggcag cgcaccgaca gccccgaagc cttctactcc    600
tgctcggacg tcgtctttga tgaagccctc tctctctcct ccaccatc                648
```

<210> SEQ ID NO 101
<211> LENGTH: 657
<212> TYPE: DNA
<213> ORGANISM: Lygodium flexuosum

<400> SEQUENCE: 101

```
atggggagct ggcagtgggg atcagtgaat gtggccattg ttgtttttat gatgttgtgc    60
ggcgtagcga gcggccatgg caccatgggg gaccccatca gtcgcgtcta caggtgctac   120
cttgagaatc cggagaggcc cacgtcggca gcttgccaag cggcggtggc gctgagtggg   180
acccaagcct tctacgactg gaatgaggta aacctgccca cgccgctgg ccggcaccgc     240 cagctcattc cggatggcca actgtgcagc gccgggcggg ccaagtatca gggcctcgac    300
ctggcacgcg ccgactggct agccgccagc ctgtcctccg gcgtctccta cacattcctc    360
tacagggtca ccgcccagca ccgtggcttc ttcgagttct acgtcacccg ggatggttac    420
gagcccactg agccgctcaa atggtcagac ttggaggagt cgccgttcat caacgtcacc    480
gaccccacgg ctgtcagcgg ctcctaccag atccccggca ccacgcctgc cggcaagtcc    540
ggccgccacc tcatctacgt catttggcag cgctccgaca gccccgaggc cttctactcc    600
tgctccgacg tcgacttcga cgtcgagggc gccgccgtct ctctccgctc taccacc      657
```

<210> SEQ ID NO 102
<211> LENGTH: 645
<212> TYPE: DNA
<213> ORGANISM: Polystichum polyblepharum

<400> SEQUENCE: 102

```
atgaacaggt catggggagt tgtggctatt atggtgctgt gcgctagcgg cctgctcggc    60
gtagcgagcg gccatggcac catgaatgac cccatcagcc gtgtctacaa ctgccgcctg   120
gagaatccgg agagtccac gtcagcagct tgcatagcgg cggtggcgct gagtgggacc     180
caagcgttct atgattggaa tgaggtgaac ctggccaacg tcgctggccg gcaccgcgag    240
ctcattccgg atggcaaact gtgcagcgcc gggcgggaca gtataagggg cctcgacctc    300
gcacgctccg actgggtagc caccaacttg tcctccggcg tcgccttcac attcctctac    360
agggtcaccg cccagcacag gggcttcttc gagttctacg tcaccgtgga tgattacgac    420
cccactgagc tgctcaaatg gaagacttg gaggaaacgc cgttcatgaa tgtcaccgac     480 ccacgcttg taggcctcaa ctacgaaatg cccggcacca cgcctgccaa caagaccggc    540
cgccatctca tctatgtcat ttggcagcgc tccgacagcc ccgaggcctt ctactcctgc    600
tccgacgtcg acttcgtcga tgccgtgtct ctccactcca gcacc                   645
```

<210> SEQ ID NO 103
<211> LENGTH: 654
<212> TYPE: DNA
<213> ORGANISM: Diplazium pycnocarpon

<400> SEQUENCE: 103

```
atggggaagt catggggagt tgtggctatt atattggtgt tgtgcgccag cggcctgctg    60
```

-continued

```
ggtgtagcga gcggccatgg cagcatggcg acccccatca gtcgcattta caactgcaga    120
caggagaatc cggagcgtcc cacgtcggca gcttgccaag cggcagtggc gctgagtgga    180
acccaagcgt tctatgattg gaatgaggtg aaccagccca acgccgctgg ccggcaccgc    240
gagatcattc cggatggcca actgtgcagc gccgggcggt acaagtatcg gggcctcgac    300
ctggcaagcg ccgactggca gtggcctgcc acctccttgt cctccggcgt ctccttcaca    360
taccgctaca gggccaccgc cgcgcactac ggctacttcc agttctatat cacccgggat    420
ggttaccagc ccactcagcc gctcaaatgg gcagacttgg agcagctgcc attccttacc    480
gtctacaacc ccacgcttgt caacggcttc tacgaaatgc aggggaccac gcctgctggc    540
aagaccggcc gccacctcat ctatgtcatc tggcagcgct ccgacagccc cgaggccttc    600
tactcctgct ccgacgtcga cttcgtgggt gccctctctc tccattccac cacc          654
```

<210> SEQ ID NO 104
<211> LENGTH: 648
<212> TYPE: DNA
<213> ORGANISM: Polystichum braunii

<400> SEQUENCE: 104

```
atggggaggt catggggagt tgtggctatt atggtgttgt gtgctagcgg cctgctgggc    60
gcagcgagcg gccatggcac catgtacgac ccattcagcc gcgtctacaa ctgccgcttc    120
cgggagaatc cggagcgtcc cacgtcagca gcttgcatag cggcggtggc gttgagtggg    180
acccaagcgt tctatgattg gaatgaggtg aacctggcca acgccgctgg ccggcaccgc    240
gagctcattc cggatggcaa actgtgcagc gccgggcggg acaagtataa gggcctcgac    300
ctggcacgct ccgactgggt agccaccaac ttgtcctccg gcgtcgcctt cacattcctc    360
tacagggtca ccgcccagca caggggcttc ttcgagttct acgtcaccgt ggatgattac    420 gacccccactg agtcgctcaa atgggaagac ttggaggaaa cgccgttcct caacgtcacc    480
gaccccacgg ttgtaggcgt caactaccaa atctccggca ccacgcctgc cagcaagacc    540
ggccgccacc tcatctacgt tatatggcag cgctccgata gccctgaggc cttctactcc    600
tgctccgacg tcgacttcgt cgatgccctg tctctccaat ccaccacc                 648
```

<210> SEQ ID NO 105
<211> LENGTH: 645
<212> TYPE: DNA
<213> ORGANISM: Platycerium hillii

<400> SEQUENCE: 105

```
atggggaagc cgtggagagt ggtggtggcc attgtggtgg tgtgcgccag cggcctgctg    60
ggcgtagcga gcggccatgg cagcatgggt gaacccatca gtcgcgtcta taattgctac    120
ctggagaatc cggagagacc cacgtcggca gcgtgcatcg cggcggtggc gcttagtggc    180
acccaagcct tctacgactg gaatgaggtg aacctgccct cgccgctgg ccggcaccgc    240 gagctcattc ctgacggcca gctctgcagc gccgggcggg acaagtataa aggcctggac    300
ctggcacgcg ccgactgggt tgccacctcc ttgtcttcgg cgtcagcta caccttcctc    360 tacagggtta ccgcccccca ccggggctac tttgagttct acgtcaccaa ggatagctac    420
gaccccactg agccgctggc ctgggcagac ctggaggaca cgcccttcat taacatcacc    480
gacccgacca ttgtcagcgg ctcttaccag atctccagca ccacgccttc cgacaagacc    540
ggccgccacc tcatctacgt catttggcag cgcaccgaca gccctgaggc cttctactcc    600
```

```
tgctccgata tcgactttga cgacaccctc ccctacact ccacc            645
```

```
<210> SEQ ID NO 106
<211> LENGTH: 681
<212> TYPE: DNA
<213> ORGANISM: Drynaria rigidula (whitei)

<400> SEQUENCE: 106
atggggagga cgtactcatg gggggctgtg gctgttatgg tggtgctgtg cgccagcggc    60
ctgctgggca tagcgagcgg ccatggcagc atggacagcc catcagtcg cgtctaccgg   120
tgctatctag agaatccgga gaatcccacg tcggcagcct gccaagcggc ggtggcgctg   180
agtgggaccc aagccttcta cgactggaat gaggtgaaca tcgccgacgc tgcgggccgc   240
caccgcgagc tcattccgga tggccaactg tgcagcgccg gcgggaaaa gtatcaaggt   300
ctcgacctgg cacgcgccga ctggctagcc gactccttgt cctccggcgt ctccttcact   360
ttcctctaca aggctactgc cgcgcacttg ggcttcttcg agttctacgt cacccgggat   420
gcctacgacc ccactgagcc gctcaaatgg gcagacctgg aggactcgcc cttcctcaac   480
gtcaccgacc ccacgcttgt cagcggctac taccagatcc ctggcaccac gcctgccggc   540
aagtccggcc gccacctcct ctacgtcatc tggcagcgct ccgacagccc cgaggccttc   600
tactcctgct ccgacgtcga ctttgacgac gatgccgctg ccgcccagca catgataatc   660
tctctccgcc actccaccac c                                             681
```

```
<210> SEQ ID NO 107
<211> LENGTH: 687
<212> TYPE: DNA
<213> ORGANISM: Adiantum monocolor

<400> SEQUENCE: 107
atggggatga agatgtcatg ggaagttgca ctagcagaaa tagtagcttt gtgcctactg    60
ggcatggcaa gcagccatgg caccatgcag gaccccataa gtcgtgtcta caactgcttt   120
ctggagaacc cggagaggcc aacgtcggca gcttgtcaag ctgcagtagc gttgggtggc   180
acacaaccac tctatgattg aatgaggtg aacatccatg atgccgctgg caaccaccgc   240
gatctcatcc ccgatggcaa gctctgcagc gccggccgcc aaaagtttca gggcctcgac   300
ttggcgcgcg cggattggat agcaacctcc ctatcctctg cgtcgactac acattcctc   360
taccgcgcca ccgccccgca cttgggcttc tttgaatttt acatcacccg tgacacctac   420
gaccccaccc agccgctcgc atggggtgac ctggaagact cgcccttcat caacattacc   480
aatccctcca tcgtcagtac gactttgggt cccgcctact cgatcccag cactacacca   540
ttcagcaaaa gtggtcgcca cctcatctac gtcatctggc agcgcaccga cagcctcgag   600
gcgttctact cctgctccga cgtcgacttc tcgacatctt ccatcgagga tgatgtcatc   660
gtctctctcc gttctgcagc tctactc                                       687
```

```
<210> SEQ ID NO 108
<211> LENGTH: 669
<212> TYPE: DNA
<213> ORGANISM: Pellaea rotundifolia

<400> SEQUENCE: 108
atgcagaggt catgcatgtg gggggaatcc gtagtggcta ttatgtgcat ggtgttgggc    60
cttctgggcg acgtagcgag cggccatggc agcatggcca gcccatcag tcgcgtcttc   120
aactgctacc tcgagaatcc agagagtccc acctcggaag cttgcaaagc ggctgtggag   180
```

```
gagagtggca cccaagcttt ctatgattgg gctgaggtga gcctgcccaa cgccgctgga    240
cgccaccgcg agctcattcc ggatggccaa ctctgcagcg ccgggctggc caagtatgcg    300
ggcctcgacc tggcgcgcgc cgactggaca gccacctcct tgacctccaa catctcctac    360
acgttcatct tcgaggccac cgccggcccg cacttgggct ccttcgagtt ctacgtcacc    420
aatgatgatt acgagcccgc tgaggcgctc aactgggcag acttggagga cactccgttc    480
atcatcgtca ccaaccccac gcttgtgagc ggctcctacc tcatcccggg cactacgcct    540
gccggcaaga ccggccgcca catcatctac gtcatttggc agcgctccga cagccccgag    600
gctttctact cctgctccga catcgacttc gtggaggagg atcccgtggt ccctctccac    660
tctaccacc                                                            669
```

<210> SEQ ID NO 109
<211> LENGTH: 645
<212> TYPE: DNA
<213> ORGANISM: Platycerium bifurcatum

<400> SEQUENCE: 109

```
atggggaagc cgtggagagt ggtggtggcc attgtggtgg tgtgcgccag cggcctgctg     60
ggcgtagcga gcggccatgg cagcatgggt gaacccatca gtcgcgtcta taattgctac    120
ctggagaatc cggagagacc cacgtcggca gcgtgcatcg cggcggtggc gcttagtggc    180
acccaagcct tctacgactg gaatgaggtg aacctgccct cgccgctgg ccggcaccgc    240 gagctcattc ctgacggcca gctctgcagc gccgggcggg acaagtataa aggcctggac    300
ctggcacgcg ccgactgggt tgccacctcc ctgtcttcgg gcgtcagcta caccttcctc    360
tacagggcca ccgccccccca ccagggctac tttgagttct acgtcaccaa ggatagctac    420
gaccccactg agccgctggc ctgggcggac ctggaggaca cgcccttcat taacatcacc    480
gatccgaccc ttgtcagcgg ctcttaccag atccccagca ccacgccttc cgacaagacc    540
ggccgccacc tcatctacgt catttggcag cgcaccgaca gccctgaggc cttctactcc    600
tgctccgata tcgactttga cgacaccctc cccctacact ccacc                    645
```

<210> SEQ ID NO 110
<211> LENGTH: 648
<212> TYPE: DNA
<213> ORGANISM: Microsorum punctatum

<400> SEQUENCE: 110

```
atgaggaggt catggggagt tctggctatt gtggtggccg tgtgcgcaag cggcctgttt     60
ggcgtcgcga gtggtcatgg ctccatggag gaccccatta gtcgcgtcta tcaatgctac    120
gacgagggtc cggaaaatcc caagtcgcca gcctgcatcg cggcggtggg gcttagcggc    180
gctcaagcct tctacgattg gaatgaagtg aatcagccct cgccgctgg ccagcacaag    240 gagatcatcc atgacggcca tctttgcagc ggcgggcgcg acaagtatag aggcctcgac    300
ctgccacgtg ccgactgggt ggctacctct ttgtctgccg gcgcacccta cacattcctc    360
taccgcgcca ccgcccacca cctgggctac ttcgagttct acgtcactcg ggacggctac    420
gaccccacta agccgctcgc atgggcggac ttggaggact cgccgtttat caatgtcacc    480
aacccgcccc tcgtcagcgg cagctaccga attccagaca ccacgcccgc cctcaaaact    540
ggccggcacc tcatctacgt catttggcag cgcaccgaca gccccgaagc cttctactcc    600
tgctcggacg tcgtctttgc tgaggccctc tctctttcct ccaccacc                 648
```

<210> SEQ ID NO 111
<211> LENGTH: 651
<212> TYPE: DNA
<213> ORGANISM: Woodwardia fimbriata

<400> SEQUENCE: 111

```
atggggaggt caatatgggg agttgtggct atgatggtgt tgtgcgccag cggcctgctg      60
cgcatagcga gcgggcatgg cagcatggag aacccatca gtcgcgtcta caactgctat     120
ctggagggtc cggagaatcc caagtcggca gcttgcaaag cggcggtggc ggcgagtggg    180
acccaagcgt tctatgattg gaatgaggtg aacctggcca acgccgctgg ccgccaccgc    240
gagctcattc cggatggcca actgtgcagc gccgggcggc agaagtatca gggcctcgac    300
ctcgtacgct ccgactggcc agccacctcc ttgtcctccg cgtcccctt cacattcctc     360
tacaggatca ccgcccagca cttgggcttc ttcgagttct acgtcacccg cgatggttac    420
cagcccactg cggcgctcac ttgggcagac ttggaggact ccccgttcat gaacgtcacc    480
ggcgacccca cgtttatcac cggctcctgg gaaatccccg gcacctcgcc tgccggcaag    540
tctggccgcc accttatcta cgtcatctgg cagcgctccg acagccccga ggccttctac    600
gcctgctgcg acgtcgactt cgtcgacgcc ctctctctcc actccaccac t              651
```

<210> SEQ ID NO 112
<211> LENGTH: 639
<212> TYPE: DNA
<213> ORGANISM: Dryopteris celsa

<400> SEQUENCE: 112

```
atggggaggt catcattggg agttgtggct attatggtgt tgtgcctggt gggcgtagcg      60
agcggtcatg gcagcatgca ggaccccatc agtcgcgtct acaactgcta cctcgagaat    120
ccggagagtc ccacgtcggc agcttgccaa gcggcggtgg cgctgagtgg cacccaagcg    180
ttctatgact ggaatgaggt gaaccagccc gaagccgatg tcggtcccg cgaaatcatt    240
ccggatggcc aactgtgcag cggcgggcgg gagaagtatc agggcctgga cctggcgcgc    300
tccgactggg aagccaccac cttgtcctcc agcgtcaact acacattcct ctacaaggcc    360
acagccccgc acttgggctt cttcgagttc tacgtcaccc aggatggtta cgatcccact    420
gaggtgctca atgggcaga tctggaggac tcgccgttcc tcaacgtcac cgaccccacg    480
cttgacagcg gcgcctacca aatccccggc accacgcctg ccggtaagac cggccgccac    540
ctcatctacg tcatttggca gcgctccgac agccccgagg ccttctactc ctgctccgac    600
gtcgacttcc ccgatgccct ctctctccac tccaccacc                            639
```

<210> SEQ ID NO 113
<211> LENGTH: 648
<212> TYPE: DNA
<213> ORGANISM: Campyloneurum angustifolium

<400> SEQUENCE: 113

```
atgaggaggt catgggaggt tgtggggatg atggtgctgt gcgcctgcgg cctgctgggt      60
gtagcgagcg gccatggcag catggaggac cccatcagtc gcgtctatag gtgccgcctt    120
gagaatccgg agagacccac gtcaccagct tgcagagcgg cggtggcgtt gagtggcact    180
caggccttct acgactggaa tgaggtgaat cagcccttcg ccgctgggcg gcaccgtgag    240
atcattcccg acgccagct ctgcagcgcc gggcgggaca agtataaagg gttggacctg    300
gcgcgcgccg actggctagc cgtctccttg tcttccggcg ccgactacac attcctctac    360
```

```
ctagccaccg ccacccacag gggctacttc gagttctacg tcactcggga tagctacgat    420
cccactgagc cgctcaaatg gtcggacttg gaggactccc cgttcatcaa cgtcacggat    480
cccacagaag tcggccccgt gtaccaaatt cccggcacca cgcctgccgg caaaactggc    540
cgccacctca tctacgtcat ttggcagcgc accgacagcc ccgaagcctt ctactcctgc    600
tccgacgtcg actttggcga gtctctctcc ctctactccg tcaccgag                 648
```

<210> SEQ ID NO 114
<211> LENGTH: 654
<212> TYPE: DNA
<213> ORGANISM: Onoclea sensibilis

<400> SEQUENCE: 114

```
atggggaggt catggggagt ggtgcaggct ataattatgg tgttgtgcgg cagcggcctg     60
ctgggcgtag cgagcggcca tgcagcatg gaggacccca tcagtcgcgt ctacaactgc    120
tacctggaga atcccgagag tcccacgtcg gcagcttgcc aagcggcggt ggcgctgagt    180
ggggcccaag cgttctatga ttggaatgag gtgaacctgg ccgacgccgc tggccggcat    240
cgcgagctca ttccggatgg ccaactgtgc agcgccgggc gggagaagta tcagggcctc    300
gacctggcac gctccgactg gacagccact tccttgtcct ccggcgtctc cttcacatac    360
ctctacaagg ccaccgcccc gcacttgggc ttcttcgagt tctacgtcac caaggatggt    420
tacgagccca ctgagccgct caaatgggca gacttggagg actcgcccct catcaacgtc    480 accgaccca cgcttgtcag cggctcctac caaatcccg gcaccacgcc ttccggcaag    540
tccggccgcc acctcatcta cgtcatttgg cagcgctccg acagcccga ggccttctac    600 tcctgctccg acgtcgactt cgacgtcgat gccctctctc tccactccac cacc         654
```

<210> SEQ ID NO 115
<211> LENGTH: 705
<212> TYPE: DNA
<213> ORGANISM: Onoclea sensibilis

<400> SEQUENCE: 115

```
atggggaggt catggggagt ggtgcaggct ataattatgg tgttgtgcgg cagcggcctg     60
ctgggcgtag cgagcggcca tgcagcatg gaggacccca tcagtcgcgt ctacaactgc    120
tacctggaga atcccgagag tcccacgtcg gcagcttgcc aagcggcggt ggcgctgagt    180
ggggcccaag cgttctatga ttggaatgag gtgaacctgg ccgacgccgc tggccggcat    240
cgcgagctca ttccggatgg ccaactgtgc agcgccgggc gggagaagta tcagggcctc    300
gacctggcac gctccgactg gacagccact tccttgtcct ccggcgtctc cttcacatac    360
ctctacaagg ccaccgcccc gcacttgggc ttcttcgagt tctacgtcac caaggatggt    420
tacgagccca ctgagccgct caaatgggca gacttggagg actcgcccctt catcaacgtc    480 accgaccca cgcttgtcag cggctcctac caaatcccg gcaccacgcc ttccggcaag    540
tccggccgcc acctcatcta cgtcatttgg cagcgctccg acagcccga ggccttctac    600 tcctgctccg acgtcgactt cgacgtcgat gccctctctc tccactccac acctaatcta    660
gacttgtcat cttctggatt ggccaactta attaatgtat gtgta                    705
```

<210> SEQ ID NO 116
<211> LENGTH: 688
<212> TYPE: DNA
<213> ORGANISM: Onoclea sensibilis

<400> SEQUENCE: 116

```
atggggaggt catggggagt ggtgcaggct ataattatgg tgttgtgcgg cagcggcctg     60
ctgggcgtag cgagcggcca tggcagcatg gaggacccca tcagtcgcgt ctacaactgc    120
tacctggaga atcccgagag tcccacgtcg gcagcttgcc aagcggcggt ggcgctgagt    180
ggggcccaag cgttctatga ttggaatgag gtgaacctgg ccgacgccgc tggccggcat    240
cgcgagctca ttccggatgg ccaactgtgc agcgccgggc gggagaagta tcagggcctc    300
gacctggcac gctccgactg gacagccact tccttgtcct ccggcgtctc cttcacatac    360
ctctacaagg ccaccgcccc gcacttgggc ttcttcgagt tctacgtcac caaggatggt    420
tacgagccca ctgagccgct caaatgggca gacttggagg actcgccctt catcaacgtc    480
accgacccca cgcttgtcag cggctcctac caaatccccg gcaccacgcc ttccggcaag    540
tccggccgcc acctcatcta cgtcatttgg cagcgctccg acagcccga ggccttctac     600
tcctgctccg acgtcgactt cgacgtcgat gccctctctc tccactccac acctaatcta    660
gacttgtcca ttctggattg gccaactt                                       688
```

<210> SEQ ID NO 117
<211> LENGTH: 645
<212> TYPE: DNA
<213> ORGANISM: Polystichum tripteron

<400> SEQUENCE: 117

```
atgggcaggt catggggagt tgtggctatt atggtgttgt gcgccagcgg cctgctgggc     60
gtagcgagcg gccatggcac catgaacgac cccatcagtc gcgtctacgc ctgcaggcag    120
gagaatccgg agcgacccac tacgccggct tgcatagcgg cggtggcgct gagtggggcc    180
caagcgttct atgattggaa tgaggtgaac ctgccctttg tcaatggccg gcaccgccag    240
ttcattccgg atgggaaact ctgcagcgcc gggcggaaca agtatagggg tctcgacctg    300
gcacgctccg actggacagc cacaaacttg tcctccggcg tcgcctacac attcctctac    360
agggtcaccg cccagcacag gggcttcttc gagttctacg tcaccgtgga tggttacgac    420
cccactgagc cgctcaaatg gcagacttg gaggaaacgc cgttcatcaa cgtcaccgac     480
cccacagttg taggcctcaa ctatgtaatc cccggtacca cgcctgccag caagaccggc    540
cgccacctca tctacgtcat ttggcagcgc tccgacagcc ccgaggcctt ctactcctgc    600
tccgacgtca actttcccga tgccctgtct ctccactccg ccacc                    645
```

<210> SEQ ID NO 118
<211> LENGTH: 645
<212> TYPE: DNA
<213> ORGANISM: Polystichum tripteron

<400> SEQUENCE: 118

```
atgggcaggt catggggagt tgtggctatt atggtgttgt gcgccagcgg cctgctgggc     60
gtagcgagcg gccatggcac catgaacgac cccatcagtc gcgtctacgc ctgcaggcag    120
gagaatccgg agcgacccac tacgccggct tgcatagcgg cggtggcgct gagtggggcc    180
caagcgttct atgattggaa tgaggtgaac ctgccctttg tcaatggccg gcaccgccag    240
ttcattccgg atgggaaact ctgcagcgcc gggcggaaca agtatagggg tctcgacctg    300
gcacgctccg actggacagc cacaaacttg tcctccggcg tcgcctacac attcctctac    360
agggtcaccg cccagcacag gggcttcttc gagttctacg tcaccgtgga tggttacgac    420
cccactgagc cgctcaaatg gcagacttg gaggaaacgc cgttcatcaa cgtcaccgac     480
```

```
cccacagttg taggcctcaa ctatgtaatc tccggcacca cgcctgccag caagaccggc      540
cgccacctca tctacgtcat ttggcagcgt accgacagcc cgaggccttt ctactcctgc      600
tccgacgtca actttcccga tgccctgtct ctccactccg ccacc                      645
```

<210> SEQ ID NO 119
<211> LENGTH: 645
<212> TYPE: DNA
<213> ORGANISM: Polystichum tripteron

<400> SEQUENCE: 119

```
atgggcaggt catggggagt gtgtgctatt atgatgttgt gcgccagcgg cctgctgggc       60
gtagcgagcg gccatggcac catgaacgac cccatcagtc gcgtctacgc ctgcaggcag      120
gagaatccgg agcgacccac tacgccggct gcatagcgg cggtggcgct gagtgggggcc      180 caagcgttct atgattggaa tgaggtgaac ctgcccttTg tcaatggccg gcaccgccag      240
ttcattccgg atgggaaact ctgcagcgcc gggcggaaca agtatagggg tctcgacctg      300
gcacgctccg actggacagc cacaaacttg tcctccggcg tcgcctacac attcctctac      360
agggtcaccg cccagcacag gggcttcttc gagttctacg tcaccgtgga tggttacgac      420
cccactgagc cgctcaaatg gcagacttg gaggaaacgc cgttcatcaa cgtcaccgac      480
cccacagttg taggcctcaa ctatgtaatc cccggtacca cgcctgccag caagaccggc      540
cgccacctca tctacgtcat ttggcagcgc tccgacagcc cgaggccttt ctactcctgc      600
tccgacgtca actttcccga tgccctgtct ctccactccg ccacc                      645
```

<210> SEQ ID NO 120
<211> LENGTH: 645
<212> TYPE: DNA
<213> ORGANISM: Polystichum tripteron

<400> SEQUENCE: 120

```
atgggcaggt catggggagt gtgtggctatt atggtgttgt gcgccagcgg cctgctgggc      60
gtagcgagcg gccatggcac catgaacgac cccatcagtc gcgtctacgc ctgcaggcag      120
gagaatccgg agcgacccac tacgccggct gcatagcgg cggtggcgct gagtgggggcc      180 caagcgttct atgattggaa tgaggtgaac ctgcccttTg tcaatggccg gcaccgccag      240
ttcattccgg atgggaaact ctgcagcgcc gggcggaaca agtatagggg tctcgacctg      300
gcacgctccg actggacagc cacaaacttg tcctccggcg tcgcctacac attcctctac      360
agggtcaccg cccagcacag gggcttcttc gagttctacg tcaccgtgga tggttacgac      420
cccactgagc cgctcaaatg gcagacttg gaggaaacgc cgttcatcaa cgtcgccaac      480
cccacagttg taggcctcaa ctatgtaatc tccggcacca cgcctgccag caagaccggc      540
cgccacctca tctacgtcat ttggcagcgt accgacagcc cgaggccttt ctactcctgc      600
tccgacgtca acttcgtcga tgccctgtct ctccactccg ccacc                      645
```

<210> SEQ ID NO 121
<211> LENGTH: 651
<212> TYPE: DNA
<213> ORGANISM: Tectaria milnei

<400> SEQUENCE: 121

```
atggggaggt catggggagt ggtggctgtt atggtggtgt gcgcaagcgg cctattgagc       60
gtagtgaggg gccatggaag catggaggac cccatcagtc gtgtgtatgc atgcttccta      120
```

```
gagaatccgg agcgtcccat atcagcagct tgccaggcgg cagtggcaat gggtgggacg    180
caagccttct atgattggaa tgcggtaagc ctgccctatg ctgctgggcg gcaccgtgaa    240
ctcatcccgg atggccaatt gtgcagtgct gggcgggcca agtatcgggg cctggacctg    300
cctcgtgacg attggccagg cacctccaat atgacctccg cgtcgcctt cacatacagg      360 tacaaggcca ccgccccaca cttgggctcc ttccagttct atgtcactcg ggatggctac    420
gatcccaccg agccgctcaa atgggcagac ttggaggact cgcctttcat gaacgccacc    480
agcacgcttg ccccggactc ctacctaatg tccggcacca ccctagcgg caaggctggc     540 caccacctca tctacgccat ttggcagcgc agcgacagcc ctgaggcctt ctactcctgc    600
tccgatgtca ccttcgacgt cgctgctgtc tctgatctcc actccaccac c              651
```

<210> SEQ ID NO 122
<211> LENGTH: 651
<212> TYPE: DNA
<213> ORGANISM: Tectaria milnei

<400> SEQUENCE: 122

```
atggggaggt catggggagt ggtggctgtt atggtggtgt gcgcaagcgg cctattgagc    60
gtagtgaggg gccatggaag catggaggac cccatcagtc gtgtgtatgc atgcttccta    120
gagaatccgg agcgtcccat atcagcagct tgccaggcgg cagtggcaat gggtgggacg    180
caagccttct atgattggaa tgcggtaagc ctgccctatg ctgctgggcg gcaccgtgaa    240
ctcatcccgg atggccaatt gtgcagtgct gggcgggcca agtatcgggg cctggacctg    300
cctcgtgacg attggccagg cacctccaat atgacctccg cgtcgcctt cacatacagg      360 tacaaggcca ccgccccaca cttgggctcc ttccagttcc atgtcactcg ggatggctac    420
gatcccaccg agccgctcaa atgggcagac ttggaggact cgcctttcat gaacgccacc    480
agcacgcttg ccccggactc ctacctaatg tccggcacca ccctagcgg caaggctggc     540 caccacctca tctacgccat ttggcagcgc agcgacagcc ctgaggcctt ctactcctgc    600
tccgatgtca ccttcgacgt cgctgctgtc tctgatctcc actccaccac c              651
```

<210> SEQ ID NO 123
<211> LENGTH: 651
<212> TYPE: DNA
<213> ORGANISM: Tectaria milnei

<400> SEQUENCE: 123

```
atggggaggt catggggagt ggtggctgtt atggtggtgt gcgcaagcgg cctattgagc    60
gtagtgaggg gccatggaag catggaggac cccatcagtc gtgtgtatgc atgcttccta    120
gagaatccgg agcgtcccat atcagcagct tgccaggcgg cagtggcaat gggtgggacg    180
caagccttct atgattggaa tgcggtaagc ctgccctatg ctgctgggcg gcaccgtgaa    240
ctcatcccgg atggccaatt gtgcagtgct gggcgggcca agtatcgggg cctggacctg    300
cctcgtgacg attggccagg cacctccaat atgacctccg cgtcgcctt cacatacagg      360 tacaaggcca ccgccccaca cttgggctcc ttccagttct atgtcactcg ggatggctac    420
gatcccaccg agccgctcaa atgggcagac ttggaggact cgcctctcat gaacgccacc    480
agcacgcttg ccccggactc ctacctaatg tccggcacca ccctagcgg caaggctggc     540 caccacctca tctacgccat ttggcagcgc agcgacagcc ctgaggcctt ctactcctgc    600
tccgatgtca ccttcgacgt cgctgctgtc tctgatctcc actccaccac c              651
```

```
<210> SEQ ID NO 124
<211> LENGTH: 215
<212> TYPE: PRT
<213> ORGANISM: Polystichum tripteron

<400> SEQUENCE: 124

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Ala Cys Arg Gln Glu Asn Pro Glu Arg Pro Thr Thr
        35                  40                  45

Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
        115                 120                 125

Phe Phe Glu Phe Tyr Val Thr Val Asp Gly Tyr Asp Pro Thr Glu Pro
    130                 135                 140

Leu Lys Trp Ala Asp Leu Glu Glu Thr Pro Phe Ile Asn Val Thr Asp
145                 150                 155                 160

Pro Thr Val Val Gly Leu Asn Tyr Val Ile Pro Gly Thr Thr Pro Ala
                165                 170                 175

Ser Lys Thr Gly Arg His Leu Ile Tyr Val Ile Trp Gln Arg Ser Asp
            180                 185                 190

Ser Pro Glu Ala Phe Tyr Ser Cys Ser Asp Val Asn Phe Pro Asp Ala
        195                 200                 205

Leu Ser Leu His Ser Thr Thr
    210                 215

<210> SEQ ID NO 125
<211> LENGTH: 212
<212> TYPE: PRT
<213> ORGANISM: Polystichum tripteron

<400> SEQUENCE: 125

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Ala Cys Arg Gln Glu Asn Pro Glu Arg Pro Thr Thr
        35                  40                  45

Pro Ala Cys Ile Ala Ala Val Ala Leu Ser Gly Ala Gln Ala Phe Tyr
    50                  55                  60

Asp Trp Asn Glu Val Asn Ile Pro Asn Ala Pro Gly Arg His Arg Glu
65                  70                  75                  80

Leu Ile Ser Asp Gly Tyr Leu Cys Ser Ala Asn Arg Thr Lys Tyr Ala
            85                  90                  95

Gly Leu Asp Leu Ala Arg Ser Asp Trp Thr Ala Thr Asn Leu Ser Ser
        100                 105                 110

Gly Val Ala Tyr Thr Phe Leu Tyr Arg Val Thr Ala Gln His Arg Gly
```

```
            115                 120                 125
Phe Phe Glu Phe Tyr Val Thr Val Asp Gly Tyr Asp Pro Thr Glu Pro
        130                 135                 140

Leu Lys Trp Ala Asp Leu Glu Glu Thr Pro Phe Ile Asn Val Thr Asp
145                 150                 155                 160

Pro Thr Val Val Gly Leu Asn Tyr Val Ile Pro Gly Thr Thr Pro Ala
                165                 170                 175

Ser Lys Thr Gly Arg His Leu Ile Tyr Val Ile Trp Gln Arg Ser Asp
                180                 185                 190

Ser Pro Glu Ala Phe Tyr Ser Cys Ser Asp Val Asn Phe Pro Asp Ala
                195                 200                 205

Leu Ser Leu His
        210

<210> SEQ ID NO 126
<211> LENGTH: 214
<212> TYPE: PRT
<213> ORGANISM: Davallia fejeensis

<400> SEQUENCE: 126

Met Gly Arg Ser Trp Gly Val Val Ala Ile Met Val Val Cys Ile Met
1               5                   10                  15

Ser Gly Leu Val Gly Ile Val Ser Gly His Gly Ser Met Glu Asp Pro
                20                  25                  30

Ile Ser Arg Val Tyr Arg Cys Tyr Leu Glu Asn Pro Glu Arg Pro Val
                35                  40                  45

Ser Ala Ala Cys Gln Ala Val Ala Met Ser Gly Thr Gln Ala Phe
        50                  55                  60

Tyr Asp Trp Asn Glu Val Asn Ile Pro Asn Ala Ala Gly Arg His Arg
65                  70                  75                  80

Glu Leu Ile Ser Asp Gly Gln Leu Cys Ser Ala Asn Arg Thr Lys Tyr
                85                  90                  95

Ala Gly Leu Asp Leu Ala Arg Ala Asp Trp Leu Gly Thr Pro Leu Ser
                100                 105                 110

Ser Gly Val Ser Phe Thr Phe Ala Tyr Lys Ala Thr Ala Pro His Leu
                115                 120                 125

Gly Phe Phe Glu Phe Tyr Val Thr Arg Asp Gly Tyr Glu Pro Thr Glu
        130                 135                 140

Pro Leu Lys Trp Ala Asp Leu Glu Asp Ser Pro Phe Ile Asn Val Thr
145                 150                 155                 160

Asp Pro Thr Leu Glu Asn Gly Ala Tyr Gln Ile Ser Gly Thr Thr Pro
                165                 170                 175

Ser Gly Lys Ser Gly Arg His Leu Met Tyr Val Ile Trp Gln Arg Ser
                180                 185                 190

Asp Ser Pro Glu Ala Phe Tyr Ser Cys Ser Asp Val Asp Phe Asp Val
                195                 200                 205

Asp Ala Leu Ser Leu His
        210

<210> SEQ ID NO 127
<211> LENGTH: 212
<212> TYPE: PRT
<213> ORGANISM: Didymochlaena truncatula

<400> SEQUENCE: 127

Met Gly Arg Ser Trp Gly Val Val Ala Ile Met Val Leu Cys Ala Ser
```

```
1               5                   10                  15
Gly Leu Leu Gly Val Ala Ser Gly His Gly Ser Met Glu Asp Pro Ile
            20                  25                  30

Ser Arg Val Tyr Ala Cys Tyr Leu Glu Asn Pro Glu Arg Pro Thr Ser
            35                  40                  45

Ala Ala Cys Gln Ala Ala Val Ala Val Ser Gly Thr Gln Ala Phe Tyr
            50                  55                  60

Asp Trp Asn Glu Val Asn Gln Pro Phe Ala Ala Gly Arg His Arg Glu
 65                 70                  75                  80

Leu Ile Pro Asp Gly Glu Leu Cys Ser Gly Gly Arg Glu Lys Tyr Lys
                    85                  90                  95

Gly Leu Asp Leu Ala Arg Ala Asp Trp Pro Ala Thr Ser Leu Pro Ser
                100                 105                 110

Gly Val Asn Tyr Thr Tyr Leu Tyr Lys Ala Thr Ala Pro His Leu Gly
                115                 120                 125

Phe Phe Glu Phe Tyr Ile Thr Arg Asp Gly Tyr Glu Pro Thr Glu Pro
            130                 135                 140

Leu Lys Trp Ala Asp Leu Glu Asp Leu Pro Phe Ile Asn Ile Thr Asn
145                 150                 155                 160

Pro Thr Leu Val Ser Gly Ser Tyr Gln Ile Pro Gly Thr Thr His Ala
                165                 170                 175

Ser Lys Thr Gly Arg His Leu Leu Tyr Val Ile Trp Gln Arg Ser Asp
                180                 185                 190

Ser Phe Glu Ala Phe Tyr Ser Cys Ser Asp Val Asp Phe Val Asn Ala
                195                 200                 205

Leu Ser Leu His
            210

<210> SEQ ID NO 128
<211> LENGTH: 212
<212> TYPE: PRT
<213> ORGANISM: Didymochlaena truncatula

<400> SEQUENCE: 128

Met Gly Arg Ser Trp Gly Val Val Ala Ile Met Val Leu Cys Ala Ser
 1               5                  10                  15

Gly Leu Leu Gly Val Ala Ser Gly His Gly Ser Met Glu Asp Pro Ile
            20                  25                  30

Ser Arg Val Tyr Ala Cys Tyr Leu Glu Asn Pro Glu Arg Pro Thr Ser
            35                  40                  45

Ala Ala Cys Gln Ala Ala Val Ala Val Ser Gly Thr Gln Ala Phe Tyr
            50                  55                  60

Asp Trp Asn Glu Val Asn Gln Pro Phe Ala Ala Gly Arg His Arg Glu
 65                 70                  75                  80

Leu Ile Pro Asp Gly Glu Leu Cys Ser Gly Gly Arg Glu Lys Tyr Lys
                    85                  90                  95

Gly Leu Asp Leu Ala Arg Ala Asp Trp Pro Ala Thr Ser Leu Pro Ser
                100                 105                 110

Gly Val Asn Tyr Thr Tyr Leu Tyr Lys Ala Thr Ala Pro His Leu Gly
                115                 120                 125

Phe Phe Glu Phe Tyr Ile Thr Arg Asp Gly Tyr Glu Pro Thr Glu Pro
            130                 135                 140

Leu Lys Trp Ala Asp Leu Glu Asp Leu Pro Phe Ile Asn Ile Thr Asn
145                 150                 155                 160
```

```
Pro Thr Leu Val Ser Gly Ser Tyr Gln Ile Pro Gly Thr Thr Pro Ala
            165                 170                 175

Ser Lys Thr Gly Arg His Leu Leu Tyr Val Ile Trp Gln Arg Ser Asp
        180                 185                 190

Ser Phe Glu Ala Phe Tyr Ser Cys Ser Asp Val Asp Phe Val Asn Ala
            195                 200                 205

Leu Ser Leu His
        210

<210> SEQ ID NO 129
<211> LENGTH: 212
<212> TYPE: PRT
<213> ORGANISM: Humata tyermanii

<400> SEQUENCE: 129

Met Gly Arg Ser Trp Gly Val Val Ala Ile Met Val Met Tyr Ile Gly
1               5                   10                  15

Gly Leu Leu Ser Ile Ala Ser Gly His Gly Ser Met Glu Asp Pro Ile
            20                  25                  30

Ser Arg Val Tyr Arg Cys Tyr Leu Glu Asn Pro Glu Ser Pro Thr Ser
        35                  40                  45

Ala Ala Cys Gln Ala Ala Val Ala Val Ser Gly Ala Gln Ala Phe Tyr
    50                  55                  60

Asp Trp Asn Glu Val Asn Ile Asp Ala Asn Gly Arg His Arg Glu
65                  70                  75                  80

Leu Ile Ser Asp Gly Gln Leu Cys Ser Ala Asn Arg Ser Lys Tyr Ala
                85                  90                  95

Gly Leu Asp Leu Ala Arg Ala Asp Trp Leu Gly Thr Thr Leu Ser Ser
            100                 105                 110

Gly Ala Ser Phe Thr Phe Ala Tyr Lys Ala Thr Ala Pro His Leu Gly
        115                 120                 125

Phe Phe Glu Phe Tyr Val Thr Arg Asp Gly Tyr Glu Pro Thr Asp Pro
    130                 135                 140

Leu Lys Trp Ala Asp Leu Glu Asp Ser Pro Phe Ile Asn Val Thr Asn
145                 150                 155                 160

Pro Thr Leu Asp Asn Gly Ala Tyr Gln Ile Ser Gly Thr Thr Pro Ala
                165                 170                 175

Gly Lys Ser Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Leu Ser Leu His
        210

<210> SEQ ID NO 130
<211> LENGTH: 215
<212> TYPE: PRT
<213> ORGANISM: Cyrtomium fortunei

<400> SEQUENCE: 130

Met Gly Arg Ser Trp Gly Val Val Ala Ile Met Val Leu Cys Thr Ser
1               5                   10                  15

Gly Leu Leu Gly Val Ala Ser Gly His Gly Thr Met Gly Asp Pro Ile
            20                  25                  30

Ser Arg Val Tyr Asn Cys Phe Gln Glu Asn Pro Glu Arg Pro Thr Ser
        35                  40                  45
```

```
Ala Ala Cys Ile Ala Ala Val Ala Leu Ser Gly Thr Gln Ala Phe Tyr
    50                  55                  60

Asp Trp Asn Glu Val Asn Leu Pro Asp Val Asn Gly Arg His Arg Glu
 65                  70                  75                  80

Phe Ile Pro Asp Gly Gln Leu Cys Ser Ala Gly Arg Asp Lys Tyr Lys
                 85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
        115                 120                 125

Phe Phe Glu Phe Tyr Val Thr Val Asp Asp Tyr Asp Pro Thr Val Ala
130                 135                 140

Leu Lys Trp Glu Asp Leu Glu Glu Thr Pro Phe Leu Asn Val Thr Asp
145                 150                 155                 160

Pro Thr Val Val Gly Val Asn Tyr Gln Ile Ser Gly Thr Thr Pro Ala
                165                 170                 175

Ser Lys Thr Gly Arg His Leu Ile Tyr Val Ile Trp Gln Arg Ser Asp
            180                 185                 190

Ser Pro Glu Ala Phe Tyr Ala Cys Ser Asp Val Asp Phe Val Asp Ala
        195                 200                 205

Val Ser Leu His Ser Thr Thr
210                 215

<210> SEQ ID NO 131
<211> LENGTH: 229
<212> TYPE: PRT
<213> ORGANISM: Adiantum hispidulum

<400> SEQUENCE: 131

Met Lys Lys Ser Trp Gly Val Ala Val Val Gly Val Val Ala Leu
 1               5                  10                  15

Cys Leu Leu Gly Met Ala Ser Gly His Gly Ser Met Gln Asp Pro Ile
            20                  25                  30

Ser Arg Val Tyr Asn Cys Tyr Leu Glu Gly Pro Glu Arg Pro Thr Ser
        35                  40                  45

Ala Ala Cys Ile Ala Ala Val Ala Met Ser Gly Thr Gln Pro Phe Tyr
    50                  55                  60

Asp Trp Asn Glu Val Asn Leu Pro Asp Ala Ala Gly Arg His Arg Glu
 65                  70                  75                  80

Leu Ile Pro Asp Gly Lys Leu Cys Ser Ala Gly Arg Asp Lys Tyr Gln
                 85                  90                  95

Gly Leu Asp Leu Ala Arg Asp Asp Trp Val Ala Ser Leu Ser Ser Gly
            100                 105                 110

Val Ala Tyr Thr Phe Leu Tyr Arg Val Thr Ala Gln His Leu Gly Phe
        115                 120                 125

Phe Glu Ile Tyr Val Thr Arg Asp Thr Tyr Asp Pro Thr Gln Ala Leu
130                 135                 140

Thr Trp Asp Asp Leu Glu Asp Ser Pro Phe Ile Asn Val Thr Asn Pro
145                 150                 155                 160

Ser Val Val Ser Thr Thr Leu Gly Asn Ala Tyr Ala Ile Pro Thr Pro
                165                 170                 175

Thr Pro Ser Gly Lys Thr Gly Arg His Leu Ile Tyr Val Ile Trp Gln
            180                 185                 190

Arg Ser Asp Ser Pro Glu Ala Phe Tyr Ser Cys Ser Asp Val Glu Phe
        195                 200                 205
```

```
Asp Val Ala Ser Thr Val Glu Asp Val Ile Ile Ser Leu Arg Ser
    210                 215                 220

Ala Ala Leu Asp Val
225
```

```
<210> SEQ ID NO 132
<211> LENGTH: 215
<212> TYPE: PRT
<213> ORGANISM: Polystichum acrostichoides

<400> SEQUENCE: 132

Met Gly Arg Ser Trp Gly Val Val Ala Ile Met Val Leu Cys Ala Ser
1               5                   10                  15

Gly Leu Leu Gly Val Ala Ser Gly His Gly Ser Met Asn Asp Pro Ile
            20                  25                  30

Ser Arg Val Tyr Asn Cys Arg Leu Glu Asn Pro Glu Ser Pro Thr Ser
        35                  40                  45

Ala Ala Cys Ile Ala Ala Val Ala Leu Ser Gly Thr Gln Ala Phe Tyr
    50                  55                  60

Asp Trp Asn Glu Val Asn Leu Pro Asp Val Asn Gly Arg His Arg Gln
65                  70                  75                  80

Leu Ile Pro Asp Gly Lys Leu Cys Ser Ala Gly Arg Asp Lys Tyr Lys
                85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Gln His Arg Gly
        115                 120                 125

Phe Phe Glu Phe Tyr Val Thr Val Asp Asp Tyr Asp Pro Thr Glu Leu
    130                 135                 140

Leu Lys Trp Glu Asp Leu Glu Glu Thr Pro Phe Met Asn Val Thr Asp
145                 150                 155                 160

Pro Thr Val Val Gly Val Asn Tyr Glu Ile Pro Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Val Ser Leu His Ser Thr Thr
    210                 215
```

```
<210> SEQ ID NO 133
<211> LENGTH: 217
<212> TYPE: PRT
<213> ORGANISM: Thelypteris kunthii

<400> SEQUENCE: 133

Met Glu Arg Ala Ala Trp Gly Val Val Gly Ile Ile Met Val Leu Cys
1               5                   10                  15

Ala Ser Gly Leu Leu Gly Val Ala Ser Gly His Gly Ser Met Glu Asp
            20                  25                  30

Pro Ile Ser Arg Val Tyr Leu Cys Tyr Leu Glu Asn Pro Glu Arg Pro
        35                  40                  45

Thr Ser Ala Ala Cys Gln Ala Ala Val Ala Leu Ser Gly Thr Gln Ala
    50                  55                  60

Phe Tyr Asp Trp Asn Glu Val Asn Ile Ala Asp Ala Ala Gly Arg His
65                  70                  75                  80
```

```
Arg Glu Leu Ile Pro Asp Gly Gln Leu Cys Ser Ala Gly Arg Asp Lys
                85                  90                  95

Tyr Lys Gly Leu Asp Leu Ala Arg Ser Asp Trp Val Ala Thr Asn Leu
            100                 105                 110

Ser Ser Gly Val Ala Phe Thr Phe Leu Tyr Arg Val Thr Ala Glu His
        115                 120                 125

Arg Gly Phe Phe Glu Phe Tyr Val Thr Val Asp Asp Tyr Asp Pro Thr
    130                 135                 140

Glu Leu Leu Lys Trp Glu Asp Leu Glu Ala Thr Pro Phe Met Asn Val
145                 150                 155                 160

Thr Asp Pro Thr Val Val Gly Asp Asn Tyr Glu Ile Pro Gly Thr Thr
                165                 170                 175

Pro Ala Asn Lys Thr Gly Arg His Leu Ile Tyr Val Ile Trp Gln Arg
            180                 185                 190

Ser Asp Ser Pro Glu Ala Phe Tyr Ser Cys Ser Asp Val Val Phe Ala
        195                 200                 205

Asp Ala Val Ser Leu His Ser Thr Thr
    210                 215

<210> SEQ ID NO 134
<211> LENGTH: 222
<212> TYPE: PRT
<213> ORGANISM: Cyrtomium fortune (clivicola)

<400> SEQUENCE: 134

Met Gly Thr Leu Gly Arg Ser Trp Gly Ala Val Ala Ile Met Val Leu
1               5                   10                  15

Cys Ala Ser Gly Leu Leu Gly Val Ala Ser Gly His Gly Ser Met Asn
            20                  25                  30

Asp Pro Ile Ser Arg Val Tyr Asn Cys Tyr Leu Glu Asn Pro Glu Arg
        35                  40                  45

Pro Thr Ser Ala Ala Cys Ile Ala Ala Val Ala Leu Ser Gly Thr Gln
    50                  55                  60

Ala Phe Tyr Asp Trp Asn Glu Val Asn Leu Pro Asp Ala Asn Gly Arg
65                  70                  75                  80

His Arg Gln Leu Ile Pro Asp Gly Gln Leu Cys Ser Ala Gly Arg Asp
                85                  90                  95

Lys Tyr Lys Gly Leu Asp Leu Ala Arg Ser Asp Trp Thr Ala Thr Asn
            100                 105                 110

Leu Ser Ser Gly Val Ala Phe Thr Phe Leu Tyr Arg Val Thr Ala Gln
        115                 120                 125

His Arg Gly Phe Phe Glu Phe Tyr Val Thr Val Asp Asp Tyr Asp Pro
    130                 135                 140

Thr Val Ala Leu Lys Trp Glu Asp Leu Glu Glu Thr Pro Phe Leu Asn
145                 150                 155                 160

Val Thr Asp Pro Thr Val Val Gly Val Asn Tyr Gln Ile Ser Gly Thr
                165                 170                 175

Thr Pro Ala Ser Lys Thr Gly Arg His Leu Ile Tyr Val Ile Trp Gln
            180                 185                 190

Arg Ser Asp Ser Pro Glu Ala Phe Tyr Ala Cys Ser Asp Val Asp Phe
        195                 200                 205

Val Asp Ala Val Ser Leu His Ser Thr Thr Leu Thr Leu Ile
    210                 215                 220
```

<210> SEQ ID NO 135
<211> LENGTH: 215
<212> TYPE: PRT
<213> ORGANISM: Polystichum tripteron

<400> SEQUENCE: 135

Met Gly Arg Ser Trp Gly Val Val Ala Ile Met Val Leu Phe Ser Ser
1               5                   10                  15

Gly Leu Leu Gly Val Ala Ser Gly His Gly Ser Met Gly Asp Pro Ile
            20                  25                  30

Ser Arg Val Tyr Asn Cys Arg Gln Glu Asn Pro Glu Arg Pro Thr Thr
        35                  40                  45

Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
        115                 120                 125

Phe Phe Glu Phe Tyr Val Thr Val Asp Gly Tyr Asp Pro Thr Glu Pro
    130                 135                 140

Leu Lys Trp Ala Asp Leu Glu Glu Thr Pro Phe Ile Asn Val Thr Asp
145                 150                 155                 160

Pro Thr Val Glu Gly Leu Asn Tyr Val Arg Val Leu Arg His Arg Gly
                165                 170                 175

Cys Lys Ser Gly Arg His Leu Ile Tyr Val Ile Trp Gln Arg Ser Asp
            180                 185                 190

Ser Pro Glu Ala Phe Tyr Ser Cys Ser Asp Val Asn Phe Pro Asp Ala
        195                 200                 205

Leu Ser Leu His Ser Ala Thr
    210                 215

<210> SEQ ID NO 136
<211> LENGTH: 215
<212> TYPE: PRT
<213> ORGANISM: Didymochlaena truncatula

<400> SEQUENCE: 136

Met Gly Arg Ser Trp Gly Val Val Ala Ile Met Val Leu Cys Ala Ser
1               5                   10                  15

Gly Leu Leu Gly Val Ala Ser Gly His Gly Ser Met Glu Asp Pro Ile
            20                  25                  30

Ser Arg Val Tyr Ala Cys Tyr Leu Glu Asn Pro Glu Arg Pro Thr Ser
        35                  40                  45

Ala Ala Cys Gln Ala Ala Val Ala Val Ser Gly Thr Gln Ala Phe Tyr
    50                  55                  60

Asp Trp Asn Glu Val Asn Gln Pro Phe Ala Ala Gly Arg His Arg Glu
65                  70                  75                  80

Leu Ile Pro Asp Gly Glu Leu Cys Ser Gly Gly Arg Glu Lys Tyr Lys
                85                  90                  95

Gly Leu Asp Leu Ala Arg Ala Asp Trp Pro Ala Thr Ser Leu Pro Ser
            100                 105                 110

Gly Val Asn Tyr Thr Tyr Leu Tyr Lys Ala Thr Ala Pro His Leu Gly

```
            115                 120                 125
Phe Phe Glu Phe Tyr Ile Thr Arg Asp Gly Tyr Glu Pro Thr Glu Pro
    130                 135                 140
Leu Lys Trp Ala Asp Leu Glu Asp Leu Pro Phe Ile Asn Ile Thr Asn
145                 150                 155                 160
Pro Thr Leu Val Ser Gly Ser Tyr Gln Ile Pro Gly Thr Thr Pro Ala
                165                 170                 175
Ser Lys Thr Gly Arg His Leu Leu Tyr Val Ile Trp Gln Arg Ser Asp
                180                 185                 190
Ser Phe Glu Ala Phe Tyr Ser Cys Ser Asp Val Asp Phe Val Asn Ala
                195                 200                 205
Leu Ser Leu His Ser Thr Thr
                210                 215
```

<210> SEQ ID NO 137
<211> LENGTH: 229
<212> TYPE: PRT
<213> ORGANISM: Asplenium antiquum

<400> SEQUENCE: 137

```
Met Arg Met Gly Arg Ser Ala Ser Cys Ile Arg Ala Asn Met Ala Ile
1               5                   10                  15
Met Leu Val Leu Phe Trp Ala Ser Cys Ser Cys Leu Leu Gly Ile Val
            20                  25                  30
Ser Gly His Gly Ser Met Glu Asp Pro Ile Ser Arg Val Tyr Ala Cys
        35                  40                  45
Phe Leu Glu Asn Pro Glu Arg Pro Thr Ser Ala Ala Cys Ile Ala Ala
    50                  55                  60
Val Ala Leu Ser Gly Thr Gln Ala Phe Tyr Asp Trp Asn Glu Val Asn
65                  70                  75                  80
Gln Pro Asn Ala Ala Gly Arg His Arg Glu Ile Ile Pro Asp Gly Gln
                85                  90                  95
Leu Cys Gly Ala Gly Arg Asp Lys Tyr Lys Gly Leu Asn Leu Ala Arg
            100                 105                 110
Ala Asp Trp Pro Ala Thr Thr Leu Ser Ser Asp Ile Ser Phe Thr Tyr
        115                 120                 125
Leu Phe Lys Ala Thr Ala Pro His Arg Gly Phe Phe Glu Phe Tyr Val
    130                 135                 140
Thr Arg Asp Gly Tyr Asp Pro Thr Glu Pro Leu Lys Trp Ala Asp Leu
145                 150                 155                 160
Glu Asp Pro Pro Phe Leu Asn Val Thr Asp Pro Thr Leu Ala Ser Gly
                165                 170                 175
Ser Tyr Gln Ile Pro Gly Thr Thr Pro Ala Gly Lys Thr Gly Arg His
                180                 185                 190
Leu Ile Tyr Val Ile Trp Gln Arg Ser Asp Ser Pro Glu Ala Phe Tyr
                195                 200                 205
Ser Cys Ser Asp Val Asp Phe Asp Ser Asp Thr Val Ile Ser Leu
                210                 215                 220
Arg Ser Ala Thr Thr
225
```

<210> SEQ ID NO 138
<211> LENGTH: 215
<212> TYPE: PRT
<213> ORGANISM: Cyrtomium falcatum (Butterfieldii)

<400> SEQUENCE: 138

```
Met Gly Arg Ser Trp Gly Val Val Ala Ile Met Val Leu Cys Ala Thr
1               5                   10                  15
Gly Leu Leu Gly Val Ala Ser Gly His Gly Ser Met Gly Asp Pro Ile
            20                  25                  30
Ser Arg Val Tyr Asn Cys Phe Leu Glu Asn Pro Glu Arg Pro Thr Ser
        35                  40                  45
Ala Ala Cys Ile Ala Ala Val Ala Leu Ser Gly Thr Gln Ala Phe Tyr
    50                  55                  60
Asp Trp Asn Glu Val Asn Leu Pro Asp Val Asn Gly Arg His Arg Gln
65                  70                  75                  80
Phe Ile Pro Asp Gly Gln Leu Cys Ser Ala Gly Arg Asp Lys Tyr Lys
                85                  90                  95
Gly Leu Asp Leu Ala Arg Ser Asp Trp Thr Ala Thr Asn Leu Ser Ser
            100                 105                 110
Gly Ile Ala Tyr Thr Phe Leu Tyr Arg Val Thr Ala Gln His Arg Gly
        115                 120                 125
Phe Phe Glu Phe Tyr Val Thr Val Asp Asp Tyr Asp Pro Thr Val Ala
    130                 135                 140
Leu Lys Trp Glu Asp Leu Glu Glu Thr Pro Phe Leu Asn Val Thr Asp
145                 150                 155                 160
Pro Thr Val Val Gly Val Asn Tyr Gln Ile Asn Gly Thr Thr Pro Ala
                165                 170                 175
Ser Lys Thr Gly Arg His Leu Ile Tyr Val Ile Trp Gln Arg Ser Asp
            180                 185                 190
Ser Pro Glu Ala Phe Tyr Ala Cys Ser Asp Val Asp Phe Val Asp Ala
        195                 200                 205
Val Ser Leu His Ser Thr Thr
    210                 215
```

<210> SEQ ID NO 139
<211> LENGTH: 218
<212> TYPE: PRT
<213> ORGANISM: Onoclea sensibilis

<400> SEQUENCE: 139

```
Met Gly Arg Ser Trp Gly Val Val Gln Ala Ile Ile Met Val Leu Cys
1               5                   10                  15
Gly Ser Gly Leu Leu Gly Val Ala Ser Gly His Gly Ser Met Glu Asp
            20                  25                  30
Pro Ile Ser Arg Val Tyr Asn Cys Tyr Leu Glu Asn Pro Glu Ser Pro
        35                  40                  45
Thr Ser Ala Ala Cys Gln Ala Val Ala Leu Ser Gly Ala Gln Ala
    50                  55                  60
Phe Tyr Asp Trp Asn Glu Val Asn Leu Ala Asp Ala Ala Gly Arg His
65                  70                  75                  80
Arg Glu Leu Ile Pro Asp Gly Gln Leu Cys Ser Ala Gly Arg Glu Lys
                85                  90                  95
Tyr Gln Gly Leu Asp Leu Ala Arg Ser Asp Trp Thr Ala Thr Ser Leu
            100                 105                 110
Ser Ser Gly Val Ser Phe Thr Tyr Leu Tyr Lys Ala Thr Ala Pro His
        115                 120                 125
Leu Gly Phe Phe Glu Phe Tyr Val Thr Lys Asp Gly Tyr Glu Pro Thr
    130                 135                 140
```

```
Glu Pro Leu Lys Trp Ala Asp Leu Glu Asp Ser Pro Phe Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
            195                 200                 205

Val Asp Ala Leu Ser Leu His Ser Thr Thr
    210                 215
```

<210> SEQ ID NO 140
<211> LENGTH: 216
<212> TYPE: PRT
<213> ORGANISM: Platycerium superbum

<400> SEQUENCE: 140

```
Met Arg Arg Ser Trp Val Ala Val Ala Val Thr Leu Val Val Cys Ala
1               5                   10                  15

Gly Ser Leu Leu Gly Val Ala Ser Gly His Gly Ser Met Glu Asp Pro
            20                  25                  30

Ile Ser Arg Val Tyr Gly Cys Tyr Leu Glu Asn Pro Glu Asn Pro Thr
        35                  40                  45

Ser Ala Ala Cys Ile Ala Ala Val Ala Ala Ser Gly Thr Gln Ala Phe
    50                  55                  60

Tyr Asp Trp Asn Glu Val Asn Gln Pro Phe Ala Ala Gly Gln His Arg
65                  70                  75                  80

Gln Ile Ile Pro Asp Gly Gln Leu Cys Ser Ala Gly Arg Asp Lys Tyr
                85                  90                  95

Lys Gly Leu Asp Leu Ala Arg Ala Asp Trp Pro Ala Thr Ser Leu Ser
            100                 105                 110

Ser Gly Val Asp Tyr Thr Phe Leu Phe Lys Ala Thr Ala Pro His Arg
        115                 120                 125

Gly Tyr Phe Glu Phe Tyr Val Thr Arg Asp Ser Tyr Asp Pro Thr Glu
    130                 135                 140

Pro Leu Ala Trp Ala Asp Leu Glu Asp Thr Pro Phe Ile Asn Val Thr
145                 150                 155                 160

Asp Pro Thr Leu Val Ser Gly Ser Tyr Gln Ile Ser Thr Thr Pro
                165                 170                 175

Ser Gly Lys Thr Gly Arg His Leu Ile Tyr Val Ile Trp Gln Arg Thr
            180                 185                 190

Asp Ser Thr Glu Ala Phe Tyr Ser Cys Ser Asp Val Asp Phe Asp Glu
            195                 200                 205

Thr Leu Arg Leu His Ser Ala Thr
    210                 215
```

<210> SEQ ID NO 141
<211> LENGTH: 215
<212> TYPE: PRT
<213> ORGANISM: Davallia tyermannii

<400> SEQUENCE: 141

```
Met Gly Arg Ser Trp Gly Val Val Ala Ile Met Val Met Tyr Ile Gly
1               5                   10                  15

Gly Leu Leu Ser Ile Ala Ser Gly His Gly Ser Met Glu Asp Pro Ile
            20                  25                  30
```

```
Ser Arg Val Tyr Arg Cys Tyr Leu Glu Asn Pro Glu Ser Pro Thr Ser
        35                  40                  45

Ala Ala Cys Gln Ala Ala Val Ala Val Ser Gly Ala Gln Ala Phe Tyr
 50                  55                  60

Asp Trp Asn Glu Val Asn Ile Ala Asp Ala Asn Gly Arg His Arg Glu
65                  70                  75                  80

Leu Ile Ser Asp Gly His Leu Cys Ser Ala Asn Arg Thr Lys Tyr Ala
                85                  90                  95

Gly Leu Asp Leu Ala Cys Pro Asp Trp Leu Gly Thr Leu Leu Phe Ser
            100                 105                 110

Gly Val Ser Tyr Thr Phe Ser Tyr Lys Ala Thr Ala Pro His Leu Gly
            115                 120                 125

Phe Phe Glu Phe Tyr Val Thr Arg Asp Gly Tyr Glu Pro Thr Asp Pro
        130                 135                 140

Leu Lys Trp Ala Asp Leu Glu Asp Ser Pro Phe Ile Asn Val Thr Asn
145                 150                 155                 160

Pro Thr Leu Asp Asn Gly Ala Tyr Gln Ile Ser Gly Thr Thr Pro Ala
                165                 170                 175

Gly Lys Ser Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Leu Ser Leu His Ser Thr Thr
        210                 215

<210> SEQ ID NO 142
<211> LENGTH: 217
<212> TYPE: PRT
<213> ORGANISM: Tectaria milnei

<400> SEQUENCE: 142

Met Gly Arg Ser Trp Gly Val Val Ala Val Met Val Val Cys Ala Ser
1               5                   10                  15

Gly Leu Leu Ser Val Val Arg Gly His Gly Ser Met Glu Asp Pro Ile
            20                  25                  30

Ser Arg Val Tyr Ala Cys Phe Leu Glu Asn Pro Glu Arg Pro Ile Ser
        35                  40                  45

Ala Ala Cys Gln Ala Ala Val Ala Met Gly Gly Thr Gln Ala Phe Tyr
 50                  55                  60

Asp Trp Asn Ala Val Ser Leu Pro Tyr Ala Ala Gly Gln His Arg Glu
65                  70                  75                  80

Leu Ile Pro Asp Gly Gln Leu Cys Ser Ala Gly Arg Ala Lys Tyr Arg
                85                  90                  95

Gly Leu Asp Leu Pro Arg Asp Asp Trp Pro Gly Thr Ser Asn Met Thr
            100                 105                 110

Ser Gly Val Ala Phe Thr Tyr Arg Tyr Lys Ala Thr Ala Pro His Leu
            115                 120                 125

Gly Ser Phe Gln Phe Tyr Val Thr Arg Asp Gly Tyr Asp Pro Thr Glu
        130                 135                 140

Pro Leu Lys Trp Ala Asp Leu Glu Asp Ser Pro Phe Met Asn Ala Thr
145                 150                 155                 160

Ser Thr Leu Ala Pro Asp Ser Tyr Leu Met Ser Gly Thr Thr Pro Ser
                165                 170                 175

Gly Lys Ala Gly His His Leu Ile Tyr Ala Ile Trp Gln Arg Ser Asp
            180                 185                 190
```

Ser Pro Glu Ala Phe Tyr Ser Cys Ser Asp Val Thr Phe Asp Val Ala
        195                 200                 205

Ala Val Ser Asp Leu His Ser Thr Thr
    210                 215

<210> SEQ ID NO 143
<211> LENGTH: 216
<212> TYPE: PRT
<213> ORGANISM: Polystichium tsus-simense

<400> SEQUENCE: 143

Met Gly Arg Ser Trp Trp Gly Val Leu Ala Val Met Val Leu Cys Ala
1               5                   10                  15

Ser Gly Leu Leu Gly Val Ala Ser Gly His Gly Thr Met Asn Asp Pro
            20                  25                  30

Ile Ser Arg Val Tyr Asn Cys Phe Leu Glu Asn Pro Glu Ser Pro Thr
        35                  40                  45

Ser Ala Ala Cys Ile Ala Ala Val Ala Leu Ser Gly Thr Gln Ala Phe
    50                  55                  60

Tyr Asp Trp Asn Glu Val Asn Leu Ala Asn Ala Ala Gly Arg His Arg
65                  70                  75                  80

Glu Leu Ile Pro Asp Gly Gln Leu Cys Ser Ala Gly Arg Asp Lys Tyr
                85                  90                  95

Lys Gly Leu Asp Leu Ala Arg Ser Asp Trp Thr Ala Thr Asn Leu Ser
            100                 105                 110

Ser Gly Val Ala Phe Thr Phe Leu Tyr Arg Val Thr Ala Gln His Arg
        115                 120                 125

Gly Phe Phe Glu Phe Tyr Val Thr Val Asp Asp Tyr Asp Pro Thr Glu
    130                 135                 140

Leu Leu Lys Trp Glu Asp Leu Glu Glu Thr Pro Phe Leu Asn Val Thr
145                 150                 155                 160

Asp Pro Thr Val Val Gly Val Asn Tyr Glu Ile Ser Gly Thr Thr Pro
                165                 170                 175

Ala Ser Lys Thr Gly Arg His Leu Ile Tyr Val Ile Trp Gln Arg Ser
            180                 185                 190

Asp Ser Pro Glu Ala Phe Tyr Ser Cys Ser Asp Val Asp Phe Val Asp
        195                 200                 205

Ser Leu Ser Leu His Ser Thr Thr
    210                 215

<210> SEQ ID NO 144
<211> LENGTH: 216
<212> TYPE: PRT
<213> ORGANISM: Nephrolepis falcata

<400> SEQUENCE: 144

Met Gly Arg Ser Trp Trp Gly Ala Val Ala Ile Val Leu Ala Val Cys
1               5                   10                  15

Ala Ser Gly Leu Leu Ser Val Val Ser Gly Gln Gly Ser Met Ala Tyr
            20                  25                  30

Pro Ile Ser Arg Val Tyr Gly Cys Phe Leu Glu Asn Pro Leu Ser Pro
        35                  40                  45

Thr Ser Ala Ala Cys Asn Ala Ala Val Ala Leu Ser Gly Thr Gln Ala
    50                  55                  60

Phe Tyr Asp Trp Asn Glu Val Ser Leu Ala Asn Ala Ser Gly Gln His
65                  70                  75                  80

```
Arg Gln Leu Ile Pro Asp Gly Gln Leu Cys Ser Ala Gly Gln Ala Lys
                85                  90                  95

Tyr Arg Gly Leu Asp Leu Ala Arg Asp Asp Trp Pro Gly Thr Ser Leu
            100                 105                 110

Thr Ser Gly Val Ala Tyr Thr Phe Tyr Tyr Ala Thr Thr Leu His
            115                 120                 125

Leu Gly Phe Phe Glu Phe Tyr Val Thr Arg Asp Gly Tyr Asp Ala Thr
    130                 135                 140

Gln Pro Leu Lys Trp Ala Asp Leu Glu Asp Ser Pro Phe Leu Asn Val
145                 150                 155                 160

Thr Ser Thr Leu Ala Ala Ser Ser Phe Gln Trp Ser Ser Ile Thr Pro
                165                 170                 175

Ser Asp Lys Ser Gly Arg His Leu Ile Tyr Val Ile Trp Gln Arg Thr
            180                 185                 190

Asp Ser Pro Glu Ala Phe Tyr Ser Cys Ser Asp Val Asp Phe Asp Tyr
            195                 200                 205

Ala Val Ser Leu His Ser Thr Thr
    210                 215

<210> SEQ ID NO 145
<211> LENGTH: 213
<212> TYPE: PRT
<213> ORGANISM: Nephrolepis exaltata (compacta)

<400> SEQUENCE: 145

Met Gly Arg Ser Trp Gly Val Ala Ala Ile Val Val Ala Val Cys Ala
1               5                   10                  15

Ser Gly Leu Leu Ser Val Val Ser Gly His Gly Ser Met Gln Asp Pro
            20                  25                  30

Ile Ser Arg Val Tyr Ala Cys Tyr Leu Glu Asn Pro Glu Arg Pro Thr
            35                  40                  45

Ser Ala Ala Cys Gln Ala Ala Val Ala Leu Ser Gly Thr Gln Ala Phe
    50                  55                  60

Tyr Asp Trp Asn Glu Val Asn Leu Pro Asn Ala Ala Gly Arg His Arg
65                  70                  75                  80

Glu Leu Ile Pro Asp Gly Gln Leu Cys Ser Ala Gly Arg Ala Lys Tyr
                85                  90                  95

Gln Gly Leu Asp Gln Ala Arg Asn Asp Trp Pro His Thr Asp Leu Ile
            100                 105                 110

Ser Gly Val Ala Phe Thr Phe Asn Tyr Arg Ala Thr Ala Pro His Leu
            115                 120                 125

Gly Ile Phe Glu Phe Tyr Val Thr Arg Asp Gly Tyr Asp Ala Thr Gln
    130                 135                 140

Pro Leu Lys Trp Ala Asp Leu Glu Asp Ser Pro Phe Leu Thr Ala Thr
145                 150                 155                 160

Ser Thr Leu Ala Pro Ser Ser Tyr Gln Trp Pro Gly Thr Thr Pro Ser
                165                 170                 175

Gly Lys Ser Gly Arg His Leu Ile Tyr Val Ile Trp Gln Arg Thr Asp
            180                 185                 190

Ser Pro Glu Ala Phe Tyr Ser Cys Ser Asp Val Glu Phe Val Asp Ala
            195                 200                 205

Val Ser Leu His Ser
    210
```

```
<210> SEQ ID NO 146
<211> LENGTH: 215
<212> TYPE: PRT
<213> ORGANISM: Nephrolepis exaltata (Tiger Fern)

<400> SEQUENCE: 146

Met Gly Arg Ser Trp Gly Val Ala Ala Ile Val Val Ala Val Cys Ala
1               5                   10                  15

Ser Gly Leu Leu Ser Val Val Ser Gly His Gly Ser Met Gln Asp Pro
            20                  25                  30

Ile Ser Arg Val Tyr Ala Cys Tyr Leu Glu Asn Pro Glu Arg Pro Thr
        35                  40                  45

Ser Ala Ala Cys Gln Ala Ala Val Ala Leu Ser Gly Thr Gln Ala Phe
    50                  55                  60

Tyr Asp Trp Asn Glu Val Asn Leu Pro Asn Ala Ala Gly Arg His Arg
65                  70                  75                  80

Glu Leu Ile Pro Asp Gly Gln Leu Cys Ser Ala Gly Arg Ala Lys Tyr
                85                  90                  95

Gln Gly Leu Asp Gln Ala Arg Asn Asp Trp Pro His Thr Asp Leu Ile
            100                 105                 110

Ser Gly Val Ala Phe Thr Phe Asn Tyr Arg Ala Thr Ala Pro His Leu
        115                 120                 125

Gly Ile Phe Glu Phe Tyr Val Thr Arg Asp Gly Tyr Asp Ala Thr Gln
    130                 135                 140

Pro Leu Lys Trp Ala Asp Leu Glu Asp Ser Pro Phe Leu Thr Ala Thr
145                 150                 155                 160

Ser Thr Leu Ala Pro Ser Ser Tyr Gln Trp Pro Gly Thr Thr Pro Ser
                165                 170                 175

Gly Lys Ser Gly Arg His Leu Ile Tyr Val Ile Trp Gln Arg Thr Asp
            180                 185                 190

Ser Pro Glu Ala Phe Tyr Ser Cys Ser Asp Val Glu Phe Val Asp Ala
        195                 200                 205

Val Ser Leu His Ser Thr Thr
    210                 215

<210> SEQ ID NO 147
<211> LENGTH: 215
<212> TYPE: PRT
<213> ORGANISM: Humata termanii

<400> SEQUENCE: 147

Met Gly Arg Ser Trp Gly Val Val Ala Ile Met Val Met Tyr Ile Gly
1               5                   10                  15

Gly Leu Leu Ser Ile Ala Ser Gly His Gly Ser Met Glu Asp Pro Ile
            20                  25                  30

Ser Arg Val Tyr Arg Cys Tyr Leu Glu Asn Pro Glu Ser Pro Thr Ser
        35                  40                  45

Ala Ala Cys Gln Ala Ala Val Ala Val Ser Gly Ala Gln Ala Phe Tyr
    50                  55                  60

Asp Trp Asn Glu Val Asn Ile Ala Asp Ala Asn Gly Arg His Arg Glu
65                  70                  75                  80

Leu Ile Ser Asp Gly Gln Leu Cys Ser Ala Asn Arg Ser Lys Tyr Ala
                85                  90                  95

Gly Leu Asp Leu Ala Arg Ala Asp Trp Leu Gly Thr Thr Leu Ser Ser
            100                 105                 110

Gly Ala Ser Phe Thr Phe Ala Tyr Lys Ala Thr Ala Pro His Leu Gly
```

```
                115                 120                 125
Phe Phe Glu Phe Tyr Val Thr Arg Asp Gly Tyr Glu Pro Thr Asp Pro
            130                 135                 140
Leu Lys Trp Ala Asp Leu Glu Asp Ser Pro Phe Ile Asn Val Thr Asn
145                 150                 155                 160
Pro Thr Leu Asp Asn Gly Ala Tyr Gln Ile Ser Gly Thr Thr Pro Ala
                165                 170                 175
Gly Lys Ser Gly Arg His Leu Ile Tyr Val Ile Trp Gln Arg Ser Asp
            180                 185                 190
Ser Pro Glu Ala Phe Tyr Ser Cys Ser Asp Val Asp Phe Val Asp Ala
                195                 200                 205
Leu Ser Leu His Ser Thr Thr
210                 215
```

<210> SEQ ID NO 148
<211> LENGTH: 220
<212> TYPE: PRT
<213> ORGANISM: Adiantum tenerum (Scutum Roseum)

<400> SEQUENCE: 148

```
Met Gly Trp Cys Arg Ser Trp Gly Val Val Ala Val Met Val Leu Cys
1               5                   10                  15
Thr Ser Gly Leu Leu Gly Val Ala Ser Gly His Gly Ser Met Lys Asp
                20                  25                  30
Pro Ile Ser Arg Val Tyr Asn Cys Tyr Leu Glu Asn Pro Glu Arg Pro
            35                  40                  45
Thr Ser Ala Ala Cys Gln Ala Val Ala Leu Ser Gly Thr Gln Ala
        50                  55                  60
Phe Tyr Asp Trp Asn Glu Val Asn Leu Pro Asn Ala Ala Gly Arg His
65                  70                  75                  80
Arg Glu Leu Ile Pro Asp Gly Leu Cys Ser Ala Gly Arg Glu Lys
                85                  90                  95
Tyr Gln Gly Leu Asp Leu Ala Arg Ala Asp Trp Thr Ala Thr Ser Leu
                100                 105                 110
Thr Ser Gly Leu Asp Ser Phe Thr Trp Leu Tyr Lys Ala Thr Ala Pro
            115                 120                 125
His Leu Gly Phe Phe Glu Phe Tyr Val Thr Arg Asp Gly Tyr Asp Pro
        130                 135                 140
Thr Glu Ala Leu Thr Trp Ala Asp Leu Glu Asp Ser Pro Phe Ile Asn
145                 150                 155                 160
Val Thr Asn Pro Ala Leu Val Ser Gly Asp Tyr Gln Ile Ser Gly Thr
                165                 170                 175
Ile Pro Ala Gly Lys Ser Gly Arg His Leu Ile Tyr Val Ile Trp Gln
            180                 185                 190
Arg Ser Asp Ser Pro Glu Ala Phe Tyr Ser Cys Ser Asp Val Asp Phe
        195                 200                 205
Val Asp Asp Ala Leu Ile Ser Leu Arg Ser Ala Thr
    210                 215                 220
```

<210> SEQ ID NO 149
<211> LENGTH: 215
<212> TYPE: PRT
<213> ORGANISM: Polystichum setiferum (compacta)

<400> SEQUENCE: 149

Met Gly Arg Ser Trp Gly Val Ala Ala Ile Met Val Leu Cys Ala Ser

```
                1               5                  10                 15
            Gly Leu Leu Gly Val Ala Ser Gly His Gly Thr Met His Asp Pro Ile
                            20                 25                 30

Ser Arg Val Tyr Asn Cys Phe Leu Glu Asn Pro Glu Ser Pro Thr Ser
                        35                 40                 45

Ala Ala Cys Ile Glu Ala Val Glu Val Ser Gly Thr Gln Pro Phe Tyr
                    50                 55                 60

Asp Trp Asn Glu Val Asn Leu Ala Asn Ala Gly Arg His Arg Glu
            65                 70                 75                 80

Leu Ile Pro Asp Gly Lys Leu Cys Ser Ala Gly Arg Asp Lys Tyr Lys
                            85                 90                 95

Gly Leu Asp Leu Ala Arg Ser Asp Trp Val Ala Thr Asn Leu Ser Ser
                            100                105                110

Gly Val Ala Phe Thr Phe Leu Tyr Arg Val Thr Ala Glu His Arg Gly
                            115                120                125

Phe Phe Glu Phe Tyr Val Thr Val Asp Asp Tyr Asp Pro Thr Glu Leu
                            130                135                140

Leu Lys Trp Glu Asp Leu Glu Glu Thr Pro Phe Met Asn Val Thr Asp
            145                150                155                160

Pro Thr Val Val Gly Ala Asn Tyr Glu Ile Pro Gly Thr Thr Pro Ala
                                165                170                175

Asn Lys Thr Gly Arg His Leu Ile Tyr Val Ile Trp Gln Arg Ser Asp
                        180                185                190

Ser Pro Glu Ala Phe Tyr Ser Cys Ser Asp Val Val Phe Ala Asp Ala
                            195                200                205

Val Ser Leu His Ser Thr Thr
                        210                215

<210> SEQ ID NO 150
<211> LENGTH: 215
<212> TYPE: PRT
<213> ORGANISM: Polystichum setiferum (compacta)

<400> SEQUENCE: 150

Met Gly Arg Ser Trp Gly Val Ala Ala Ile Met Val Leu Cys Ala Ser
            1               5                  10                 15

Gly Leu Leu Gly Val Ala Ser Gly His Gly Thr Met His Asp Pro Ile
                            20                 25                 30

Ser Arg Val Tyr Asn Cys Phe Leu Glu Asn Pro Glu Ser Pro Thr Ser
                        35                 40                 45

Ala Ala Cys Ile Glu Ala Val Glu Val Ser Gly Thr Gln Pro Phe Tyr
                    50                 55                 60

Asp Trp Asn Glu Val Asn Leu Pro Asp Val Asn Gly Arg His Arg Glu
            65                 70                 75                 80

Leu Ile Pro Asp Gly Lys Leu Cys Ser Ala Gly Arg Glu Lys Tyr Lys
                            85                 90                 95

Gly Leu Asp Leu Ala Arg Ser Asp Trp Val Ala Thr Asn Leu Ser Ser
                            100                105                110

Gly Val Ala Phe Thr Phe Leu Tyr Arg Val Thr Ala Glu His Arg Gly
                            115                120                125

Phe Phe Glu Phe Tyr Val Thr Val Asp Asp Tyr Asp Pro Thr Glu Leu
                            130                135                140

Leu Lys Trp Glu Asp Leu Glu Ala Thr Pro Phe Met Asn Val Thr Asp
            145                150                155                160
```

Pro Thr Val Val Gly Asp Asn Tyr Glu Ile Pro Gly Thr Thr Pro Ala
              165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Val Phe Ala Asp Ala
        195                 200                 205

Val Ser Leu His Ser Thr Thr
        210             215

<210> SEQ ID NO 151
<211> LENGTH: 215
<212> TYPE: PRT
<213> ORGANISM: Lepisorus bicolor

<400> SEQUENCE: 151

Met Arg Ser Trp Gly Val Val Ala Ile Met Val Ala Val Cys Ala Ser
1               5                   10                  15

Gly Leu Leu Gly Val Ala Ser Gly His Gly Ser Met Ser Asp Pro Ile
            20                  25                  30

Ser Arg Val Tyr Arg Cys Arg Leu Glu Asn Pro Glu Arg Pro Thr Ser
        35                  40                  45

Ala Ala Cys Ile Ala Ala Val Ala Leu Ser Gly Lys Gln Ala Phe Tyr
    50                  55                  60

Asp Trp Asn Glu Val Asn Leu Pro Phe Ala Asn Gly Arg His Arg Glu
65                  70                  75                  80

Leu Ile Pro Asp Gly Lys Leu Cys Ser Ala Gly Arg Asp Lys Tyr Lys
                85                  90                  95

Gly Leu Asp Leu Pro Arg Ala Asp Trp Leu Ala Thr Ser Leu Ser Ser
            100                 105                 110

Gly Ser Ala Tyr Thr Phe Leu Tyr Arg Ala Thr Ala Pro His Leu Gly
        115                 120                 125

Tyr Phe Glu Phe Tyr Val Thr Arg Asp Ser Tyr Asp Pro Thr Gln Pro
    130                 135                 140

Leu Ala Trp Ser Asp Leu Glu Asp Ser Pro Phe Ile Lys Val Thr Asn
145                 150                 155                 160

Pro Pro Leu Val Ser Gly Phe Tyr Glu Phe Pro Gly Thr Thr Pro Ser
                165                 170                 175

Gly Lys Thr Gly Arg His Leu Ile Tyr Val Ile Trp Gln Arg Thr Asp
            180                 185                 190

Ser Thr Glu Ala Phe Tyr Ser Cys Ser Asp Val Asp Phe Asp Glu Ala
        195                 200                 205

Leu Ser Leu Ser Ser Thr Ile
        210             215

<210> SEQ ID NO 152
<211> LENGTH: 217
<212> TYPE: PRT
<213> ORGANISM: Pyrrosia lingua (Ogon)

<400> SEQUENCE: 152

Met Arg Thr Arg Val Trp Gly Val Val Ala Phe Met Val Ala Val Cys
1               5                   10                  15

Ala Cys Asp Leu Leu Gly Leu Ala Ser Gly His Gly Ser Met Gly Asp
            20                  25                  30

Pro Val Ser Arg Val Leu Asn Cys Tyr Leu Glu Asn Pro Glu Arg Pro
        35                  40                  45

-continued

```
Thr Ser Ala Ala Cys Ile Ala Ala Val Ala Leu Ser Gly Thr Gln Ala
    50                  55                  60
Phe Tyr Asp Trp Asn Glu Val Asn Leu Ala Ser Ala Cys Gly Arg His
65                  70                  75                  80
Arg Glu Leu Ile Ser Asp Gly Glu Leu Cys Ser Ala Gly Arg Asp Lys
                85                  90                  95
Tyr Lys Gly Leu Asn Leu Ala Arg Ala Asp Trp Val Ala Thr Ser Leu
            100                 105                 110
Ser Ser Gly Val Asp Tyr Thr Phe Leu Phe Asn Ala Thr Ala Ala His
        115                 120                 125
Leu Gly Tyr Phe Glu Phe Trp Val Thr Arg Asp Ser Tyr Asp Pro Thr
    130                 135                 140
Gln Pro Leu Ala Trp Ala Asp Leu Glu Asp Ser Pro Phe Ile Asn Ile
145                 150                 155                 160
Thr Asn Pro Thr Ile Val Ser Asp Ala Tyr Gln Val Pro Ala Thr Thr
                165                 170                 175
Pro Ser Gly Lys Thr Gly Arg His Leu Ile Tyr Val Ile Trp Gln Arg
            180                 185                 190
Thr Asp Ser Thr Glu Ala Phe Tyr Ser Cys Ser Asp Val Asp Phe Asp
        195                 200                 205
Glu Ala Leu Pro Leu Ser Thr Thr
    210                 215

<210> SEQ ID NO 153
<211> LENGTH: 224
<212> TYPE: PRT
<213> ORGANISM: Blechnum appendiculatum

<400> SEQUENCE: 153

Met Lys Lys Ser Ser Gly Val Val Val Val Ala Ala Ile Leu
1               5                   10                  15
Leu Leu Cys Leu Leu Gly Val Ala Asn Gly His Gly Ser Met Gln Asp
            20                  25                  30
Pro Ile Ser Arg Val Tyr Asn Cys Phe Leu Glu Asn Pro Glu Ser Pro
        35                  40                  45
Thr Ser Ala Ala Cys Gln Ala Ala Val Ala Val Ala Gly Thr Gln Pro
    50                  55                  60
Phe Tyr Asp Trp Asn Glu Val Asn Leu Ala Asn Ala Asn Gly Arg His
65                  70                  75                  80
Arg Glu Leu Ile Ser Asp Gly Met Leu Cys Ser Ala Asn Arg Ser Lys
                85                  90                  95
Tyr His Gly Leu Asp Leu Ala Arg Ala Asp Trp Thr Ala Thr Ser Leu
            100                 105                 110
Ser Ser Gly Val Ala Tyr Thr Phe Leu Tyr Arg Val Thr Ala His His
        115                 120                 125
Arg Gly Phe Phe Glu Phe Tyr Ile Thr Arg Asp Ser Tyr Asp Pro Thr
    130                 135                 140
Gln Pro Leu Ala Trp Ala Asp Leu Glu Asp Ser Pro Phe Ile Asn Ile
145                 150                 155                 160
Thr Asp Pro Thr Thr Val Ser Thr Thr Leu Gly Glu Ala Tyr Glu Ile
                165                 170                 175
Ser Gly Thr Thr Pro Ala Ser Lys Ser Gly Arg His Leu Ile Tyr Val
            180                 185                 190
Ile Trp Gln Arg Ser Asp Ser Pro Glu Ala Phe Tyr Ser Cys Ser Asp
        195                 200                 205
```

-continued

Val Asp Phe Ser Ala Asp Ala Leu Ile Ser Leu Arg Ser Ala Val Leu
    210                 215                 220

<210> SEQ ID NO 154
<211> LENGTH: 215
<212> TYPE: PRT
<213> ORGANISM: Polystichum munitum

<400> SEQUENCE: 154

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asn Pro Ile
            20                  25                  30

Ser Arg Val Tyr Asn Cys Arg Leu Glu Asn Pro Glu Arg Pro Thr Ser
        35                  40                  45

Ala Ala Cys Ile Ala Ala Val Ala Leu Ser Gly Thr Gln Ala Phe Tyr
    50                  55                  60

Asp Trp Asn Glu Val Asn Leu Pro Asp Val Asn Gly Arg His Arg Glu
65                  70                  75                  80

Leu Ile Pro Asp Gly Lys Leu Cys Ser Ala Gly Arg Asp Lys Tyr Lys
                85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Gln His Arg Gly
        115                 120                 125

Phe Phe Glu Phe Tyr Val Thr Val Asp Asp Tyr Asp Pro Thr Glu Leu
    130                 135                 140

Leu Lys Trp Glu Asp Leu Glu Glu Thr Pro Phe Met Asn Val Thr Asp
145                 150                 155                 160

Pro Thr Val Val Gly Val Asn Tyr Glu Ile Pro Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Val Ser Leu His Ser Thr Thr
    210                 215

<210> SEQ ID NO 155
<211> LENGTH: 217
<212> TYPE: PRT
<213> ORGANISM: Stenochiaena tenuifolia

<400> SEQUENCE: 155

Met Gly Met Gly Arg Ser Asn Ser Ser Lys Val Val Ala Ile Val Val
1               5                   10                  15

Leu Cys Ser Gly Leu Leu Ser Leu Val Ser Gly His Gly Ser Met Gln
            20                  25                  30

Asn Pro Ile Ser Arg Val Leu Asn Cys Tyr Leu Glu Asn Pro Glu Arg
        35                  40                  45

Pro Thr Ser Ala Ala Cys Gln Ala Ala Val Ala Met Ser Gly Thr Gln
    50                  55                  60

Ala Phe Tyr Asp Trp Asn Glu Val Asn Leu Pro Asn Ala Ala Gly Arg
65                  70                  75                  80

His Arg Gln Leu Ile Pro Asp Gly Gln Leu Cys Ser Ala Gly Arg Gln
                85                  90                  95

```
Lys Tyr Arg Gly Leu Asp Leu Ala Arg Asp Asp Trp Glu Ala Thr Thr
                100                 105                 110

Leu Ser Ser Gly Thr Ala Phe Thr Tyr Asn Tyr Arg Ala Thr Ala Pro
            115                 120                 125

His Leu Gly Phe Phe Glu Phe Tyr Val Thr Arg Asp Gly Tyr Glu Pro
        130                 135                 140

Thr Glu Pro Leu Lys Trp Ser Asp Leu Gln Asp Ser Pro Phe Ile Asn
145                 150                 155                 160

Val Thr Thr Thr Leu Ser Ser Asp Ser Tyr Gln Ile Thr Gly Thr Thr
                165                 170                 175

Pro Ala Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Glu Phe Asp
            195                 200                 205

Val Ala Leu Ser Leu His Ser Ala Thr
            210                 215

<210> SEQ ID NO 156
<211> LENGTH: 231
<212> TYPE: PRT
<213> ORGANISM: Asplenium bulbiferum (G.Forst.)

<400> SEQUENCE: 156

Met Arg Met Gly Arg Ser Thr Ser Cys Met Gly Ala Asn Met Ala Phe
1               5                   10                  15

Met Leu Leu Leu Leu Leu Phe Trp Ala Ser Cys Cys Cys Leu Leu Gly
                20                  25                  30

Lys Val Ser Gly His Gly Ser Met Glu Asp Pro Ile Ser Arg Val Tyr
            35                  40                  45

Ala Cys Phe Leu Glu Asn Pro Glu Arg Pro Thr Ser Ala Ala Cys Gln
        50                  55                  60

Ala Ala Val Ala Leu Ser Gly Thr Gln Ala Phe Tyr Asp Trp Asn Glu
65                  70                  75                  80

Val Asn Gln Pro Asn Ala Ala Gly Arg His Arg Glu Ile Ile Pro Asp
                85                  90                  95

Gly Gln Leu Cys Ser Gly Gly Arg Glu Lys Tyr Gln Gly Leu Asp Leu
            100                 105                 110

Ala Arg Asp Asp Trp Thr Ala Thr Ser Leu Ser Pro Asn Val Ser Phe
            115                 120                 125

Thr Phe Leu Tyr Lys Ala Thr Ala Pro His Arg Gly Phe Phe Glu Phe
        130                 135                 140

Tyr Val Thr Arg Asp Gly Tyr Asp Pro Thr Glu Ala Leu Thr Trp Ala
145                 150                 155                 160

Asp Leu Glu Glu Pro Pro Phe Ile Asn Val Thr Asp Pro Thr Val Ala
                165                 170                 175

Ser Gly Ala Tyr Gln Ile Pro Gly Thr Thr Pro Ala Gly Lys Thr Gly
            180                 185                 190

Arg His Leu Ile Tyr Val Ile Trp Gln Arg Ser Asp Ser Pro Glu Ala
        195                 200                 205

Phe Tyr Ser Cys Ser Asp Val Asp Phe Glu Ser Ala Asp Thr Val Asn
        210                 215                 220

Ile Ser Leu Arg Ser Thr Thr
225                 230
```

```
<210> SEQ ID NO 157
<211> LENGTH: 221
<212> TYPE: PRT
<213> ORGANISM: Athyrium filix-femina

<400> SEQUENCE: 157
```

| | | | | | | | | | | | | | | |
|---|---|---|---|---|---|---|---|---|---|---|---|---|---|---|
|Met|Gly|Arg|Ser|Trp|Gly|Val|Val|Ala|Ile|Leu|Met|Val|Leu|Cys|Gly
1| | | |5| | | | |10| | | | |15|

Cys Leu Leu Gly Val Ala Ser Gly His Gly Ser Met Glu Asp Pro Ile
            20                  25                  30

Ser Arg Val Tyr Asn Cys Tyr Leu Glu Asn Pro Glu Ser Pro Thr Ser
        35                  40                  45

Ala Ala Cys Gln Ala Ala Val Ala Leu Gly Gly Pro Gln Pro Phe Tyr
    50                  55                  60

Asp Trp Asn Glu Val Asn Gln Pro Asn Ala Asp Gly His Ser Arg Glu
65                  70                  75                  80

Ile Ile Pro Asp Gly Gln Leu Cys Ser Gly Gly Arg Glu Lys Tyr Lys
                85                  90                  95

Gly Leu Asp Leu Ala Arg Ser Asp Trp Thr Ala Thr Ser Leu Ser Ser
            100                 105                 110

Gly Val Ala Phe Thr Phe Leu Phe Lys Ala Thr Ala Pro His Ala Gly
        115                 120                 125

Phe Phe Glu Phe Tyr Val Thr Gln Asp Gly Tyr Asp Pro Thr Glu Pro
    130                 135                 140

Leu Lys Trp Ala Asp Leu Glu Asp Ser Pro Phe Ile Asn Val Thr Asp
145                 150                 155                 160

Pro Thr Leu Leu Ser Gly Ser Tyr Gln Ile Pro Gly Thr Thr Pro Ala
                165                 170                 175

Gly Lys Ser Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Leu Ser Ser Asp Leu His Ser Thr Met Ala Pro Ile Ala
    210                 215                 220

```
<210> SEQ ID NO 158
<211> LENGTH: 231
<212> TYPE: PRT
<213> ORGANISM: Adiantum capillus-veneris

<400> SEQUENCE: 158
```

Met Gly Met Lys Met Ser Trp Glu Val Ala Leu Ala Glu Ile Val Ala
1               5                   10                  15

Leu Cys Leu Leu Gly Met Ala Ser Ser His Gly Thr Met Gln Asp Pro
            20                  25                  30

Ile Ser Arg Val Tyr Asn Cys Phe Leu Glu Asn Pro Glu Arg Pro Thr
        35                  40                  45

Ser Ala Ala Cys Gln Ala Ala Val Ala Leu Gly Gly Thr Gln Pro Leu
    50                  55                  60

Tyr Asp Trp Asn Glu Val Asn Ile His Asp Ala Gly Asn His Arg
65                  70                  75                  80

Asp Leu Ile Pro Asp Gly Lys Leu Cys Ser Ala Gly Arg Gln Lys Phe
                85                  90                  95

Gln Gly Leu Asp Leu Ala Arg Ala Asp Trp Ile Ala Thr Ser Leu Ser
            100                 105                 110

Ser Gly Val Asp Val Asp Tyr Thr Phe Leu Tyr Arg Ala Thr Ala Pro

```
            115                 120                 125
His Leu Gly Phe Phe Glu Phe Tyr Ile Thr Arg Asp Thr Tyr Asp Pro
        130                 135                 140

Thr Gln Pro Leu Ala Trp Gly Asp Leu Glu Asp Ser Pro Phe Ile Asn
145                 150                 155                 160

Ile Thr Asn Pro Ser Ile Val Ser Thr Thr Leu Gly Pro Ala Tyr Ser
                165                 170                 175

Ile Pro Ser Thr Thr Pro Phe Ser Lys Ser Gly Arg His Leu Ile Tyr
            180                 185                 190

Val Ile Trp Gln Arg Thr Asp Ser Leu Glu Ala Phe Tyr Ser Cys Ser
        195                 200                 205

Asp Val Asp Phe Ser Thr Ser Ser Ile Glu Asp Val Ile Val Ser
    210                 215                 220

Leu Arg Ser Ala Ala Leu Leu
225                 230

<210> SEQ ID NO 159
<211> LENGTH: 231
<212> TYPE: PRT
<213> ORGANISM: Asplenium nidus var plicatum

<400> SEQUENCE: 159

Met Arg Met Gly Arg Ser Ile Ser Arg Met Ala Ala Arg Met Ala Ile
1               5                   10                  15

Met Leu Val Leu Cys Trp Ala Ile Ser Cys Cys Leu Leu Gly Thr Val
            20                  25                  30

Ser Gly His Gly Ser Ser Glu Asp Pro Met Ser Arg Val Tyr Gly Cys
        35                  40                  45

Tyr Leu Gln Asn Pro Glu Arg Pro Ala Ser Ala Ala Cys Arg Ala Ala
    50                  55                  60

Val Ala Met Ser Gly Thr Gln Ala Phe Tyr Asp Trp Asn Glu Val Asn
65                  70                  75                  80

Gln Pro His Ala Ala Gly Arg His Arg Glu Ile Ile Pro Asp Gly Gln
                85                  90                  95

Leu Cys Gly Gly Gly Arg Ala Lys Tyr Arg Gly Leu Asn Leu Ala Arg
            100                 105                 110

Ala Asp Trp Trp Ser Thr Pro Leu Tyr Ser Asn Thr Pro Phe Met Phe
        115                 120                 125

Leu Tyr Arg Ala Thr Ala Pro His Arg Gly Phe Phe Glu Phe Tyr Val
    130                 135                 140

Thr Arg Asp Gly Tyr Asp Pro Thr Glu Pro Leu Lys Trp Ser Asp Leu
145                 150                 155                 160

Glu Tyr Pro Pro Phe Ile Asn Val Thr Asp Pro Thr Leu Ala Phe Gly
                165                 170                 175

Ala Tyr Lys Ile Pro Gly Phe Thr Pro Tyr Gly Lys Thr Gly Arg His
            180                 185                 190

Leu Ile Tyr Ile Ile Trp Gln Arg Ser Asp Ser Pro Glu Ala Phe Tyr
        195                 200                 205

Ser Cys Ser Asp Val Asp Phe Val Asp Phe Lys Ser Asp Glu Thr Val
    210                 215                 220

Ile Pro Leu His Ser Thr Thr
225                 230

<210> SEQ ID NO 160
<211> LENGTH: 215
```

<212> TYPE: PRT
<213> ORGANISM: Polystichum polyblepharum

<400> SEQUENCE: 160

Met Gly Arg Ser Trp Gly Val Val Ala Ile Met Val Leu Cys Ala Ser
1               5                   10                  15

Gly Leu Leu Asp Val Ala Ser Gly His Gly Ser Met Asn Asp Pro Ile
            20                  25                  30

Ser Arg Val Tyr Asn Cys Arg Leu Glu Asn Pro Glu Ser Pro Thr Ser
        35                  40                  45

Asp Ala Cys Ile Ala Ala Val Ala Leu Ser Gly Thr Gln Ala Phe Tyr
    50                  55                  60

Asp Trp Asn Glu Val Asn Leu Pro Asn Ala Ala Gly Arg His Arg Glu
65                  70                  75                  80

Leu Ile Pro Asp Gly Lys Leu Cys Ser Ala Gly Arg Asp Lys Tyr Lys
                85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Gln His Arg Gly
        115                 120                 125

Phe Phe Glu Phe Tyr Val Thr Val Asp Asp Tyr Asp Pro Thr Glu Leu
    130                 135                 140

Leu Lys Trp Glu Asp Leu Glu Glu Thr Pro Phe Met Asn Val Thr Asp
145                 150                 155                 160

Pro Thr Val Val Gly Val Asn Tyr Glu Met Ala Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Val Ser Leu His Ser Ser Thr
    210                 215

<210> SEQ ID NO 161
<211> LENGTH: 215
<212> TYPE: PRT
<213> ORGANISM: Adiantum venustum

<400> SEQUENCE: 161

Met Gly Arg Ser Trp Gly Asp Val Val Ala Ile Met Val Leu Cys Ala
1               5                   10                  15

Ser Gly Leu Leu Gly Val Ala Ser Gly His Gly Ser Met Gln Asp Pro
            20                  25                  30

Ile Ser Arg Val Tyr Asn Cys Tyr Leu Glu Gly Pro Glu Ser Pro Thr
        35                  40                  45

Ser Ala Ala Cys Ile Ala Ala Val Ala Leu Ser Gly Thr Gln Ala Phe
    50                  55                  60

Tyr Asp Trp Asn Glu Val Asn Gln Pro Asn Ala Ala Gly Arg His Arg
65                  70                  75                  80

Glu Ile Ile Pro Asp Gly Gln Leu Cys Ser Gly Gly Arg Asp Lys Tyr
                85                  90                  95

Ser Gly Leu Asp Leu Ala Arg Ser Asp Trp Thr Ala Thr Ser Leu Ser
            100                 105                 110

Ser Asn Val Ser Tyr Thr Tyr Leu Phe Lys Ala Thr Ala Pro His Lys
        115                 120                 125

Gly Phe Phe Glu Phe Tyr Val Thr Arg Asp Ser Tyr Glu Pro Thr Glu
            130                 135                 140

Ala Leu Lys Trp Ala Asp Leu Glu Asp Ser Pro Phe Ile Asn Ile Thr
145                 150                 155                 160

Asp Pro Thr Leu Asp Ser Gly Ala Tyr Gln Ile Pro Gly Thr Thr Pro
                165                 170                 175

Ala Gly Lys Ser Gly Arg His Leu Ile Tyr Val Ile Trp Gln Arg Ser
            180                 185                 190

Asp Ser Gly Glu Ala Phe Tyr Ala Cys Cys Asp Val Asp Phe Asp Val
            195                 200                 205

Asp Val Leu His Ser Thr Thr
            210                 215

<210> SEQ ID NO 162
<211> LENGTH: 233
<212> TYPE: PRT
<213> ORGANISM: Actiniopteris australis

<400> SEQUENCE: 162

Met Arg Gln Gly Ser Ser Ile Ala Asp Met Ser Val Arg Met Gly Gly
1               5                   10                  15

Val Asn Ala Val Ala Ile Ile Leu Leu Leu Cys Cys Ala Ser Ser Gly
            20                  25                  30

Leu Leu Gly Ile Ala Arg Gly His Gly Ser Met Gln Asp Pro Ile Ser
        35                  40                  45

Arg Val Tyr Ala Cys Tyr Leu Glu Asn Pro Glu Arg Pro Thr Ser Ala
    50                  55                  60

Ala Cys Gln Ala Ala Val Ala Leu Ser Gly Thr Gln Ala Phe Tyr Asp
65                  70                  75                  80

Trp Asn Glu Val Asn Gln Pro Phe Ala Ala Gly Arg His Arg Glu Ile
                85                  90                  95

Ile Pro Asp Gly Gln Leu Cys Ser Gly Gly Arg Thr Lys Tyr Ala Gly
            100                 105                 110

Leu Asp Leu Ala Arg Asp Asp Trp Thr Ala Thr Ser Leu Ser Ala Gly
        115                 120                 125

Ile Ser Tyr Thr Phe Leu Tyr Arg Gly Thr Ala Pro His Leu Gly Phe
    130                 135                 140

Phe Glu Phe Tyr Val Thr Arg Asp Gly Tyr Asp Pro Thr Glu Pro Leu
145                 150                 155                 160

Lys Trp Ala Asp Leu Glu Asp Pro Pro Phe Ile Asn Ile Thr Asn Pro
                165                 170                 175

Thr Leu Val Ser Gly Val Tyr Gln Ile Pro Gly Thr Thr Pro Ala Gly
            180                 185                 190

Lys Thr Gly Arg His Leu Ile Tyr Val Ile Trp Gln Arg Thr Asp Ser
        195                 200                 205

Pro Glu Ala Phe Tyr Ser Cys Ser Asp Val Val Phe Ser Asp Asp Ala
    210                 215                 220

Ala Leu Tyr Leu Arg Ser Thr Thr Glu
225                 230

<210> SEQ ID NO 163
<211> LENGTH: 231
<212> TYPE: PRT
<213> ORGANISM: Marsilea crenata

<400> SEQUENCE: 163

```
Met Arg Arg Ser Gly Met Ser Ser Val Leu Ala Ala Val Ala Ala
1               5                   10                  15

Gly Val Leu Leu Val Ala Ala Leu Gly Ser His Val Ala Tyr Gly His
                20                  25                  30

Gly Ser Met Lys Glu Pro Ile Ser Arg Ala Tyr Asn Cys Tyr Leu Glu
            35                  40                  45

Ile Ala Asp Asn Ala Thr Ser Asp Ala Cys Gly Ala Ala Ala Ala Leu
50                  55                  60

Cys Ile Pro Glu Ala Phe Asn Asp Trp Asn Ala Val Leu Ile Pro Asp
65                  70                  75                  80

Val Ala Gly Arg His Arg Gln Leu Ile Pro Asp Gly Gln Leu Cys Ser
                85                  90                  95

Ala Gly Arg Ala Lys Tyr Ala Gly Leu Asn Leu Ala Ser Val Asp Trp
            100                 105                 110

Glu Ala Ala Thr Leu Ala Ala Gly Val Asn Tyr Thr Phe Leu Tyr Lys
            115                 120                 125

Ala Val Val Val His Lys Gly Tyr Phe Glu Phe Tyr Val Thr Lys Asp
        130                 135                 140

Gly Tyr Asp Ala Thr Gln Ala Leu Thr Trp Ser Asp Leu Glu Asp Ala
145                 150                 155                 160

Pro Phe Val Asn Val Thr Asp Pro Ile Val Asn Ser Asp Ser Asp Phe
                165                 170                 175

Glu Ile Pro Gly Thr Ile Pro Ser Gly Lys Ser Gly Arg His Val Ile
            180                 185                 190

Tyr Val Ile Trp Gln Arg Thr Asp Ser Pro Glu Ala Phe Tyr Ser Cys
        195                 200                 205

Ser Asp Val Asp Phe Asp Asp Thr Ile Ser Asp Thr Ile Ser Asp
        210                 215                 220

Thr Val Leu His Ala Ser Ser
225                 230

<210> SEQ ID NO 164
<211> LENGTH: 229
<212> TYPE: PRT
<213> ORGANISM: Asplenium prolongatum x Asplenium antiquum (Kurata)

<400> SEQUENCE: 164

Met Arg Met Gly Arg Ser Ala Ser Cys Ile Arg Ala Asn Met Ala Ile
1               5                   10                  15

Met Leu Val Leu Phe Trp Ala Ser Cys Cys Leu Leu Gly Ile Val
                20                  25                  30

Ser Gly His Gly Ser Met Glu Asp Pro Ile Ser Arg Val Tyr Ala Cys
            35                  40                  45

Tyr Leu Glu Asn Pro Glu Arg Pro Thr Ser Ala Ala Cys Ile Ala Ala
        50                  55                  60

Val Ala Leu Ser Gly Thr Gln Ala Phe Tyr Asp Trp Asn Glu Val Asn
65                  70                  75                  80

Gln Pro Asn Ala Ala Gly Arg His Arg Glu Ile Ile Pro Asp Gly Gln
                85                  90                  95

Leu Cys Ser Gly Gly Arg Glu Lys Tyr Gln Gly Leu Asp Leu Ala Arg
            100                 105                 110

Ala Asp Trp Thr Ala Thr Ser Leu Thr Ser Gly Ile Thr Phe Thr Phe
            115                 120                 125

Leu Tyr Lys Ala Thr Ala Pro His Arg Gly Phe Glu Phe Tyr Val
        130                 135                 140
```

```
Thr Arg Asp Thr Tyr Asp Pro Thr Glu Pro Leu Thr Trp Ala Asp Leu
145                 150                 155                 160

Glu Asp Thr Pro Phe Ile Asn Ala Thr Asp Pro Thr Leu Ala Ser Gly
                165                 170                 175

Ser Tyr Gln Ile Pro Gly Thr Thr Pro Ala Gly Lys Thr Gly Arg His
            180                 185                 190

Leu Ile Tyr Val Ile Trp Gln Arg Ser Asp Ser Pro Glu Ala Phe Tyr
            195                 200                 205

Ser Cys Ser Asp Val Asp Phe Glu Ser Ser Asp Thr Val Ile Ser Leu
            210                 215                 220

Arg Ser Ala Thr Thr
225
```

```
<210> SEQ ID NO 165
<211> LENGTH: 229
<212> TYPE: PRT
<213> ORGANISM: Adiantum raddianum (Fritz Luthi)

<400> SEQUENCE: 165

Met Gly Met Lys Met Ser Trp Glu Val Ala Leu Ala Glu Ile Val Ala
1               5                   10                  15

Leu Cys Leu Leu Gly Met Ala Ser Ser His Gly Thr Met Gln Asp Pro
                20                  25                  30

Ile Ser Arg Val Tyr Asn Cys Phe Leu Glu Asn Pro Glu Arg Pro Thr
            35                  40                  45

Ser Ala Ala Cys Gln Ala Val Ala Leu Gly Gly Thr Gln Pro Leu
        50                  55                  60

Tyr Asp Trp Asn Glu Val Asn Ile His Asp Ala Ala Gly Asn His Arg
65                  70                  75                  80

Asp Leu Ile Pro Asp Gly Lys Leu Cys Ser Ala Gly Arg Gln Lys Phe
                85                  90                  95

Gln Gly Leu Asp Leu Ala Arg Ala Asp Trp Ile Ala Thr Ser Leu Ser
            100                 105                 110

Ser Gly Val Asp Tyr Thr Phe Leu Tyr Arg Ala Thr Ala Pro His Leu
            115                 120                 125

Gly Phe Phe Glu Phe Tyr Ile Thr Arg Asp Thr Tyr Asp Pro Thr Gln
        130                 135                 140

Pro Leu Ala Trp Gly Asp Leu Glu Asp Ser Pro Phe Ile Asn Ile Thr
145                 150                 155                 160

Asn Pro Ser Ile Val Ser Thr Thr Leu Gly Pro Ala Tyr Ser Ile Pro
                165                 170                 175

Ser Thr Thr Pro Phe Ser Lys Ser Gly Arg His Leu Ile Tyr Val Ile
            180                 185                 190

Trp Gln Arg Thr Asp Ser Leu Glu Ala Phe Tyr Ser Cys Ser Asp Val
            195                 200                 205

Asp Phe Ser Thr Ser Ile Glu Asp Val Ile Val Ser Leu Arg
        210                 215                 220

Ser Ala Ala Leu Leu
225
```

```
<210> SEQ ID NO 166
<211> LENGTH: 227
<212> TYPE: PRT
<213> ORGANISM: Asplenium australasicum

<400> SEQUENCE: 166
```

Met Arg Met Gly Arg Ser Thr Ser Arg Met Ala Ala Arg Met Ala Ile
1               5                   10                  15

Thr Leu Leu Leu Cys Trp Ala Ser Cys Cys Leu Leu Gly Thr Val Ser
            20                  25                  30

Gly His Gly Ser Met Leu Asp Pro Ile Ser Arg Ile Tyr Ala Cys Phe
        35                  40                  45

Leu Glu Asn Pro Glu Arg Pro Thr Ser Ala Ala Cys Gln Ala Ala Val
    50                  55                  60

Ala Leu Gly Gly Thr Gln Pro Leu Tyr Asp Trp Asn Glu Val Asn Gln
65                  70                  75                  80

Pro Asn Ala Ala Gly Arg His Arg Glu Ile Ile Pro Asp Gly Gln Leu
                85                  90                  95

Cys Gly Gly Arg Glu Lys Tyr Gln Gly Leu Asn Leu Ala Arg Ala
            100                 105                 110

Asp Trp Pro Ala Thr Ser Leu Ser Ser Asn Thr Ala Phe Thr Phe Leu
            115                 120                 125

Tyr Ile Ala Thr Ala Pro His Arg Gly Phe Phe Glu Phe Tyr Val Thr
    130                 135                 140

Arg Asp Gly Tyr Asp Pro Thr Glu Leu Leu Lys Trp Ala Asp Leu Glu
145                 150                 155                 160

Tyr Pro Pro Phe Leu Asn Val Thr Asp Pro Thr Leu Ala Ser Gly Asn
                165                 170                 175

Tyr Gln Ile Pro Gly Thr Thr Pro Ala Gly Lys Thr Gly Arg His Leu
            180                 185                 190

Ile Tyr Val Ile Trp Gln Arg Ser Asp Ser Pro Glu Ala Phe Tyr Ser
        195                 200                 205

Cys Ser Asp Ile Asp Phe Glu Ser Asp Glu Thr Val Ile Ser Leu His
210                 215                 220

Ser Thr Thr
225

<210> SEQ ID NO 167
<211> LENGTH: 227
<212> TYPE: PRT
<213> ORGANISM: Asplenium australasicum

<400> SEQUENCE: 167

Met Arg Met Gly Arg Ser Thr Ser Arg Met Ala Ala Arg Met Ala Ile
1               5                   10                  15

Thr Leu Leu Leu Cys Trp Ala Ser Cys Cys Leu Leu Gly Thr Val Ser
            20                  25                  30

Gly His Gly Ser Met Leu Asp Pro Ile Ser Arg Ile Tyr Ala Cys Phe
        35                  40                  45

Leu Glu Asn Pro Glu Arg Pro Thr Ser Ala Ala Cys Gln Ala Ala Val
    50                  55                  60

Ala Leu Gly Gly Thr Gln Pro Leu Tyr Asp Trp Asn Glu Val Asn Gln
65                  70                  75                  80

Pro Asn Ala Ala Gly Arg His Arg Glu Ile Ile Pro Asp Gly Gln Leu
                85                  90                  95

Cys Ser Gly Gly Arg Glu Lys Tyr Lys Gly Phe Asp Leu Pro Arg Ala
            100                 105                 110

Asp Trp Pro Ala Thr Thr Leu Val Ser Asn Ile Ser Phe Thr Tyr Leu
            115                 120                 125

Tyr Lys Ala Thr Ala Pro His Arg Gly Phe Phe Glu Phe Tyr Val Thr

```
Arg Asp Gly Tyr Asp Pro Thr Glu Leu Leu Lys Trp Ala Asp Leu Glu
145                 150                 155                 160

Tyr Pro Pro Phe Leu Asn Val Thr Asp Pro Thr Leu Ala Ser Gly Asn
                165                 170                 175

Tyr Gln Ile Pro Gly Thr Thr Pro Ala Gly Lys Thr Gly Arg His Leu
            180                 185                 190

Ile Tyr Val Ile Trp Gln Arg Ser Asp Ser Pro Glu Ala Phe Tyr Ser
        195                 200                 205

Cys Ser Asp Ile Asp Phe Glu Ser Asp Glu Thr Val Ile Ser Leu His
    210                 215                 220

Ser Ile Thr
225

<210> SEQ ID NO 168
<211> LENGTH: 216
<212> TYPE: PRT
<213> ORGANISM: Thelypteris palustris

<400> SEQUENCE: 168

Met Gly Arg Ser Trp Gly Val Val Gly Ile Met Val Leu Cys Leu Leu
1               5                   10                  15

Gly Val Ala Ser Gly His Gly Thr Met Gln Asp Pro Ile Ser Arg Val
            20                  25                  30

Tyr Asn Cys Arg Leu Glu Asn Pro Glu Arg Pro Thr Ser Ala Ala Cys
        35                  40                  45

Ile Ala Ala Val Ala Leu Ser Gly Thr Gln Ala Phe Tyr Asp Trp Asn
    50                  55                  60

Glu Val Asn Leu Ala Asn Ala Ala Gly Arg His Arg Glu Leu Ile Pro
65                  70                  75                  80

Asp Gly Gln Leu Cys Ser Ala Gly Arg Val Lys Tyr Gln Gly Leu Asp
                85                  90                  95

Leu Ala Arg Ser Asp Trp Thr Ala Thr Ser Leu Ser Ser Gly Val Ser
            100                 105                 110

Phe Thr Phe Leu Tyr Arg Val Thr Ala Gln His Leu Gly Phe Phe Glu
        115                 120                 125

Phe Tyr Val Thr Gln Asp Gly Tyr Asp Pro Thr Glu Pro Leu Lys Trp
    130                 135                 140

Ala Asp Leu Glu Asp Ser Pro Phe Ile Asn Val Thr Asn Pro Thr Val
145                 150                 155                 160

Val Ser Thr Ser Leu Gly Pro Ala Tyr Gln Ile Ala Gly Thr Thr Pro
                165                 170                 175

Ala Gly Lys Ser Gly Arg His Leu Ile Tyr Val Ile Trp Gln Arg Ser
            180                 185                 190

Asp Ser Pro Glu Ala Phe Tyr Ser Cys Ser Asp Val Asp Phe Val Asp
        195                 200                 205

Ala Leu Ser Leu His Ser Thr Ala
    210                 215

<210> SEQ ID NO 169
<211> LENGTH: 230
<212> TYPE: PRT
<213> ORGANISM: Asplenium dimorphum x Asplenium difforme

<400> SEQUENCE: 169

Met Arg Met Gly Arg Ser Thr Ser Cys Met Gly Ala Asn Met Ala Ile
```

```
 1               5                  10                 15
Val Leu Leu Leu Leu Phe Trp Ala Ser Cys Cys Leu Leu Gly
            20                  25                  30

Lys Val Ser Gly His Gly Ser Met Glu Asp Pro Ile Ser Arg Val Tyr
            35                  40                  45

Ala Cys Phe Leu Glu Asn Pro Glu Arg Pro Thr Ser Ala Ala Cys Gln
 50                  55                  60

Ala Ala Val Ala Leu Ser Gly Thr Gln Ala Phe Tyr Asp Trp Asn Glu
 65                  70                  75                  80

Val Asn Leu Pro Asn Ala Ala Gly Arg His Arg Glu Ile Ile Pro Asp
                85                  90                  95

Gly Gln Leu Cys Ser Gly Gly Arg Glu Lys Tyr Lys Gly Leu Asp Leu
            100                 105                 110

Ala Arg Ala Asp Trp Thr Ala Thr Ser Leu Ser Pro Asn Val Ser Phe
            115                 120                 125

Thr Phe Leu Tyr Lys Gly Thr Ala Pro His Arg Gly Phe Phe Glu Phe
            130                 135                 140

Tyr Val Thr Arg Asp Gly Tyr Asp Pro Thr Glu Ala Leu Thr Trp Ala
145                 150                 155                 160

Asp Leu Glu Glu Pro Pro Phe Ile Asn Val Thr Asp Pro Thr Leu Ala
                165                 170                 175

Ser Gly Ala Tyr Gln Ile Pro Gly Thr Thr Pro Ala Gly Lys Thr Gly
            180                 185                 190

Arg His Leu Ile Tyr Val Ile Trp Gln Arg Ser Asp Ser Pro Glu Ala
            195                 200                 205

Phe Tyr Ser Cys Ser Asp Val Asp Phe Glu Ser Asp Asp Thr Val Val
210                 215                 220

Ser Leu Arg Ser Thr Thr
225                 230

<210> SEQ ID NO 170
<211> LENGTH: 215
<212> TYPE: PRT
<213> ORGANISM: Matteuccia struthiopteris

<400> SEQUENCE: 170

Met Gly Arg Ser Trp Gly Val Val Ala Ile Met Val Leu Cys Ala Ser
 1               5                  10                  15

Ser Leu Leu Gly Val Val Ser Gly His Gly Ser Met Ala Asp Pro Ile
            20                  25                  30

Ser Arg Val Tyr Gly Cys Arg Leu Glu Gly Pro Glu Ser Pro Thr Ser
            35                  40                  45

Ala Ala Cys Gln Ala Ala Val Ala Leu Ser Gly Thr Gln Ala Phe Tyr
 50                  55                  60

Asp Trp Asn Glu Val Asn Gln Pro Phe Ala Ala Gly Arg His Arg Glu
 65                  70                  75                  80

Leu Ile Pro Asp Gly Gln Leu Cys Ser Gly Gly Arg Val Lys Tyr Gln
                85                  90                  95

Gly Leu Asp Leu Ala Arg Ser Asp Trp Pro Ala Thr Asn Leu Ser Ser
            100                 105                 110

Gly Val Ser Phe Thr Phe Leu Tyr Glu Val Thr Ala Thr His Leu Gly
            115                 120                 125

Tyr Phe Glu Phe Tyr Val Thr Arg Asp Gly Tyr Gln Pro Thr Glu Pro
            130                 135                 140
```

Leu Lys Trp Ala Asp Leu Glu Asp Ser Pro Phe Leu Thr Ala Thr Thr
145                 150                 155                 160

Thr His Glu Ser Ser Ser Tyr Ile Ile Pro Gly Thr Pro Ser Ala
            165                 170                 175

Lys Ser Gly Arg His Leu Ile Tyr Leu Ile Trp Gln Arg Thr Asp Ser
            180                 185                 190

Pro Glu Ala Phe Tyr Ser Cys Ser Asp Val Asp Phe Val Asp Ala Leu
            195                 200                 205

Ser Ser Leu His Ser Thr Asn
    210                 215

<210> SEQ ID NO 171
<211> LENGTH: 217
<212> TYPE: PRT
<213> ORGANISM: Athyrium filix-femina (angustum)

<400> SEQUENCE: 171

Met Gly Arg Ser Trp Gly Val Val Ala Ile Leu Met Val Leu Cys Gly
1               5                   10                  15

Cys Leu Leu Gly Val Ala Ser Gly His Gly Ser Met Glu Asp Pro Ile
                20                  25                  30

Ser Arg Val Tyr Asn Cys Tyr Leu Glu Asn Pro Glu Ser Pro Thr Ser
            35                  40                  45

Ala Ala Cys Gln Ala Ala Val Ala Leu Gly Gly Thr Gln Pro Leu Tyr
        50                  55                  60

Asp Trp Asn Glu Val Asn Gln Pro Asn Ala Ala Gly Gln Ser Arg Glu
65                  70                  75                  80

Ile Ile Pro Asp Gly Gln Leu Cys Ser Gly Gly Arg Glu Lys Tyr Gln
                85                  90                  95

Gly Leu Asp Leu Ala Arg Ser Asp Trp Thr Ala Thr Ser Leu Ser Ser
            100                 105                 110

Gly Val Ala Phe Thr Phe Leu Phe Lys Ala Thr Ala Pro His Leu Gly
        115                 120                 125

Phe Phe Glu Phe Tyr Val Thr Gln Asp Gly Tyr Asp Pro Thr Glu Pro
130                 135                 140

Leu Lys Trp Ala Asp Leu Glu Asp Ser Pro Phe Ile Asn Val Thr Asp
145                 150                 155                 160

Pro Thr Leu Leu Ser Gly Ser Tyr Gln Ile Pro Gly Thr Thr Pro Ala
                165                 170                 175

Gly Lys Ser Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Leu Ser Ser Asp Leu His Ser Thr Thr
    210                 215

<210> SEQ ID NO 172
<211> LENGTH: 228
<212> TYPE: PRT
<213> ORGANISM: Adiantum pubescens (Bronze)

<400> SEQUENCE: 172

Met Lys Lys Ser Trp Gly Val Thr Ala Val Val Gly Val Ile Ala Leu
1               5                   10                  15

Cys Leu Leu Asp Val Ala Ser Gly His Gly Ser Met Gln Asp Pro Ile
                20                  25                  30

```
Ser Arg Val Tyr Asn Cys Phe Leu Glu Asn Pro Glu Arg Pro Thr Ser
         35                  40                  45

Ala Ala Cys Ile Ala Ala Val Ala Met Ser Gly Thr Gln Pro Phe Tyr
 50                      55                  60

Asp Trp Asn Glu Val Asn Leu Ala Asp Ala Asn Gly Arg His Arg Glu
 65                  70                  75                  80

Leu Ile Pro Asp Gly Lys Leu Cys Ser Ala Gly Arg Asp Lys Tyr Gln
                 85                  90                  95

Gly Leu Asp Gln Ala Arg Asp Asp Trp Val Ala Thr Ser Leu Ser Ser
             100                 105                 110

Gly Val Ala Tyr Thr Phe Leu Tyr Arg Val Thr Ala Pro His Leu Gly
             115                 120                 125

Phe Phe Glu Phe Tyr Val Thr Arg Asp Thr Tyr Asp Pro Thr Gln Ala
 130                 135                 140

Leu Ala Trp Asp Asp Leu Glu Asp Ser Pro Phe Ile Asn Ile Thr Asn
 145                 150                 155                 160

Pro Ser Val Val Ser Thr Thr Leu Gly Asn Ala Tyr Ser Ile Pro Gly
                 165                 170                 175

Thr Thr Pro Ser Gly Lys Thr Gly Arg His Leu Ile Tyr Val Ile Trp
             180                 185                 190

Gln Arg Ser Asp Ser Arg Glu Ala Phe Tyr Ser Cys Ser Asp Val Asp
             195                 200                 205

Phe Pro Ala Ser Thr Val Glu Asp Val Ile Ile Ser Leu Arg Ser
 210                 215                 220

Ala Ala Leu Val
225

<210> SEQ ID NO 173
<211> LENGTH: 215
<212> TYPE: PRT
<213> ORGANISM: Blechnum niponicum

<400> SEQUENCE: 173

Met Gly Arg Ser Trp Gly Val Val Ala Ile Met Val Leu Cys Ala Ser
 1               5                  10                  15

Gly Leu Leu Gly Val Ala Ser Gly His Gly Ser Met Asp Asp Pro Ile
             20                  25                  30

Ser Arg Val Tyr Asn Cys Tyr Leu Glu Asn Pro Glu Arg Pro Thr Ser
         35                  40                  45

Ala Ala Cys Gln Ala Ala Val Ala Leu Ser Gly Thr Gln Ala Phe Tyr
 50                      55                  60

Asp Trp Asn Glu Val Asn Gln Pro Phe Ala Ala Gly Arg His Arg Glu
 65                  70                  75                  80

Ile Ile Pro Asp Gly Gln Leu Cys Ser Gly Gly Arg Glu Lys Tyr Gln
                 85                  90                  95

Gly Leu Asp Leu Ala Arg Ser Asp Trp Thr Ala Thr Ser Leu Ser Ser
             100                 105                 110

Gly Val Ser Phe Thr Tyr Leu Tyr Lys Ala Thr Ala Pro His Leu Gly
             115                 120                 125

Phe Phe Glu Phe Tyr Val Thr Val Asp Gly Tyr Gln Pro Thr Glu Pro
 130                 135                 140

Leu Lys Trp Ser Asp Leu Glu Asp Pro Phe Ile Asn Val Thr Asn
 145                 150                 155                 160

Pro Thr Leu Val Ser Gly Ser Tyr Gln Ile Pro Gly Thr Thr Pro Ala
                 165                 170                 175
```

Gly Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Ala Asp Ala
        195                 200                 205

Leu Ser Leu His Ser Thr Thr
    210                 215

<210> SEQ ID NO 174
<211> LENGTH: 215
<212> TYPE: PRT
<213> ORGANISM: Platycerium wandae

<400> SEQUENCE: 174

Met Gly Lys Pro Trp Arg Val Val Ala Ile Val Val Cys Ala
1               5                   10                  15

Ser Gly Leu Leu Gly Val Ala Ser Gly His Gly Ser Met Gly Glu Pro
            20                  25                  30

Ile Ser Arg Val Tyr Asn Cys Tyr Leu Glu Asn Pro Glu Arg Pro Thr
        35                  40                  45

Ser Ala Ala Cys Ile Ala Ala Val Ala Leu Ser Gly Thr Gln Ala Phe
50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Asp Lys Tyr
                85                  90                  95

Lys Gly Leu Asp Leu Ala Arg Ala Asp Trp Val Ala Thr Ser Leu Ser
            100                 105                 110

Ser Gly Val Ser Tyr Thr Phe Leu Tyr Arg Ala Thr Ala Pro His Gln
        115                 120                 125

Gly Tyr Phe Glu Phe Tyr Val Thr Lys Asp Ser Tyr Asp Pro Thr Glu
    130                 135                 140

Pro Leu Ala Trp Ala Asp Leu Glu Asp Thr Pro Phe Ile Asn Ile Thr
145                 150                 155                 160

Asp Pro Thr Leu Val Ser Gly Ser Tyr Gln Ile Pro Ser Thr Thr Pro
                165                 170                 175

Ser Asp Lys Thr Gly Arg His Leu Ile Tyr Val Ile Trp Gln Arg Thr
            180                 185                 190

Asp Ser Pro Glu Ala Phe Tyr Ser Cys Ser Asp Ile Asp Phe Asp Asp
        195                 200                 205

Thr Leu Pro Leu His Ser Thr
    210                 215

<210> SEQ ID NO 175
<211> LENGTH: 214
<212> TYPE: PRT
<213> ORGANISM: Nephrolepis cordifolia (Duffii)

<400> SEQUENCE: 175

Met Gly Arg Ser Trp Arg Val Val Ala Ile Met Val Val Cys Ala Ser
1               5                   10                  15

Gly Leu Leu Ser Val Val Arg Gly His Gly Ser Met Glu Asp Pro Leu
            20                  25                  30

Ser Arg Val Tyr Gly Cys Phe Leu Glu Asn Pro Glu Ser Pro Thr Ser
        35                  40                  45

Ala Ala Cys Gln Ala Ala Val Ala Met Ser Gly Thr Leu Ala Phe Tyr
50                  55                  60

```
Asp Trp Phe Asp Val Ser Leu Pro Asn Ala Ser Gly Arg His Arg Glu
65                  70                  75                  80

Leu Ile Pro Asp Gly Gln Leu Cys Gly Ala Gly Leu Thr Lys Tyr Gln
                85                  90                  95

Gly Leu Asn Leu Ala Arg Asp Asp Trp Thr Ala Thr Ser Leu Thr Ser
            100                 105                 110

Gly Val Ser Phe Thr Tyr Leu Tyr Lys Ala Ala Arg His Leu Gly
            115                 120                 125

Phe Phe Glu Phe Tyr Val Thr Arg Asp Gly Tyr Asp Pro Thr Glu Pro
130                 135                 140

Leu Lys Trp Ala Asp Leu Glu Asp Leu Pro Phe Met Asn Val Thr Ser
145                 150                 155                 160

Thr Leu Asp Glu Glu Ser Tyr Gln Ile Pro Gly Thr Thr Pro Ser Gly
                165                 170                 175

Lys Ala Gly Arg His Leu Ile Tyr Val Ile Trp Gln Arg Ser Asp Ser
            180                 185                 190

Pro Glu Ala Phe Tyr Ser Cys Ser Asp Val Asp Phe Val Asp Ala Val
            195                 200                 205

Ser Leu His Ser Thr Thr
            210
```

```
<210> SEQ ID NO 176
<211> LENGTH: 224
<212> TYPE: PRT
<213> ORGANISM: Adiantum raddianum (Fragrans)

<400> SEQUENCE: 176

Met Gly Met Lys Met Ser Trp Glu Val Ala Leu Ala Glu Ile Val Ala
1               5                   10                  15

Leu Cys Leu Leu Gly Met Ala Ser Ser His Gly Thr Met Gln Asp Pro
                20                  25                  30

Ile Ser Arg Val Tyr Asn Cys Phe Leu Glu Asn Pro Glu Arg Pro Thr
            35                  40                  45

Ser Ala Ala Cys Gln Ala Ala Val Ala Leu Gly Gly Thr Gln Pro Leu
        50                  55                  60

Tyr Asp Trp Asn Glu Val Asn Ile His Asp Ala Ala Gly Asn His Arg
65                  70                  75                  80

Asp Leu Ile Pro Asp Gly Lys Leu Cys Ser Ala Gly Arg Gln Lys Phe
                85                  90                  95

Gln Gly Leu Asp Leu Ala Arg Ala Asp Trp Ile Ala Thr Ser Leu Ser
            100                 105                 110

Ser Gly Val Asp Tyr Thr Phe Leu Tyr Arg Ala Thr Ala Pro His Leu
            115                 120                 125

Gly Phe Phe Glu Phe Tyr Ile Thr Arg Asp Thr Tyr Asp Pro Thr Gln
130                 135                 140

Pro Leu Ala Trp Gly Asp Leu Glu Asp Ser Pro Phe Ile Asn Ile Thr
145                 150                 155                 160

Asn Pro Ser Ile Val Ser Thr Thr Leu Gly Pro Ala Tyr Ser Ile Pro
                165                 170                 175

Ser Thr Thr Pro Phe Ser Lys Ser Gly Arg His Leu Ile Tyr Val Ile
            180                 185                 190

Trp Gln Arg Ser Asp Ser Pro Glu Ala Phe Tyr Ala Cys Ser Asp Ile
            195                 200                 205

Asp Phe Ser Thr Ser Ser Asp Met Ile Ser Leu Arg Ser Ala Val Leu
```

<210> SEQ ID NO 177
<211> LENGTH: 216
<212> TYPE: PRT
<213> ORGANISM: Platycerium bifurcatum (Netherlands)

<400> SEQUENCE: 177

Met Gly Lys Pro Trp Arg Val Val Ala Ile Val Val Cys Ala
1               5                   10                  15

Ser Gly Leu Leu Gly Val Ala Ser Gly His Gly Ser Met Gly Asp Pro
            20                  25                  30

Ile Ser Arg Val Tyr Asn Cys Tyr Leu Glu Asn Pro Glu Arg Pro Thr
        35                  40                  45

Ser Ala Ala Cys Ile Ala Ala Val Ala Leu Ser Gly Thr Gln Ala Phe
    50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Asp Lys Tyr
                85                  90                  95

Lys Gly Leu Asp Leu Ala Arg Ala Asp Trp Val Ala Thr Ser Leu Ser
            100                 105                 110

Ser Gly Val Ser Tyr Thr Phe Leu Tyr Arg Val Thr Ala Pro His Arg
        115                 120                 125

Gly Tyr Phe Glu Phe Tyr Val Thr Lys Asp Ser Tyr Asp Pro Thr Glu
    130                 135                 140

Pro Leu Ala Trp Ala Asp Leu Glu Asp Thr Pro Phe Ile Asn Ile Thr
145                 150                 155                 160

Asp Pro Thr Ile Val Ser Gly Ser Tyr Gln Ile Ser Ser Thr Thr Pro
                165                 170                 175

Ser Asp Lys Thr Gly Arg His Leu Ile Tyr Val Ile Trp Gln Arg Thr
            180                 185                 190

Asp Ser Pro Glu Ala Phe Tyr Ser Cys Ser Asp Val Asp Phe Asp Asp
        195                 200                 205

Thr Leu Pro Leu His Ser Ser Thr
    210                 215

<210> SEQ ID NO 178
<211> LENGTH: 221
<212> TYPE: PRT
<213> ORGANISM: Pyrrosia polydactyla

<400> SEQUENCE: 178

Met Arg Met Gly Met Arg Met Arg Leu Trp Gly Val Val Ala Phe Met
1               5                   10                  15

Val Ala Val Cys Ala Gly Glu Leu Leu Asp Gln Ala Ser Gly His Gly
            20                  25                  30

Ser Met Gly Asp Pro Val Ser Arg Val Leu Asn Cys Tyr Leu Glu Asn
        35                  40                  45

Pro Glu Asn Pro Ser Ser Ala Ala Cys Ile Ala Ala Val Ala Ala Ser
    50                  55                  60

Gly Thr Gln Ala Phe Tyr Asp Trp Asn Glu Val Asn Leu Ala Phe Ala
65                  70                  75                  80

Ala Gly Gln His Arg Thr Leu Ile Pro Asp Gly Glu Leu Cys Ser Ala
                85                  90                  95

Gly Arg Glu Lys Tyr Lys Gly Leu Asn Leu Ala Arg Ala Asp Trp Val

```
                100             105             110
Ala Thr Ser Leu Ser Ser Gly Ala Asn Tyr Thr Phe Leu Tyr Arg Ala
            115                 120                 125

Thr Ala Pro His Leu Gly Tyr Phe Glu Phe Tyr Val Thr Gln Asp Ser
        130                 135                 140

Tyr Asp Pro Thr Glu Pro Leu Ala Trp Ala Asp Leu Glu Asp Ser Pro
145                 150                 155                 160

Phe Ile Asn Val Thr Asn Pro Ala Leu Val Ser Gly Ser Tyr Arg Ile
                165                 170                 175

Ala Gly Thr Thr Pro Ser Gly Lys Thr Gly Arg His Leu Ile Tyr Val
            180                 185                 190

Ile Trp Gln Arg Thr Asp Ser Pro Glu Ala Phe Tyr Ser Cys Ser Asp
        195                 200                 205

Val Asp Phe Asp Glu Ala Val Ser Leu Ser Ser Thr Thr
210                 215                 220
```

<210> SEQ ID NO 179
<211> LENGTH: 222
<212> TYPE: PRT
<213> ORGANISM: Blechnum brasiliense

<400> SEQUENCE: 179

```
Met Lys Lys Pro Trp Gly Val Val Val Ala Ile Leu Leu Leu
1               5                   10                  15

Cys Leu Leu Gly Val Ala Ser Gly His Gly Ser Met Gln Asp Pro Ile
            20                  25                  30

Ser Arg Val Tyr Asn Cys Tyr Leu Glu Asn Pro Glu Arg Pro Thr Ser
        35                  40                  45

Ala Ala Cys Gln Ala Ala Val Ala Met Ser Gly Thr Gln Ala Phe Tyr
    50                  55                  60

Asp Trp Asn Glu Val Asn Leu Ala Asn Ala Ser Gly Arg His Arg Glu
65                  70                  75                  80

Leu Ile Pro Asp Gly Lys Leu Cys Ser Ala Gly Arg Asp Lys Tyr Arg
                85                  90                  95

Gly Leu Asp Leu Ala Arg Ala Asp Trp Thr Ala Thr Ser Leu Ser Ser
            100                 105                 110

Gly Val Ala Tyr Thr Phe Leu His Arg Val Thr Ala Arg His Leu Gly
        115                 120                 125

Phe Phe Glu Phe Tyr Ile Thr Arg Asp Ser Tyr Asp Pro Thr Glu Leu
    130                 135                 140

Leu Thr Trp Ala Asp Leu Glu Asp Ser Pro Phe Ile Asn Ile Thr Asn
145                 150                 155                 160

Pro Thr Thr Val Ser Thr Ser Leu Gly Asn Ala Tyr Gln Ile Pro Gly
                165                 170                 175

Thr Thr Pro Ala Gly Lys Ser Gly Arg His Leu Ile Tyr Val Ile Trp
            180                 185                 190

Gln Arg Ser Asp Ser Pro Glu Ala Phe Tyr Ser Cys Cys Asp Val Asp
        195                 200                 205

Phe Ser Ser Asp Thr Leu Ile Ser Leu Arg Ser Ala Ala Leu
    210                 215                 220
```

<210> SEQ ID NO 180
<211> LENGTH: 222
<212> TYPE: PRT
<213> ORGANISM: Blechnum SP. (Silver Lady)

<400> SEQUENCE: 180

```
Met Lys Lys Pro Trp Gly Val Val Val Ala Ile Leu Leu Leu
1               5                   10                  15

Cys Leu Leu Gly Val Ala Ser Gly His Gly Ser Met Gln Asp Pro Ile
                20                  25                  30

Ser Arg Val Tyr Asn Cys Tyr Leu Glu Asn Pro Glu Arg Pro Thr Ser
            35                  40                  45

Ala Ala Cys Gln Ala Ala Val Ala Met Ser Gly Thr Gln Ala Phe Tyr
50                  55                  60

Asp Trp Asn Glu Val Asn Leu Ala Asn Ala Ser Gly Arg His Arg Glu
65                  70                  75                  80

Leu Ile Pro Asp Gly Lys Leu Cys Ser Ala Gly Arg Asp Lys Tyr Arg
                85                  90                  95

Gly Leu Asp Leu Ala Arg Ala Asp Trp Thr Ala Thr Ser Leu Ser Ser
            100                 105                 110

Gly Val Ala Tyr Thr Phe Leu His Arg Val Thr Ala Arg His Leu Gly
            115                 120                 125

Phe Phe Glu Phe Tyr Ile Thr Arg Asp Ser Tyr Asp Pro Thr Glu Pro
130                 135                 140

Leu Thr Trp Ala Asp Leu Glu Asp Ser Pro Phe Leu Asn Ile Thr Asp
145                 150                 155                 160

Pro Thr Thr Val Gly Thr Pro Leu Gly Asp Ala Tyr Glu Ile Pro Gly
                165                 170                 175

Thr Thr Pro Asp Gly Lys Ser Gly Arg His Leu Ile Tyr Val Ile Trp
            180                 185                 190

Gln Arg Ser Asp Ser Pro Glu Ala Phe Tyr Ser Cys Cys Asp Val Asp
            195                 200                 205

Phe Ser Ser Asp Thr Leu Ile Ser Leu Arg Ser Ala Ala Leu
            210                 215                 220
```

<210> SEQ ID NO 181
<211> LENGTH: 223
<212> TYPE: PRT
<213> ORGANISM: Pteris cretica (Mayi)

<400> SEQUENCE: 181

```
Met Gly Ser Arg Ser Val Gly Gly Gly Ala Gly Ala Ile Tyr Cys
1               5                   10                  15

Met Leu Leu Ile Cys Cys Val Ser Ser Gly Leu Leu Gly Ile Ala Ser
                20                  25                  30

Gly His Gly Thr Met Leu Asp Pro Phe Ser Arg Val Tyr Ala Cys Arg
            35                  40                  45

Phe Phe Glu Asn Pro Glu Arg Pro Thr Ser Pro Ala Cys Gln Ala Ala
50                  55                  60

Val Ala Ala Ser Gly Thr Gln Ala Phe Tyr Asp Trp Asn Glu Val Asn
65                  70                  75                  80

Gln Pro Phe Ala Ala Gly Arg His Arg Glu Ile Ile Pro Asp Gly Gln
                85                  90                  95

Leu Cys Ser Gly Gly Arg Asp Lys Tyr Lys Gly Leu Asp Leu Ala Arg
            100                 105                 110

Asn Asp Trp Pro Ala Thr Ser Leu Ser Ser Asn Ile Pro Phe Thr Tyr
            115                 120                 125

Leu Tyr Ile Ala Ser Ala Pro His Arg Gly Phe Glu Phe Tyr Val
130                 135                 140
```

```
Thr Gln Asp Gly Tyr Asp Pro Thr Gln Pro Leu Lys Trp Ala Asp Leu
145                 150                 155                 160

Glu Tyr Pro Pro Phe Ile Asn Ile Thr Asp Pro Thr Leu Leu Ser Gly
                165                 170                 175

Ser Tyr Gln Ile Pro Gly Thr Thr Pro Ala Gly Lys Ser Gly Arg His
            180                 185                 190

Leu Ile Tyr Val Ile Trp Gln Arg Ser Asp Ser Pro Glu Ala Phe Tyr
                195                 200                 205

Ser Cys Ser Asp Val Asp Phe Val Asp Ser Leu His Ala Ser Val
        210                 215                 220

<210> SEQ ID NO 182
<211> LENGTH: 221
<212> TYPE: PRT
<213> ORGANISM: Cystopteris fragilis

<400> SEQUENCE: 182

Met Gly Arg Val Asn Leu Leu Ala Ile Leu Val Leu Cys Ala Ser Cys
1               5                   10                  15

Cys Ala Gly Leu Leu Gly Val Ala Ser Gly His Gly Thr Met Glu Asp
            20                  25                  30

Pro Ile Ser Arg Val Tyr Asn Cys Phe Leu Glu Asn Pro Glu Arg Pro
        35                  40                  45

Thr Ser Ala Ala Cys Gln Ala Val Ala Leu Ser Gly Thr Gln Ala
    50                  55                  60

Phe Tyr Asp Trp Asn Glu Val Asn Leu Ala Asp Ala Ala Gly Arg His
65                  70                  75                  80

Arg Glu Leu Ile Pro Asp Gly Gln Leu Cys Ser Ala Gly Arg Glu Lys
                85                  90                  95

Tyr Arg Gly Leu Asp Leu Ala Arg Ser Asp Trp Val Ala Thr Ser Leu
            100                 105                 110

Ser Ser Gly Val Ser Thr Thr Phe Leu Tyr Lys Ala Thr Ala Pro His
        115                 120                 125

Leu Gly Phe Phe Glu Phe Tyr Val Thr Arg Asp Gly Tyr Asp Pro Thr
    130                 135                 140

Glu Ala Leu Lys Trp Ser Asp Leu Glu Asp Ser Pro Phe Leu Asn Val
145                 150                 155                 160

Thr Asp Pro Thr Leu Leu Ser Ser Pro Tyr Val Tyr Gln Ile Pro Gly
                165                 170                 175

Thr Thr Pro Ala Gly Lys Ser Gly Arg His Leu Ile Tyr Val Ile Trp
            180                 185                 190

Gln Arg Ser Asp Ser Pro Glu Ala Phe Tyr Ser Cys Ser Asp Val Ala
        195                 200                 205

Phe Asp Asp Ala Gln Leu Val Ser Leu His Ser Thr Thr
    210                 215                 220

<210> SEQ ID NO 183
<211> LENGTH: 220
<212> TYPE: PRT
<213> ORGANISM: Dryopteris filix-mas

<400> SEQUENCE: 183

Met Gly Arg Ser Trp Gly Val Val Gln Ala Ile Ile Met Val Leu Cys
1               5                   10                  15

Gly Ser Gly Leu Leu Gly Val Ala Ser Gly His Gly Ser Met Glu Asp
            20                  25                  30
```

Pro Ile Ser Arg Val Tyr Asn Cys Tyr Leu Glu Asn Pro Glu Ser Pro
            35                  40                  45

Thr Ser Ala Ala Cys Gln Ala Val Ala Leu Ser Gly Ala Gln Ala
 50                  55                  60

Phe Tyr Asp Trp Asn Glu Val Asn Leu Ala Asp Ala Ala Gly Arg His
 65                  70                  75                  80

Arg Glu Leu Ile Pro Asp Gly Gln Leu Cys Ser Ala Gly Arg Glu Lys
                 85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
            115                 120                 125

Leu Gly Phe Phe Glu Phe Tyr Val Thr Lys Asp Gly Tyr Glu Pro Thr
            130                 135                 140

Glu Pro Leu Lys Trp Ala Asp Leu Glu Asp Ser Pro Phe Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Ser
            195                 200                 205

Ser Asp Ala Leu Ile Ser Leu Gly Ser Ala Val Leu
            210                 215                 220

<210> SEQ ID NO 184
<211> LENGTH: 219
<212> TYPE: PRT
<213> ORGANISM: Bolbitis cladorrhizans

<400> SEQUENCE: 184

Met Gly Arg Ser Leu Gly Ala Val Val Ile Thr Leu Val Leu Cys Ala
 1               5                  10                  15

Gly Gly Leu Leu Ser Leu Ala Ser Gly His Gly Ser Met Glu Asp Pro
            20                  25                  30

Ile Ser Arg Val Tyr Arg Cys Tyr Leu Glu Asn Pro Glu Ser Pro Thr
            35                  40                  45

Ser Ala Ala Cys Gln Ala Ala Val Ala Leu Ser Gly Thr Glu Ala Phe
 50                  55                  60

Ser Gly Tyr Ala Trp Ser Ala Val Leu Ala Asn Ala Ala Gly Gln His
 65                  70                  75                  80

Arg Gln Leu Ile Pro Asp Gly Gln Leu Cys Ser Ala Gly Gln Glu Leu
                 85                  90                  95

Tyr Ala Gly Leu Asp Leu Pro Arg Ala Asp Trp Pro Ala Thr Ser Leu
            100                 105                 110

Ser Ser Gly Val Ala Phe Thr Tyr Leu Tyr Lys Ala Ala Ile Pro His
            115                 120                 125

Met Gly Phe Phe Glu Phe Tyr Ile Thr Arg Asp Gly Tyr Glu Pro Thr
            130                 135                 140

Glu Pro Leu Lys Trp Ala Asp Leu Glu Asp Ser Pro Phe Leu Asn Val
145                 150                 155                 160

Thr Asp Pro Pro Leu Val Ser Ser Tyr Gln Ile Pro Gly Ser Thr
                165                 170                 175

Pro Ala Gly Lys Ser Gly Arg His Leu Ile Tyr Val Ile Trp Gln Arg
            180                 185                 190

```
Ser Asp Ser Pro Gln Ala Phe Tyr Ser Cys Ser Asp Val Asp Phe Val
        195                 200                 205

Asp Ala Thr Leu Ser Gln Leu His Ser Thr Thr
    210                 215
```

<210> SEQ ID NO 185
<211> LENGTH: 220
<212> TYPE: PRT
<213> ORGANISM: Dryopteris filix-mas

<400> SEQUENCE: 185

```
Met Lys Lys Ser Trp Gly Val Val Val Val Val Ala Leu Val
1               5                   10                  15

Leu Leu Cys Leu Leu Gly Thr Ala Ser Gly His Gly Ser Met Gln Asp
            20                  25                  30

Pro Ile Ser Arg Val Tyr Asn Cys Tyr Leu Glu Asn Pro Glu Asn Pro
        35                  40                  45

Thr Ser Ala Ala Cys Lys Ala Val Val Ala Val Gly Gly Thr Gln Pro
    50                  55                  60

Leu Tyr Asp Trp Asn Glu Val Asn Leu Ala Asn Ala Ala Gly Arg His
65                  70                  75                  80

Arg Glu Leu Ile Pro Asp Gly Arg Leu Cys Ser Ala Gly Arg Asp Lys
                85                  90                  95

Tyr Arg Gly Leu Asp Leu Ala Arg Asp Asp Trp Pro Ala Thr Ser Leu
            100                 105                 110

Ser Ser Gly Val Asp Tyr Thr Phe Leu Tyr Arg Ala Thr Ala Pro His
        115                 120                 125

Leu Gly Phe Phe Glu Phe Tyr Val Thr Arg Asp Ser Tyr Asp Pro Thr
    130                 135                 140

Gln Pro Leu Ala Trp Ala Asp Leu Glu Asp Leu Pro Phe Ile Asn Val
145                 150                 155                 160

Thr Asn Pro Ala Leu Asn Ala Gly Ala Tyr Gln Ile Pro Gly Thr Met
                165                 170                 175

Pro Ala Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Ser
        195                 200                 205

Ser Asp Ala Leu Ile Ser Leu Arg Ser Ala Val Leu
    210                 215                 220
```

<210> SEQ ID NO 186
<211> LENGTH: 218
<212> TYPE: PRT
<213> ORGANISM: Pyrrosia lanceolata

<400> SEQUENCE: 186

```
Met Arg Thr Arg Ser Trp Gly Val Val Ala Phe Met Val Ala Val Cys
1               5                   10                  15

Ala Gly Asp Leu Leu Gly Leu Ala Ser Gly His Gly Ser Met Gly Tyr
            20                  25                  30

Pro Val Ser Arg Val Leu Asn Cys Phe Leu Glu Asn Pro Glu Ser Pro
        35                  40                  45

Thr Ser Ala Ala Cys Thr Ala Ala Val Ala Met Ser Gly Thr Gln Ala
    50                  55                  60

Phe Tyr Asp Trp Asn Glu Val Asn Leu Pro Phe Ala Asn Gly Gln His
65                  70                  75                  80
```

```
Arg Asp Leu Ile Pro Asp Gly Gln Leu Cys Ser Ala Gly Arg Ala Lys
                85                  90                  95

Tyr Ala Gly Leu Asp Leu Ala Arg Asp Asp Trp Glu Ala Thr Phe Leu
            100                 105                 110

Ser Ser Ala Thr Ser Tyr Thr Leu Leu Tyr Arg Val Thr Ala Arg His
            115                 120                 125

Leu Gly Tyr Phe Glu Phe Tyr Val Thr Arg Asp Ser Tyr Asn Ser Thr
    130                 135                 140

Gln Pro Leu Ala Trp Ala Asp Leu Glu Asp Ser Pro Phe Ile Asn Ile
145                 150                 155                 160

Thr Asn Pro Thr Val Asp Ser Gly Tyr Tyr Gln Val Pro Val Asp Thr
                165                 170                 175

Pro Ser Gly Lys Thr Gly Arg His Leu Ile Tyr Val Ile Trp Gln His
            180                 185                 190

Thr Asp Ser Leu Glu Ala Phe Tyr Ser Cys Ser Asp Val Glu Phe Asp
            195                 200                 205

Val Glu Val Pro Ser Leu Arg Ser Thr Thr
    210                 215
```

<210> SEQ ID NO 187
<211> LENGTH: 218
<212> TYPE: PRT
<213> ORGANISM: Athyrium filix-femina

<400> SEQUENCE: 187

```
Met Gly Arg Ser Trp Gly Gly Val Val Ala Ile Met Val Leu Cys Gly
1               5                   10                  15

Cys Leu Leu Gly Val Ala Ser Gly His Gly Ser Met Glu Asp Pro Ile
            20                  25                  30

Ser Arg Val Tyr Asn Cys Tyr Leu Glu Asn Pro Glu Ser Pro Thr Ser
        35                  40                  45

Ala Ala Cys Gln Ala Ala Val Ala Leu Ser Gly Thr Gln Ala Phe Tyr
    50                  55                  60

Asp Trp Asn Glu Val Asn Gln Pro Phe Ala Ala Gly Gln Ser Arg Glu
65                  70                  75                  80

Ile Ile Pro Asp Gly Gln Leu Cys Ser Gly Arg Glu Lys Tyr Lys
                85                  90                  95

Gly Leu Asp Leu Ala Arg Ser Asp Trp Thr Ala Thr Ser Leu Ser Ser
            100                 105                 110

Gly Val Ala Phe Thr Phe Leu Phe Lys Ala Thr Ala Pro His Ala Gly
            115                 120                 125

Phe Phe Glu Phe Tyr Val Thr Gln Asp Gly Tyr Asp Pro Thr Glu Pro
    130                 135                 140

Leu Lys Trp Ala Asp Leu Glu Asp Ser Pro Phe Ile Asn Val Thr Asp
145                 150                 155                 160

Pro Thr Leu Val Ser Gly Ser Tyr Gln Ile Ser Gly Thr Thr Pro Ala
                165                 170                 175

Gly Lys Ser Gly Arg His Leu Ile Tyr Val Ile Trp Gln Arg Ser Asp
            180                 185                 190

Ser Pro Glu Ala Phe Tyr Ser Cys Ser Asp Val Glu Phe Val Asp Asp
            195                 200                 205

Ala Leu Ser Ser Asp Leu His Ser Thr Thr
    210                 215
```

-continued

```
<210> SEQ ID NO 188
<211> LENGTH: 218
<212> TYPE: PRT
<213> ORGANISM: Colysis wrightii (Monstifera)

<400> SEQUENCE: 188

Met Gly Arg Ala Trp Val Val Ala Ile Met Val Ala Val Cys Ala
1               5                   10                  15

Ser Gly Leu Leu Ser Phe Ala Ser Arg Thr Arg Gly His Gly Ser Met
                20                  25                  30

Gly Asp Pro Ile Ser Arg Val Leu Arg Cys Arg Glu Glu Asn Pro Glu
            35                  40                  45

Asn Pro Thr Ser Pro Ala Cys Ile Ala Ala Val Ala Leu Ser Gly Lys
        50                  55                  60

Gln Ala Phe Tyr Asp Trp Asn Glu Val Asn Leu Pro Phe Ala Asp Gly
65                  70                  75                  80

Gln His Gln Lys Leu Ile Pro Asp Gly Gln Leu Cys Gly Ala Gly Arg
                85                  90                  95

Asp Lys Tyr Lys Gly Leu Asn Leu Ala Arg Ala Asp Trp Leu Ala Thr
            100                 105                 110

Ser Leu Ser Ala Gly Ala Pro Tyr Thr Phe Leu Phe Leu Ala Ser Ala
        115                 120                 125

Pro His Leu Gly Tyr Phe Glu Phe Tyr Val Thr Arg Asp Ser Tyr Asp
130                 135                 140

Pro Thr Gln Pro Leu Ala Trp Ala Asp Leu Glu Asp Ser Pro Phe Leu
145                 150                 155                 160

Thr Thr Thr Thr Thr Leu Asp Ser Ser Ser Tyr Ile Ile Pro Gly Thr
                165                 170                 175

Thr Pro Ala Gly Lys Thr Gly Arg His Leu Ile Tyr Leu Ile Trp Gln
            180                 185                 190

Arg Thr Asp Ser Pro Glu Ala Phe Tyr Ser Cys Ser Asp Val Asp Phe
        195                 200                 205

Glu Glu Ala Ile Ser Leu Ser Ser Thr Thr
210                 215

<210> SEQ ID NO 189
<211> LENGTH: 219
<212> TYPE: PRT
<213> ORGANISM: Coniogramme venusta

<400> SEQUENCE: 189

Met Gly Arg Ser Ser Trp Glu Gly Val Leu Val Val Val Cys
1               5                   10                  15

Cys Ala Ser Gly Leu Leu Gly Val Ala Ser Gly His Gly Ser Met Gly
                20                  25                  30

Ser Pro Ile Ser Arg Val Tyr Asn Cys Arg Gln Glu Asn Pro Glu Arg
            35                  40                  45

Pro Thr Ser Ala Ala Cys Arg Glu Ala Val Arg Ile Ser Gly Thr Gln
        50                  55                  60

Ala Phe Tyr Asp Trp Asn Glu Val Asn Leu Pro Val Ala Ser Gly Arg
65                  70                  75                  80

His Arg Glu Leu Ile Pro Asp Gly Lys Leu Cys Ser Ala Gly Arg Thr
                85                  90                  95

Lys Tyr Ala Gly Leu Asp Leu Ala Arg Ser Asp Trp Val Ser Thr Val
            100                 105                 110

Leu Pro Ser Gly Val Pro Tyr Thr Phe Leu Tyr Arg Val Thr Ala Arg
```

```
            115                 120                 125
His Val Gly Phe Phe Glu Phe Tyr Val Thr Arg Asp Gly Tyr Gln Pro
            130                 135                 140

Ser Glu Pro Leu Lys Trp Ser Asp Leu Glu Glu Pro Pro Phe Ile Asn
145                 150                 155                 160

Val Thr Asn Pro Thr Met Ser Gly Gly Phe Tyr Arg Ile Pro Gly Thr
                    165                 170                 175

Thr Pro Pro Ala Lys Ala Gly Arg His Leu Ile Tyr Val Ile Trp Gln
                180                 185                 190

Arg Ser Asp Ser Pro Glu Ala Phe Tyr Ser Cys Ser Asp Ala Val Phe
                195                 200                 205

Gly Asp Ala Leu Ser Leu Gln Tyr Ser Ser Thr
            210                 215

<210> SEQ ID NO 190
<211> LENGTH: 217
<212> TYPE: PRT
<213> ORGANISM: Platycerium coronarium

<400> SEQUENCE: 190

Met Arg Arg Ser Trp Gly Val Val Ala Val Ile Met Leu Ala Val Cys
1               5                   10                  15

Ala Val Gly Met Leu Gly Val Ala Ser Gly His Gly Ser Met Glu Asp
                20                  25                  30

Pro Ile Ser Arg Val Tyr Arg Cys Phe Leu Glu Asn Pro Glu Arg Pro
            35                  40                  45

Thr Ser Ala Ala Cys Ile Ala Val Ala Leu Ser Gly Thr Gln Ala
        50                  55                  60

Phe Tyr Asp Trp Asn Glu Val Asn Leu Pro Phe Ala Ala Gly Arg His
65              70                  75                  80

Arg Glu Leu Ile Pro Asp Gly Gln Leu Cys Ser Ala Gly Arg Asp Lys
                85                  90                  95

Tyr Lys Gly Leu Asp Leu Ala Arg Asp Asp Trp Val Ala Thr Ser Leu
            100                 105                 110

Ser Ser Gly Val Asn Tyr Thr Phe Leu Tyr Lys Ala Thr Ala Pro His
            115                 120                 125

Arg Gly Tyr Phe Glu Phe Tyr Val Thr Arg Asp Ser Tyr Asp Pro Thr
            130                 135                 140

Glu Pro Leu Ala Trp Ala Asp Leu Glu Asp Thr Pro Phe Ile Asn Val
145                 150                 155                 160

Thr Asp Pro Asp Leu Ala Ser Gly Ser Tyr Gln Ile Ser Ser Thr Thr
                    165                 170                 175

Pro Ser Gly Lys Thr Gly Arg His Leu Ile Tyr Val Ile Trp Gln Arg
                180                 185                 190

Thr Asp Ser Pro Glu Ala Phe Tyr Ser Cys Ser Asp Ile Leu Phe Asp
                195                 200                 205

Glu Ala Val Ala Leu Tyr Ser Thr Ala
            210                 215

<210> SEQ ID NO 191
<211> LENGTH: 218
<212> TYPE: PRT
<213> ORGANISM: Cystopteris bulbifera

<400> SEQUENCE: 191

Met Gly Arg Val Asn Leu Met Ala Ile Leu Ala Leu Cys Ala Ser Phe
```

```
                 1               5                  10                 15
            Cys Ala Ala Leu Leu Gly Val Ala Ser Gly His Gly Ser Met Gln Asp
                             20                 25                 30

Pro Ile Ser Arg Val Tyr Asn Cys Phe Leu Glu Asn Pro Glu Arg Pro
                             35                 40                 45

Thr Ser Ala Ala Cys Gln Ala Ala Val Ala Leu Ser Gly Thr Gln Ala
                         50                 55                 60

Phe Tyr Asp Trp Asn Glu Val Asn Leu Ala Asn Ala Asp Gly Arg His
             65                 70                 75                 80

Arg Glu Leu Ile Pro Asp Gly Gln Leu Cys Ser Ala Gly Arg Glu Lys
                             85                 90                 95

Tyr Gln Gly Leu Asp Leu Ala Arg Ala Asp Trp Thr Ala Thr Ser Leu
                             100                105                110

Ser Ser Gly Ile Ser Tyr Thr Phe Leu Tyr Lys Ala Thr Ala Pro His
                         115                120                125

Leu Gly Phe Phe Glu Phe Tyr Val Thr Arg Asp Gly Tyr Asp Pro Thr
                         130                135                140

Glu Ala Leu Lys Trp Ser Asp Leu Glu Asp Ser Pro Phe Leu Asn Val
            145                150                155                160

Thr Asn Pro Thr Leu Val Ser Gly Ser Tyr Gln Ile Pro Val Thr Thr
                             165                170                175

Pro Ala Ala Lys Ser Gly Arg His Leu Ile Tyr Val Ile Trp Gln Arg
                         180                185                190

Ser Asp Ser Pro Glu Ala Phe Tyr Ser Cys Ser Asp Val Asp Phe Asp
                         195                200                205

Asp Ala Leu Val Ser Leu His Ser Thr Thr
                         210                215

<210> SEQ ID NO 192
            <211> LENGTH: 217
            <212> TYPE: PRT
            <213> ORGANISM: Platycerium ridleyi

<400> SEQUENCE: 192

Met Arg Arg Ser Trp Gly Val Met Ala Val Ile Leu Leu Ala Val Cys
            1                5                  10                 15

Ala Cys Gly Leu Leu Gly Val Ala Ser Gly His Gly Ser Met Glu Asp
                             20                 25                 30

Pro Ile Ser Arg Val Tyr Gly Cys Tyr Leu Glu Asn Pro Glu Arg Pro
                             35                 40                 45

Thr Ser Ala Ala Cys Ile Ala Ala Val Ala Leu Ser Gly Thr Gln Ala
                         50                 55                 60

Phe Tyr Asp Trp Asn Glu Val Asn Gln Pro Phe Ala Ala Gly Arg His
             65                 70                 75                 80

Arg Glu Leu Ile Pro Asp Gly Gln Leu Cys Ser Gly Gly Arg Asp Lys
                             85                 90                 95

Tyr Lys Gly Leu Asp Leu Ala Arg Asp Asp Trp Glu Ala Thr Ser Leu
                             100                105                110

Ser Ser Gly Ala Asn Tyr Ser Phe Leu Phe Lys Ala Thr Ala Pro His
                         115                120                125

Arg Gly Tyr Phe Glu Phe Tyr Val Thr Gln Asp Ser Tyr Asp Pro Thr
                         130                135                140

Glu Pro Leu Ala Trp Gly Asp Leu Glu Ser Thr Pro Phe Ile Asn Val
            145                150                155                160
```

```
Thr Asp Pro Asp Leu Phe Ser Gly Ser Tyr Gln Ile Ser Ser Thr Thr
            165                 170                 175

Pro Pro Gly Lys Thr Gly Arg His Leu Ile Tyr Val Ile Trp Gln Arg
            180                 185                 190

Thr Asp Ser Pro Glu Ala Phe Tyr Ser Cys Ser Asp Val Leu Phe Asp
            195                 200                 205

Glu Ala Val Ala Leu Tyr Ser Thr Ala
        210                 215
```

<210> SEQ ID NO 193
<211> LENGTH: 215
<212> TYPE: PRT
<213> ORGANISM: Dryopteris marginalis

<400> SEQUENCE: 193

```
Met Gly Arg Ser Trp Gly Val Val Ala Ile Ile Met Val Leu Cys Gly
1               5                   10                  15

Ser Gly Leu Leu Gly Val Ala Ser Gly His Gly Ser Met Gln Asp Pro
            20                  25                  30

Ile Ser Arg Val Tyr Asn Cys Tyr Leu Glu Asn Pro Glu Arg Pro Thr
        35                  40                  45

Ser Ala Ala Cys Gln Ala Ala Val Ala Leu Ser Gly Thr Gln Ala Phe
    50                  55                  60

Tyr Asp Trp Asn Glu Val Asn Gln Pro Phe Ala Ala Gly Arg His Arg
65                  70                  75                  80

Glu Ile Ile Pro Asp Gly Gln Leu Cys Ser Ala Gly Arg Glu Lys Tyr
                85                  90                  95

Arg Gly Leu Asp Leu Ala Arg Ser Asp Trp Val Ala Thr Ser Leu Ser
            100                 105                 110

Ser Gly Val Asn Tyr Thr Tyr Leu Tyr Lys Ala Thr Ala Pro His Leu
        115                 120                 125

Gly Phe Phe Glu Phe Tyr Val Thr Gln Asp Gly Tyr Asn Ser Ser Glu
    130                 135                 140

Pro Leu Lys Trp Ala Asp Leu Glu Asp Ser Pro Phe Ile Asn Val Thr
145                 150                 155                 160

Thr Thr Leu Asp Ser Ala Ser Tyr Gln Ile Pro Gly Thr Thr Pro Ala
                165                 170                 175

Gly Lys Asn Gly Arg His Leu Ile Tyr Val Ile Trp Gln Arg Ser Asp
            180                 185                 190

Ser Pro Glu Ala Phe Tyr Ser Cys Ser Asp Val Asp Phe Ala Asp Ala
        195                 200                 205

Leu Ser Leu His Ser Thr Thr
    210                 215
```

<210> SEQ ID NO 194
<211> LENGTH: 216
<212> TYPE: PRT
<213> ORGANISM: Microsorum musifolium (Blume)

<400> SEQUENCE: 194

```
Met Arg Arg Ser Trp Gly Val Leu Ala Ile Val Met Ala Val Cys Ala
1               5                   10                  15

Ser Gly Leu Phe Gly Val Ala Ser Gly His Gly Ser Met Glu His Pro
            20                  25                  30

Ile Ser Arg Val Tyr Gln Cys Tyr Arg Glu Gly Pro Gly Asn Pro Lys
        35                  40                  45
```

```
Ser Pro Ala Cys Ile Ala Ala Lys Gly Leu Ser Gly Ala Gln Ala Phe
    50                  55                  60

Tyr Asp Trp Asn Glu Val Asn Gln Pro Phe Ala Asp Gly Arg His Gln
65                  70                  75                  80

Glu Ile Ile His Asp Gly His Leu Cys Ser Gly Gly Arg Asp Lys Tyr
                85                  90                  95

Arg Gly Leu Asp Leu Pro Arg Ala Asp Trp Val Ala Thr Ser Leu Ser
            100                 105                 110

Ala Gly Lys Pro Tyr Thr Phe Leu Tyr Arg Ala Thr Ala His His Leu
        115                 120                 125

Gly Tyr Phe Glu Phe Tyr Val Thr Arg Asp Gly Tyr Asp Pro Thr Lys
    130                 135                 140

Pro Leu Ala Trp Ala Asp Leu Glu Asp Ser Pro Phe Ile Asn Val Thr
145                 150                 155                 160

Asn Pro Thr Leu Val Ser Gly Ser Tyr Arg Ile Pro His Thr Thr Pro
                165                 170                 175

Ala Ser Lys Thr Gly Arg His Leu Ile Tyr Val Ile Trp Gln Arg Thr
            180                 185                 190

Asp Ser Phe Glu Ala Phe Tyr Ser Cys Ser Asp Val Val Phe Asp Glu
        195                 200                 205

Ala Leu Ser Leu Ser Ser Thr Ile
    210                 215

<210> SEQ ID NO 195
<211> LENGTH: 216
<212> TYPE: PRT
<213> ORGANISM: Elaphoglossum SP.

<400> SEQUENCE: 195

Met Arg Arg Ser Trp Glu Val Val Ala Leu Ile Met Val Val Cys Ala
1               5                   10                  15

Cys Gly Leu Leu Gly Val Ala Ser Gly His Gly Ser Met Glu Asp Pro
            20                  25                  30

Ile Ser Arg Val Tyr Arg Cys Tyr Leu Glu Gly Val Glu Asn Pro Thr
        35                  40                  45

Ser Ala Ala Cys Ile Ala Ala Ile Glu Val Ser Gly Lys Gln Ala Phe
    50                  55                  60

Tyr Asp Trp Asn Glu Val Asn Gln Pro Leu Ala Ala Gly Arg His Arg
65                  70                  75                  80

Glu Ile Ile Pro Asp Gly Glu Leu Cys Ser Gly Gly Arg Glu Lys Tyr
                85                  90                  95

Lys Gly Leu Asp Leu Ala Arg Ala Asp Trp Leu Ala Thr Ser Leu Ser
            100                 105                 110

Ser Gly Val Asp Tyr Thr Phe Leu Tyr Lys Ala Thr Ala Glu His Lys
        115                 120                 125

Gly Tyr Phe Glu Phe Tyr Val Thr Gln Asp Ser Tyr Asp Pro Thr Glu
    130                 135                 140

Pro Leu Lys Trp Ser Asp Leu Glu Asp Thr Pro Phe Ile Asn Val Thr
145                 150                 155                 160

Gln Pro Leu Leu Val Ser Gly Ser Tyr Gln Ile Pro Gly Thr Thr Pro
                165                 170                 175

Ser Gly Lys Thr Gly Arg His Leu Ile Tyr Val Ile Trp Gln Arg Thr
            180                 185                 190

Asp Ser Ala Glu Ala Phe Tyr Ser Cys Ser Asp Val Asn Phe Asp Asp
        195                 200                 205
```

Ala Leu Pro Ile Tyr Ser Ala Thr
         210             215

<210> SEQ ID NO 196
<211> LENGTH: 214
<212> TYPE: PRT
<213> ORGANISM: Dryopteris lepidopoda

<400> SEQUENCE: 196

Met Gly Arg Ser Trp Gly Val Val Ala Ile Met Val Leu Cys Gly Ser
1               5                   10                  15

Gly Leu Leu Gly Val Ala Ser Gly His Gly Ser Met Glu Asp Pro Ile
            20                  25                  30

Ser Arg Val Tyr Asn Cys Tyr Leu Glu Asn Pro Glu Arg Pro Thr Ser
        35                  40                  45

Ala Ala Cys Gln Ala Ala Val Ala Leu Ser Gly Thr Gln Ala Phe Tyr
    50                  55                  60

Asp Trp Asn Glu Val Asn Gln Pro Phe Ala Ala Gly Arg His Arg Glu
65                  70                  75                  80

Ile Ile Pro Asp Gly Gln Leu Cys Ser Gly Gly Arg Glu Lys Tyr Arg
                85                  90                  95

Gly Leu Asp Leu Ala Arg Ser Asp Trp Glu Ala Thr Ser Leu Ser Ser
            100                 105                 110

Gly Val Ser Tyr Thr Tyr Leu Tyr Lys Ala Thr Ala Pro His Leu Gly
        115                 120                 125

Phe Phe Glu Phe Tyr Val Thr Gln Asp Gly Tyr Asn Ser Ser Glu Pro
    130                 135                 140

Leu Glu Trp Ala Asp Leu Glu Asp Ser Pro Phe Ile Asn Val Thr Thr
145                 150                 155                 160

Thr Leu Asp Ser Ala Ser Tyr Gln Ile Pro Gly Thr Pro Ala Gly
                165                 170                 175

Lys Thr Gly Arg His Leu Ile Tyr Val Ile Trp Gln Arg Ser Asp Ser
            180                 185                 190

Pro Glu Ala Phe Tyr Ser Cys Ser Asp Val Asp Phe Val Asp Ala Leu
        195                 200                 205

Ser Leu His Ser Thr Thr
    210

<210> SEQ ID NO 197
<211> LENGTH: 214
<212> TYPE: PRT
<213> ORGANISM: Polystichum lepidocaulon

<400> SEQUENCE: 197

Met Gly Arg Ser Trp Gly Val Val Ala Ile Met Val Leu Phe Ala Ser
1               5                   10                  15

Ala Ser Gly Leu Leu Gly Val Ala Asn Gly His Gly Ser Met Gly Asn
            20                  25                  30

Pro Ile Ser Arg Val Tyr Asn Cys Arg Leu Glu Asn Pro Glu Arg Pro
        35                  40                  45

Thr Ser Ala Ala Cys Ile Ala Val Ala Leu Ser Gly Thr Tyr Asp
    50                  55                  60

Trp Ser Glu Val Asn Leu Pro Asn Ala Asn Gly Arg His Arg Glu Leu
65                  70                  75                  80

Ile Pro Asp Gly Lys Leu Cys Ser Ala Gly Arg Asp Lys Tyr Lys Gly
                85                  90                  95

```
Leu Asp Leu Ala Arg Ser Asp Trp Thr Ala Thr Asn Leu Ser Ser Gly
            100                 105                 110

Val Ala Tyr Thr Phe Leu Tyr Arg Val Thr Ala Glu His Arg Gly Phe
        115                 120                 125

Phe Glu Phe Tyr Val Thr Val Asp Asp Tyr Glu Pro Thr Glu Leu Leu
    130                 135                 140

Lys Trp Glu Asp Leu Glu Glu Thr Pro Phe Leu Asn Val Ser Asp Pro
145                 150                 155                 160

Thr Val Val Gly Asn Asn Tyr Glu Ile Ser Gly Thr Thr Pro Ala Ser
                165                 170                 175

Lys Thr Gly Arg His Leu Ile Tyr Val Ile Trp Gln Arg Ser Asp Ser
            180                 185                 190

Pro Glu Ala Phe Tyr Ser Cys Ser Asp Val Asp Phe Val Asp Thr Leu
        195                 200                 205

Ser Leu His Ser Thr Thr
    210

<210> SEQ ID NO 198
<211> LENGTH: 215
<212> TYPE: PRT
<213> ORGANISM: Polystichum polyblepharum (C.)

<400> SEQUENCE: 198

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Asn Cys Arg Leu Glu Asn Pro Glu Ser Pro Thr Ser
        35                  40                  45

Ala Ala Cys Ile Ala Ala Val Ala Leu Ser Gly Thr Gln Ala Phe Tyr
    50                  55                  60

Asp Trp Asn Glu Val Asn Leu Pro Asn Ala Ala Gly Arg His Arg Glu
65                  70                  75                  80

Leu Ile Pro Asp Gly Lys Leu Cys Ser Ala Gly Arg Asp Lys Tyr Lys
            85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Gln His Arg Gly
        115                 120                 125

Phe Phe Glu Phe Tyr Val Thr Val Asp Asp Tyr Asp Pro Thr Glu Leu
    130                 135                 140

Leu Lys Trp Glu Asp Leu Glu Glu Thr Pro Phe Met Asn Val Thr Asp
145                 150                 155                 160

Pro Thr Val Val Gly Val Asn Tyr Glu Met Ala Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Val Ser Leu His Ser Ser Thr
    210                 215

<210> SEQ ID NO 199
<211> LENGTH: 216
<212> TYPE: PRT
```

<213> ORGANISM: Lecanopteris sinuosa

<400> SEQUENCE: 199

Met Met Arg Ser Trp Gly Val Ala Ala Ile Met Met Ala Val Cys Ala
1               5                   10                  15

Ser Gly Leu Leu Gly Val Ala Ser Gly His Gly Ser Met Ala Asp Pro
            20                  25                  30

Ile Ser Arg Val Tyr Arg Cys Arg Leu Glu Asn Pro Glu Arg Pro Thr
        35                  40                  45

Ser Pro Ala Cys Ile Ala Ala Val Ala Leu Ser Gly Thr Gln Ala Phe
    50                  55                  60

Tyr Asp Trp Asn Glu Val Asn Leu Pro Phe Ala Ala Gly Arg His Arg
65                  70                  75                  80

Gln Leu Ile Pro Asp Gly Gln Leu Cys Ser Ala Gly Arg Asn Lys Tyr
                85                  90                  95

Lys Gly Leu Asp Leu Ala Arg Ala Asp Trp Leu Ala Thr Ser Leu Ser
            100                 105                 110

Pro Gly Ala Asn Tyr Thr Phe Leu Tyr Arg Ala Thr Ala Pro His Ala
        115                 120                 125

Gly Tyr Phe Glu Phe Tyr Val Thr Arg Asp Ser Tyr Asp Pro Thr Glu
    130                 135                 140

Gln Leu Ala Trp Ala Asp Leu Glu Asp Ser Pro Phe Ile Thr Ile Thr
145                 150                 155                 160

Asn Pro Thr Leu Val Asn Gly Tyr Tyr Gln Ile Pro Asn Thr Val Pro
                165                 170                 175

Ala Gly Lys Thr Gly Arg His Leu Ile Tyr Val Ile Trp Gln Arg Thr
            180                 185                 190

Asp Ser Pro Glu Ala Phe Tyr Ser Cys Ser Asp Val Asp Phe Asp Asp
        195                 200                 205

Ala Leu Arg Leu His Tyr Ser Thr
    210                 215

<210> SEQ ID NO 200
<211> LENGTH: 215
<212> TYPE: PRT
<213> ORGANISM: Aglaomorpha splendens

<400> SEQUENCE: 200

Met Arg Arg Ser Trp Gly Val Val Val Ile Leu Val Val Cys Val Cys
1               5                   10                  15

Gly Leu Leu Gly Val Ala Ser Gly His Gly Ser Met Gly Asp Pro Ile
            20                  25                  30

Ser Arg Val Tyr Gly Cys Arg Leu Glu Asn Pro Glu Ser Pro Thr Ser
        35                  40                  45

Ala Ala Cys Ile Ala Ala Val Ala Val Ser Gly Thr Gln Ala Phe Tyr
    50                  55                  60

Asp Trp Asn Glu Val Asn Gln Pro Asn Ala Asn Gly Arg His Arg Glu
65                  70                  75                  80

Ile Ile Pro Asp Gly Glu Leu Cys Ser Ala Gly Arg Val Lys Tyr Ala
                85                  90                  95

Gly Leu Asp Leu Ala Arg Asp Asp Trp Val Ala Thr Ser Leu Ser Ser
            100                 105                 110

Gly Val Asn Tyr Thr Phe Leu Phe Val Ala Thr Ala Pro His Leu Gly
        115                 120                 125

Tyr Phe Glu Phe Tyr Val Thr Gln Asp Ser Tyr Asp Pro Thr Gln Pro

```
            130                 135                 140
Leu Lys Trp Ser Asp Leu Glu Ala Thr Pro Phe Ile Asn Val Thr Asp
145                 150                 155                 160

Pro Thr Leu Leu Asn Gly Ser Tyr Gln Ile Pro Ser Ser Thr Pro Ser
                165                 170                 175

Gly Lys Thr Gly Arg His Leu Ile Tyr Val Ile Trp Gln Arg Thr Asp
            180                 185                 190

Ser Pro Glu Ala Phe Tyr Ser Cys Ser Asp Val Asp Phe Asp Val Ala
        195                 200                 205

Leu Pro Leu Tyr Ser Ser Thr
    210                 215

<210> SEQ ID NO 201
<211> LENGTH: 216
<212> TYPE: PRT
<213> ORGANISM: Polypodium formosanum

<400> SEQUENCE: 201

Met Lys Arg Ser Trp Gly Val Ala Ala Ile Val Met Ala Leu Ser Thr
1               5                   10                  15

Cys Gly Leu Ile Gly Val Ala Ser Gly His Gly Ser Met Gly Asp Pro
            20                  25                  30

Ile Ser Arg Val Tyr Arg Cys Tyr Arg Glu Asn Pro Glu Arg Pro Thr
        35                  40                  45

Ser Pro Ala Cys Ile Ala Ala Val Ala Leu Ser Gly Lys Gln Ala Phe
    50                  55                  60

Tyr Asp Trp Asn Ala Val Asn Leu Phe Asn Ala Asn Gly Arg His Arg
65                  70                  75                  80

Glu Leu Ile Pro Asp Gly Gln Leu Cys Ser Ala Gly Arg Ala Lys Tyr
                85                  90                  95

Lys Gly Leu Asp Leu Pro Arg Ala Asp Trp Leu Ala Thr Ser Leu Ser
            100                 105                 110

Ser Gly Val Asn Phe Thr Phe Leu Tyr Arg Val Thr Ala Arg His Leu
        115                 120                 125

Gly Tyr Phe Glu Phe Tyr Val Thr Arg Asp Gly Tyr Asp Pro Ser Glu
    130                 135                 140

Pro Leu Ala Trp Ala Asp Leu Glu Asp Ser Pro Phe Ile Lys Ile Thr
145                 150                 155                 160

Asn Pro Ser Val Val Ser Asn Ser Tyr Val Ile Pro Gly Ile Thr Pro
                165                 170                 175

Ala Gly Lys Thr Gly Arg His Leu Ile Tyr Val Ile Trp Gln Arg Thr
            180                 185                 190

Asp Ser Gln Glu Ala Phe Tyr Ser Cys Ser Asp Ile Asp Phe Asp Glu
        195                 200                 205

Ala Val Pro Leu Tyr Ser Thr Thr
    210                 215

<210> SEQ ID NO 202
<211> LENGTH: 214
<212> TYPE: PRT
<213> ORGANISM: Nephrolepis obliterata (Sunjest)

<400> SEQUENCE: 202

Met Gly Arg Ser Trp Gly Val Val Ala Ile Met Val Val Cys Ala Cys
1               5                   10                  15

Gly Leu Leu Ser Val Val Arg Gly His Gly Ser Met Glu Asp Pro Ile
```

```
            20                  25                  30
Ser Arg Val Tyr Gly Cys Tyr Leu Glu Asn Pro Glu Ser Pro Lys Ser
        35                  40                  45

Ala Ala Cys Gln Ala Ala Val Ala Leu Ser Gly Thr Gln Ala Phe Tyr
    50                  55                  60

Asp Trp Asn Glu Val Asn Leu Pro Asp Val Ala Gly Arg His Arg Ala
65                  70                  75                  80

Val Ile Pro Asp Gly Gln Leu Cys Ser Ala Gly Arg Ala Lys Tyr Gln
                85                  90                  95

Gly Leu Asn Leu Ala Arg Ala Asp Trp Pro Ala Thr Ser Leu Thr Ser
            100                 105                 110

Gly Val Ser Phe Thr Tyr Leu Tyr Lys Val Thr Ala Lys His Leu Gly
            115                 120                 125

Phe Phe Glu Phe Tyr Val Thr Gln Asp Gly Tyr Asp Pro Thr Glu Pro
        130                 135                 140

Leu Lys Trp Ala Asp Leu Glu Asp Leu Pro Phe Met Asn Val Thr Ser
145                 150                 155                 160

Thr Phe Asp Asp Glu Ser Tyr Gln Met Ser Gly Thr Thr Pro Ser Gly
                165                 170                 175

Lys Ala Gly Arg His Leu Ile Tyr Val Ile Trp Gln Arg Ser Asp Ser
            180                 185                 190

Pro Glu Ala Phe Tyr Ser Cys Ser Asp Val Asp Phe Val Asp Ala Val
        195                 200                 205

Ser Leu Arg Ser Thr Thr
    210

<210> SEQ ID NO 203
<211> LENGTH: 215
<212> TYPE: PRT
<213> ORGANISM: Deparia acrostichoides

<400> SEQUENCE: 203

Met Gly Arg Ser Trp Gly Val Val Ala Ile Met Val Leu Cys Ala Ser
1               5                   10                  15

Gly Leu Leu Gly Val Ala Ser Gly His Gly Ser Met Glu Gly Pro Ile
            20                  25                  30

Ser Arg Val Leu Asn Cys Tyr Leu Glu Asn Pro Glu Arg Pro Thr Ser
        35                  40                  45

Gly Ala Cys Ile Ala Ala Val Ala Leu Gly Gly Thr Gln Pro Phe Tyr
    50                  55                  60

Asp Trp Asn Glu Val Asn Leu Ala Asp Ala Asp Gly Arg His Arg Glu
65                  70                  75                  80

Leu Ile Pro Asp Gly Gln Leu Cys Ser Ala Gly Arg Glu Lys Phe Lys
                85                  90                  95

Gly Leu Asp Leu Ala Arg Ser Asp Trp Pro Ala Thr Ser Leu Ser Ser
            100                 105                 110

Gly Val Ala Phe Thr Tyr Leu Tyr Lys Ala Thr Ala Pro His Ala Gly
            115                 120                 125

Phe Phe Glu Phe Tyr Val Thr Arg Asp Gly Tyr Lys Pro Thr Glu Pro
        130                 135                 140

Leu Lys Trp Ala Asp Leu Glu Glu Pro Pro Phe Ile Asn Val Thr Asp
145                 150                 155                 160

Pro Lys Leu Val Ser Gly Ser Tyr Gln Ile Pro Gly Thr Thr Pro Ala
                165                 170                 175
```

Gly Lys Ala Gly Arg His Leu Ile Tyr Val Ile Trp Gln Arg Ser Asp
                180                 185                 190

Ser Pro Glu Ala Phe Tyr Ser Cys Ser Asp Val Asp Phe Val Glu Ala
            195                 200                 205

Leu Ser Leu His Ser Thr Thr
        210                 215

<210> SEQ ID NO 204
<211> LENGTH: 216
<212> TYPE: PRT
<213> ORGANISM: Aglaomorpha sp. (Roberts)

<400> SEQUENCE: 204

Met Arg Arg Ser Trp Pro Gly Val Val Ala Ile Met Val Val Cys Ala
1               5                   10                  15

Cys Gly Leu Leu Gly Val Ala Ser Gly His Gly Ser Met Gln Asp Pro
            20                  25                  30

Ile Ser Arg Val Tyr Arg Cys Arg Leu Glu Asn Pro Glu Arg Pro Thr
        35                  40                  45

Ser Ala Ala Cys Ile Ala Ala Val Ala Leu Ser Gly Thr Gln Ala Phe
    50                  55                  60

Tyr Asp Trp Asn Glu Val Asn Gln Pro Phe Ala Asn Gly Arg His Arg
65                  70                  75                  80

Glu Ile Ile Pro Asp Gly Gln Leu Cys Ser Ala Gly Arg Ala Lys Tyr
                85                  90                  95

Arg Gly Leu Asp Leu Ala Arg Ala Asp Trp Leu Ala Pro Ser Leu Ser
            100                 105                 110

Ser Gly Val Asp Tyr Thr Phe Leu Tyr Ile Ala Thr Ala Pro His Leu
        115                 120                 125

Gly Tyr Phe Glu Phe Tyr Ile Thr Arg Asp Ser Tyr Asp Pro Thr Glu
    130                 135                 140

Pro Leu Lys Trp Ser Asp Leu Glu Asp Ser Pro Phe Ile Asn Val Thr
145                 150                 155                 160

Asn Pro Ser Leu Val Ser Gly Ser Tyr Gln Ile Pro Gly Thr Thr Pro
                165                 170                 175

Ser Asn Lys Thr Gly Arg His Leu Met Tyr Val Ile Trp Gln Arg Thr
            180                 185                 190

Asp Ser Pro Glu Ala Phe Tyr Ala Cys Ser Asp Val Asp Phe Asp Val
        195                 200                 205

Ala Leu Pro Leu Tyr Ser Thr Thr
    210                 215

<210> SEQ ID NO 205
<211> LENGTH: 215
<212> TYPE: PRT
<213> ORGANISM: Polypodium attenuatum (Falax)

<400> SEQUENCE: 205

Met Gly Lys Gly Trp Glu Val Val Gly Ile Met Val Val Cys Ala Cys
1               5                   10                  15

Gly Leu Leu Gly Val Ala Ser Gly His Gly Thr Met Glu Asp Pro Ile
            20                  25                  30

Ser Arg Val Tyr Arg Cys Arg Leu Glu Asn Pro Glu Arg Pro Thr Ser
        35                  40                  45

Pro Ala Cys Ile Ala Ala Val Ala Leu Ser Gly Thr Gln Ala Phe Tyr
    50                  55                  60

-continued

```
Asp Trp Asn Glu Val Asn Leu Pro Phe Ala Ala Gly Arg His Arg Glu
 65                  70                  75                  80

Ile Ile Pro Asp Gly Gln Leu Cys Ser Ala Gly Arg Ala Lys Tyr Arg
                 85                  90                  95

Gly Leu Asp Leu Ala Arg Asp Asp Trp Leu Ala Thr Ser Leu Ser Ser
            100                 105                 110

Gly Val Asp Tyr Thr Phe Val Tyr Arg Val Thr Ala Pro His Arg Gly
            115                 120                 125

Tyr Phe Glu Phe Tyr Val Thr Arg Asp Thr Tyr Asp Pro Thr Glu Pro
            130                 135                 140

Leu Lys Trp Ser Asp Leu Glu Glu Pro Pro Phe Ile Asn Val Thr Gln
145                 150                 155                 160

Pro Ser Leu Val Ser Gly Ser Tyr Gln Ile Pro Gly Ala Thr Pro Thr
                165                 170                 175

Gly Lys Thr Gly Arg His Leu Ile Tyr Val Ile Trp Gln Arg Thr Asp
                180                 185                 190

Ser Pro Glu Ala Phe Tyr Ser Cys Ser Asp Val Asp Phe Gly Glu Ala
                195                 200                 205

Leu Arg Leu Asp Ala Thr Ala
210                 215

<210> SEQ ID NO 206
<211> LENGTH: 215
<212> TYPE: PRT
<213> ORGANISM: Arachniodes simplicior (variegata)

<400> SEQUENCE: 206

Met Gly Arg Ser Trp Gly Val Val Ala Ile Ile Val Leu Cys Ala Ser
  1               5                  10                  15

Gly Leu Leu Gly Val Ala Ser Gly His Gly Ser Met Glu Asp Pro Ile
                 20                  25                  30

Ser Arg Val Tyr Asn Cys Phe Leu Glu Gly Pro Glu Asn Pro Thr Ser
             35                  40                  45

Asp Ala Cys Ile Ala Ala Val Ala Leu Ser Gly Thr Gln Ala Phe Tyr
 50                  55                  60

Asp Trp Thr Glu Val Asn Leu Ala Asp Ala Asp Gly His His Arg Glu
 65                  70                  75                  80

Leu Ile Pro Asp Gly Gln Leu Cys Ser Ala Gly Arg Asp Lys Tyr Lys
                 85                  90                  95

Gly Leu Asp Leu Ala Arg Ser Asp Trp Thr Ala Thr Ser Leu Ser Ser
            100                 105                 110

Gly Val Asp Tyr Thr Phe Leu Phe Lys Ala Thr Ala Pro His Leu Gly
            115                 120                 125

Ser Phe Glu Phe Tyr Val Thr Val Asp Gly Tyr Glu Pro Thr Glu Pro
            130                 135                 140

Leu Lys Trp Ala Asp Leu Glu Ala Thr Pro Phe Ile Asn Val Thr Asp
145                 150                 155                 160

Pro Thr Leu Asp Ser Gly Ser Tyr Gln Ile Pro Gly Thr Thr Pro Ala
                165                 170                 175

Gly Lys Thr Gly Arg His Leu Ile Tyr Val Ile Trp Gln Arg Ser Asp
                180                 185                 190

Ser Ala Glu Ala Phe Tyr Ser Cys Ser Asp Val Asp Phe Thr Asp Ala
                195                 200                 205

Leu Ser Leu His Ser Thr Thr
210                 215
```

<210> SEQ ID NO 207
<211> LENGTH: 216
<212> TYPE: PRT
<213> ORGANISM: Campyloneurum angustifolium

<400> SEQUENCE: 207

| Met | Arg | Arg | Ser | Trp | Glu | Val | Gly | Met | Met | Val | Leu | Cys | Ala | Cys |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Gly Leu Leu Gly Val Ala Ser Gly His Gly Ser Met Glu Asp Pro Ile
            20                  25                  30

Ser Arg Val Tyr Arg Cys Arg Leu Glu Gly Pro Glu Arg Pro Thr Ser
            35                  40                  45

Pro Ala Cys Ile Ala Ala Val Ala Val Asn Gly Thr Gln Ala Phe Tyr
    50                  55                  60

Asp Trp Asn Glu Val Asn Gln Pro Phe Ala Ala Gly Arg His Arg Glu
65                  70                  75                  80

Ile Ile Pro Asp Gly Gln Leu Cys Ser Ala Gly Arg Asp Lys Tyr Lys
            85                  90                  95

Gly Leu Asp Leu Ala Arg Ala Asp Trp Leu Ala Val Ser Leu Ser Ser
            100                 105                 110

Gly Ala Asp Tyr Thr Phe Leu Tyr Leu Ala Thr Ala Thr His Arg Gly
            115                 120                 125

Tyr Phe Glu Phe Tyr Val Thr Arg Asp Ser Tyr Asp Pro Thr Glu Pro
    130                 135                 140

Leu Lys Trp Ser Asp Leu Glu Asp Ser Pro Phe Ile Asn Val Thr Asp
145                 150                 155                 160

Pro Thr Glu Val Gly Pro Val Tyr Gln Ile Pro Gly Thr Thr Pro Ala
            165                 170                 175

Gly Lys Thr Gly Arg His Leu Ile Tyr Val Ile Trp Gln Arg Thr Asp
            180                 185                 190

Ser Pro Glu Ala Phe Tyr Ser Cys Ser Asp Val Asp Phe Gly Glu Ser
    195                 200                 205

Leu Ser Leu Tyr Ser Val Thr Glu
    210                 215

<210> SEQ ID NO 208
<211> LENGTH: 215
<212> TYPE: PRT
<213> ORGANISM: Colysis wrightii (Ching)

<400> SEQUENCE: 208

Met Arg Lys Ser Leu Glu Val Val Ala Ile Met Val Ala Val Cys Ala
1               5                   10                  15

Ser Gly Leu Leu Gly Val Ala Ser Gly His Gly Thr Met Leu Asp Pro
            20                  25                  30

Ile Ser Arg Val Tyr Arg Cys Tyr Leu Glu Asn Pro Glu Arg Pro Thr
            35                  40                  45

Ser Pro Ala Cys Ile Ala Ala Val Ala Leu Ser Gly Lys Gln Ala Phe
    50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Asp Lys Tyr
            85                  90                  95

Lys Gly Leu Asp Gln Ala Arg Asp Asp Trp Leu Ala Thr Ser Leu Pro
            100                 105                 110

-continued

```
Ser Gly Ala Asn Tyr Ile Phe Arg Phe Glu Val Thr Ala Val His Arg
        115                 120                 125

Gly Tyr Phe Glu Phe Tyr Val Thr Arg Asp Gly Tyr Asp Pro Thr Gln
    130                 135                 140

Pro Leu Ala Trp Ala Asp Leu Glu Asp Ser Pro Phe Leu Thr Thr Thr
145                 150                 155                 160

Thr Thr Leu Asp Ser Ser Ser Tyr Ile Ile Pro Gly Thr Thr Pro Ala
                165                 170                 175

Gly Lys Thr Gly Arg His Leu Ile Tyr Leu Ile Trp Gln Arg Thr Asp
                180                 185                 190

Ser Pro Glu Ala Phe Tyr Ser Cys Ser Asp Val Asp Phe Glu Glu Ala
            195                 200                 205

Ile Ser Leu Ser Ser Thr Thr
        210                 215

<210> SEQ ID NO 209
<211> LENGTH: 246
<212> TYPE: PRT
<213> ORGANISM: Colysis wrightii (Ching)

<400> SEQUENCE: 209

Met Gly Arg Ser Trp Val Val Ala Ile Met Val Thr Val Cys Ala
1               5                   10                  15

Ser Gly Leu Leu Gly Phe Ala Ser Gly His Gly Ser Met Gly Asp Pro
            20                  25                  30

Ile Ser Arg Val Leu Arg Cys Arg Glu Glu Asn Pro Glu Asn Pro Thr
        35                  40                  45

Ser Pro Ala Cys Ile Ala Ala Val Ala Leu Ser Gly Lys Gln Ala Phe
    50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Ala Lys Tyr
                85                  90                  95

Lys Gly Leu Asp Leu Ala Arg Asp Asp Trp Leu Ala Thr Pro Leu Pro
            100                 105                 110

Ser Gly Ala Ala Tyr Thr Phe Arg Tyr Arg Val Thr Ala Ala His Arg
        115                 120                 125

Gly Tyr Phe Glu Phe Tyr Val Thr Arg Asp Gly Tyr Asp Pro Thr Gln
    130                 135                 140

Pro Leu Ala Trp Ala Asp Leu Glu Asp Ser Pro Phe Leu Thr Thr Thr
145                 150                 155                 160

Thr Thr Leu Asp Ser Ser Ser Tyr Ile Ile Pro Gly Thr Thr Pro Ala
                165                 170                 175

Gly Lys Thr Gly Arg His Leu Ile Tyr Leu Ile Trp Gln Arg Thr Asp
                180                 185                 190

Ser Pro Glu Ala Phe Tyr Ser Cys Ser Asp Val Asp Phe Glu Glu Ala
            195                 200                 205

Ile Ser Leu Ser Ser Thr Thr Leu Ser Leu Ala Gly Gly Leu Ser Gly
        210                 215                 220

Met Ala Thr Tyr Cys Lys Gly His Ala Ala Ala Pro Val Leu Thr Trp
225                 230                 235                 240

Arg Met Glu Cys Cys Cys
                245
```

```
<210> SEQ ID NO 210
<211> LENGTH: 216
<212> TYPE: PRT
<213> ORGANISM: Platycerium elephantotis

<400> SEQUENCE: 210

Met Arg Arg Ser Trp Gly Val Val Ala Val Met Leu Ala Ile Cys Ala
1               5                   10                  15

Ser Gly Leu Leu Gly Val Ala Ser Gly His Gly Ser Met Leu Asp Pro
            20                  25                  30

Ile Ser Arg Val Tyr Thr Cys Tyr Leu Glu Asn Pro Glu Arg Pro Thr
        35                  40                  45

Ser Ala Ala Cys Ile Ala Ala Val Ala Val Ser Gly Ser Gln Ala Phe
    50                  55                  60

Tyr Asp Trp Asn Glu Val Asn Leu Ala Asp Ala Asp Gly Gln His Arg
65                  70                  75                  80

Gln Leu Ile Pro Asp Gly Lys Leu Cys Ser Ala Gly Arg Glu Lys Tyr
                85                  90                  95

Arg Gly Leu Asp Leu Ala Arg Asp Asp Trp Pro Ala Thr Ser Leu Ser
            100                 105                 110

Ser Gly Val Asn Tyr Thr Phe Leu Tyr Arg Ala Thr Ala Pro His Leu
        115                 120                 125

Gly Phe Phe Glu Phe Tyr Val Thr Arg Asp Ser Tyr Asp Pro Thr Gln
    130                 135                 140

Pro Leu Ala Trp Ala Asp Leu Glu Asp Pro Pro Phe Ile Asn Ile Thr
145                 150                 155                 160

Asp Pro Thr Leu Ala Ser Gly Ser Tyr Gln Ile Val Asn Thr Thr Pro
                165                 170                 175

Ser Asn Lys Thr Gly Arg His Leu Ile Tyr Val Ile Trp Gln Arg Thr
            180                 185                 190

Asp Ser Pro Glu Ala Phe Tyr Ser Cys Ser Asp Val Asp Phe Asp Glu
        195                 200                 205

Asp Asp Ser Leu Leu Ser Ala Val
    210                 215

<210> SEQ ID NO 211
<211> LENGTH: 215
<212> TYPE: PRT
<213> ORGANISM: Platycerium madagascariense

<400> SEQUENCE: 211

Met Arg Arg Ser Trp Gly Val Val Ala Val Ile Leu Ala Met Cys Ala
1               5                   10                  15

Gly Ser Leu Leu Gly Val Ala Ser Gly His Gly Ser Met Glu Asp Pro
            20                  25                  30

Ile Ser Arg Val Tyr Ala Cys Phe Leu Glu Asn Pro Glu Arg Pro Thr
        35                  40                  45

Ser Ala Ala Cys Ile Ala Ala Val Ala Leu Ser Gly Thr Gln Ala Phe
    50                  55                  60

Tyr Asp Trp Asn Glu Val Asn Gln Pro Asn Ala Ala Gly Asn His Thr
65                  70                  75                  80

Ile Ile Pro Asp Gly Gln Leu Cys Ser Ala Gly Arg Glu Lys Tyr Lys
                85                  90                  95

Gly Leu Asp Leu Pro Arg Ala Asp Trp Ser Ala Ile Ser Leu Ser Ser
            100                 105                 110

Gly Val Asn Tyr Thr Phe Leu Tyr Lys Ala Thr Ala Pro His Arg Gly
```

```
            115                 120                 125
Tyr Phe Glu Phe Tyr Val Thr Arg Asp Ser Tyr Asp Pro Thr Glu Pro
        130                 135                 140

Leu Ala Trp Ala Asp Leu Glu Asp Thr Pro Phe Ile Asn Ile Thr Asp
145                 150                 155                 160

Pro Asp Leu Val Ser Gly Ser Tyr Arg Ile Ala Asn Thr Thr Pro Ser
                165                 170                 175

Gly Lys Thr Gly Arg His Leu Ile Tyr Val Ile Trp Gln Arg Thr Asp
            180                 185                 190

Ser Pro Glu Ala Phe Tyr Ser Cys Ser Asp Val Val Phe Asp Glu Asp
        195                 200                 205

Val Ser Leu Val Ser Ala Ala
    210                 215
```

<210> SEQ ID NO 212
<211> LENGTH: 216
<212> TYPE: PRT
<213> ORGANISM: Microsorum musifolium (Blume)

<400> SEQUENCE: 212

```
Met Arg Arg Ser Trp Gly Val Leu Ala Ile Val Val Ala Val Cys Ala
1               5                   10                  15

Ser Gly Leu Phe Gly Val Ala Ser Gly His Gly Ser Met Glu His Pro
            20                  25                  30

Ile Ser Arg Val Tyr Gln Cys Tyr Arg Glu Gly Pro Glu Asn Pro Lys
        35                  40                  45

Ser Pro Ala Cys Ile Ala Ala Lys Gly Leu Ser Gly Ala Gln Ala Phe
    50                  55                  60

Tyr Asp Trp Asn Glu Val Asn Gln Pro Phe Ala Asp Gly Arg His Gln
65                  70                  75                  80

Glu Ile Ile His Asp Gly His Leu Cys Ser Gly Gly Arg Asp Lys Tyr
                85                  90                  95

Arg Gly Leu Asp Leu Pro Arg Ala Asp Trp Val Ala Thr Ser Leu Ser
            100                 105                 110

Ala Gly Lys Pro Tyr Thr Phe Leu Tyr Arg Ala Thr Ala Pro His Leu
        115                 120                 125

Gly Tyr Phe Gln Phe Tyr Val Thr Arg Asp Gly Tyr Asn Pro Thr Lys
    130                 135                 140

Pro Leu Ala Trp Ala Asp Leu Glu Asp Ser Pro Phe Ile Asn Val Thr
145                 150                 155                 160

Asn Pro Thr Leu Val Ser Gly Ser Tyr Arg Ile Pro His Thr Thr Pro
                165                 170                 175

Ala Ser Lys Thr Gly Arg His Leu Ile Tyr Val Ile Trp Gln Arg Thr
            180                 185                 190

Asp Ser Pro Glu Ala Phe Tyr Ser Cys Ser Asp Val Val Phe Asp Glu
        195                 200                 205

Ala Leu Ser Leu Ser Ser Thr Ile
    210                 215
```

<210> SEQ ID NO 213
<211> LENGTH: 219
<212> TYPE: PRT
<213> ORGANISM: Lygodium flexuosum

<400> SEQUENCE: 213

Met Gly Ser Trp Gln Trp Gly Ser Val Asn Val Ala Ile Val Val Phe

```
            1               5                  10                 15
         Met Met Leu Cys Gly Val Ala Ser Gly His Gly Thr Met Gly Asp Pro
                         20                 25                 30

Ile Ser Arg Val Tyr Arg Cys Tyr Leu Glu Asn Pro Glu Arg Pro Thr
                         35                 40                 45

Ser Ala Ala Cys Gln Ala Ala Val Ala Leu Ser Gly Thr Gln Ala Phe
                         50                 55                 60

Tyr Asp Trp Asn Glu Val Asn Leu Pro Asn Ala Ala Gly Arg His Arg
          65                 70                 75                 80

Gln Leu Ile Pro Asp Gly Gln Leu Cys Ser Ala Gly Arg Ala Lys Tyr
                         85                 90                 95

Gln Gly Leu Asp Leu Ala Arg Ala Asp Trp Leu Ala Ala Ser Leu Ser
                         100                105                110

Ser Gly Val Ser Tyr Thr Phe Leu Tyr Arg Val Thr Ala Gln His Arg
                         115                120                125

Gly Phe Phe Glu Phe Tyr Val Thr Arg Asp Gly Tyr Glu Pro Thr Glu
                         130                135                140

Pro Leu Lys Trp Ser Asp Leu Glu Glu Ser Pro Phe Ile Asn Val Thr
         145                150                155                160

Asp Pro Thr Ala Val Ser Gly Ser Tyr Gln Ile Pro Gly Thr Thr Pro
                         165                170                175

Ala Gly Lys Ser Gly Arg His Leu Ile Tyr Val Ile Trp Gln Arg Ser
                         180                185                190

Asp Ser Pro Glu Ala Phe Tyr Ser Cys Ser Asp Val Asp Phe Asp Val
                         195                200                205

Glu Gly Ala Ala Val Ser Leu Arg Ser Thr Thr
                         210                215

<210> SEQ ID NO 214
<211> LENGTH: 215
<212> TYPE: PRT
<213> ORGANISM: Polystichum polyblepharum

<400> SEQUENCE: 214

Met Asn Arg Ser Trp Gly Val Val Ala Ile Met Val Leu Cys Ala Ser
          1               5                  10                 15

Gly Leu Leu Gly Val Ala Ser Gly His Gly Thr Met Asn Asp Pro Ile
                         20                 25                 30

Ser Arg Val Tyr Asn Cys Arg Leu Glu Asn Pro Glu Ser Pro Thr Ser
                         35                 40                 45

Ala Ala Cys Ile Ala Ala Val Ala Leu Ser Gly Thr Gln Ala Phe Tyr
                         50                 55                 60

Asp Trp Asn Glu Val Asn Leu Ala Asn Val Ala Gly Arg His Arg Glu
          65                 70                 75                 80

Leu Ile Pro Asp Gly Lys Leu Cys Ser Ala Gly Arg Asp Lys Tyr Lys
                         85                 90                 95

Gly Leu Asp Leu Ala Arg Ser Asp Trp Val Ala Thr Asn Leu Ser Ser
                         100                105                110

Gly Val Ala Phe Thr Phe Leu Tyr Arg Val Thr Ala Gln His Arg Gly
                         115                120                125

Phe Phe Glu Phe Tyr Val Thr Val Asp Asp Tyr Asp Pro Thr Glu Leu
                         130                135                140

Leu Lys Trp Glu Asp Leu Glu Glu Thr Pro Phe Met Asn Val Thr Asp
         145                150                155                160
```

```
Pro Thr Leu Val Gly Leu Asn Tyr Glu Met Pro Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Val Ser Leu His Ser Ser Thr
    210                 215

<210> SEQ ID NO 215
<211> LENGTH: 218
<212> TYPE: PRT
<213> ORGANISM: Diplazium pycnocarpon

<400> SEQUENCE: 215

Met Gly Lys Ser Trp Gly Val Val Ala Ile Ile Leu Val Leu Cys Ala
1               5                   10                  15

Ser Gly Leu Leu Gly Val Ala Ser Gly His Gly Ser Met Ala Asp Pro
            20                  25                  30

Ile Ser Arg Ile Tyr Asn Cys Arg Gln Glu Asn Pro Glu Arg Pro Thr
        35                  40                  45

Ser Ala Ala Cys Gln Ala Ala Val Ala Leu Ser Gly Thr Gln Ala Phe
    50                  55                  60

Tyr Asp Trp Asn Glu Val Asn Gln Pro Asn Ala Ala Gly Arg His Arg
65                  70                  75                  80

Glu Ile Ile Pro Asp Gly Gln Leu Cys Ser Ala Gly Arg Tyr Lys Tyr
                85                  90                  95

Arg Gly Leu Asp Leu Ala Ser Ala Asp Trp Gln Trp Pro Ala Thr Ser
            100                 105                 110

Leu Ser Ser Gly Val Ser Phe Thr Tyr Arg Tyr Arg Ala Thr Ala Ala
        115                 120                 125

His Tyr Gly Tyr Phe Gln Phe Tyr Ile Thr Arg Asp Gly Tyr Gln Pro
    130                 135                 140

Thr Gln Pro Leu Lys Trp Ala Asp Leu Glu Gln Leu Pro Phe Leu Thr
145                 150                 155                 160

Val Tyr Asn Pro Thr Leu Val Asn Gly Phe Tyr Glu Met Gln Gly Thr
                165                 170                 175

Thr Pro Ala Gly Lys Thr Gly Arg His Leu Ile Tyr Val Ile Trp Gln
            180                 185                 190

Arg Ser Asp Ser Pro Glu Ala Phe Tyr Ser Cys Ser Asp Val Asp Phe
        195                 200                 205

Val Gly Ala Leu Ser Leu His Ser Thr Thr
    210                 215

<210> SEQ ID NO 216
<211> LENGTH: 216
<212> TYPE: PRT
<213> ORGANISM: Polystichum braunii

<400> SEQUENCE: 216

Met Gly Arg Ser Trp Gly Val Val Ala Ile Met Val Leu Cys Ala Ser
1               5                   10                  15

Gly Leu Leu Gly Ala Ala Ser Gly His Gly Thr Met Tyr Asp Pro Phe
            20                  25                  30

Ser Arg Val Tyr Asn Cys Arg Phe Arg Glu Asn Pro Glu Arg Pro Thr
        35                  40                  45
```

```
Ser Ala Ala Cys Ile Ala Ala Val Ala Leu Ser Gly Thr Gln Ala Phe
 50                  55                  60

Tyr Asp Trp Asn Glu Val Asn Leu Ala Asn Ala Ala Gly Arg His Arg
 65                  70                  75                  80

Glu Leu Ile Pro Asp Gly Lys Leu Cys Ser Ala Gly Arg Asp Lys Tyr
                 85                  90                  95

Lys Gly Leu Asp Leu Ala Arg Ser Asp Trp Val Ala Thr Asn Leu Ser
                100                 105                 110

Ser Gly Val Ala Phe Thr Phe Leu Tyr Arg Val Thr Ala Gln His Arg
                115                 120                 125

Gly Phe Phe Glu Phe Tyr Val Thr Val Asp Asp Tyr Asp Pro Thr Glu
            130                 135                 140

Ser Leu Lys Trp Glu Asp Leu Glu Glu Thr Pro Phe Leu Asn Val Thr
145                 150                 155                 160

Asp Pro Thr Val Val Gly Val Asn Tyr Gln Ile Ser Gly Thr Thr Pro
                165                 170                 175

Ala Ser Lys Thr Gly Arg His Leu Ile Tyr Val Ile Trp Gln Arg Ser
                180                 185                 190

Asp Ser Pro Glu Ala Phe Tyr Ser Cys Ser Asp Val Asp Phe Val Asp
                195                 200                 205

Ala Leu Ser Leu Gln Ser Thr Thr
210                 215

<210> SEQ ID NO 217
<211> LENGTH: 215
<212> TYPE: PRT
<213> ORGANISM: Platycerium hillii

<400> SEQUENCE: 217

Met Gly Lys Pro Trp Arg Val Val Ala Ile Val Val Cys Ala
 1               5                  10                  15

Ser Gly Leu Leu Gly Val Ala Ser Gly His Gly Ser Met Gly Glu Pro
                 20                  25                  30

Ile Ser Arg Val Tyr Asn Cys Tyr Leu Glu Asn Pro Glu Arg Pro Thr
                 35                  40                  45

Ser Ala Ala Cys Ile Ala Ala Val Ala Leu Ser Gly Thr Gln Ala Phe
 50                  55                  60

Tyr Asp Trp Asn Glu Val Asn Leu Pro Phe Ala Ala Gly Arg His Arg
 65                  70                  75                  80

Glu Leu Ile Pro Asp Gly Gln Leu Cys Ser Ala Gly Arg Asp Lys Tyr
                 85                  90                  95

Lys Gly Leu Asp Leu Ala Arg Ala Asp Trp Val Ala Thr Ser Leu Ser
                100                 105                 110

Ser Gly Val Ser Tyr Thr Phe Leu Tyr Arg Val Thr Ala Pro His Arg
                115                 120                 125

Gly Tyr Phe Glu Phe Tyr Val Thr Lys Asp Ser Tyr Asp Pro Thr Glu
            130                 135                 140

Pro Leu Ala Trp Ala Asp Leu Glu Asp Thr Pro Phe Ile Asn Ile Thr
145                 150                 155                 160

Asp Pro Thr Ile Val Ser Gly Ser Tyr Gln Ile Ser Thr Thr Pro
                165                 170                 175

Ser Asp Lys Thr Gly Arg His Leu Ile Tyr Val Ile Trp Gln Arg Thr
                180                 185                 190

Asp Ser Pro Glu Ala Phe Tyr Ser Cys Ser Asp Ile Asp Phe Asp Asp
                195                 200                 205
```

```
Thr Leu Pro Leu His Ser Thr
    210                 215
```

```
<210> SEQ ID NO 218
<211> LENGTH: 227
<212> TYPE: PRT
<213> ORGANISM: Drynaria rigidula (whitei)

<400> SEQUENCE: 218
```

```
Met Gly Arg Thr Tyr Ser Trp Gly Ala Val Ala Met Val Val Leu
1               5                   10                  15

Cys Ala Ser Gly Leu Leu Gly Ile Ala Ser Gly His Gly Ser Met Asp
                20                  25                  30

Ser Pro Ile Ser Arg Val Tyr Arg Cys Tyr Leu Glu Asn Pro Glu Asn
                35                  40                  45

Pro Thr Ser Ala Ala Cys Gln Ala Val Ala Leu Ser Gly Thr Gln
    50                  55                  60

Ala Phe Tyr Asp Trp Asn Glu Val Asn Ile Ala Asp Ala Ala Gly Arg
65                  70                  75                  80

His Arg Glu Leu Ile Pro Asp Gly Gln Leu Cys Ser Ala Gly Arg Glu
                85                  90                  95

Lys Tyr Gln Gly Leu Asp Leu Ala Arg Ala Asp Trp Leu Ala Asp Ser
                100                 105                 110

Leu Ser Ser Gly Val Ser Phe Thr Phe Leu Tyr Lys Ala Thr Ala Ala
                115                 120                 125

His Leu Gly Phe Phe Glu Phe Tyr Val Thr Arg Asp Ala Tyr Asp Pro
    130                 135                 140

Thr Glu Pro Leu Lys Trp Ala Asp Leu Glu Asp Ser Pro Phe Leu Asn
145                 150                 155                 160

Val Thr Asp Pro Thr Leu Val Ser Gly Tyr Tyr Gln Ile Pro Gly Thr
                165                 170                 175

Thr Pro Ala Gly Lys Ser Gly Arg His Leu Leu Tyr Val Ile Trp Gln
                180                 185                 190

Arg Ser Asp Ser Pro Glu Ala Phe Tyr Ser Cys Ser Asp Val Asp Phe
                195                 200                 205

Asp Asp Asp Ala Ala Ala Gln His Met Ile Ile Ser Leu Arg His
    210                 215                 220

Ser Thr Thr
225
```

```
<210> SEQ ID NO 219
<211> LENGTH: 229
<212> TYPE: PRT
<213> ORGANISM: Adiantum monocolor

<400> SEQUENCE: 219
```

```
Met Gly Met Lys Met Ser Trp Glu Val Ala Leu Ala Glu Ile Val Ala
1               5                   10                  15

Leu Cys Leu Leu Gly Met Ala Ser Ser His Gly Thr Met Gln Asp Pro
                20                  25                  30

Ile Ser Arg Val Tyr Asn Cys Phe Leu Glu Asn Pro Glu Arg Pro Thr
                35                  40                  45

Ser Ala Ala Cys Gln Ala Ala Val Ala Leu Gly Gly Thr Gln Pro Leu
    50                  55                  60

Tyr Asp Trp Asn Glu Val Asn Ile His Asp Ala Ala Gly Asn His Arg
65                  70                  75                  80
```

```
Asp Leu Ile Pro Asp Gly Lys Leu Cys Ser Ala Gly Arg Gln Lys Phe
                85                  90                  95

Gln Gly Leu Asp Leu Ala Arg Ala Asp Trp Ile Ala Thr Ser Leu Ser
            100                 105                 110

Ser Gly Val Asp Tyr Thr Phe Leu Tyr Arg Ala Thr Ala Pro His Leu
        115                 120                 125

Gly Phe Phe Glu Phe Tyr Ile Thr Arg Asp Thr Tyr Asp Pro Thr Gln
    130                 135                 140

Pro Leu Ala Trp Gly Asp Leu Glu Asp Ser Pro Phe Ile Asn Ile Thr
145                 150                 155                 160

Asn Pro Ser Ile Val Ser Thr Thr Leu Gly Pro Ala Tyr Ser Ile Pro
                165                 170                 175

Ser Thr Thr Pro Phe Ser Lys Ser Gly Arg His Leu Ile Tyr Val Ile
            180                 185                 190

Trp Gln Arg Thr Asp Ser Leu Glu Ala Phe Tyr Ser Cys Ser Asp Val
        195                 200                 205

Asp Phe Ser Thr Ser Ser Ile Glu Asp Asp Val Ile Val Ser Leu Arg
    210                 215                 220

Ser Ala Ala Leu Leu
225

<210> SEQ ID NO 220
<211> LENGTH: 223
<212> TYPE: PRT
<213> ORGANISM: Pellaea rotundifolia

<400> SEQUENCE: 220

Met Gln Arg Ser Cys Met Trp Gly Glu Ser Val Val Ala Ile Met Cys
1               5                   10                  15

Met Val Leu Gly Leu Leu Gly Asp Val Ala Ser Gly His Gly Ser Met
                20                  25                  30

Ala Ser Pro Ile Ser Arg Val Phe Asn Cys Tyr Leu Glu Asn Pro Glu
            35                  40                  45

Ser Pro Thr Ser Glu Ala Cys Lys Ala Ala Val Glu Glu Ser Gly Thr
        50                  55                  60

Gln Ala Phe Tyr Asp Trp Ala Glu Val Ser Leu Pro Asn Ala Ala Gly
65                  70                  75                  80

Arg His Arg Glu Leu Ile Pro Asp Gly Gln Leu Cys Ser Ala Gly Leu
                85                  90                  95

Ala Lys Tyr Ala Gly Leu Asp Leu Ala Arg Ala Asp Trp Thr Ala Thr
            100                 105                 110

Ser Leu Thr Ser Asn Ile Ser Tyr Thr Phe Ile Phe Glu Ala Thr Ala
        115                 120                 125

Gly Pro His Leu Gly Ser Phe Glu Phe Tyr Val Thr Asn Asp Asp Tyr
    130                 135                 140

Glu Pro Ala Glu Ala Leu Asn Trp Ala Asp Leu Glu Asp Thr Pro Phe
145                 150                 155                 160

Ile Ile Val Thr Asn Pro Thr Leu Val Ser Gly Ser Tyr Leu Ile Pro
                165                 170                 175

Gly Thr Thr Pro Ala Gly Lys Thr Gly Arg His Ile Ile Tyr Val Ile
            180                 185                 190

Trp Gln Arg Ser Asp Ser Pro Glu Ala Phe Tyr Ser Cys Ser Asp Ile
        195                 200                 205

Asp Phe Val Glu Glu Asp Pro Val Val Pro Leu His Ser Thr Thr
```

```
                210                 215                 220

<210> SEQ ID NO 221
<211> LENGTH: 216
<212> TYPE: PRT
<213> ORGANISM: Microsorum punctatum

<400> SEQUENCE: 221

Met Arg Arg Ser Trp Gly Val Leu Ala Ile Val Val Ala Val Cys Ala
1               5                   10                  15

Ser Gly Leu Phe Gly Val Ala Ser Gly His Gly Ser Met Glu Asp Pro
            20                  25                  30

Ile Ser Arg Val Tyr Gln Cys Tyr Asp Glu Gly Pro Glu Asn Pro Lys
        35                  40                  45

Ser Pro Ala Cys Ile Ala Ala Val Gly Leu Ser Gly Ala Gln Ala Phe
    50                  55                  60

Tyr Asp Trp Asn Glu Val Asn Gln Pro Phe Ala Ala Gly Gln His Lys
65                  70                  75                  80

Glu Ile Ile His Asp Gly His Leu Cys Ser Gly Gly Arg Asp Lys Tyr
                85                  90                  95

Arg Gly Leu Asp Leu Pro Arg Ala Asp Trp Val Ala Thr Ser Leu Ser
            100                 105                 110

Ala Gly Ala Pro Tyr Thr Phe Leu Tyr Arg Ala Thr Ala His His Leu
        115                 120                 125

Gly Tyr Phe Glu Phe Tyr Val Thr Arg Asp Gly Tyr Asp Pro Thr Lys
    130                 135                 140

Pro Leu Ala Trp Ala Asp Leu Glu Asp Ser Pro Phe Ile Asn Val Thr
145                 150                 155                 160

Asn Pro Pro Leu Val Ser Gly Ser Tyr Arg Ile Pro Asp Thr Thr Pro
                165                 170                 175

Ala Leu Lys Thr Gly Arg His Leu Ile Tyr Val Ile Trp Gln Arg Thr
            180                 185                 190

Asp Ser Pro Glu Ala Phe Tyr Ser Cys Ser Asp Val Val Phe Ala Glu
        195                 200                 205

Ala Leu Ser Leu Ser Ser Thr Thr
    210                 215

<210> SEQ ID NO 222
<211> LENGTH: 217
<212> TYPE: PRT
<213> ORGANISM: Woodwardia fimbriata

<400> SEQUENCE: 222

Met Gly Arg Ser Ile Trp Gly Val Val Ala Met Met Val Leu Cys Ala
1               5                   10                  15

Ser Gly Leu Leu Arg Ile Ala Ser Gly His Gly Ser Met Glu Asn Pro
            20                  25                  30

Ile Ser Arg Val Tyr Asn Cys Tyr Leu Glu Gly Pro Glu Asn Pro Lys
        35                  40                  45

Ser Ala Ala Cys Lys Ala Ala Val Ala Ala Ser Gly Thr Gln Ala Phe
    50                  55                  60

Tyr Asp Trp Asn Glu Val Asn Leu Ala Asn Ala Gly Arg His Arg
65                  70                  75                  80

Glu Leu Ile Pro Asp Gly Gln Leu Cys Ser Ala Gly Arg Gln Lys Tyr
                85                  90                  95

Gln Gly Leu Asp Leu Val Arg Ser Asp Trp Pro Ala Thr Ser Leu Ser
```

```
              100                 105                 110
Ser Gly Val Pro Phe Thr Phe Leu Tyr Arg Ile Thr Ala Gln His Leu
            115                 120                 125

Gly Phe Phe Glu Phe Tyr Val Thr Arg Asp Gly Tyr Gln Pro Thr Ala
        130                 135                 140

Ala Leu Thr Trp Ala Asp Leu Glu Asp Ser Pro Phe Met Asn Val Thr
145                 150                 155                 160

Gly Asp Pro Thr Phe Ile Thr Gly Ser Trp Glu Ile Pro Gly Thr Ser
                165                 170                 175

Pro Ala Gly Lys Ser Gly Arg His Leu Ile Tyr Val Ile Trp Gln Arg
            180                 185                 190

Ser Asp Ser Pro Glu Ala Phe Tyr Ala Cys Cys Asp Val Asp Phe Val
        195                 200                 205

Asp Ala Leu Ser Leu His Ser Thr Thr
    210                 215

<210> SEQ ID NO 223
<211> LENGTH: 213
<212> TYPE: PRT
<213> ORGANISM: Dryopteris celsa

<400> SEQUENCE: 223

Met Gly Arg Ser Ser Leu Gly Val Val Ala Ile Met Val Leu Cys Leu
1               5                   10                  15

Val Gly Val Ala Ser Gly His Gly Ser Met Gln Asp Pro Ile Ser Arg
            20                  25                  30

Val Tyr Asn Cys Tyr Leu Glu Asn Pro Glu Ser Pro Thr Ser Ala Ala
        35                  40                  45

Cys Gln Ala Ala Val Ala Leu Ser Gly Thr Gln Ala Phe Tyr Asp Trp
    50                  55                  60

Asn Glu Val Asn Gln Pro Glu Ala Asp Gly Arg Ser Arg Glu Ile Ile
65                  70                  75                  80

Pro Asp Gly Gln Leu Cys Ser Gly Gly Arg Glu Lys Tyr Gln Gly Leu
                85                  90                  95

Asp Leu Ala Arg Ser Asp Trp Glu Ala Thr Thr Leu Ser Ser Ser Val
            100                 105                 110

Asn Tyr Thr Phe Leu Tyr Lys Ala Thr Ala Pro His Leu Gly Phe Phe
        115                 120                 125

Glu Phe Tyr Val Thr Gln Asp Gly Tyr Asp Pro Thr Glu Val Leu Lys
    130                 135                 140

Trp Ala Asp Leu Glu Asp Ser Pro Phe Leu Asn Val Thr Asp Pro Thr
145                 150                 155                 160

Leu Asp Ser Gly Ala Tyr Gln Ile Pro Gly Thr Thr Pro Ala Gly Lys
                165                 170                 175

Thr Gly Arg His Leu Ile Tyr Val Ile Trp Gln Arg Ser Asp Ser Pro
            180                 185                 190

Glu Ala Phe Tyr Ser Cys Ser Asp Val Asp Phe Pro Asp Ala Leu Ser
        195                 200                 205

Leu His Ser Thr Thr
    210

<210> SEQ ID NO 224
<211> LENGTH: 216
<212> TYPE: PRT
<213> ORGANISM: Campyloneurum angustifolium
```

-continued

<400> SEQUENCE: 224

Met Arg Arg Ser Trp Glu Val Val Gly Met Val Leu Cys Ala Cys
1               5                   10                  15

Gly Leu Leu Gly Val Ala Ser Gly His Gly Ser Met Glu Asp Pro Ile
            20                  25                  30

Ser Arg Val Tyr Arg Cys Arg Leu Glu Asn Pro Glu Arg Pro Thr Ser
        35                  40                  45

Pro Ala Cys Arg Ala Ala Val Ala Leu Ser Gly Thr Gln Ala Phe Tyr
    50                  55                  60

Asp Trp Asn Glu Val Asn Gln Pro Phe Ala Ala Gly Arg His Arg Glu
65                  70                  75                  80

Ile Ile Pro Asp Gly Gln Leu Cys Ser Ala Gly Arg Asp Lys Tyr Lys
                85                  90                  95

Gly Leu Asp Leu Ala Arg Ala Asp Trp Leu Ala Val Ser Leu Ser Ser
            100                 105                 110

Gly Ala Asp Tyr Thr Phe Leu Tyr Leu Ala Thr Ala Thr His Arg Gly
        115                 120                 125

Tyr Phe Glu Phe Tyr Val Thr Arg Asp Ser Tyr Asp Pro Thr Glu Pro
    130                 135                 140

Leu Lys Trp Ser Asp Leu Glu Asp Ser Pro Phe Ile Asn Val Thr Asp
145                 150                 155                 160

Pro Thr Glu Val Gly Pro Val Tyr Gln Ile Pro Gly Thr Thr Pro Ala
                165                 170                 175

Gly Lys Thr Gly Arg His Leu Ile Tyr Val Ile Trp Gln Arg Thr Asp
            180                 185                 190

Ser Pro Glu Ala Phe Tyr Ser Cys Ser Asp Val Asp Phe Gly Glu Ser
        195                 200                 205

Leu Ser Leu Tyr Ser Val Thr Glu
    210                 215

<210> SEQ ID NO 225
<211> LENGTH: 218
<212> TYPE: PRT
<213> ORGANISM: Onoclea sensibilis

<400> SEQUENCE: 225

Met Gly Arg Ser Trp Gly Val Val Gln Ala Ile Ile Met Val Leu Cys
1               5                   10                  15

Gly Ser Gly Leu Leu Gly Val Ala Ser Gly His Gly Ser Met Glu Asp
            20                  25                  30

Pro Ile Ser Arg Val Tyr Asn Cys Tyr Leu Glu Asn Pro Glu Ser Pro
        35                  40                  45

Thr Ser Ala Ala Cys Gln Ala Val Ala Leu Ser Gly Ala Gln Ala
    50                  55                  60

Phe Tyr Asp Trp Asn Glu Val Asn Leu Ala Asp Ala Ala Gly Arg His
65                  70                  75                  80

Arg Glu Leu Ile Pro Asp Gly Gln Leu Cys Ser Ala Gly Arg Glu Lys
                85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
        115                 120                 125

Leu Gly Phe Phe Glu Phe Tyr Val Thr Lys Asp Gly Tyr Glu Pro Thr
    130                 135                 140

```
Glu Pro Leu Lys Trp Ala Asp Leu Glu Asp Ser Pro Leu Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
            195                 200                 205

Val Asp Ala Leu Ser Leu His Ser Thr Thr
        210                 215

<210> SEQ ID NO 226
<211> LENGTH: 235
<212> TYPE: PRT
<213> ORGANISM: Onoclea sensibilis

<400> SEQUENCE: 226

Met Gly Arg Ser Trp Gly Val Val Gln Ala Ile Ile Met Val Leu Cys
1               5                   10                  15

Gly Ser Gly Leu Leu Gly Val Ala Ser Gly His Gly Ser Met Glu Asp
                20                  25                  30

Pro Ile Ser Arg Val Tyr Asn Cys Tyr Leu Glu Asn Pro Glu Ser Pro
            35                  40                  45

Thr Ser Ala Ala Cys Gln Ala Val Ala Leu Ser Gly Ala Gln Ala
    50                  55                  60

Phe Tyr Asp Trp Asn Glu Val Asn Leu Ala Asp Ala Ala Gly Arg His
65                  70                  75                  80

Arg Glu Leu Ile Pro Asp Gly Gln Leu Cys Ser Ala Gly Arg Glu Lys
                85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
            115                 120                 125

Leu Gly Phe Phe Glu Phe Tyr Val Thr Lys Asp Gly Tyr Glu Pro Thr
130                 135                 140

Glu Pro Leu Lys Trp Ala Asp Leu Glu Asp Ser Pro Phe Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
            195                 200                 205

Val Asp Ala Leu Ser Leu His Ser Thr Pro Asn Leu Asp Leu Ser Ser
        210                 215                 220

Ser Gly Leu Ala Asn Leu Ile Asn Val Cys Val
225                 230                 235

<210> SEQ ID NO 227
<211> LENGTH: 229
<212> TYPE: PRT
<213> ORGANISM: Onoclea sensibilis

<400> SEQUENCE: 227

Met Gly Arg Ser Trp Gly Val Val Gln Ala Ile Ile Met Val Leu Cys
1               5                   10                  15
```

```
Gly Ser Gly Leu Leu Gly Val Ala Ser Gly His Gly Ser Met Glu Asp
                20                  25                  30

Pro Ile Ser Arg Val Tyr Asn Cys Tyr Leu Glu Asn Pro Glu Ser Pro
            35                  40                  45

Thr Ser Ala Ala Cys Gln Ala Val Ala Leu Ser Gly Ala Gln Ala
 50                  55                  60

Phe Tyr Asp Trp Asn Glu Val Asn Leu Ala Asp Ala Ala Gly Arg His
 65                  70                  75                  80

Arg Glu Leu Ile Pro Asp Gly Gln Leu Cys Ser Ala Gly Arg Glu Lys
                85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
        115                 120                 125

Leu Gly Phe Phe Glu Phe Tyr Val Thr Lys Asp Gly Tyr Glu Pro Thr
130                 135                 140

Glu Pro Leu Lys Trp Ala Asp Leu Glu Asp Ser Pro Phe Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
        195                 200                 205

Val Asp Ala Leu Ser Leu His Ser Thr Pro Asn Leu Asp Leu Ser Ile
210                 215                 220

Leu Asp Trp Pro Thr
225

<210> SEQ ID NO 228
<211> LENGTH: 215
<212> TYPE: PRT
<213> ORGANISM: Polystichum tripteron

<400> SEQUENCE: 228

Met Gly Arg Ser Trp Gly Val Val Ala Ile Met Val Leu Cys Ala Ser
 1               5                  10                  15

Gly Leu Leu Gly Val Ala Ser Gly His Gly Thr Met Asn Asp Pro Ile
                20                  25                  30

Ser Arg Val Tyr Ala Cys Arg Gln Glu Asn Pro Glu Arg Pro Thr Thr
            35                  40                  45

Pro Ala Cys Ile Ala Ala Val Ala Leu Ser Gly Ala Gln Ala Phe Tyr
 50                  55                  60

Asp Trp Asn Glu Val Asn Leu Pro Phe Val Asn Gly Arg His Arg Gln
 65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
        115                 120                 125

Phe Phe Glu Phe Tyr Val Thr Val Asp Gly Tyr Asp Pro Thr Glu Pro
130                 135                 140

Leu Lys Trp Ala Asp Leu Glu Glu Thr Pro Phe Ile Asn Val Thr Asp
145                 150                 155                 160
```

```
Pro Thr Val Val Gly Leu Asn Tyr Val Ile Pro Gly Thr Thr Pro Ala
            165                 170                 175

Ser Lys Thr Gly Arg His Leu Ile Tyr Val Ile Trp Gln Arg Ser Asp
            180                 185                 190

Ser Pro Glu Ala Phe Tyr Ser Cys Ser Asp Val Asn Phe Pro Asp Ala
            195                 200                 205

Leu Ser Leu His Ser Ala Thr
            210                 215

<210> SEQ ID NO 229
<211> LENGTH: 215
<212> TYPE: PRT
<213> ORGANISM: Polystichum tripteron

<400> SEQUENCE: 229

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Ala Cys Arg Gln Glu Asn Pro Glu Arg Pro Thr Thr
            35                  40                  45

Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
            85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
            115                 120                 125

Phe Phe Glu Phe Tyr Val Thr Val Asp Gly Tyr Asp Pro Thr Glu Pro
    130                 135                 140

Leu Lys Trp Ala Asp Leu Glu Glu Thr Pro Phe Ile Asn Val Thr Asp
145                 150                 155                 160

Pro Thr Val Val Gly Leu Asn Tyr Val Ile Ser Gly Thr Thr Pro Ala
            165                 170                 175

Ser Lys Thr Gly Arg His Leu Ile Tyr Val Ile Trp Gln Arg Thr Asp
            180                 185                 190

Ser Pro Glu Ala Phe Tyr Ser Cys Ser Asp Val Asn Phe Pro Asp Ala
            195                 200                 205

Leu Ser Leu His Ser Ala Thr
            210                 215

<210> SEQ ID NO 230
<211> LENGTH: 215
<212> TYPE: PRT
<213> ORGANISM: Polystichum tripteron

<400> SEQUENCE: 230

Met Gly Arg Ser Trp Gly Val Val Ala Ile Met Met Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Ala Cys Arg Gln Glu Asn Pro Glu Arg Pro Thr Thr
            35                  40                  45
```

```
Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
                100                 105                 110

Gly Val Ala Tyr Thr Phe Leu Tyr Arg Val Thr Ala Gln His Arg Gly
                115                 120                 125

Phe Phe Glu Phe Tyr Val Thr Val Asp Gly Tyr Asp Pro Thr Glu Pro
                130                 135                 140

Leu Lys Trp Ala Asp Leu Glu Glu Thr Pro Phe Ile Asn Val Thr Asp
145                 150                 155                 160

Pro Thr Val Val Gly Leu Asn Tyr Val Ile Pro Gly Thr Thr Pro Ala
                165                 170                 175

Ser Lys Thr Gly Arg His Leu Ile Tyr Val Ile Trp Gln Arg Ser Asp
                180                 185                 190

Ser Pro Glu Ala Phe Tyr Ser Cys Ser Asp Val Asn Phe Pro Asp Ala
                195                 200                 205

Leu Ser Leu His Ser Ala Thr
                210                 215

<210> SEQ ID NO 231
<211> LENGTH: 215
<212> TYPE: PRT
<213> ORGANISM: Polystichum tripteron

<400> SEQUENCE: 231

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
                20                  25                  30

Ser Arg Val Tyr Ala Cys Arg Gln Glu Asn Pro Glu Arg Pro Thr Thr
                35                  40                  45

Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
                100                 105                 110

Gly Val Ala Tyr Thr Phe Leu Tyr Arg Val Thr Ala Gln His Arg Gly
                115                 120                 125

Phe Phe Glu Phe Tyr Val Thr Val Asp Gly Tyr Asp Pro Thr Glu Pro
                130                 135                 140

Leu Lys Trp Ala Asp Leu Glu Glu Thr Pro Phe Ile Asn Val Ala Asn
145                 150                 155                 160

Pro Thr Val Val Gly Leu Asn Tyr Val Ile Ser Gly Thr Thr Pro Ala
                165                 170                 175

Ser Lys Thr Gly Arg His Leu Ile Tyr Val Ile Trp Gln Arg Thr Asp
                180                 185                 190

Ser Pro Glu Ala Phe Tyr Ser Cys Ser Asp Val Asn Phe Val Asp Ala
```

195                 200                 205
Leu Ser Leu His Ser Ala Thr
    210                 215

<210> SEQ ID NO 232
<211> LENGTH: 217
<212> TYPE: PRT
<213> ORGANISM: Tectaria milnei

<400> SEQUENCE: 232

Met Gly Arg Ser Trp Gly Val Val Ala Val Met Val Val Cys Ala Ser
1               5                   10                  15

Gly Leu Leu Ser Val Val Arg Gly His Gly Ser Met Glu Asp Pro Ile
            20                  25                  30

Ser Arg Val Tyr Ala Cys Phe Leu Glu Asn Pro Glu Arg Pro Ile Ser
        35                  40                  45

Ala Ala Cys Gln Ala Ala Val Ala Met Gly Gly Thr Gln Ala Phe Tyr
    50                  55                  60

Asp Trp Asn Ala Val Ser Leu Pro Tyr Ala Ala Gly Arg His Arg Glu
65                  70                  75                  80

Leu Ile Pro Asp Gly Gln Leu Cys Ser Ala Gly Arg Ala Lys Tyr Arg
                85                  90                  95

Gly Leu Asp Leu Pro Arg Asp Asp Trp Pro Gly Thr Ser Asn Met Thr
            100                 105                 110

Ser Gly Val Ala Phe Thr Tyr Arg Tyr Lys Ala Thr Ala Pro His Leu
        115                 120                 125

Gly Ser Phe Gln Phe Tyr Val Thr Arg Asp Gly Tyr Asp Pro Thr Glu
    130                 135                 140

Pro Leu Lys Trp Ala Asp Leu Glu Asp Ser Pro Phe Met Asn Ala Thr
145                 150                 155                 160

Ser Thr Leu Ala Pro Asp Ser Tyr Leu Met Ser Gly Thr Thr Pro Ser
                165                 170                 175

Gly Lys Ala Gly His His Leu Ile Tyr Ala Ile Trp Gln Arg Ser Asp
            180                 185                 190

Ser Pro Glu Ala Phe Tyr Ser Cys Ser Asp Val Thr Phe Asp Val Ala
        195                 200                 205

Ala Val Ser Asp Leu His Ser Thr Thr
    210                 215

<210> SEQ ID NO 233
<211> LENGTH: 217
<212> TYPE: PRT
<213> ORGANISM: Tectaria milnei

<400> SEQUENCE: 233

Met Gly Arg Ser Trp Gly Val Val Ala Val Met Val Val Cys Ala Ser
1               5                   10                  15

Gly Leu Leu Ser Val Val Arg Gly His Gly Ser Met Glu Asp Pro Ile
            20                  25                  30

Ser Arg Val Tyr Ala Cys Phe Leu Glu Asn Pro Glu Arg Pro Ile Ser
        35                  40                  45

Ala Ala Cys Gln Ala Ala Val Ala Met Gly Gly Thr Gln Ala Phe Tyr
    50                  55                  60

Asp Trp Asn Ala Val Ser Leu Pro Tyr Ala Ala Gly Arg His Arg Glu
65                  70                  75                  80

Leu Ile Pro Asp Gly Gln Leu Cys Ser Ala Gly Arg Ala Lys Tyr Arg

```
                  85                  90                  95

Gly Leu Asp Leu Pro Arg Asp Asp Trp Pro Gly Thr Ser Asn Met Thr
            100                 105                 110

Ser Gly Val Ala Phe Thr Tyr Arg Tyr Lys Ala Thr Ala Pro His Leu
            115                 120                 125

Gly Ser Phe Gln Phe His Val Thr Arg Asp Gly Tyr Asp Pro Thr Glu
            130                 135                 140

Pro Leu Lys Trp Ala Asp Leu Glu Asp Ser Pro Phe Met Asn Ala Thr
145                 150                 155                 160

Ser Thr Leu Ala Pro Asp Ser Tyr Leu Met Ser Gly Thr Thr Pro Ser
                165                 170                 175

Gly Lys Ala Gly His His Leu Ile Tyr Ala Ile Trp Gln Arg Ser Asp
            180                 185                 190

Ser Pro Glu Ala Phe Tyr Ser Cys Ser Asp Val Thr Phe Asp Val Ala
            195                 200                 205

Ala Val Ser Asp Leu His Ser Thr Thr
            210                 215

<210> SEQ ID NO 234
<211> LENGTH: 217
<212> TYPE: PRT
<213> ORGANISM: Tectaria milnei

<400> SEQUENCE: 234

Met Gly Arg Ser Trp Gly Val Val Ala Val Met Val Val Cys Ala Ser
1               5                   10                  15

Gly Leu Leu Ser Val Val Arg Gly His Gly Ser Met Glu Asp Pro Ile
            20                  25                  30

Ser Arg Val Tyr Ala Cys Phe Leu Glu Asn Pro Glu Arg Pro Ile Ser
            35                  40                  45

Ala Ala Cys Gln Ala Ala Val Ala Met Gly Gly Thr Gln Ala Phe Tyr
            50                  55                  60

Asp Trp Asn Ala Val Ser Leu Pro Tyr Ala Ala Gly Arg His Arg Glu
65                  70                  75                  80

Leu Ile Pro Asp Gly Gln Leu Cys Ser Ala Gly Arg Ala Lys Tyr Arg
                85                  90                  95

Gly Leu Asp Leu Pro Arg Asp Asp Trp Pro Gly Thr Ser Asn Met Thr
            100                 105                 110

Ser Gly Val Ala Phe Thr Tyr Arg Tyr Lys Ala Thr Ala Pro His Leu
            115                 120                 125

Gly Ser Phe Gln Phe Tyr Val Thr Arg Asp Gly Tyr Asp Pro Thr Glu
            130                 135                 140

Pro Leu Lys Trp Ala Asp Leu Glu Asp Ser Pro Leu Met Asn Ala Thr
145                 150                 155                 160

Ser Thr Leu Ala Pro Asp Ser Tyr Leu Met Ser Gly Thr Thr Pro Ser
                165                 170                 175

Gly Lys Ala Gly His His Leu Ile Tyr Ala Ile Trp Gln Arg Ser Asp
            180                 185                 190

Ser Pro Glu Ala Phe Tyr Ser Cys Ser Asp Val Thr Phe Asp Val Ala
            195                 200                 205

Ala Val Ser Asp Leu His Ser Thr Thr
            210                 215

<210> SEQ ID NO 235
<211> LENGTH: 51
```

```
<212> TYPE: DNA
<213> ORGANISM: Unknown
<220> FEATURE:
<223> OTHER INFORMATION: Synthetic sequence

<400> SEQUENCE: 235
gtttaacttt aagaaggaga tatacatatg ggcaggtcat ggggagttgt g      51

<210> SEQ ID NO 236
<211> LENGTH: 49
<212> TYPE: DNA
<213> ORGANISM: Unknown
<220> FEATURE:
<223> OTHER INFORMATION: Synthetic sequence

<400> SEQUENCE: 236
gtgatggtga tggtgatggt gggatccggt ggtggagtgg agagatagg           49

<210> SEQ ID NO 237
<211> LENGTH: 49
<212> TYPE: DNA
<213> ORGANISM: Unknown
<220> FEATURE:
<223> OTHER INFORMATION: Synthetic sequence

<400> SEQUENCE: 237
gtttaacttt aagaaggaga tatacatatg gggagatcat ggggagttg           49

<210> SEQ ID NO 238
<211> LENGTH: 49
<212> TYPE: DNA
<213> ORGANISM: Unknown
<220> FEATURE:
<223> OTHER INFORMATION: Synthetic sequence

<400> SEQUENCE: 238
gtgatggtga tggtgatggt gggatccggt ggtggagtgg agagagagg           49

<210> SEQ ID NO 239
<211> LENGTH: 49
<212> TYPE: DNA
<213> ORGANISM: Unknown
<220> FEATURE:
<223> OTHER INFORMATION: Synthetic sequence

<400> SEQUENCE: 239
gtttaacttt aagaaggaga tatacatatg gggaggtcat ggggagttg           49

<210> SEQ ID NO 240
<211> LENGTH: 50
<212> TYPE: DNA
<213> ORGANISM: Unknown
<220> FEATURE:
<223> OTHER INFORMATION: Synthetic sequence

<400> SEQUENCE: 240
gtgatggtga tggtgatggt gggatccggt ggtagagtgg agagagagag          50

<210> SEQ ID NO 241
<211> LENGTH: 51
<212> TYPE: DNA
<213> ORGANISM: Unknown
<220> FEATURE:
<223> OTHER INFORMATION: Synthetic sequence

<400> SEQUENCE: 241
```

```
gtttaacttt aagaaggaga tatacatatg gggaggccat ggggagttgt g              51
```

<210> SEQ ID NO 242
<211> LENGTH: 49
<212> TYPE: DNA
<213> ORGANISM: Unknown
<220> FEATURE:
<223> OTHER INFORMATION: Synthetic sequence

<400> SEQUENCE: 242

```
gtgatggtga tggtgatggt gggatccggt ggtggagtgg agagagagg                49
```

<210> SEQ ID NO 243
<211> LENGTH: 55
<212> TYPE: DNA
<213> ORGANISM: Unknown
<220> FEATURE:
<223> OTHER INFORMATION: Synthetic sequence

<400> SEQUENCE: 243

```
aatctctcat ctaagaggct ggatcctagg atggggaggt catggggagt ggtgc         55
```

<210> SEQ ID NO 244
<211> LENGTH: 55
<212> TYPE: DNA
<213> ORGANISM: Unknown
<220> FEATURE:
<223> OTHER INFORMATION: Synthetic sequence

<400> SEQUENCE: 244

```
tggccaatcc agaagatgga caagtctaga ttaggtggtg gagtggagag agagg         55
```

<210> SEQ ID NO 245
<211> LENGTH: 55
<212> TYPE: DNA
<213> ORGANISM: Unknown
<220> FEATURE:
<223> OTHER INFORMATION: Synthetic sequence

<400> SEQUENCE: 245

```
aatctctcat ctaagaggct ggatcctagg atggggaggt catggggagt ggtgg         55
```

<210> SEQ ID NO 246
<211> LENGTH: 55
<212> TYPE: DNA
<213> ORGANISM: Unknown
<220> FEATURE:
<223> OTHER INFORMATION: Synthetic sequence

<400> SEQUENCE: 246

```
tggccaatcc agaagatgga caagtctaga ttaggtggtg gagtggagat cagag         55
```

<210> SEQ ID NO 247
<211> LENGTH: 55
<212> TYPE: DNA
<213> ORGANISM: Unknown
<220> FEATURE:
<223> OTHER INFORMATION: Synthetic sequence

<400> SEQUENCE: 247

```
aatctctcat ctaagaggct ggatcctagg atgggcaggt catggggagt tgtgg         55
```

<210> SEQ ID NO 248
<211> LENGTH: 55
<212> TYPE: DNA
<213> ORGANISM: Unknown

```
<220> FEATURE:
<223> OTHER INFORMATION: Synthetic sequence

<400> SEQUENCE: 248
tggccaatcc agaagatgga caagtctaga ttaggtggcg gagtggagag acagg        55

<210> SEQ ID NO 249
<211> LENGTH: 5
<212> TYPE: PRT
<213> ORGANISM: Unknown
<220> FEATURE:
<223> OTHER INFORMATION: Synthetic sequence

<400> SEQUENCE: 249

Glu Glu Lys Lys Asn
1               5
```